US009476082B2

(12) United States Patent
Hansen

(10) Patent No.: US 9,476,082 B2
(45) Date of Patent: Oct. 25, 2016

(54) METHOD OF PRODUCING ISOPRENOID COMPOUNDS IN YEAST

(75) Inventor: Jorgen Hansen, Frederiksberg (DK)

(73) Assignee: Evolva SA, Reinach (CH)

( * ) Notice: Subject to any disclaimer, the term of this patent is extended or adjusted under 35 U.S.C. 154(b) by 0 days.

(21) Appl. No.: 13/699,198

(22) PCT Filed: May 20, 2011

(86) PCT No.: PCT/US2011/037337
§ 371 (c)(1),
(2), (4) Date: Feb. 6, 2013

(87) PCT Pub. No.: WO2011/146833
PCT Pub. Date: Nov. 24, 2011

(65) Prior Publication Data
US 2013/0137138 A1 May 30, 2013

Related U.S. Application Data

(60) Provisional application No. 61/346,853, filed on May 20, 2010.

(51) Int. Cl.
| C12P 23/00 | (2006.01) |
| C12P 5/00 | (2006.01) |
| C12N 15/51 | (2006.01) |
| C12N 1/19 | (2006.01) |
| C12N 9/10 | (2006.01) |
| C12N 9/12 | (2006.01) |
| C12N 15/52 | (2006.01) |

(52) U.S. Cl.
CPC .............. *C12P 23/00* (2013.01); *C12N 9/1025* (2013.01); *C12N 9/1241* (2013.01); *C12N 15/52* (2013.01); *C12P 5/007* (2013.01); *C12Y 203/03008* (2013.01); *Y02P 20/52* (2015.11)

(58) Field of Classification Search
None
See application file for complete search history.

(56) References Cited

U.S. PATENT DOCUMENTS

| 4,464,472 A | 8/1984 | Carbon et al. |
| 4,870,013 A | 9/1989 | Gelfand et al. |
| 4,945,046 A | 7/1990 | Horii et al. |
| 5,035,996 A | 7/1991 | Hartley |
| 5,089,398 A | 2/1992 | Rosenberg et al. |
| 5,270,201 A | 12/1993 | Richards et al. |
| 5,436,136 A | 7/1995 | Hinnen et al. |
| 5,559,027 A | 9/1996 | Filmus et al. |
| 5,641,661 A | 6/1997 | Kumagai et al. |
| 5,667,986 A | 9/1997 | Goodey et al. |
| 5,763,239 A | 6/1998 | Short et al. |
| 5,798,227 A | 8/1998 | Hoffman et al. |
| 5,877,018 A | 3/1999 | Filmus et al. |
| 5,888,732 A | 3/1999 | Hartley et al. |
| 5,952,195 A | 9/1999 | Nacken et al. |
| 5,977,439 A | 11/1999 | Hamilton |
| 6,072,050 A | 6/2000 | Bowen et al. |
| 6,077,697 A | 6/2000 | Hadlaczky et al. |
| 6,133,503 A | 10/2000 | Scheffler |
| 7,561,972 B1 | 7/2009 | Welch et al. |
| 7,561,973 B1 | 7/2009 | Welch et al. |
| 7,659,097 B2 | 2/2010 | Renninger et al. |
| 2008/0274523 A1* | 11/2008 | Renninger et al. ........... 435/157 |
| 2013/0171328 A1* | 7/2013 | Kishore et al. ............... 426/658 |

FOREIGN PATENT DOCUMENTS

| EP | 0329203 B | 9/1993 |
| EP | 2226383 | 9/2010 |
| WO | WO 95/08647 | 3/1995 |
| WO | WO 95/11986 | 5/1995 |
| WO | WO 97/44470 | 11/1997 |
| WO | WO 98/54339 | 12/1998 |
| WO | WO 02/059290 | 8/2002 |
| WO | WO 02/059296 | 8/2002 |
| WO | WO 02/059297 | 8/2002 |
| WO | WO 03/062419 | 7/2003 |
| WO | WO 2004/016791 | 2/2004 |
| WO | WO 2006/014837 | 2/2006 |
| WO | WO 2008/008256 | 1/2008 |
| WO | WO 2008042338 A2 * | 4/2008 |
| WO | WO 2009/042070 | 4/2009 |
| WO | WO 2010/141452 | 12/2010 |
| WO | WO 2011/063350 | 5/2011 |

OTHER PUBLICATIONS

Chen et al., Aconitase couples metabolic regulation to mitochondrial DNA maintenance, Science, 2005, 307, 714-17.*
Lange et al., Isoprenoid biosynthesis: the evolution of two ancient and distinct pathways across genomes, Proc. Natl. Acad. Sci. USA, 2000, 97, 13172-77.*
Heinzelman et al., A family of thermostable fungal cellulases created by structure-guided recombination, Proc. Natl. Acad. Sci. USA, 2009, 106, 5610-15.*
GenBank NCBI Reference Sequence NM_001022609.1, 2008, www.ncbi.nih.gov.*
GenBank Reference Sequence NC_002758.2, 2009, www.ncbi.nlm.nih.gov.*
Finogenova et al., Properties of Candida lipolytica mutants with the modified glyoxylate cycle and their ability to produce citric and isocitric acid, Appl. Microbiol. Biotechnol., 1986, 23, 378-83.*

(Continued)

*Primary Examiner* — Robert Mondesi
*Assistant Examiner* — Todd M Epstein
(74) *Attorney, Agent, or Firm* — McDonnell Boehnen Hulbert & Berghoff LLP

(57) ABSTRACT

Yeast strains capable of increased prenyl phosphate production are provided, enabling increased terpenoid molecule production. Heterologous yeast strains with high prenyl phosphate availability are prepared using one or both of two different strategies for increasing the availability of prenyl phosphates for terpenoid production. First, by co-expressing multiple mevalonate pathway gene analogs, a novel heterologous combination of genes results, some of which increases the inherent availability of prenyl phosphates in yeast. Second, by expressing the non-endogenous enzyme ATP citrate lyase (ACL), a buildup of high cytosolic concentration of acetyl-CoA is produced in the cytosol of *S. cerevisiae*.

16 Claims, 3 Drawing Sheets

(56) References Cited

OTHER PUBLICATIONS

Pagot et al., Peroxisomal β-oxidation activities and γ-decalactone production by the yeast Yarrowia lipolytica, Appl. Microbiol. Biotechnol., 1998, 49, 295-300.*
Mascorro-Gallardo et al., Construction of a CUP1 promote—based vector to modulate gene expression in Saccharomyces cerevisiae, Gene, 1996, 172, 169-70.*
International Search Report and Written Opinion in International Application No. PCT/US2011/037337, mailed Aug. 23, 2011, 11 pages.
International Preliminary Report on Patentability in International Application No. PCT/US2011/037337, mailed Nov. 20, 2012, 7 pages.
Blattner et al., "The Completed Genome Sequence of *Escherichia coli* K-12," *Science*, Sep. 1997, 277:1453-1462.
Bonaldo et al., "Normalization and subtraction: two approaches to facilitate gene discovery," *Genome Res.*, 1996, 6:791-806.
Caminci et al., "Normalization and Subtraction of Cap-Trapper-Selected cDNAs to Prepare Full-Length cDNA Libraries for Rapid Discovery of New Genes," *Genome Res.*, 2000, 10:1617-1630.
Chang and Bollum, "Chemistry and Metabolism of Macromolecules," *J Biol Chem.*, 1971, 246:909-916.
Chen and Struhl, "Yeast mRNA initiation sites are determined primarily by specific sequences, not by the distrance from the TATA element," *EMBO J.*, 1985, 4:3273-3280.
Cordier et al., "Heterologous expression in *Saccharomyces cerevisiae* of an Arabidopsis thanliana cDNA encoding mevalonate diphosphate decarboxylase," *Plant Molecular Bio.*, Mar. 1999, 39(5):953-967 (Abstract Only).
Davis et al., "Test of intron predictions reveals novel splice sites, alternatively spliced mRNAs and new introns in meiotically regulated genes of yeast," *Nucleic Acids Res.*, Apr. 2000, 28(8):1700-1706.

DeJong et al., "Genetic Engineering of Taxol Biosynthetic Genes in *Saccharomyces cerevisiae*," Biotechnol. Bioeng., Feb. 2006, 93(2):212-224.
Diatchenko eta l., "Suppression subtractive hybridization: a method for generating differentially regulated or tissue-specific cDNA probes and libraries," *PNAS*, 1996, 93(12):6025-6030.
Kunst et al., "The completed genome sequence of the Gram-positive bacterium *Bacillus subtilis,*" *Nature*, 1997, 390:249-256.
Lotan and Hirschberg, "Cloning and expression in *Escherichia coli* of the gene encoding β-C-4-oxygenase, that converts β-carotene to the ketocarotenoid canthaxanthin in *Haematococcus pluvialis*," *FEBS Letters*, 1995, 364:125-128.
Naesby et al., "Yeast artificial chromosomes employed for random assembly pathways and production of diverse compounds in *Saccharomyces cerevisiea,*" *Microbial Cell Factories*, 2009, 8:45.
Olesen et al., "The pYC plasmids, a series of cassette-based yeast plasmid vectors providing means of counter-selection," *Yeast*, 2000, 16:1035-1043.
Paradise et al., "Redirection of flux through the FPP Branch-Point in *Saccharomyces cerevisiae* by down-regulating squalene synthase," *Biotechnol. Bioeng.*, Jun. 2008, 100(2):371-378.
Ro et al., "Production of the antimalarial drug precursor artemisinic acid in engineered yeast," *Nature*, Apr. 2006, 440(13):940-943.
Shiba et al., "Engineering of the pyruvate dehydrogenase bypass in *Saccharromyces cerevisiae* from high-level production of isoprenoids," *Metabolic Engineering*, 2007, 9:160-168.
Sive and John, "A simple subtractive hybridization technique employing photoactivatable biotin and phenol extraction," *Nucleic Acid Res.*, 1988, 16:10937.
Spingola et al., "Genome-wide bioinformatics and molecular analysis of introns in *Saccharomyces cerevisiae*," *RNA*, Feb. 1999, 5(2):221-234.

\* cited by examiner

SEQUENCE LISTING

<160> NUMBER OF SEQ ID NOS: 90

<210> SEQ ID NO 1
<211> LENGTH: 1188
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| atggtcaaca | ctgaagttta | catcgtatct | gctgttagaa | cacctatggg | gtcatttggt | 60 |
| ggctctttcg | cttcattgcc | agctactaaa | ctgggctcta | tcgcaatcaa | aggggcactt | 120 |
| gaacgtgtca | atatcaagcc | ttctgatgta | gatgaggttt | tcatgggaaa | tgtggtttcc | 180 |
| gctaacctag | acaaaaccc | agctagacaa | tgcgccttgg | gtgcaggatt | accaagatca | 240 |
| attgtttgta | ccacagtaaa | caaggtttgt | gcctctggca | tgaaggccac | tatcttgggt | 300 |
| gcccagacta | ttatgactgg | taatgctgaa | attgtagttg | ctggtgggac | agaatcaatg | 360 |
| agtaacgccc | cttactatgc | tcctaaaaac | agattcggtg | ctaagtacgg | taatgttgaa | 420 |
| ttagtcgatg | gcctgttgag | agacggcttg | tccgacgcct | atgacggctt | accaatgggt | 480 |
| aatgcagctg | aactatgtgc | tgaagagcac | tccatcgata | gagcatctca | agatgccttt | 540 |
| gctatctctt | catacaagag | agctcaaaat | gctcaagcaa | caaaagcctt | cgaacaagag | 600 |
| atagtcccag | tcgaagtgcc | agttggaaga | gggaagccaa | acaaacttgt | tacagaagat | 660 |
| gaggagccta | aaaacttaaa | cgaagataag | ctgaagagtg | ttagagctgt | ctttaagtca | 720 |
| aacggaacag | ttactgccgc | taatgcctct | acactaaatg | atggtgcatc | tgctttagta | 780 |
| ttgatgtcag | cagcaaaggt | taaggaactg | ggtttgaagc | cttggcaaa | gataataggc | 840 |
| tggggcgagg | cagctcaaga | tccagaaaga | ttcactacaa | gtccttccct | tgctattcca | 900 |
| aaggccctaa | acatgcagg | tattgaagca | tcccaggtag | attactatga | gattaatgag | 960 |
| gcattctctg | ttgtcgcagt | ggccaatacc | aaaatcctag | gtcttgaccc | agaaagagtg | 1020 |
| aacataaacg | gcggtggtgt | cgctatgggt | catccttag | gatcttcagg | atcaaggatc | 1080 |
| atctgtactt | tggcctacat | tttagcacaa | aaagatgcta | agattggtgt | cgctgcagtg | 1140 |
| tgcaacggag | gaggtggggc | ttcttctatc | gttatagaaa | gagtataa | | 1188 |

<210> SEQ ID NO 2
<211> LENGTH: 1269
<212> TYPE: DNA
<213> ORGANISM: Artificial Sequence
<220> FEATURE:
<223> OTHER INFORMATION: Synthetic

<400> SEQUENCE: 2

| | | | | | |
|---|---|---|---|---|---|
| atgccagttt | tggctgcact | acttagaaga | ggtcctttat | tgcaaaggag | ggtacaggaa | 60 |
| attagatatg | ctgaaagatc | ctacgttagt | aagccaacac | tgaatgaggt | agttatagtc | 120 |
| tcagcaatta | gaactccaat | tggctccttc | ttgggttctt | tatcatcact | acctgctacc | 180 |
| aaattggggt | ccattgccat | acaaggcgct | atcgaaaagg | ctggtatacc | taaggaggaa | 240 |
| gtaaaagagg | cctacatggg | aaacgttctg | caaggtggag | aagggcaagc | ccctacaaga | 300 |
| caagctgtgt | gggtgctgg | cttaccaata | tctacaccat | gcactacaat | caataaggtg | 360 |
| tgtgcttctg | gtatgaaggc | tatcatgatg | gcatctcaaa | atctgatgtg | tggccaccaa | 420 |
| gatgttatgt | tgctggtgg | tatggaatct | atgtctaatg | ttccttatgt | catgaataga | 480 |
| ggagccacac | catatggcgg | tgtaaaactt | gaggatctga | tcgtgaagga | cggattaact | 540 |

```
gatgtctaca acaaaattca tatggggaac tgtgcagaaa acactgccaa aaagttgaac      600
attacaagag aggaacaaga tacctacgcc ttaaacagtt acacaagatc taaagccgct      660
tgggaagctg gtagattcgg taatgaggtg gttccagtga caattactgt aaagggcaaa      720
cctgatgttg tcgtgaagga agatgaggaa tacaagaggg tcgactttc caagatccca      780 aaactaaaga cggtgttcca agagaaaac ggcacggtta cagccgccaa tgcttctact      840
ttgaatgacg gtgcagccgc tgttgtcttg atgacggctg acgccgctaa gagattaaac      900
gtcaaacctt tagctagaat tgcagctttt gctgatgccg ctgttgaacc aatcgatttc      960
ccacttgcac ctgcatacgc cgtacctaaa gtcttgaaag acgcagggtt gaaaaaggaa     1020
gatataacca tgtgggaagt aaacgaggcc ttttctgttg tagttctagc taacatcaaa     1080
atgttagaaa tggatccaca aaaggttaac attaatggtg gtgccgtctc attgggccat     1140
ccaataggaa tgagtggagc cagaattgtg gtacatctag cccacgcttt gaaacagggt     1200
gaatatggac ttgcctcaat ttgcaatggt ggaggagggg caagtgccat gctaatccag     1260
aaattgtaa                                                              1269

<210> SEQ ID NO 3
<211> LENGTH: 1221
<212> TYPE: DNA
<213> ORGANISM: Artificial Sequence
<220> FEATURE:
<223> OTHER INFORMATION: Synthetic

<400> SEQUENCE: 3
atggcccatt ccgctgattc atctgacaac ccaagagatg tttgcatcgt aggcgtggct       60 agaacccccaa tgggtggttt cttagggtca ctttcatctt tgccagccac taaattgggc     120
tccttggcca ttacagctgc attgaaaaga gagatgttaa ctagactgtg gagtaaggag     180
gtcgttttcg gtaatgtttt aagtgctaat ctgggtcaag cccctgccag gcaggctgcc     240
ctgggcgctg gtataagtaa cagtgtcatc tgtacaacag taaacaaagt gtgtgcctcc     300
ggcatgaaag ctgttatgat agccgctcaa agtatccaat taggtataaa cgatgtcgta     360
gtggccggtg gcatggaatc catgtctaat actccaaagt atcttgctga agccagaaaa     420
gggtctagat ttggccacga ctcattggta gacggcatgc tgaaggacgg actatgggat     480
gtttacaatg attgtggtat gggttcatgc gccgaactgt gcgcagagaa gtttgaaatc     540
acaagagaac aacaagatga ttatgcagta caatcttttg aaagaggaat cgctgcccag     600
gagtctggtc cattcacatg ggaaattgtt ccagtgaag tttctggtgg aagaggtaga      660
ccttcaacaa ttgtagataa agacgaaggg ttagggaaat tcgatgccgc caagttaagg     720 aagttgagc cttcctttaa agagaacggt ggaacggtca cagccgggaa cgcatcttcc     780
atctccgatg gtgcagctgc tatcgttcta gtgtcaggag aaaaggcctt gcaactaggg     840
ttgcaagtgt tagctaaggt taaggggtac ggagatgccg ctcaggaacc agagttcttc     900
acgaccgcac cagctcttgc tattccaaaa gctattgcac ctaattcacc ttactctgaa     960
tcctatcaag ttgattacta tgagattaac gaagcctttg ctgtcgtcgc tttagctaac    1020
caaaagttat gggaatttc acctgaaaaa gtgaacgtga tggcggagc cgtttctcta    1080 ggtcatcctc taggttgctc tggcgctaga attcttataa cttgcttgg cattctgaaa    1140 aagagaaacg gaaagtacgg tgtaggagga gtctgtaatg gaggtggtgg tgcttctgca    1200 ttggtttttgg aagttgtcta a                                             1221
```

<210> SEQ ID NO 4
<211> LENGTH: 1323
<212> TYPE: DNA
<213> ORGANISM: Artificial Sequence
<220> FEATURE:
<223> OTHER INFORMATION: Synthetic

<400> SEQUENCE: 4

```
atgcattcta ccagacatat cttaagacaa agggccgtcc tagttacagg cgctagaaca      60
ccattcgtga atcatttgg ggctcttatg aaagcagata ccttggaatt ggcatcagca     120
tcagtcgctg ggttgctgaa caagacctca ctggacccta gagatatcga tcatatcgtt     180
tggggtaatg ttgtacttca aggatcagct cataactgcg ccagagaaat agttatcgac     240
cttaacatgc taaaaagat catcggtaat ttgacatcta tggcctgtgc ttcaggctta     300
tcttctttgt cacaagcctg tatgctaata gagggtggtc atgccgatgt cgtcattgct     360
ggcggttctg attcagtctc caacactgaa gtgcctttgc caagatccgt cacttacggt     420
ctaatgatgg cccaaaggaa gggtgttatg ggcttcttta aggaagcagg atacaaccca     480
ttcaaatggt ttccaggcgg tattgcttta accgaacgta gtacaggaaa aactatgggt     540
tggcatggag acttaattgc tgagttaaac tctatatcta gagatgacca ggaagccctg     600
gctgtggctt tcatgcaaa tgctgctaga gcagaaaaag ctgggtactt aaggaggaa     660
attgtacctg tgacaatcga caaaaagggc aaaaagactg aagtaacatg tgatgatgtt     720
atgcaaagag atacagaaaa gatgaaggcc aagatgccat cattgaagcc tgttttcaga     780
aaagagggag gtacaataac agcagccact tccagtactc tgactgatgg tggctctgca     840
atgttggtta tgtcagagga aaaggccaaa agttgggtt atccaactga tgtctgcgtg     900
aagtcttggt atttcagtgg tatcgatcct tacccacaac ttttgttagc accagttcta     960
ggttggggtc agctttgaa aaaggccgga ttaaccccta agatatcga tttgtacgaa    1020
attcacgaag catttgctgc acaagttcta gccacaatta agtgtttgaa gtctcaggaa    1080
ttcttcgata ggtacgctaa cggtgcaaag ccagtattaa ctgaggatat tgatctttct    1140
aaactaaatg ttaatggcgg ttccttagca cttggccacc cattcgccgc tacaggaggt    1200
agaatcgtaa tctctctagc aaatgagttg agaagatccg gaaagagaca cgggctggtc    1260
agtatttgtg cagctggagg gttaggcgga gtagctatac ttgagcatac agcaagtaag    1320
taa                                                                  1323
```

<210> SEQ ID NO 5
<211> LENGTH: 1140
<212> TYPE: DNA
<213> ORGANISM: Artificial Sequence
<220> FEATURE:
<223> OTHER INFORMATION: Synthetic

<400> SEQUENCE: 5

```
atgaaccaag cagtcatcgt tgctgccaag agaacagctt tcggaaagta cggtggcaca      60
ctaaaacaca tcgagccaga gcaactgtta aagccacttt ccaacatttt caaggagaaa     120
tatccagagg ttatatccaa gattgatgat gttgtgttag gaatgttgt aggtaacgga     180
ggcaacatcg ccagaaaggc tctgcttgaa gctggcctga agacagtat tccaggtgtt     240
acaattgata gacaatgcgg tagtggttta gaatctgtcc agtatagttg tagaatgata     300
caggccggag ccggcaaagt ctacattgct ggtggtgttg agtctacgtc cagagctcct     360
tggaagatca aaagacctca ttctgtctac gaaacagctt taccagaatt ctatgaaaga     420
```

-continued

```
gcttcatttg cccctgagat gtccgatcct tcaatgattc aaggtgccga aaatgcagct      480
aaaatgtacg acgtatcaag agaattgcaa gatgaatttg cctacagatc tcaccagctt      540
acggcagaaa atgtcaaaaa tggtaatatc tctcaagaga tccttccaat tacagttaag      600
ggagaaatct ttaacactga cgaatcacta aaaagtcata tacctaagga taacttcggg      660
aggtttaaac cagtaatcaa gggcggtact gtgaccgcag ccaactcttg tatgaaaaat      720
gatggtgccg tcctgttgtt gattatggag aaagacatgg cctacgaatt agattttgaa      780
cacgggctgt tgttcaagga tggagtaact gtgggagtgg actctaatttt ccctggtatt      840 ggcccagtac cagctatctc taatttgttg aagagaaacc aattgactat cgaaaacatt      900
gaagtcattg agataaacga agccttctca gcacaagttg tggcctgtca caggccttg       960 aacatctcaa acactcaatt gaacatatgg ggaggagctc tagcctctgg gcatccttac     1020
ggagcttccg gtgctcaact agtgaccaga ttgttctata tgtttgataa ggaaacaatg     1080
atagcttcca tgggaattgg cggtggctta ggtaatgctg ctttattcac aaggttctaa     1140
```

<210> SEQ ID NO 6
<211> LENGTH: 1422
<212> TYPE: DNA
<213> ORGANISM: Artificial Sequence
<220> FEATURE:
<223> OTHER INFORMATION: Synthetic

<400> SEQUENCE: 6

```
atgactatcc ctttggccac agctgttgca gatattgaat taccaagacc aaaggatgtt       60
ggcgttttgg gtatcgaagt atactttcct aggagatgtg tttcagaagc cgacctggaa      120
gtgttcgatg gcgtttccac aggaaagtac actattggac tgggtcagga atacatggca      180
tggcctgatg accgtgaaga tatcaattct tttgccctta cgctgtatc tggtctgttg       240 gaaaagtaca acattgatcc aaaatcaatt ggcagaatcg atgtaggcac agaaactatc      300
attgataagt caaaatctgt taaaacaaca ctgatggatc ttttcgcaga agctggaaac      360
tacgatatcg aaggtattga cagtaaaaac gcttgttacg gaggtactgc tgccttgttc      420
aatgcaatca attggataga gtcctcttct tgggacggta gaaacgctat agttgtatcc      480
ggagatatag ctgtctacgc cgaaggtgct gcaagaccag caggtggtgc aggggcttgt      540
gcaatcttaa tcggaccaaa tgctccagtt gtctttgaac cagtgcatgg tacctacatg      600
gctaacacat atgacttcta caagccaaat ttgtcatcag agtatccaga ggttgatggc      660
ccagtgagtg tcgtcacata tgtcgccgct cttgatgccg catatactac tttcaaggaa      720
aagttcgcta agctgcaaa gagagctcaa gttgctggaa aggaagtaag ttctgcaact      780
ttctctttag aggatttgga ttatgccatt tttcactccc cttatggtaa acaagcagtc      840
aaggggcatg ctagaatgtt atacaacgat ttcatcacta tcctaaagaa tcctagattc     900
gccaacgttc caaatccaga gtccttcata tcacaatcac atgcacaatc tttgactgac     960
aaaaacgttg aaaagacttt cgtggcacta agtaaagcat cttttgctaa aaagacagat    1020
cctgggatgg catgctcaaa gagactaggg aacatgtaca cagcatctct atacggttgt    1080
ttggcatcat tgttaggtac tgttgaacca tccgagttag gcgtaagag agtttctttg      1140 tttttctttg gctcagggtg cgctgctaca ttcttcaccg ccaggattaa aggcgacacc     1200
agtgagataa aggaaaagtt aaagctaaag gaaagactag ctgctatgac agttgcccct     1260
cctgaagagt tcgtggctgc cttggccttg agagagaaaa atcataacgc agtagatttt    1320
```

| | |
|---|---|
| acccccagaag gatctgtgga taacatctgg ccaggtgctt actaccttga gcacgtagat | 1380 |
| tctaagtttc gtagaaaata cgtcagagcc cctgttgcat aa | 1422 |

<210> SEQ ID NO 7
<211> LENGTH: 1527
<212> TYPE: DNA
<213> ORGANISM: Artificial Sequence
<220> FEATURE:
<223> OTHER INFORMATION: Synthetic

<400> SEQUENCE: 7

| | |
|---|---|
| atgcaaagat tattgacacc agtcagacag gtacttcaag ttaagagggt tatgcaggaa | 60 |
| gccagtcttt taccagctag acttttgcca gctgcacacc cttctttctc aacagttcca | 120 |
| gctgtaccac ttgcaaagac tgacacatg ccaaaggacg tcggcatact ggcaatggag | 180 |
| gtttactttc cagcccagta cgtggatcaa actgaacttg aaaagttcaa taaggtagaa | 240 |
| gcaggtagat acaccgtagg tttgggtcaa acacaaatgg gattttgtag tgttcaagag | 300 |
| gatgtaaatt cactatgctt aactgtggtt caacaattga tggagagaac ccaactgcca | 360 |
| tgggattccg tgggcagatt agaagttggc acagaaacaa tcattgataa gtctaaagca | 420 |
| gttaagacag tgttaatgga actatttcag gattctggta atacagatat cgaaggtatc | 480 |
| gatactacaa acgcctgtta tggaggaaca gcttcattgt ttaacgcagc aaactggatg | 540 |
| gaatcttcat cttgggatgg tagatacgct ttggtagtat gcgagatat cgctgtctat | 600 |
| ccttcaggta acgcaagacc aacaggcggt gctgggctg tcgcaatgtt ggttggtcca | 660 |
| gaagctccat tagttttaga aagaggtttg aggggtacac acatggaaaa tgtttatgac | 720 |
| ttctataaac ctgatgtcac ttctgaatac cctttagtcg acggaaaact ttccattcaa | 780 |
| tgttacctaa gagcccttga taatgttac gcattctaca gacaaaagat tgaaaagcaa | 840 |
| tggaagcaag ccggaattga tagacctttc accttagatg atgttcaata catgatcttc | 900 |
| catactccat tctgtaagtt ggttcaaaag tccttagcta gattgatgtt taatgatttc | 960 |
| ttgctagcat ctggcgatac tcaaaccgga atatacaaag gcttagaggc tttcagaggt | 1020 |
| cttaaactgg aggacaccta cactaataag gatgtagata aggcctttct gaaggcttct | 1080 |
| ctgaatatgt tcaacaaaaa gactaaaaac tctctttact tgtccacata taacggaaac | 1140 |
| atgtacacta gttctctgta cggttgctta gcctccctat tagctcatca ttcagctcag | 1200 |
| gatttggctg gtctagaat aggtgctttt tcatacggct caggcctagc agcaagtttc | 1260 |
| ttttccttcc gtgttagtca agatgcctct ccagggtccc ctctggaaaa gttagtctca | 1320 |
| tctacttctg acttgcagaa aagactagcc agtagaaaac gtgtttctcc tgaggaattc | 1380 |
| acagagatta tgaatcaaag agagcagtat taccataaga tgaacttctc accaccaggt | 1440 |
| gacaaaaact cattgtttcc tgggacatgg tatttggaaa gagtcgatga gttgtacaga | 1500 |
| aggaaatatg cccgtagacc agtttaa | 1527 |

<210> SEQ ID NO 8
<211> LENGTH: 1389
<212> TYPE: DNA
<213> ORGANISM: Artificial Sequence
<220> FEATURE:
<223> OTHER INFORMATION: Synthetic

<400> SEQUENCE: 8

| | |
|---|---|
| atggcttctc aacctaaaaa cgttggtatc ttggcaatgg aaatatattt tcctcctacc | 60 |
| tgtctgcaac aggaagtgtt agaagctcac gatggtgcat ctaaaggtaa atacactatt | 120 |

```
ggtctgggtc aagattgtat gggcttttgt acagaagtcg aggatgtaat atctatgtcc      180
ttgactgctg ttacatcatt gcctgagaag tacgccattg atccaaagca aatagggaga      240
cttgaggttg gctccgaaac ggttattgat aaatccaaga gtattaagac gttttttgatg    300 cagatctttg aaaaacatgg taataccgat atagaaggtg tagactcaac aaatgcctgt      360
tatggaggaa ctgccgcctt gttcaactgc gtgaactggg ttgaatcttc ttcctgggat      420
ggaagatacg gccttgtagt ctgtacagat agtgccgtgt atgccgaagg ccagccaga       480 ccaacaggag gtgctgctgc catagcaatg ctagtgggcc ctgacgctcc tattgttttc      540
gagagtaaaa tcagagcctc acatatgtct catgcttatg acttctataa acctatctta     600
gattccgaat acccagtggt cgatgggaag ttatctcaga catgttattt gatggctttg      660
gattcttgtt acaaaagtct atgcaataag tacgaaaaac tggagggggaa gcagttctcc    720 atggctgacg ctgcatactt tgtctttcat tctccataca caaattagt gcaaaaatca      780 tttggtagac tgttgttcaa tgacttcctt aggaacgcct cttctgtaga tgaatcagca     840
aagcaaatct tagctccttt cgagtctttg gccggagacg aatcttacca atctagagat     900
ttggaaaagg cctcccaaca ggttgctaag ccattctatg atgagaaagt tcaaccaaca     960
actctaattc ctaaacaagt aggtaacatg tataccgcca gtctgtacgc tgcctttgct    1020
tcattgatcc acaataagca taatacactg gcaggtcaaa gagtgattgt tttcagttac    1080
ggttccggac taacagcaac aatgttctct ttgaagttca cgaaggaca acatccattt     1140 tctttgagta acattgcttc agtcatgaat gtttcagaga agctaaaatc aaggcatgag    1200
ttcactccag aaaagttcgt agagattatg aagttaatgg aacacagata tggcgccaag    1260
gattttgtta cttctaagga ctgctcctta ttggcaccag ggacttacta ccttacggaa    1320
gtcgattcaa aatacagaag attctacgct caaaaagccc cagaacacgg attagttaat    1380
ggccactaa                                                             1389

<210> SEQ ID NO 9
<211> LENGTH: 1506
<212> TYPE: DNA
<213> ORGANISM: Artificial Sequence
<220> FEATURE:
<223> OTHER INFORMATION: Synthetic

<400> SEQUENCE: 9
atgatgagaa acacatgttt atctttggct ggagtttcag gtatggcagt ttacgcacct       60
cattgcagag tcgatttgga acaatggtgt aagtggactg gaactcctg ggataaagtc      120 tctagtgttg tcggtcagag ttttagaatc acctcccaca acgaaaatgc ctacacaatg      180
gctgccaatg ctgtgttgag actaatcgtt aacaacaata ttgatcctac caaaataggg     240
ttcctgggat taggcactga atcaagttcc gataactctg ccggtgccat aatcgtaaaa     300
ggtatggttg acaaaggctt gagagctatg aatatgcctg ctatgtcaag acattgtgag    360
gttcctgaat tcaagcacgc ttgtttagca ggtgtgtatg caatggagtc agcaacaaga    420
tttgtcaacg cagatggcaa ggacagaatg gcaatagccg tggcctctga tatagctgag    480
tacgccctag gctcaactgg ggaacagact caaggtgccg gtgcaactgc aatggtcctt    540
gaacatgacc ctaagctgtt tgaagtacaa ttacaacatt cagggtctgc ctccgactac    600
agaggaccag attttagaaa accacaccgt agacatttca tgaatttgga ggaatacacc    660
aaatcttccg ctaatggtaa gatggctgat ttcccagtct ttagtggacc ttattctact    720
```

```
ttagtatatc aggaagaggt tacagtagct gtcgaacaca tgctagaaag attgcaacaa    780
tctcctggta aatactacga tgatgttaca gcattattct tccatcgtcc atacaacatg    840
atgccaatcc aagccatgag tttcttatat gctagaggat tagcaagagc tacatctgaa    900
gagcacaagg cacatttcgc tgaattgtgt aagcagggca aggccgatcc agcagctgtt    960
gttaaggaat tagatgttaa tccacattac ttccaacaaa tcgaatcagg aggagaacca   1020
aaggatgcat tcccagccac tggcaaagta gctaaggtgt tgagaaagga caaaaagttt   1080
attgatctac tagagaaaaa gatgtctatg ggttccccag caatgggaaa cttcggcaat   1140
ctgtatactg cttctctacc ttgttggctt gcagctggtt tcgaggaagc atacacaagg   1200
aagttagata ttacaggtaa gccaatggtt atggtgggtt acgggtcagg tgatgcttca   1260
atgtctattc caattttgcc agtaccagga tgggaaaacg ccgctgctaa tatcaacgta   1320
tcaaaggcct tggaaaatcc tgttaacctt gataaagctc aatacgaagc attgcataca   1380
ggtgctgaga aaacgacct tgctaaggat cgtagaaaga tggagttcgt tatcgatagg   1440
cttggcaata gaaacgaagc tgcatttcaa gatgttggca ttgagtatta cagatacatc   1500
caataa                                                              1506

<210> SEQ ID NO 10
<211> LENGTH: 1167
<212> TYPE: DNA
<213> ORGANISM: Artificial Sequence
<220> FEATURE:
<223> OTHER INFORMATION: Synthetic

<400> SEQUENCE: 10
atgacaatcg gtattgataa gataaacttc tatgttccaa atactatgt tgatatggca     60
aagttagctg aggccaggca agtagatcct aacaaatttc taattggcat tggacagact    120
gagatggcag tcagtcctgt taatcaagat atcgtctcta tgggtgctaa tgcagctaaa    180
gacatcatca ccgatgagga caagaagaaa atcggtatgg ttatagttgc cacagaatct    240
gcagttgatg ccgcaaaggc tgctgctgtc caaattcata acctgttagg tatacaacca    300
ttcgccagat gtttcgagat gaaagaggcc tgctacgccg ctactcctgc catccaattg    360
gctaaggatt acttagcaac aagaccaaac gaaaaggttt tggtaatagc tacagatact    420
gctagatatg ggttgaattc tggaggtgaa ccaacacagg gagccggtgc tgttgcaatg    480
gtgatcgctc acaatccatc aattttggct ttgaatgagg atgcagtggc ttacactgag    540
gacgtttacg acttctggcg tccaactggt cataagtacc ctttggtaga cggcgcactt    600
tcaaaagatg cttacattag atcattccaa caatcctgga acgaatacgc taagagacaa    660
ggcaaatctc tagctgactt cgccagtttta tgttttcatg tacctttac taagatgggc    720
aaaaaggccc tagaatccat tatcgataac gcagatgaaa ccacacagga aaggctaaga    780
tctggttacg aggatgcagt agattacaac agatacgtcg gaacatctca cacaggatcc    840
ttatacttat ctcttatttc acttctggaa aacagagatc tgcaagcagg tgaaacaatc    900
ggtttgttct catatggatc tggttctgtc ggggaattct attcagcaac acttgttgaa    960
ggatacaaag atcatctgga tcaagctgct cacaaggcct tattgaataa cagaactgaa   1020
gtgagtgttg atgcatatga acatttttc aaaagattcg atgatgttga atttgatgaa   1080
gagcaagacg cagttcatga ggatagacac atattctact tgtccaatat agaaaacaat   1140
gtcagagaat atcatcgtcc agaataa                                       1167
```

```
<210> SEQ ID NO 11
<211> LENGTH: 3681
<212> TYPE: DNA
<213> ORGANISM: Artificial Sequence
<220> FEATURE:
<223> OTHER INFORMATION: Synthetic

<400> SEQUENCE: 11
atgagagctg tccttagatt gttatcaaca catactgttt tctctcctat tgaaacaatt      60
gtatctgttt tcgtgttagc tacattagct tacttccaca tcttgtccgg aatcaagcac     120
tcaagtttct ttgcatcttc tcatcctcct gctatcagac ctgcttttgc acatctgacc     180
aacggggaat gggttgccgt ctcccaacat gattggactg aagcatggaa gcatcctggc     240
ggttcacttg atgcattaga acttcaacaa gtagttttca ctttagatga caagactcaa     300
ccatctgctg tgctagatgc atccgcaatt agtcagcact agtttccaa tgttcctgca      360 ttatctggaa aagcctactc ttcattgtgc caccatccaa atgtatcagg cacctcctgt     420
tttacatcag tttctggtcc aggagcttca ccaatcttga cactgagttt taagcctgga     480
actagagacg attggttagg atcattaagg aaggagaaaa ctatcacact agatggggtt     540
aagtacgacg ttggagccgg aaaaagacaa gagtcaatcg gcgatatgga atcatctaag     600
tgggttgctt atgcattatc agctttggta cttagatttt gggaattaac aaaggcagat     660
tccttagata tactagtggt tctaactggg tacatcctaa tgcacgtaac attcatgaga     720
ttgttcttgg catccagagc acttggcagt aacttttggt tatcagctgg catattctcc     780
tccgcaacaa tttctttcct attcacttta ccaatgtgta gatctatgga tattccactt     840
gatccaattg ccttgacaga agccctgcca ttcttggtgt gtaccgtagg ttttgacaaa     900
ccacttagat tggcaagagc tgtgatggct catcctaata tccttaaacc tcaagatgat     960
ggtaggatga agctgccgg agatgtcatt cttgaggcac tggacagagt tggtaacatg    1020
atattgagag attacgcttt agagatcgca gttctattcg ttggcgttaa ctccagagtt    1080
ggcggtctta aggaattttg tgctgtagct gcagcattac ttgctatgga cagattaatg    1140
acattcacac tttatacagc agtgttaacc atcatggttg aggtaaggcg tatcaaaaag    1200
gtcagagata tgactaaggc tagatctaga agttcttcta ttaccgccgt tacagccaac    1260
ggcaccgcca taagaggcgt tttgagtaga aaatcttcaa acaatctgt gacagaacca     1320 gagacaacta aaaacctaag acaaagagcc actgattcag ccatcggtgt taagggttca    1380
ttgctgaaag atggaggcag attgcaggaa gccgaggaga atccaatggc aagattaaag    1440
ctattgttaa tcgcttcctt cttaacacta cacatcttga acttttgtac tactttgact    1500
tcagccacag ctaacgcaag acatcaaaga catccttta gaaccgttca agaggtagta     1560
ccaattccta gagttgacat tactaccccca gccatagcca atatcttgtc tcatctagct    1620
gtggctcagg aacctatgtt cactgttgtt ggcagtgaac ctatcgaact tcttgttaaa    1680
gtcgctgctc cagtctacgt ccatgctcta ccattggccc ctgctttaag gcttcaaac    1740 actaatactg agaagctat tgaaaacttt atgagttcat ggtctagtct ggtaggtgac      1800
ccagttgtta gtaagtggat cgtagcattg ctagctgtct ctgttgcatt gaatggatac    1860
ttgttaaagg gtatagccgc aggttccggg ttggctgcca tgagctgt tagatctcaa      1920 ggtgttcgtt tcagatctag agctagaagt atcgtaaaga tatctgatga acctgagcca    1980
gagccagaac actctatcga cccagcacca gtagtgttct tcgcttccgc agcaccagct    2040
gtagaggccc ctgctccagc tcctgcacct gaaccagaac caccagtcaa cagaccacca    2100
```

| | |
|---|---|
| ccattgacta ttttctcaag accactgaac ttagaaacag tggacaaaaa gttacaagat | 2160 |
| gctctgccaa taagatcccc accacctgtt gaaccaatca ctccagaatc tagagaagtg | 2220 |
| gaaccaaccc aagtagaagt aagatctcta gctgaatgtg tggatgtgtt cgagaatggg | 2280 |
| ccaagaccag tctcagtggc tttaaagact ctgaatgatg aggaagttat cctgctttgc | 2340 |
| caaacaggta agatagctcc atatgcattg gttaagatgt tggctgattt cgatagggcc | 2400 |
| gtacgtgtca aagagcact tattagtaga gcttcacgta caaaaacttt agaaaactca | 2460 |
| ctggttccta tgaaagatta tgattacgcc agagtcatgg gtgcctgttg tgaaaacgtt | 2520 |
| atcggataca tgccattacc actagggatt gcaggtccat tgaagattga tggcttgatg | 2580 |
| tatcctatac caatggcaac cgcagaaggt accttggttg catctacttc tagggctgt | 2640 |
| aaggccttaa atgctggtgg aggggtcaca actgtcttga cagcagatgg catgacaaga | 2700 |
| gggccagcta tagactttcc ttccatcgtc agagctgcag aggctaaggc cttcattgaa | 2760 |
| tcagaagatg gatacgctac aatcagggag gctttcgagt ctacttctag atttgccaag | 2820 |
| ttgcaaaaga tcaagtgtgc actagctggt cgtactcttt tgtcagatt tgctactaga | 2880 |
| acaggagatg ccatgggtat gaacatgatt tctaaggcta ccgaaaaggc acttgatgtc | 2940 |
| ctgagtcacg agttccctga atggtcgtc cttgctttgt ctggtaacta ctgcacagac | 3000 |
| aaaaagcctg cagctatttc atggatcgaa ggtaggggaa aatctattgt agcagaagca | 3060 |
| gttattcctg gtaaggtcgt taagtcagtc ctgaaaacaa cagtcgagtc tctttgcaat | 3120 |
| gtcaacacta agaaaaacct gattggttca gccatggcag ttctgttgg tggtttcaac | 3180 |
| gctcatgccg ccaacatcct aacagctgtg ttcctagcca caggtcagga tcctgctcaa | 3240 |
| aatgtcgaat cttctaattg catgacttta atggaaccaa caaacggcgg tgaggatttg | 3300 |
| ctaatgacaa tttcaatgcc atgtatagag gtaggaaccg ttggtggagg acaattctg | 3360 |
| gaaccacaag gtgcagtttt ggatttgttg ggcgttagag gggctcaccc tactaatcct | 3420 |
| ggtcaaaacg ctcaacagtt agccagaatt atcgcatcag ctgtaatggc aggcgaattg | 3480 |
| tctttgataa gtgccttagc cgcaggtcat ttggttagag ctcatcttgc ccacaatcgt | 3540 |
| tctcaattga atacaccaat gccatccaga ccacatactc ctggccctga ggatgtctca | 3600 |
| catgtgcagc agctacctac accatctgca tctgatgata aggtgttac agctcaaggt | 3660 |
| tacgttgtcg aagcaaaata a | 3681 |

<210> SEQ ID NO 12
<211> LENGTH: 2667
<212> TYPE: DNA
<213> ORGANISM: Artificial Sequence
<220> FEATURE:
<223> OTHER INFORMATION: Synthetic

<400> SEQUENCE: 12

| | |
|---|---|
| atgttatcaa gattgttcag aatgcatggt ctatttgttg cttctcaccc ttgggaagta | 60 |
| atagttggta ctgtaacatt aacgatctgt atgatgtcta tgaacatgtt taccggaaac | 120 |
| aacaagattt gtggttggaa ttatgagtgt cctaagctgg aagaggatgt gttgagttca | 180 |
| gacatcatca tacttactat aacaagatgc attgcaatat tgtatatcta cttccaattt | 240 |
| caaaacctta gacaattggg tagtaaatac atcctaggca tcgccggatt gttcactatt | 300 |
| ttctctagtt ttgtttttctc aaccgtcgtt attcacttt tggacaaaga gttaactggt | 360 |
| ttgaacgaag ctctaccatt cttccttgctg ctggtagatt tgtccagagc ttccgcttta | 420 |
| gctaaattcg ctctgtcctc taattctcaa gatgaagtta gagagaatat agcaagggga | 480 |

```
atggccatac ttggacctac tttcacactt gatgcccttg tcgaatgttt ggttattggg      540
gttggcacaa tgtccggcgt tagacagtta gaaatcatgt gttgttttgg ctgtatgagt      600
gtcttggcta actactttgt ctttatgaca ttctttccag cttgcgtttc tttggtattg      660
gagctgtcaa gagaatcaag agaaggcaga ccaatatggc aactatcaca tttcgccaga      720
gtgttagaag aggaggaaaa caaacctaat cctgtcacac agagagtgaa atgatcatg       780
tctttgggtt tagtcctagt gcatgctcat tctagatgga tcgcagatcc atcccctcag      840
aattctacag ctgataactc taaagttagt ttaggtttag atgaaaatgt aagtaagagg      900
attgaacctt ccgtgtcttt gtggcaattc tacttatcaa aaatgatttc catggatatt      960
gaacaagtga taacgttgtc tttggcttta ttgttagccg ttaagtacat tttctttgag     1020
caagccgaaa cggaatctac attatcactg aaaaacccaa ttacatcccc agtcgttacc     1080
cagaaaaaga taactgatga ttgctgtaga agagatccag tgttggtcag gaatgatcaa     1140
aagttccacg ccatggagga ggaaactagg aaaaacagag aaggaaagt tgaagttatc      1200
aagcctctat tagcagaaaa tgacacttca catagggcca ctttcgttgt cggcaattca     1260
tctcttttag gtacgtcatt ggagctgaaa acacaggaac cagaaatgga actaccagtt     1320
gaaccaagac caaatgagga atgtttgcaa atactagaga acgctgaaaa gggagccaag     1380
ttcctatctg atgccgagat tatccagctg gtcaatgcca agcacattcc tgcctacaag     1440
ttggaaaccc ttatggagac acatgagaga ggtgtgtcta ttaggagaca attactatct     1500
aaaaagttac ctgaaccaag ttccctacaa tacctgcctt atagagatta caattactcc     1560
ttggtaatgg gagcttgttg tgaaaatgtc attgggtaca tgccaattcc agtgggtgtc     1620
gccggtccac tatgtttgga cggtaaggaa tttcaagtac ctatggcaac gactgaaggc     1680
tgcttagttg catctacaaa cagaggttgt agagccattg gattaggtgg cggtgcttct     1740
tcaagagtct tggctgacgg tatgactaga ggtcctgttg tgagatttcc tagggcctgt     1800
gactctgcag aagttaaggc ttggttggaa actccagaag gtttcaccgt aatcaaagag     1860
gcctttgatt ccacatcaag ggtggccaga ttacaaaaac tacacatgtc tgtcgctggg     1920
agaaatctgt atatcagatt tcaatccaga tccggcgacg caatgggtat gaatatgatt     1980
tcaaagggga cagaaaaggc tttgtcaaag ctgcaggagt atttcccaga gatgcaaatc     2040
ttggccgtat ctggcaacta ttgcacagac aaaaagcctg ccgccatcaa ctggattgaa     2100
ggaagaggca atctgtggt tgtgaagct gtaattccag ccaaagttgt tagagaagtg       2160
ttaaagacca caacagaagc tatgattgaa gtaaacataa acaaaaactt agtagggtct     2220
gccatggctg gttcaattgg aggatacaac gctcatgctg ccaatattgt aaccgctatc     2280
tacatcgcat gtggacaaga tgctgcccaa aatgtcggtt cctcaaattg catcacattg     2340
atggaagcat ctggccctac aaacgaggat ttgtatatca gttgcacaat gccatctata     2400
gaaatagga ctgtgggagg aggaactaac ttacttccac agcaagcctg cttacaaatg      2460
ctgggtgtac aaggagcctg tagagataat ccaggggaga acgctagaca acttgccaga     2520
attgttgtg gacagttat ggctggtgaa cttagtctaa tggcagcttt ggctgctggg        2580
cacctggtga gatctcatat gattcataat agaagtaaga ttaaccttca agatttgcaa     2640
ggtacgtgta cgaaaaaggc tgcctaa                                          2667
```

<210> SEQ ID NO 13
<211> LENGTH: 1704
<212> TYPE: DNA

<213> ORGANISM: Artificial Sequence
<220> FEATURE:
<223> OTHER INFORMATION: Synthetic

<400> SEQUENCE: 13

| | | | | | |
|---|---|---|---|---|---|
| atggatttga | gaaggaaatt | accacctaag | cctccatctt | caacaacaac | aaaacagcca | 60 |
| agtcataggt | cccattctcc | tacgccaatt | ccaaaggctt | cagatgcatt | gcctcttcca | 120 |
| ttgtacctga | ccaatacgtt | tttcttcact | cttttctttt | ccgtagcata | ttacctgttg | 180 |
| cataggtgga | gagacaagat | tagatccgga | acacctttac | acgttgtgac | actgactgaa | 240 |
| ctatccgcaa | ttgtactgct | gattgcttcc | ttcatctatc | ttttaggctt | tttcggtatt | 300 |
| gattttgtgc | aatctttcac | atcaagagaa | aatgagcaac | taaacaacga | tgatcacaac | 360 |
| gtcgtgtcaa | caaacaatgt | tttatctgat | agaaggttag | tttacgacta | tggattcgat | 420 |
| gtgacaggag | acaacgataa | cgataatgat | gacgatgtta | ttgtgaaaag | tgtcgtttct | 480 |
| ggggaagtta | attcttatag | tttggaggct | tccctaggag | attgttacag | agccgcaaag | 540 |
| attagaaaga | gagccgtcga | gagaattgtc | gggagagaag | tattaggctt | gggtttcgag | 600 |
| ggatttgatt | atgaatctat | cctggggcaa | tgttgtgaaa | tgcctatcgg | gtacgtccaa | 660 |
| gtgccagtag | gtgtcgctgg | acctttattg | ttaaatggtg | gggaattcat | ggttccaatg | 720 |
| gctacaactg | aaggctgtct | tgtagcttcc | actaatagag | gttgtaaagc | catatgctta | 780 |
| tcaggtggtg | ccactgccat | attgctaaaa | gatggtatga | caagagcccc | agtagtgaga | 840 |
| ttcgccacag | ctgagagagc | ttcacaacta | aagttttact | tggaagatgg | tgtcaatttc | 900 |
| gatacattgt | ctgttgtctt | taacaaaagt | tcaagatttg | ccagattgca | aaacatccaa | 960 |
| tgctcaattg | ccggtaaaaa | cttgtacatt | aggtttactt | gctccacagg | cgacgccatg | 1020 |
| ggtatgaaca | tggtttcaaa | aggagtacaa | aatgtattag | acttttaca | aaatgatttt | 1080 |
| cctgatatgg | acgtaattgg | gatctcttgg | aagttctgct | ctgacaaaaa | gccaacagct | 1140 |
| gtcaactgga | ttgagggcag | aggaaagtct | gtcgttttcc | aggccgtaat | taccaaaaag | 1200 |
| gtggttagaa | agtctgcact | gaaccctcaa | acttgcacat | gtagaacttt | gacctgttta | 1260 |
| agaccattat | tggttctgct | acttctggtt | ttgctagtgg | acttaatgca | tatgcttcat | 1320 |
| atcgtgtctg | ccgtgttcat | cgctaccggt | caagatccag | ctcagaatat | cgaatctagt | 1380 |
| cactgtatca | ctatgatgga | ggctgtcaac | aatggtaagg | attgcacgt | taatgttacg | 1440 |
| atgccatcta | tagaagttgg | cacggtggga | ggtggcactc | agctagcctc | tcaatcagcc | 1500 |
| tgtttgaact | tgcttggtgt | aaagggtgcc | tgtatagaat | ccccaggatc | aaacgcccag | 1560 |
| ttgttagcta | gaatcgttgc | tggttctgtt | ctggcaggcg | aattaagttt | gatgtcagct | 1620 |
| ataagtgctg | gcaactagt | taatctcat | atgaaataca | ataggtctag | tagagatatg | 1680 |
| tcagcaatag | cttctaaggt | ctaa | | | | 1704 |

<210> SEQ ID NO 14
<211> LENGTH: 1308
<212> TYPE: DNA
<213> ORGANISM: Artificial Sequence
<220> FEATURE:
<223> OTHER INFORMATION: Synthetic

<400> SEQUENCE: 14

| | | | | | |
|---|---|---|---|---|---|
| atgtttagaa | gagctatact | gttaggatgc | tctgctgcca | agacaccatg | gtctgagtgt | 60 |
| tctaacgctc | aattagttga | tgcagttaag | tctagaaaga | tctcattcta | cggtcttgaa | 120 |
| caagccttgg | aaccagatta | tagaagggct | atcgaagtaa | ggagagaggt | tgtctctgaa | 180 |

| | |
|---|---|
| atcgcctcac aacagccaga agcaaaaaag aagcaatccg cattgcacac aataccattt | 240 |
| gagaattatg attggaataa ggtcgttggc caaaactgtg aaaacattat tggatacgtc | 300 |
| ccaataccac tgggcgttgc tggccctatt ttgattgatg gtaaagagta cccaatacca | 360 |
| atggctacaa cagaaggcgc tttggtcgct agtactcata gaggtgctag agctattaca | 420 |
| agatccggag gttgtaagac attgttatta ggtgaaggta tgacaagagc accagtggtt | 480 |
| gaattgcctt cattagagga agctgggcgt ttgcacaagt actgtaatga gaacttctta | 540 |
| tctttaaagg aagcatttga atcaactacc caatatggaa aacttaattc tttaaagtgc | 600 |
| gtactagctg gtagaaaagc ataccttaga ttcagagcca ctacaggcga tgctatgggc | 660 |
| atgaacatga taacaagggg tgtagacaaa gcactgtctg ttctacagca acatttccct | 720 |
| tcaatggaaa tcctagccct aagtggtaat tactgtaccg acaaaaagcc atctgctgta | 780 |
| aattggattg atggcagagg taaatcagtg gttgcagaag ccactttatt ggctgatgtt | 840 |
| gtcgaagata ctctgaaatg tacagtcgat tctttggtat ccttgaatat cgacaaaaac | 900 |
| cttgttgggt cagctatggc tggttctgtt ggaggtttta acgcccaggc tgcaaacgct | 960 |
| gtggcagcca ttttcattgc aaccggtcaa gatcctgctc aagtggtaga agttcaatg | 1020 |
| tgtatcacta caatgtccaa ggtaggtaac gatctattga tctctgtgac catgccttct | 1080 |
| atcgaggtcg gggtcgtggg aggagggact ggtcttgctg cccaaagagg atgcttagag | 1140 |
| ttaatagggt gcggaggccc atctaaggag tctcctggta ctaatgccca acttctaagt | 1200 |
| agagttgttg cagctggcgt tttatcagcc gaactttcct tgatgtccgg actggcagca | 1260 |
| ggtcatctat tgtcagcaca tatgagattg aacagaaaga agaaataa | 1308 |

<210> SEQ ID NO 15
<211> LENGTH: 1281
<212> TYPE: DNA
<213> ORGANISM: Artificial Sequence
<220> FEATURE:
<223> OTHER INFORMATION: Synthetic

<400> SEQUENCE: 15

| | |
|---|---|
| atgcaatccc tggacaaaaa ctttagacac ttatcaagac aacagaagtt acaacagcta | 60 |
| gttgataaac aatggctatc agaggaacaa ttcaatattc tacttaacca cccacttatt | 120 |
| gatgaagagg tagcaaactc attgatagaa atgtcatcg cacagggcgc actgcctgtt | 180 |
| ggtttactac caaatatcat cgttgatgac aaagcatacg tcgtgcctat gatggtggaa | 240 |
| gagccatctg ttgttgccgc tgcttcatac ggcgctaaat tggtgaacca acaggtggt | 300 |
| ttcaaaaccg tgtcctcaga acgtatcatg ataggtcaaa tagtatttga tggagtcgat | 360 |
| gataccgaga aactgtctgc agatatcaag gctcttgaaa aacaaatcca tcagattgca | 420 |
| gatgaggctt acccttctat taaggccaga ggtggaggct atcaaaggat cgccatcgat | 480 |
| acattcccag aacaacagtt gctttcattg aaggttttcg ttgatactaa ggatgctatg | 540 |
| ggcgctaata tgttaaacac aatcctagaa gcaatcacag ccttttttgaa aaacgaattc | 600 |
| ccacaatctg atatcttgat gtctatcctt tccaaccacg caacagccag tgttgtcaag | 660 |
| gtccagggtg aaatagacgt taaggatttg caagagag aacgtactgg agaagaggtc | 720 |
| gctaagagaa tggaaagagc atctgtgtta gctcaagtgg acattcatag agcagcaaca | 780 |
| cacaataagg gtgttatgaa tggcattcat gctgtagtct tggctacagg taatgatact | 840 |
| agaggtgcag aagcctctgc tcacgcttac gcttccaaag acggtcaata tagagggata | 900 |

| | |
|---|---|
| gctacatgga gatacgatca agagagacaa aggttaatag gaactataga agttccaatg | 960 |
| actctggcca ttgttggtgg cggtaccaag gtactgccta ttgctaaggc ctctttagaa | 1020 |
| ctgttaaacg tagaaagtgc ccaagagttg ggacatgttg tcgctgccgt tggactagct | 1080 |
| caaaacttcg ctgcatgtag agctttggtt tccgaaggta ttcaacaagg gcatatgtct | 1140 |
| ttgcaataca agtctttagc catcgtagtc ggggctaagg gcgatgaaat tgctcaggta | 1200 |
| gccgaagcac taaagcaaga gccaagagca aacactcaag ttgcagagag aattttgcaa | 1260 |
| gatttgagaa gtcaacaata a | 1281 |

<210> SEQ ID NO 16
<211> LENGTH: 2745
<212> TYPE: DNA
<213> ORGANISM: Artificial Sequence
<220> FEATURE:
<223> OTHER INFORMATION: Synthetic

<400> SEQUENCE: 16

| | |
|---|---|
| atgacaccac ctaaaccatt ggaaactaag caacctttac atgatctgcc tacacctgga | 60 |
| ccagaaagtc ctttcagaga gagaaggcca tacagattct ctaccttatg tgctaccgta | 120 |
| gataatccag acatgaaaga tcaatacggt agttcttccg tgccaatata ccaaactgct | 180 |
| acattcaaag gtgtagggaa cgagtatgat tatactagat ccggtaatcc tacaaggtca | 240 |
| catttgcagc atcatattgc aaaaatctcc tctgcagcac atgcttttac tgtttcttca | 300 |
| ggtatggccg ctctggacgt catcttaaga ctactgaaac ctggggatga ggtgattgct | 360 |
| ggagatgatc tttacggcgg aacaaataga cttttaactt acattagatc ccaccttggt | 420 |
| gtaactgtcc accatgtcga tacaacagat ccaacatctc tgcataagta cattcatcca | 480 |
| acgaaaactg ggatggtttt acttgaatca ccaacaaacc cattattgaa gatagcagat | 540 |
| cttgctacaa tatcaaagga tgttaaagag agagccccaa acgccatcat cgttgttgac | 600 |
| aatacaatga tgacctctta tttgcaaaga ccactggaac atggtgccga tatcgtgtat | 660 |
| gattctgcca caaaatactt atctggacac acgatttga tggccggagt tgtcacttgt | 720 |
| aatagagacg atattgccca agattggct ttcactatca acgccgtggg caatgcttta | 780 |
| acgccaattg attcattcat gttgttgagg ggcattaaga cattagccat cagaatggat | 840 |
| agacagcaaa ccacagccca attggtggca gaatacttat acaatctagg ttttacagtt | 900 |
| cactatccag gtctaccttc acatcctggc agagacgtac acctgaggat agctgacgga | 960 |
| aatggggctg tcttgtcttt cgaaacaggt aacaaggaac tgtctgaaag gattgtcgca | 1020 |
| gccacgagac tgtggggaat tagtgtctcc ttcgggtgcg ttaattcatt gatatctatg | 1080 |
| ccttgcgtta tgtcccatgc cagtatcgac gccgctacaa gagccgccag aggactgcca | 1140 |
| gaagatctta ttagattgtg tgtaggtatt gaggatccac acgacttatt ggacgatcta | 1200 |
| gaacacgctc tactagaagc tggcgcaatt gaattgaatg ctgcccaaaa caagtttgta | 1260 |
| agggctcctg atccagacgc cttatctcaa gctgttcatg atctagattt ggatgacggt | 1320 |
| agaaaccagc ttgaatggtt tgttttctgca cctggcaagg tgattttgtt tggcgaacac | 1380 |
| gccgttgtac atggtgtaac tgctattgcc gcctcagtgg atctaagatg ttatggtcta | 1440 |
| acgacgccta gaacagataa caaactgtcc gctcacttca aagacttagg aaatttctac | 1500 |
| catgaatggg atattgattc cttaccttgg gatgccttga ctcctattcc accaggtgag | 1560 |
| gaacatcctg aggaattaga ccagagattg attgaagcct tatcacaaag tgttctggct | 1620 |
| gagctgggag atgagaacaa acaagctaga gctgccactc ttgcattctt atatctatac | 1680 |

```
atgaccctgg ccagaggtca acatagacca tcctttaact tcacagccag agcaacatta    1740
ccagtgggcg ctggactagg cagttctgcc tccttctctg cttgcgcagc tacagctttg    1800
ttattgctgc ataggaggat cagtgtccct gcaaagcctg ctccatctac ggaaacacac    1860
atccatgtct ctcatgaagg cagaagggct ctaccagcca gtgtagccga ggatgtgaat    1920
aggtgggctt ttgtcgccga aaagattttg cacgggaatc ctagtggagt cgataacagt    1980
gttgccgtat tcggtggtgc tttggcctat acaagacctg ggtttggcaa aaagggaggg    2040
atggaacaaa tccagggttt taagtccttg aaattcttgt tgactaactc tcaagttcct    2100
agagatacta aaaagctagt ggctggggtg ggtgagaaaa aggaaaacga gccagaattg    2160
gtcaacggta tattggctgc aatacaatct atctccgatg aggctagaag agccttggca    2220
gacccagaat tatctagaga tgccttgttg tctgctctac aagagcttat caaggaaaac    2280
catgaccact tagtgacatt gggagtatca cacccatctc tggaaaagat tagagaaaag    2340
acttcagaac cttacggctt aaagaccaaa cttacaggtg caggtggtgg tggctgtgct    2400
gtcacgctga tacctgatga tttcaaagag gaagttctta atggtttgat cgacgaattg    2460
atcagagaag ttttcaccc atacttaact tctgttggtg gatcaggtct agggatattg    2520
tcaccatatc cagaacacag aaccagaggt tctgaccctc agccacctag agaagatgta    2580
ggaggaggcc aagttacacc tcctgatact cctagagccg agatagttga agacatacg    2640 aagcatggag ttacttttga tccattaaga ccaaccttcg agacagctgc cacgactgat    2700
atttcagatt gggcttcatc cttagggaga tggctttacg tgtaa               2745

<210> SEQ ID NO 17
<211> LENGTH: 1191
<212> TYPE: DNA
<213> ORGANISM: Artificial Sequence
<220> FEATURE:
<223> OTHER INFORMATION: Synthetic

<400> SEQUENCE: 17
atgttgtcag aagtgctgtt agtctctgct ccaggtaagg ttattctgca tggtgagcat      60
gccgtggtcc atggtaaagt cgccctggcc gttgctctaa acctgagaac tttcttgaga     120
ttacaaccac actcaaatgg tcgtgttggg ttaaacttgc ctaacattgg tgttagaaga     180
gcatgggatg tggcttcttt gcaacttctt gatacatcat tcttgggcca tggcgattcc     240
gcagctctta ctgcaaagca tgttgaaaag ctaaaggaag tagctggttt tcctaaggac     300
tgtgtagatc cagaacactt agctgtgtta gcattccttt atctatactt gtccatttgc     360
caatctcaaa gagccttgcc atctctggat atcacagtct ggtctgaatt gcctactggc     420
gctggccttg ttctagtgc cgcctactca gtctgtttgg cagccgcatt gttaaccgct     480
tgcgaagaga tcccaaaccc attgaaagat ggagaagctg ccggtagatg gacagaggaa     540
aatctagagt taatcaacaa atgggcattc caaggcgaaa gagtaattca tggaaatcca     600
tcaggcgtgg acaatgccgt tagtacttgg ggtggtgctc taagatatca acagggaaag     660
attagttctc ttaaaagacc accagttttg aagatcttat tgataaacac aaaggttcct     720
agatccacaa aggtcctagt tgcaaatgtt agatcaagac tgctgaaatt ccagaaaatt     780
gtagccccac ttttgaccct catcgatgcc ataagtttgg aatgtgaaag ggtcttaggc     840
gaaatggcag ctgcacctac accagagcat tacttaacat tggaggagct gatcgatatg     900
aatcaacacc acttgaacgc tttgggtgtc ggacatgctt cattagacca attatgtcag     960
```

| gtaaccactg ctcatggttt acactccaag ttgacaggag caggtggagg aggttgtggg | 1020 |
| ataacactgt taagaccaga tgttgaaagg cctgcagtgg aagctactaa acgtgcttta | 1080 |
| tcaggctgtg gttttgattg ctgggagact tctgttgggg cacctggagt ttctgtccac | 1140 |
| actgctgctt cccttgatgc atctgtacaa cagggtctag actcattgta a | 1191 |

```
<210> SEQ ID NO 18
<211> LENGTH: 1161
<212> TYPE: DNA
<213> ORGANISM: Artificial Sequence
<220> FEATURE:
<223> OTHER INFORMATION: Synthetic

<400> SEQUENCE: 18
```

| atggaagtta aggctagagc tcctggtaag atcatattga gtggcgaaca tgccgtagtg | 60 |
| cacgggtcaa cagctgtcgc cgcttccatc aacttgtaca cttatgtcac gttgtccttc | 120 |
| gccactgctg aaaacgatga ttcattgaaa ttacagttaa agatctggcc cctggaattc | 180 |
| tcatggccaa ttgggagaat aagagaggcc ttgtctaatc tgggcgctcc ttcttcttca | 240 |
| actagaacca gttgttctat ggaatccatt aagactatct ctgctttagt cgaggaggag | 300 |
| aacataccag aagctaagat tgccttaact tctggggtat ctgccttcct atggttatac | 360 |
| acctctatcc aaggattcaa accagccact gtagtggtta catctgactt accattgggt | 420 |
| tccggccttg gttcttcagc agcttttttgt gtcgcccttt ctgctgcatt gctagctttt | 480 |
| tcagacagtg taaatgtcga tacaaaacat ttgggatggt caattttcgg tgaatccgac | 540 |
| ttggaactac tgaacaaatg ggccttggaa ggcgagaaga tcattcacgg taagccttct | 600 |
| ggtatcgata taccgtttc agcctatggt aacatgatta gttcaaatc tggtaatttg | 660 |
| acaaggataa agtccaacat gccattaaag atgttagtaa caaacaccag agtcggcagg | 720 |
| aatacaaaag ccttggttgc tggcgtttct gagagaacat tgagacatcc taatgctatg | 780 |
| tcctttgtgt ttaacgctgt ggatagtatt agtaacgaac tagctaacat tatacagagt | 840 |
| cctgctcctg atgacgttag tattacagaa aaagaggaaa aactggagga actgatggag | 900 |
| atgaatcaag gttacttca atgtatgggc gtgtcccatg catcaatcga acggttttg | 960 |
| agaacaactt taaagtacaa acttgccagt aagttgactg gggcaggagg tggtggatgc | 1020 |
| gttcttacgc tgcttccaac actactatct ggaacagtgg ttgataaggc tatcgccgaa | 1080 |
| ttagaatctt gcggatttca atgtttgata gcaggcattg gtggaaatgg tgtagaattc | 1140 |
| tgtttcggtg ggtcctctta a | 1161 |

```
<210> SEQ ID NO 19
<211> LENGTH: 990
<212> TYPE: DNA
<213> ORGANISM: Artificial Sequence
<220> FEATURE:
<223> OTHER INFORMATION: Synthetic

<400> SEQUENCE: 19
```

| atgcacgttg ctgtgaagga taaaacaact agacatcata ttggttacgg caaagttatc | 60 |
| ctatttgggg aacacttcgt cgtgtacggt gccgagtcaa ttgtagccgg cattaacgaa | 120 |
| tatactacgt gcgagattag tagactgaaa cataaaccaa atgtcgtgga agttatagac | 180 |
| gaaagacctg ccgttccagg gtatatcaaa gagaagaggg aagagcaaag agtggcccac | 240 |
| ggtttggttt tgagacactt aaacatagac acctccaagg atggtttact agtcaaatta | 300 |
| ggtggcccctt tggtcccatc ttctgggatt ggtgcttcag cttctgatgt agtatcattg | 360 |

```
tccagagctt taaacgagct atattccttg aacttgagtg aggaagctgt gaacagatct    420
gcttacgccg gagaatgcgg atatcacgga acaccttctg gtgttgataa cacagctgca    480
acttacggtg gcataattct attcagaaga gccttgaaaa agtctgtttt ctcaaggctt    540
gccctaggta agaccctgtc aattatcgtt tgtagtactg gaataactgc atcaacaaca    600
aaagtcgtgg ctgatgttgc taggctgaag gcagcccaac cttcttggtt tgatgactta    660
ttcgaacagt acaatgcttg tgtaagagaa gccaaaaagg ctttacaatc cggaaatctt    720
agaagagttg gtgaactgat gaatatcaat catacgttat gtcaaaagtt gacagtttcc    780
tgtccagaac ttgatgccat cgctacttgt gtagaacatc tcggagcatt gggcgctaag    840
atgtctggta cgggtagagg tgggttggtg gtagccctgg ccgcaaatac acaggaaaga    900
gatagaattg ctaaggctgt tagagaacaa tgcaaggagg caaagtttgt gtggagatac    960
tctgtacaac caggaggcag taaacttaa                                      990

<210> SEQ ID NO 20
<211> LENGTH: 921
<212> TYPE: DNA
<213> ORGANISM: Artificial Sequence
<220> FEATURE:
<223> OTHER INFORMATION: Synthetic

<400> SEQUENCE: 20
atgactagaa agggatacgg tgaatctaca ggcaaaatca ttctgattgg ggaacatgcc     60
gttacattcg gtgagcctgc tatcgccgtg ccattcaatg ctggcaagat taaggtattg    120
atagaagcct tagaaagtgg aaattactct tctataaagt cagatgtcta tgatggaatg    180
ttgtacgacg ccccagatca cctgaagtca ttagttaaca gatttgtcga gttaaacaac    240
attacagaac ctttagccgt cacaattcaa acaaacttgc caccttccag aggtttgggc    300
tcttctgctg ccgttgctgt tgctttcgtt agggcctcat acgactttct gggaaaaatct    360 ctaacaaagg aggaattgat tgaaaaagca aactgggctg aacaaatcgc tcatgggaaa    420
ccatccggga tcgatactca gacgatagtt tcaggtaaac ctgtttggtt ccaaaagggg    480
cacgctgaaa ccctgaaaac tttgtcctta gatggttata tggtggtaat cgatacagga    540
gtgaagggta gtactagaca agcagtagaa gatgttcata aactatgcga agatcctcag    600
tatatgtcac acgtcaagca cattggcaaa cttgtgctga gcttctga tgtaatagaa    660 catcacaatt tgaagcccct ggctgacatc ttcaatgagt gtcatgctga cttgaaagca    720
ttaactgtct cccatgataa gatcgaacaa cttatgaaaa ttggaaaaga gaatggtgcc    780
attgccggaa agttgacagg cgctgggaga ggaggttcta tgttgttgtt agccaaagac    840
ctaccaactg ccaaaaacat tgtaaaggca gtggagaagg caggtgctgc ccatacctgg    900
attgaaaatc ttggtggcta a                                              921

<210> SEQ ID NO 21
<211> LENGTH: 1476
<212> TYPE: DNA
<213> ORGANISM: Artificial Sequence
<220> FEATURE:
<223> OTHER INFORMATION: Synthetic

<400> SEQUENCE: 21
atggtcagaa caacagtagt ttctgcccca ggtaaggtgc taattgccgg aggttatctg     60
gtattagacc ctgcctaccc tggcacagta gtctccacga gttctagatt ttacacagta    120
```

| | |
|---|---:|
| atccaatctc aggagctact aagtaaaaac accattagag tgagatcccc acagtttttg | 180 |
| gaagcaacat ggtcatactc cgtactgttc gagccagctg ttgctgtgga ggcttctcca | 240 |
| gaaaactctt ccaaaaacaa gtttgtgcac ttagctctgc agaaaacaat agccttggcc | 300 |
| gtcgaactga gaggagctgc ccagatccag gaagccttga cacatggttt cgatattgcc | 360 |
| atagttgggg acaatgattt ctattctcaa agagccaagc tggaatcctt gggtttacct | 420 |
| agaactcttg attctcttac agaaattaca ccttttttgcg ctactgaagt tcatttgtct | 480 |
| gatgtgcaca agactggact tggatcatca gccgccttga tcacttcttt gacatctgct | 540 |
| atactagtac acctatctgt catctcagaa tcatcattag ccgaagatga ttccagagat | 600 |
| aggagacaag ctcataactt ggcccaatac gtgcattgtt tggcacaagg taaagttgga | 660 |
| tcaggcttcg atgtaagtgc tgctgttttc ggttcccatc tttactcaag gtttgatcca | 720 |
| gccgtcatcc aggacctaat gtcagatgac gctttaccat ctcaacttcc ttctgtgcta | 780 |
| tctccatcta atgccgcttg gaattacaga attgaaccat tcaaattacc accattgact | 840 |
| agaatcgttt tagccgatgt tgatgctggg tcagacactc cttctctggt gggcaaggta | 900 |
| ttgaagtgga gaaaggaaaa ttctactgaa gcagaggctt tgtggaaaaa cttagatcaa | 960 |
| caaaaccaat ctttggcaca aaccttatta catctgggca agttggcaga ggacgattat | 1020 |
| gaaaactatg cttccgccgt caagtacatt tgttcattac aaccagttca acaaatcttg | 1080 |
| tatagtcctt taaggtctaa tcaatctctt caacacagta tgaaaccaac aatttcagca | 1140 |
| atcagagaga aaatgagaga gatggggaat ttgagtggcg tgccaattga accaattgag | 1200 |
| caaacaacac tgttagatgc ctgtgccagt caagctggtg ttattggtgg tggcgttcct | 1260 |
| ggggcaggtg gatacgatgc tatatggttg ttagtgtgtg atcctcctag ttgcgctcca | 1320 |
| gatcaatctc cacttgaaag gattgaacat ctatggtccc actacgaaaa gctggatgtc | 1380 |
| tcccctttat ccgctcaaga gtctacggct aagggtgtca gagttgaagc cttggacgac | 1440 |
| atacctggat tgaaaaatgc aatttcagta agttaa | 1476 |

<210> SEQ ID NO 22
<211> LENGTH: 579
<212> TYPE: DNA
<213> ORGANISM: Artificial Sequence
<220> FEATURE:
<223> OTHER INFORMATION: Synthetic

<400> SEQUENCE: 22

| | |
|---|---:|
| atggctcctc taggcggtgt tccaggactg gtgttgttat tctccggtaa gagaaaatct | 60 |
| ggaaaggatt ttgttacaga agcactgcaa tctagattag gagccgatgt atgcgcaatc | 120 |
| ttgagattgt caggtccact gaaggaacag tacgcccagg aacatggtct tgactttcaa | 180 |
| aggcttatgg acgcttcaac ctacaaagag gcttacaggt ctgatatgat ccgttggggt | 240 |
| gaagagaaaa gacaagctga tccaggcttt ttctgtagaa agattgttga aggcgtctgt | 300 |
| caacctgttt ggttagtaag tgatactaga agagtgtcag atattcaatg gttccaagag | 360 |
| gcctatggtg ctgtcacaca aacagttaga gttgtcgcaa cagaagagtc tagacaacaa | 420 |
| agagggtggg tgttcactcc agggggttgat gacgcagaat ccgaatgtgg tttagataac | 480 |
| tttcgtactt tcgattgggt tatagaaaat cacggtgatg agcaacacct agaagagcag | 540 |
| ctagaacatt tgattgaatt catcagaagt agattgtaa | 579 |

<210> SEQ ID NO 23
<211> LENGTH: 1512

```
<212> TYPE: DNA
<213> ORGANISM: Artificial Sequence
<220> FEATURE:
<223> OTHER INFORMATION: Synthetic

<400> SEQUENCE: 23
atggccgttg tcgcatctgc tccaggaaag gtattgatga caggtggtta cttaatctta      60
gaaaggccaa acgccggtat cgtcttatct acgaatgcca gattctatgc tattgttaaa     120
ccaatctatg acgagattaa gccagattcc tgggcctggg cttggactga tgtaaagttg     180
acatccccac aactagccag agaatcttta tacaagctat cactgaaaaa tctggctctg     240
caatgtgtgt cctcttctgc ttctagaaat ccattcgtgg aacaagccgt tcagttcgca     300
gtagccgcag ctcacgccac attggataag gacaaaaaga acgtattgaa caaactacta     360
ttacagggat tggacattac cattcttggt acaaatgatt tctactctta tagaaatgag     420
atagaggctt gcgggttgcc acttacacca gaatcattag cagcattgcc atcattttca     480
tctatcacgt tcaacgtcga ggaagccaat gggcaaaatt gtaagcctga agttgctaaa     540
acaggtttag gctcatccgc tgctatgaca actgccgtcg tggcagcttt attgcaccat     600
ttgggtctgg ttgatctgtc tagttcatgt aaagagaaaa agttcagtga cttagatttg     660
gtccatatca tcgctcaaac agctcactgt attgcccaag caaggtggg tagtggtttt       720 gacgttagta gtgctgttta cggatctcat aggtacgtca gatttccccc agaagtattg     780
tcctcagcac aagatgctgg aaagggtata cctttgcagg aagtaatttc taacattcta     840
aagggcaaat gggatcatga gagaactatg ttctcattgc ctcctttgat gtctttactt     900
ctgggcgaac ctggaactgg tggttcttca accccttcta tggtgggagc tttgaaaaag     960
tggcaaaagt cagatacaca aaagagtcag gaaacgtgga gaaagctaag tgaagccaac    1020
tctgccttgg aaactcaatt caacatattg tccaaactgg ctgaagagca ctgggatgct    1080
tataagtgtg tcattgactc ttgctctacc aaaaacagtg aaaaatggat agaacaggcc    1140
acggagccat ccagagaagc cgtcgtcaaa gccttattag gctctagaaa cgccatgttg    1200
caaataagga attacatgag acaaatgggc gaggctgctg gggtgcctat tgaaccagaa    1260
tcacaaacta gacttcttga tacaaccatg aatatggatg gggttctact tgcaggagtg    1320
cctggtgccg aggatttgac gctgttttt gccgttacat tagggattc tggtacaaat      1380 gttgctaagg catggtcctc attaaacgtt cttgcattgc tggtaagaga agatccaaac    1440
ggtgttctat tggaatctgg agatcctaga acaaaagaga tcactactgc cgtgtttgcc    1500
gttcatattt aa                                                          1512

<210> SEQ ID NO 24
<211> LENGTH: 1416
<212> TYPE: DNA
<213> ORGANISM: Artificial Sequence
<220> FEATURE:
<223> OTHER INFORMATION: Synthetic

<400> SEQUENCE: 24
atggtggtcg cttcttgtcc aggaaaggtt ttgattttag gtgggtactt aattgtagag      60
gaaccaaacg ttggtatttc cgtcggcacc accgctagat cgtaactcg tgttgcctct     120 tggaaaaagt gttcagatgg caaatgtaga gttcatatcg ttagttctca attcaataag    180
gaattcactt ttgagtgtgc agctgaggaa gattcagatt caaccattaa gatcgtccaa    240
ttggaaggag caccttcacc tttcttattc tacggaatac tatattctgt agccggagct    300
```

| | |
|---|---:|
| ctgttatttg gtggggatat ctttagggat gttacattgg aattgttagc agataatgac | 360 |
| ttctattctc agagaaatta cctagagtct caaggtaagc ctgttacagc tgctaactta | 420 |
| agactaatcc caagatacac tccacttctt ggtgaagtaa gtaagacagg tttaggatct | 480 |
| tccgcagcca tgactacaag tgttgtggct tgtttgcttc aactatacgt gttcgattcc | 540 |
| aaaaaaaaca acgccactga gtcagttgaa agagctcctg aacttccact tagactggaa | 600 |
| gatgtaactg aattcattca tagaatatct caagtcgcac attgcgtggc tcaaggcaag | 660 |
| gtgggttcag gtttcgacgt ctacactgcc acctttggga catgtgttta cagaagattc | 720 |
| tctgctagag tgttagaaaa gctagttaag ggaaatgagc caccaaaaag agtcaccatc | 780 |
| ccattgctaa gagaatgcgt tgaaactgat gaggtatggg ttcagagaat accattccgt | 840 |
| ttgccaacag gtttgcaact gcttctagga gatgtacaca aaggcggtac agaaacacca | 900 |
| ggcatggtat caaaggttat gagttggagg agatctgtaa caacagatcc aaattccttg | 960 |
| tgggaaagat tgaggatgtc taacgaaaag tacgtggagg cattgcaagg tctgatcaag | 1020 |
| caatctcagg aagctccagt tgcctatact gaagctgtca aaaacttgaa atctgttgtt | 1080 |
| ttggctaagc acaacccatc aacagaggct gaaagacttt gggtagaggc agcatcagtc | 1140 |
| gcctctacat caagacgtta cctgagagaa atgggcgagg ctgcacaagt tcaaattgaa | 1200 |
| ccacctgaat tgacttcttt acttgatgcc acttgcagta ttcctggtgt ctttgctgta | 1260 |
| gggtgtcctg gagcaggtgg gtacgacgcc gttttttgcat tagttctagg tgaagaggtc | 1320 |
| tgttccgcag ttgagagatt ttgggaatgc tataacgact tacaagtctg tcctttgctg | 1380 |
| gtgagaggcg atgctaatgg attggtttta gattaa | 1416 |

<210> SEQ ID NO 25
<211> LENGTH: 1077
<212> TYPE: DNA
<213> ORGANISM: Artificial Sequence
<220> FEATURE:
<223> OTHER INFORMATION: Synthetic

<400> SEQUENCE: 25

| | |
|---|---:|
| atgattcaag ttaaggctcc aggaaaattg tacatcgcag gtgaatatgc tgtaactgaa | 60 |
| ccaggctaca atctgttttt gattgctttg acagattcg tcacagcaac catcgaggaa | 120 |
| gccgatcaat acaagggtac tatccattca aaggctttac atcataatcc tgtaactttt | 180 |
| tctagggacg aagattccat tgttatttct gatccacacg ctgcaaaaca gttgaactac | 240 |
| gtcgttacag ctatcgagat tttcgagcaa tacgctaagt cttgtgatat cgccatgaaa | 300 |
| cattttcacc ttaccatcga ttctaatttg gatgattcta atggacataa gtacggactt | 360 |
| ggttcatctg cagctgtctt agtttccgtc ataaaggtgt taaacgaatt ctatgatatg | 420 |
| aaactgtcaa acctatacat ctacaaactt gccgttattg caaatatgaa gctgcaatcc | 480 |
| ttgtcatcat gtggggacat tgcagttct gtgtatagtg ggtggttagc ctactccact | 540 |
| tttgaccacg aatgggtcaa acatcaaatc gaagatacta cagtggagga ggtactgatc | 600 |
| aaaaactggc caggtttgca tattgaacct cttcaagccc ctgaaaacat ggaggtgttg | 660 |
| ataggttgga ctggctctcc agcttcttca ccacactttg tttctgaagt taaaagacta | 720 |
| aagtcagatc caagtttcta cggcgatttc ctagaagata gtcacagatg cgtcgaaaag | 780 |
| ttaatacacg cattcaaaac aaataacatc aaggggttca aaagatggt aagacaaaat | 840 |
| agaaccatta ttcagcgtat ggataaagag gccacagtag atatagaaac tgaaaagttg | 900 |
| aagtacctgt gtgacattgc tgaaaagtat catggtgcta gtaagacatc aggagcaggt | 960 |

```
ggaggcgatt gcggtataac aatcatcaac aaagacgttg ataaggagaa aatctacgat    1020
gaatggacaa agcatggtat taagcctcta aagttcaaca tatatcatgg acaataa      1077
```

<210> SEQ ID NO 26
<211> LENGTH: 1248
<212> TYPE: DNA
<213> ORGANISM: Artificial Sequence
<220> FEATURE:
<223> OTHER INFORMATION: Synthetic

<400> SEQUENCE: 26

```
atgtcagagc caatctacga agctacagca tctgcccctg ttaacatcgc tgttatcaag      60
tactggggca agagagacac ttctctaatc ttgcctacaa actcaagttt gtctgttact     120
ctatcccaag atcatcttag atctactaca acatccagag cctcatcttc tttcgataaa     180
gataggttat ggttaaacgg tcaagaggat gtcattaaac ctggctctag actggaaact     240
tgcattagag atgaaaaaa gttgagaaag gaattagtgg aagataagga tgctaatgca     300
cctaaactgt caacattgcc agttcatatt gcttcttaca ataactttcc taccgctgca     360
ggtttggctt cttccgcatc aggattcgca gcactagttt catctttagc acatctatac     420
acattaacac ctccattgac ctccccaagt acactgtctc ttatcgctag acaaggatca     480
gggagtgcat gtagatctct tttcggtggc tttgttgctt gggaaatggg atcaactcca     540
acaggaaccg attctttagc cgtccaaatt gccgatgaag ctcattggcc agaaatgcac     600
gcacttatct gtgttgtttc cgatgacaaa aagggcacat ctagtactgc tggtatgcaa     660
aggacagtcg aaacatcaac tttgttgcaa cacagaatta aggatgttgt tccaagacgt     720
atggacgaaa tgattagagc tattaaggaa aaggattttg attctttcgc tagaataact     780
atggcagatt caaattcttt tcatgccgta gcactagaca ctgagcctcc aatattctac     840
atgaatgatg tctccagagc aattatcgca ctgatagtag agcttaacag agtctccttg     900
gagaaaggag aaggttataa ggcagcctat acttatgatg ccggaccaaa cgccgtaatc     960
tacaccttgg acaaaaatgt aaaggaagtt atacagttaa tagtaaagta cttccctcag    1020
aaagccggtg aattcaagga taacctgcag gtattgggtg gtggcgttgc cgatatcaat    1080
caagtggctc aagtgccaga gggattcaac gagaaggttg ccgtcgtgag agaagttggc    1140
gctgtgaagg ggttgatcca cacaaaagtc ggtgacggtc cacgtagact tggtgatgaa    1200
gagtcactat taggtaagga tgggtttcca aaaaccttag ttgcttaa                1248
```

<210> SEQ ID NO 27
<211> LENGTH: 1203
<212> TYPE: DNA
<213> ORGANISM: Artificial Sequence
<220> FEATURE:
<223> OTHER INFORMATION: Synthetic

<400> SEQUENCE: 27

```
atggcatcag agaaaccaat agttgttgtt acatgcactg cacctgtaaa catagccgtc      60
gttaagtact gggtaaaag agacgaggaa ctgatattac aattaactc ttcactatct      120 gtcacgcttc accaagatca gttgaaaact acaacaacag ccgctatttc aagagatttc     180
acggaagata gaatttggtt aaatggtaga gaggaggata tgggacatcc aagattacaa     240
gcctgtttga gagaaatcag aaggttggcc agaaagagaa gatcagacgg gcatgaagat     300
ccactaccct tgagtctgag ttacaaagtt cacgtggcta gtgaaaacaa ttttccaact     360
```

| | |
|---|---|
| gctgctggtc tggcttcttc tgccgctggt tacgcctgtc ttgcatatac attagccaga | 420 |
| gtgtacgggg tcgactccga tctgtctgaa gttgccagga gaggatctgg atccgcttgt | 480 |
| agaagtttgt acggcggatt cgtagaatgg caaatgggcg aaagacctga cggtaaggat | 540 |
| agtgtggctt gtcaagttgc cccagaatcc cattggccag aacttagagt attgattcta | 600 |
| gtcgtttccg ctgaaaggaa acctatgggg tccacagctg gtatgcaaac atccgtggaa | 660 |
| acttcagcat tgttaaagtt tagagctgag gcactggttc caccaaggat ggcagaaatg | 720 |
| actaggtgca tcagagagag aaactttcag gctttcggcc agttgactat gaaggactca | 780 |
| aatcaatttc acgctacttg tttggatacc ttccctccta tctcttatct atcagataca | 840 |
| tctagaagga tcattcaact agttcacaga ttcaatgccc atcacggtca acgaaagtc | 900 |
| gcatatacct tcgacgccgg acctaacgct gtcgttttca ctttggatga cacagtagcc | 960 |
| gagttcgtgg ctgccgtaag acattctttt cctccagaat caaatggtga taagtttctg | 1020 |
| aagggcttac ctgtggagcc agtactttta tctgatgagt tgaaagccgt acttggtatg | 1080 |
| gatcctgttc caggttctat tagatatatc attgcaaccc aagttggacc aggacctcaa | 1140 |
| gtgttggatg atcctggtgc ccatttgtta gggccagatg gcttacctaa gccagctgct | 1200 |
| taa | 1203 |

<210> SEQ ID NO 28
<211> LENGTH: 1293
<212> TYPE: DNA
<213> ORGANISM: Artificial Sequence
<220> FEATURE:
<223> OTHER INFORMATION: Synthetic

<400> SEQUENCE: 28

| | |
|---|---|
| atgtctggtg aacaaagaga acttaactct tgggtattca tggtaacagc tagagcacct | 60 |
| accaacatag ctgtaatcaa gtactggggt aaaagagacg aaaagttaat cttacctatc | 120 |
| aatgactcta tctctgttac attggatcca gatcacttga gtgctacaac cacggtggcc | 180 |
| gtatcaccat cctttttctag tgatagaatg tggcttaatg gtaaggaagt tagtttgggt | 240 |
| ggggagagat atcaaaattg cttgagagaa atcagatcta ggggaagaga tgtggtggat | 300 |
| gaaaagtccg gtactttgat caaaaaggag gactggcaga cactacattt gcacattgct | 360 |
| tcccataaca acttttccaac tgctgccgga ttagcctcat ctgccgctgg atttgcctgt | 420 |
| ttagtttacg ccctagcaaa attgatggat attgaggaaa gatatgctgg ggaactgtcc | 480 |
| gctattgcta gacaaggaag tggttctgct tgtagatctt tgtacggtgg cttcgtcaag | 540 |
| tgggatatgg gtaaagagag agacggctct gactctatag ctgttcaact agccacagaa | 600 |
| gagcattggg aggaactggt cattttagtt gccgtcgtct cttcaagaca aaaggaaaca | 660 |
| tcttccacta ctgggatgag agaatctgtt gaaactagtg aactattaca ccatagggca | 720 |
| caagaggtag ttcctaagag aattgttcaa atgcaggaag ctattgccaa ccatgatttc | 780 |
| gcctcttttg ccagaattac gtgtgtagat tccaatcaat tccacgccgt ctgtttggat | 840 |
| gcatctcctc caatcttcta catgaacgat acgtcccaca gaatcataaa ctgcatagaa | 900 |
| aaatggaata ggtttgaggg caccccctcaa gtatcttata catttgacgc aggaccaaac | 960 |
| gccgttatat gtgcccctag tagaaaagta gcaggcttac tacttcagag attgttgtac | 1020 |
| tattttccac cagattcatc taaagagtta tcttcatacg tgattggcga tacatcaatc | 1080 |
| cttggggaaa taggtcttaa atctatgaag gatgtgaat cactgattgc tcctccagaa | 1140 |
| ttcaggtcac aaaattcctc atcaattcat cctggtgaag tcgactactt catttgcaca | 1200 |

| | |
|---|---|
| agaccaggta aaggaccaat tatcctgagg aacgaggatc aggctttctt caacaataag | 1260 |
| actggtttcc ctttcagaat tagtgaaaca taa | 1293 |

<210> SEQ ID NO 29
<211> LENGTH: 1149
<212> TYPE: DNA
<213> ORGANISM: Artificial Sequence
<220> FEATURE:
<223> OTHER INFORMATION: Synthetic

<400> SEQUENCE: 29

| | |
|---|---|
| atgtctgatc aatgtgtgac agttgaagcc ccaattaaca tcgctttat caaatactgg | 60 |
| ggtaagagag aaggaggtga actttgata ctaccaacaa atgactcttt ctctattact | 120 |
| ttgtccgcct ctccttttag atcaaagaca tcagtagaac taagagatga catcgaaaca | 180 |
| gatacattaa gattaaacgg gacagaagtg gatgtgggca aaacaccaag agttcaatca | 240 |
| atgttattgc acctaagatc cacatgtcca gaagatctga aaaacaaaaa ggtcaatatt | 300 |
| gtaagtgaaa acaattttcc tactgctgct ggtatggctt cctcagcctc tggttattgc | 360 |
| gccatgagtg ccgctctgat tagagccttc aagtccacca caaacgtctc catgctggcc | 420 |
| aggttaggat ctggttctgc ttgtagaagt gccttcggtg gattcgtaat ctggaataag | 480 |
| ggcgaaaaac ctgatgggtc tgactgcgtt gccacgcagt ttgtagacga acacattgg | 540 |
| cctgaaatac aggtcatgtg tgcagttctt aagggagctc aaaaggatgt gtcatctact | 600 |
| aaaggtatgc aacaatctct gaaaacctct ccattgatga aaaagagaat tagtgagacg | 660 |
| gttccagaga ggatgaaaat tgcttctaga gccattaagg ctagagattt cgctacttt | 720 |
| gctgagatag ctatgctaga atctgacgac ttgcaagaga tctgtgcaac aactgaacca | 780 |
| aagataactt acgcaaccga agattcctat gccatgatca gattggtgaa agcatacaac | 840 |
| gccaaaaagg gaaggacagc attagcctat acctttgatg ctggtgccaa ctgtttctta | 900 |
| tttgttctta agaggatttt gcctgaagca gttgctatgt tgatggagca tttccctacg | 960 |
| ccatttgaga gttcttctt cggggataga gaattactag agaaggtgaa agtcgtctct | 1020 |
| ttgcctgatg aatacaaaaa gttgattgat caccctaaaa agccattcga aatgctgctt | 1080 |
| caaagtcctg ttggatgcgg cgttaagtac cttggcccat ccgaatcatt gattccacca | 1140 |
| agagtataa | 1149 |

<210> SEQ ID NO 30
<211> LENGTH: 984
<212> TYPE: DNA
<213> ORGANISM: Artificial Sequence
<220> FEATURE:
<223> OTHER INFORMATION: Synthetic

<400> SEQUENCE: 30

| | |
|---|---|
| atgatcaagt ctggtaaagc aagagctcat acaaacattg ccctaatcaa gtactggggt | 60 |
| aaaaaggatg aggctttgat tattcctatg aataactcta tcagtgtaac cttggagaaa | 120 |
| ttctacacag aaacaaaggt gactttcaac gatcaattaa cacaagacca attctggtta | 180 |
| aatggcgaaa aagtgtccgg aaggaactt gagaagatat caagtacat ggatattgtc | 240 |
| agaaacagag ctggtatcga ctggtacgct gaaatcgaat ctgataactt cgtacctaca | 300 |
| gccgctggcc tggcttcatc tgcctccgct tatgctgctt tagctgccgc atgcaaccag | 360 |
| gctttagact tacaattgtc agataaggat ctaagtagac tggctagaat tggctcaggt | 420 |

| | |
|---|---|
| tctgcctcta gatctatcta cggtggattt gccgagtggg agaaaggtta taacgatgaa | 480 |
| acgtcctacg cagtaccact agaatctaat cactttgaag atgacttggc aatgattttt | 540 |
| gttgtcataa atcaacattc caaaaaggtg ccaagtagat atggaatgtc tcttactaga | 600 |
| aacacttcaa ggttctatca atattggttg gatcatattg acgaagattt ggccgaagca | 660 |
| aaagctgcaa tacaagataa agatttcaaa agattgggtg aagtcattga ggaaaatggg | 720 |
| cttagaatgc atgccacaaa tttgggaagt accccacctt ttacttacct ggttcaggaa | 780 |
| tcctacgatg tgatggcctt agttcatgaa tgtagggaag ccggataccc atgttatttc | 840 |
| acgatggatg ccggtcctaa tgttaagatt ctggttgaga agaaaaacaa gcaacagata | 900 |
| attgataagt tgctaacaca atttgacaat aaccaaatca ttgattctga cattatcgcc | 960 |
| acagggatag aaatcattga gtaa | 984 |

<210> SEQ ID NO 31
<211> LENGTH: 684
<212> TYPE: DNA
<213> ORGANISM: Artificial Sequence
<220> FEATURE:
<223> OTHER INFORMATION: Synthetic

<400> SEQUENCE: 31

| | |
|---|---|
| atgtcatctc aacaggagaa aaaggattac gacgaggaac aattgagact aatggaggaa | 60 |
| gtgtgtatag tagttgacga gaacgatgtg ccactaagat acgggactaa aaaggaatgc | 120 |
| catctgatgg aaaacatcaa taagggcttg ttgcataggg cttttctcta tgtttatcttc | 180 |
| gatgaacaaa acagacttttt gctacaacaa agagctgagg aaaagataac attcccatct | 240 |
| ctgtggacta atacatgttg tagtcatcca cttgatgttg ctggtgaacg tggtaatacc | 300 |
| ttaccagaag ctgttgaagg tgtcaaaaac gcagctcaga gaaaattgtt ccacgaattg | 360 |
| ggtatacaag ccaagtacat ccctaaagat aagttccaat tcttgaccag aattcattac | 420 |
| cttgcacctt ctacaggagc ctggggtgag catgaaattg attacatctt attctttaag | 480 |
| ggaaaggtcg aattagacat taatcctaac gaagttcagg catataagta cgttacaatg | 540 |
| gaagagttaa aggaaatgtt ttccgatcca cagtacggct ttactccatg gttcaaactg | 600 |
| atttgcgagc actttatgtt taagtggtgg caagatgtag accatgcctc aaaattccaa | 660 |
| gatactttaa tccacagatg ttaa | 684 |

<210> SEQ ID NO 32
<211> LENGTH: 864
<212> TYPE: DNA
<213> ORGANISM: Artificial Sequence
<220> FEATURE:
<223> OTHER INFORMATION: Synthetic

<400> SEQUENCE: 32

| | |
|---|---|
| atgtggagag cattggcccc agctagagct atcggtagag ctgcatccgg aggtggcgct | 60 |
| agaattggcg gaggtgccag agcattggga agatctttga agacacacc tcctgctgtt | 120 |
| caaccaacag ttgatggctc ttgcttaagg tttcctggta agagggcgg gtgggctgct | 180 |
| atgccagaag tttcaactga tgatttggat gaaagacagg tacaactaat ggccgaaatg | 240 |
| tgtattcttg tggatgaaaa cgatagaagg attggtgctg aaacaaagaa gaattgtcat | 300 |
| ttgaacgaaa acattgaaag agggttattg catagagctt ctctgttttt cctattcaat | 360 |
| acagaaaaca gttattact acagcaaaga tctgatgcca aaatcacttt tcctggttgt | 420 |
| ttcactaata catgctgttc acatccactt tcaaatccaa gtgaattgga ggaaaacgat | 480 |

```
gccatcgggg tgagaagagc agcccaaagg agactgaagg ccgaattggg tataccaatg      540
gaggaagtcc ctccagaaga gatcaactat ctgacaagga ttcactataa agctcaatct      600
gacagtatat ggggtgaaca tgaaatcgac tacattctgc tggtcaagaa aaatgtgacc      660
ttgaatccag atcctaatga gattaagtcc tactgttacg tcacgaaaga ggaacttgag      720
gagctaattg gtaaagcagc ccatggagaa atcaagatca cgccttggtt ccaaatcata      780
gctgacactt tcttgtttaa gtggtgggac aacttaaaca gattaaactt atttgtagat      840
cacgagaaaa tacacagaat gtaa                                            864
```

<210> SEQ ID NO 33  
<211> LENGTH: 855  
<212> TYPE: DNA  
<213> ORGANISM: Artificial Sequence  
<220> FEATURE:  
<223> OTHER INFORMATION: Synthetic

<400> SEQUENCE: 33

```
atggccgaaa ccttagtttc caaatgctcc tctcagttca caaaattgag ttccttctca       60
cttacttctt catcttctaa tttgtaccag agacaattcg tcacattcaa accaaggagt      120
tcatttgctg cttcagtttc ttcatccact accattctaa ctgatgccga ctctaacatg      180
gacgccgttc aaaggagatt gatgtttgaa gatgaatgca tcctggtgga tgctaacgac      240
gcagtagttg gccatgatac aaagtataac tgtcatttga tggaaaagat tcaatctgag      300
aacctgctac acagagcttt cagtgtcttt ctgttcaatt ccaagtacga attgctgtta      360
caacaaagat ctgctacaaa agttacattt cctttggttt ggactaacac ctgttgttct      420
cacccattgt atagagaatc agagcttatt gaggagaact acttaggggt gagaaacgct      480
gctcagagaa agttgttaga tgaattaggt atcccatctg atgagctacc tgttaatgag      540
tttatcccat ggacgtat actatacaaa gcaccttctg atggaaagtg gggtgaacat      600
gaacttgatt acttgttatt catagtaaga gatgtttcta tggcaccaaa tcctgatgaa      660
gtagcagaag tcaaatacgt gaatagaaa caattgaagg agttagtcat gaaggccgat      720
cttggcgaag agggtcttaa gttatcacca tggttcagaa tcgtagtgga caatttcttg      780
tttaagtggt gggatcatgt tgaaaacggt tcactattag aagcctgtga tatgaaaaca      840
attcacaact tataa                                                      855
```

<210> SEQ ID NO 34  
<211> LENGTH: 1071  
<212> TYPE: DNA  
<213> ORGANISM: Artificial Sequence  
<220> FEATURE:  
<223> OTHER INFORMATION: Synthetic

<400> SEQUENCE: 34

```
atgacacaag ttctggatt caacaaggaa gatatcgtta aagaaggaa aaaggatcac       60 attgatatct gtttgcataa agtagtcgaa ccttacaaaa acggtccatc tatatgggag      120
aagtacaaaa taccttatac tgccttacct gaaatctcca tggggaaaat tgataccaga      180
tgcgaattca tgggctggac tctatcattt cctttgatta tcagttccat gactggcgga      240
gaagagcatg ggagaataat caacgagaat ttggccaaag cctgtgaagc cgaaggcata      300
ccattcggtt taggaagtat gagaattgtt aacagatatg ctgtggctat tcatacattt      360
gatgtcaaaa agttctgtcc atctgttcca atgttcgcca atataggatt agtacagctg      420
```

| aattatggat tcggtgtcaa ggaagtgaat aatcttatca agtgcgtaaa tgcagacgga | 480 |
| ttgtttattc atctaaacca cacacaagag gcatgtcaac cagaaggtga tacaaacttc | 540 |
| gaatccctgc tacacaagtt agaagagttg ttacctcaca ttaaagtgcc agtaatcgtt | 600 |
| aagggtgttg ggcatggtat tgaaaagaga tctgttatgg ccttgcaaag agttggtgtc | 660 |
| aaatacatcg acgtatctgg ttgtggagga acttcttggg cttggattga agggtggaga | 720 |
| catccagatc taccagatga ccaaaacttg ggttacatct tcagagatgt tggtataacg | 780 |
| acggacaggt cattgcaaga gtgtgctcct ctgacacaag catctgacct gagacttatc | 840 |
| gccggaggcg ggattagaac cggtttggat atcgccaagt ctcttatgat gggcgctgaa | 900 |
| tgcgctacag ccgctctgcc atttttgaaa gcagctttgg aatcacctga agagtcaga | 960 |
| ggcgtgattc aaagattcaa aaaggagtta atagtggcta tgtttgcttg tggtgcctct | 1020 |
| actattgaag agcttagaaa gatgtcatta agtgtttcat catctttata a | 1071 |

<210> SEQ ID NO 35
<211> LENGTH: 1050
<212> TYPE: DNA
<213> ORGANISM: Artificial Sequence
<220> FEATURE:
<223> OTHER INFORMATION: Synthetic

<400> SEQUENCE: 35

| atgtctgatt ccagagaga acaaaggaaa aacgagcatg ttgaaattgc tatggcacaa | 60 |
| tctgatgcta tgcattctga tttcgataag atgagatttg tgcatcattc aattccatca | 120 |
| attaacgtta acgatattga tttgacatca caaacacctg atttgacgat gacatatcca | 180 |
| gtttacatta acgctatgac aggtggatct gaatggacca aaaacataaa tgagaaatta | 240 |
| gctgtagtcg ccagagaaac aggcttggcc atggccgtcg ttctactca cgctgccctt | 300 |
| agaaatccta aatggctga aaccttcact attgccagaa gatgaatcc agaaggcatg | 360 |
| atttctccca atgtaggagc tgatgtacct gtagaaaagg ccttagaagc agtagaacta | 420 |
| ttggaagctc aagccttaca gatccacgtt aactcccctc aggaactggt gatgccagaa | 480 |
| ggtaatagag aatttgttac atggctagac aacattgctt ccatcgtcag tagagtctca | 540 |
| gttccagtaa tcataaagga ggtggggttt ggtatgagta aggaattgat gcacgatctt | 600 |
| caacaaattg gggtgaagta cgttgacgtg tctggcaaag gtggaacaaa cttcgtcgat | 660 |
| atagaaaatg agagaagagc aaacaaggac atggattacc tttcctcctg gggccaatcc | 720 |
| actgttgaat ctttgctaga aacgactgct taccaatctg aaatatcagt gttcgcctca | 780 |
| ggtgggctga ggactccatt agacgccatc aaatcattag ccttgggtgc taaagcaact | 840 |
| ggaatgtcta gaccttttct gaatcaagtt gagaataatg gaatcgcaca tacggtcgcc | 900 |
| tatgttgaga gtttcataga gcatatgaag tctattatga caatgttaga tgctaaaaac | 960 |
| attgatgatc taacacaaaa acagatagtt ttctctccag aaatcctgag ttggatcgag | 1020 |
| caaaggaatt tgaacatcca tagaggttaa | 1050 |

<210> SEQ ID NO 36
<211> LENGTH: 395
<212> TYPE: PRT
<213> ORGANISM: Artificial Sequence
<220> FEATURE:
<223> OTHER INFORMATION: Synthetic

<400> SEQUENCE: 36

Met Val Asn Thr Glu Val Tyr Ile Val Ser Ala Val Arg Thr Pro Met

```
  1               5                   10                  15
Gly Ser Phe Gly Gly Ser Phe Ala Ser Leu Pro Ala Thr Lys Leu Gly
              20                  25                  30
Ser Ile Ala Ile Lys Gly Ala Leu Glu Arg Val Asn Ile Lys Pro Ser
              35                  40                  45
Asp Val Asp Glu Val Phe Met Gly Asn Val Val Ser Ala Asn Leu Gly
 50                  55                  60
Gln Asn Pro Ala Arg Gln Cys Ala Leu Gly Ala Gly Leu Pro Arg Ser
 65                  70                  75                  80
Ile Val Cys Thr Thr Val Asn Lys Val Cys Ala Ser Gly Met Lys Ala
              85                  90                  95
Thr Ile Leu Gly Ala Gln Thr Ile Met Thr Gly Asn Ala Glu Ile Val
             100                 105                 110
Val Ala Gly Gly Thr Glu Ser Met Ser Asn Ala Pro Tyr Tyr Ala Pro
             115                 120                 125
Lys Asn Arg Phe Gly Ala Lys Tyr Gly Asn Val Glu Leu Val Asp Gly
             130                 135                 140
Leu Leu Arg Asp Gly Leu Ser Asp Ala Tyr Asp Gly Leu Pro Met Gly
145                 150                 155                 160
Asn Ala Ala Glu Leu Cys Ala Glu Glu His Ser Ile Asp Arg Ala Ser
                 165                 170                 175
Gln Asp Ala Phe Ala Ile Ser Ser Tyr Lys Arg Ala Gln Asn Ala Gln
             180                 185                 190
Ala Thr Lys Ala Phe Glu Gln Glu Ile Val Pro Val Glu Val Pro Val
             195                 200                 205
Gly Arg Gly Lys Pro Asn Lys Leu Val Thr Glu Asp Glu Glu Pro Lys
             210                 215                 220
Asn Leu Asn Glu Asp Lys Leu Lys Ser Val Arg Ala Val Phe Lys Ser
225                 230                 235                 240
Asn Gly Thr Val Thr Ala Ala Asn Ala Ser Thr Leu Asn Asp Gly Ala
                 245                 250                 255
Ser Ala Leu Val Leu Met Ser Ala Ala Lys Val Lys Glu Leu Gly Leu
             260                 265                 270
Lys Pro Leu Ala Lys Ile Ile Gly Trp Gly Glu Ala Ala Gln Asp Pro
             275                 280                 285
Glu Arg Phe Thr Thr Ser Pro Ser Leu Ala Ile Pro Lys Ala Leu Lys
             290                 295                 300
His Ala Gly Ile Glu Ala Ser Gln Val Asp Tyr Tyr Glu Ile Asn Glu
305                 310                 315                 320
Ala Phe Ser Val Val Ala Val Ala Asn Thr Lys Ile Leu Gly Leu Asp
                 325                 330                 335
Pro Glu Arg Val Asn Ile Asn Gly Gly Val Ala Met Gly His Pro
             340                 345                 350
Leu Gly Ser Ser Gly Ser Arg Ile Ile Cys Thr Leu Ala Tyr Ile Leu
             355                 360                 365
Ala Gln Lys Asp Ala Lys Ile Gly Val Ala Ala Val Cys Asn Gly Gly
             370                 375                 380
Gly Gly Ala Ser Ser Ile Val Ile Glu Arg Val
385                 390                 395

<210> SEQ ID NO 37
<211> LENGTH: 422
<212> TYPE: PRT
<213> ORGANISM: Artificial Sequence
```

<220> FEATURE:
<223> OTHER INFORMATION: Synthetic

<400> SEQUENCE: 37

Met Pro Val Leu Ala Ala Leu Leu Arg Arg Gly Pro Leu Leu Gln Arg
1               5                   10                  15

Arg Val Gln Glu Ile Arg Tyr Ala Glu Arg Ser Tyr Val Ser Lys Pro
            20                  25                  30

Thr Leu Asn Glu Val Val Ile Val Ser Ala Ile Arg Thr Pro Ile Gly
        35                  40                  45

Ser Phe Leu Gly Ser Leu Ser Ser Leu Pro Ala Thr Lys Leu Gly Ser
    50                  55                  60

Ile Ala Ile Gln Gly Ala Ile Glu Lys Ala Gly Ile Pro Lys Glu Glu
65                  70                  75                  80

Val Lys Glu Ala Tyr Met Gly Asn Val Leu Gln Gly Gly Glu Gly Gln
                85                  90                  95

Ala Pro Thr Arg Gln Ala Val Leu Gly Ala Gly Leu Pro Ile Ser Thr
            100                 105                 110

Pro Cys Thr Thr Ile Asn Lys Val Cys Ala Ser Gly Met Lys Ala Ile
        115                 120                 125

Met Met Ala Ser Gln Asn Leu Met Cys Gly His Gln Asp Val Met Val
130                 135                 140

Ala Gly Gly Met Glu Ser Met Ser Asn Val Pro Tyr Val Met Asn Arg
145                 150                 155                 160

Gly Ala Thr Pro Tyr Gly Gly Val Lys Leu Glu Asp Leu Ile Val Lys
            165                 170                 175

Asp Gly Leu Thr Asp Val Tyr Asn Lys Ile His Met Gly Asn Cys Ala
        180                 185                 190

Glu Asn Thr Ala Lys Lys Leu Asn Ile Thr Arg Glu Glu Gln Asp Thr
    195                 200                 205

Tyr Ala Leu Asn Ser Tyr Thr Arg Ser Lys Ala Ala Trp Glu Ala Gly
210                 215                 220

Arg Phe Gly Asn Glu Val Val Pro Val Thr Ile Thr Val Lys Gly Lys
225                 230                 235                 240

Pro Asp Val Val Val Lys Glu Asp Glu Glu Tyr Lys Arg Val Asp Phe
            245                 250                 255

Ser Lys Ile Pro Lys Leu Lys Thr Val Phe Gln Arg Glu Asn Gly Thr
        260                 265                 270

Val Thr Ala Ala Asn Ala Ser Thr Leu Asn Asp Gly Ala Ala Ala Val
    275                 280                 285

Val Leu Met Thr Ala Asp Ala Ala Lys Arg Leu Asn Val Lys Pro Leu
290                 295                 300

Ala Arg Ile Ala Ala Phe Ala Asp Ala Ala Val Glu Pro Ile Asp Phe
305                 310                 315                 320

Pro Leu Ala Pro Ala Tyr Ala Val Pro Lys Val Leu Lys Asp Ala Gly
            325                 330                 335

Leu Lys Lys Glu Asp Ile Thr Met Trp Glu Val Asn Glu Ala Phe Ser
        340                 345                 350

Val Val Val Leu Ala Asn Ile Lys Met Leu Glu Met Asp Pro Gln Lys
    355                 360                 365

Val Asn Ile Asn Gly Gly Ala Val Ser Leu Gly His Pro Ile Gly Met
370                 375                 380

Ser Gly Ala Arg Ile Val Val His Leu Ala His Ala Leu Lys Gln Gly
385                 390                 395                 400

Glu Tyr Gly Leu Ala Ser Ile Cys Asn Gly Gly Gly Ala Ser Ala
                405                 410                 415
Met Leu Ile Gln Lys Leu
            420

<210> SEQ ID NO 38
<211> LENGTH: 406
<212> TYPE: PRT
<213> ORGANISM: Artificial Sequence
<220> FEATURE:
<223> OTHER INFORMATION: Synthetic

<400> SEQUENCE: 38

Met Ala His Ser Ala Asp Ser Ser Asp Asn Pro Arg Asp Val Cys Ile
1               5                   10                  15

Val Gly Val Ala Arg Thr Pro Met Gly Gly Phe Leu Gly Ser Leu Ser
            20                  25                  30

Ser Leu Pro Ala Thr Lys Leu Gly Ser Leu Ala Ile Thr Ala Ala Leu
        35                  40                  45

Lys Arg Glu Met Leu Thr Arg Leu Trp Ser Lys Glu Val Val Phe Gly
    50                  55                  60

Asn Val Leu Ser Ala Asn Leu Gly Gln Ala Pro Ala Arg Gln Ala Ala
65                  70                  75                  80

Leu Gly Ala Gly Ile Ser Asn Ser Val Ile Cys Thr Thr Val Asn Lys
                85                  90                  95

Val Cys Ala Ser Gly Met Lys Ala Val Met Ile Ala Ala Gln Ser Ile
            100                 105                 110

Gln Leu Gly Ile Asn Asp Val Val Ala Gly Gly Met Glu Ser Met
        115                 120                 125

Ser Asn Thr Pro Lys Tyr Leu Ala Glu Ala Arg Lys Gly Ser Arg Phe
    130                 135                 140

Gly His Asp Ser Leu Val Asp Gly Met Leu Lys Asp Gly Leu Trp Asp
145                 150                 155                 160

Val Tyr Asn Asp Cys Gly Met Gly Ser Cys Ala Glu Leu Cys Ala Glu
                165                 170                 175

Lys Phe Glu Ile Thr Arg Glu Gln Gln Asp Asp Tyr Ala Val Gln Ser
            180                 185                 190

Phe Glu Arg Gly Ile Ala Ala Gln Glu Ser Gly Ala Phe Thr Trp Glu
        195                 200                 205

Ile Val Pro Val Glu Val Ser Gly Gly Arg Gly Arg Pro Ser Thr Ile
    210                 215                 220

Val Asp Lys Asp Glu Gly Leu Gly Lys Phe Asp Ala Ala Lys Leu Arg
225                 230                 235                 240

Lys Leu Arg Pro Ser Phe Lys Glu Asn Gly Gly Thr Val Thr Ala Gly
                245                 250                 255

Asn Ala Ser Ser Ile Ser Asp Gly Ala Ala Ala Ile Val Leu Val Ser
            260                 265                 270

Gly Glu Lys Ala Leu Gln Leu Gly Leu Gln Val Leu Ala Lys Val Lys
        275                 280                 285

Gly Tyr Gly Asp Ala Ala Gln Glu Pro Glu Phe Phe Thr Thr Ala Pro
    290                 295                 300

Ala Leu Ala Ile Pro Lys Ala Ile Ala Pro Asn Ser Pro Tyr Ser Glu
305                 310                 315                 320

Ser Tyr Gln Val Asp Tyr Glu Ile Asn Glu Ala Phe Ala Val Val
                325                 330                 335

```
Ala Leu Ala Asn Gln Lys Leu Gly Ile Ser Pro Glu Lys Val Asn
            340                 345                 350

Val Asn Gly Gly Ala Val Ser Leu Gly His Pro Leu Gly Cys Ser Gly
            355                 360                 365

Ala Arg Ile Leu Ile Thr Leu Leu Gly Ile Leu Lys Lys Arg Asn Gly
            370                 375                 380

Lys Tyr Gly Val Gly Val Cys Asn Gly Gly Gly Ala Ser Ala
385                 390                 395                 400

Leu Val Leu Glu Val Val
                405

<210> SEQ ID NO 39
<211> LENGTH: 440
<212> TYPE: PRT
<213> ORGANISM: Artificial Sequence
<220> FEATURE:
<223> OTHER INFORMATION: Synthetic

<400> SEQUENCE: 39

Met His Ser Thr Arg His Ile Leu Arg Gln Arg Ala Val Leu Val Thr
1               5                   10                  15

Gly Ala Arg Thr Pro Phe Val Lys Ser Phe Gly Ala Leu Met Lys Ala
            20                  25                  30

Asp Thr Leu Glu Leu Ala Ser Ala Ser Val Ala Gly Leu Leu Asn Lys
        35                  40                  45

Thr Ser Leu Asp Pro Arg Asp Ile Asp His Ile Val Trp Gly Asn Val
    50                  55                  60

Val Leu Gln Gly Ser Ala His Asn Cys Ala Arg Glu Ile Val Ile Asp
65                  70                  75                  80

Leu Asn Met Pro Lys Lys Ile Ile Gly Asn Leu Thr Ser Met Ala Cys
                85                  90                  95

Ala Ser Gly Leu Ser Ser Leu Ser Gln Ala Cys Met Leu Ile Glu Gly
            100                 105                 110

Gly His Ala Asp Val Val Ile Ala Gly Gly Ser Asp Ser Val Ser Asn
            115                 120                 125

Thr Glu Val Pro Leu Pro Arg Ser Val Thr Tyr Gly Leu Met Met Ala
    130                 135                 140

Gln Arg Lys Gly Val Met Gly Phe Phe Lys Glu Ala Gly Tyr Asn Pro
145                 150                 155                 160

Phe Lys Trp Phe Pro Gly Gly Ile Ala Leu Thr Glu Arg Ser Thr Gly
                165                 170                 175

Lys Thr Met Gly Trp His Gly Asp Leu Ile Ala Glu Leu Asn Ser Ile
            180                 185                 190

Ser Arg Asp Asp Gln Glu Ala Leu Ala Val Ala Ser His Ala Asn Ala
        195                 200                 205

Ala Arg Ala Glu Lys Ala Gly Tyr Phe Lys Glu Glu Ile Val Pro Val
    210                 215                 220

Thr Ile Asp Lys Lys Gly Lys Lys Thr Glu Val Thr Cys Asp Asp Val
225                 230                 235                 240

Met Gln Arg Asp Thr Glu Lys Met Lys Ala Lys Met Pro Ser Leu Lys
                245                 250                 255

Pro Val Phe Arg Lys Glu Gly Gly Thr Ile Thr Ala Ala Thr Ser Ser
            260                 265                 270

Thr Leu Thr Asp Gly Gly Ser Ala Met Leu Val Met Ser Glu Glu Lys
        275                 280                 285
```

```
Ala Lys Lys Leu Gly Tyr Pro Thr Asp Val Cys Val Lys Ser Trp Tyr
        290                 295                 300

Phe Ser Gly Ile Asp Pro Tyr Pro Gln Leu Leu Ala Pro Val Leu
305                 310                 315                 320

Gly Trp Gly Pro Ala Leu Lys Lys Ala Gly Leu Thr Pro Lys Asp Ile
                325                 330                 335

Asp Leu Tyr Glu Ile His Glu Ala Phe Ala Ala Gln Val Leu Ala Thr
                340                 345                 350

Ile Lys Cys Leu Lys Ser Gln Glu Phe Phe Asp Arg Tyr Ala Asn Gly
            355                 360                 365

Ala Lys Pro Val Leu Thr Glu Asp Ile Asp Leu Ser Lys Leu Asn Val
370                 375                 380

Asn Gly Gly Ser Leu Ala Leu Gly His Pro Phe Ala Ala Thr Gly Gly
385                 390                 395                 400

Arg Ile Val Ile Ser Leu Ala Asn Glu Leu Arg Arg Ser Gly Lys Arg
                405                 410                 415

His Gly Leu Val Ser Ile Cys Ala Ala Gly Gly Leu Gly Gly Val Ala
            420                 425                 430

Ile Leu Glu His Thr Ala Ser Lys
            435                 440

<210> SEQ ID NO 40
<211> LENGTH: 379
<212> TYPE: PRT
<213> ORGANISM: Artificial Sequence
<220> FEATURE:
<223> OTHER INFORMATION: Synthetic

<400> SEQUENCE: 40

Met Asn Gln Ala Val Ile Val Ala Ala Lys Arg Thr Ala Phe Gly Lys
1               5                   10                  15

Tyr Gly Gly Thr Leu Lys His Ile Glu Pro Glu Gln Leu Leu Lys Pro
                20                  25                  30

Leu Phe Gln His Phe Lys Glu Lys Tyr Pro Glu Val Ile Ser Lys Ile
            35                  40                  45

Asp Asp Val Val Leu Gly Asn Val Gly Asn Gly Asn Ile Ala
50                  55                  60

Arg Lys Ala Leu Leu Glu Ala Gly Leu Lys Asp Ser Ile Pro Gly Val
65                  70                  75                  80

Thr Ile Asp Arg Gln Cys Gly Ser Gly Leu Glu Ser Val Gln Tyr Ser
                85                  90                  95

Cys Arg Met Ile Gln Ala Gly Ala Gly Lys Val Tyr Ile Ala Gly Gly
                100                 105                 110

Val Glu Ser Thr Ser Arg Ala Pro Trp Lys Ile Lys Arg Pro His Ser
            115                 120                 125

Val Tyr Glu Thr Ala Leu Pro Glu Phe Tyr Arg Ala Ser Phe Ala
            130                 135                 140

Pro Glu Met Ser Asp Pro Ser Met Ile Gln Gly Ala Glu Asn Ala Ala
145                 150                 155                 160

Lys Met Tyr Asp Val Ser Arg Glu Leu Gln Asp Glu Phe Ala Tyr Arg
                165                 170                 175

Ser His Gln Leu Thr Ala Glu Asn Val Lys Asn Gly Asn Ile Ser Gln
            180                 185                 190

Glu Ile Leu Pro Ile Thr Val Lys Gly Glu Ile Phe Asn Thr Asp Glu
            195                 200                 205
```

```
Ser Leu Lys Ser His Ile Pro Lys Asp Asn Phe Gly Arg Phe Lys Pro
    210                 215                 220

Val Ile Lys Gly Gly Thr Val Thr Ala Ala Asn Ser Cys Met Lys Asn
225                 230                 235                 240

Asp Gly Ala Val Leu Leu Ile Met Glu Lys Asp Met Ala Tyr Glu
                245                 250                 255

Leu Asp Phe Glu His Gly Leu Leu Phe Lys Asp Gly Val Thr Val Gly
            260                 265                 270

Val Asp Ser Asn Phe Pro Gly Ile Gly Pro Val Pro Ala Ile Ser Asn
            275                 280                 285

Leu Leu Lys Arg Asn Gln Leu Thr Ile Glu Asn Ile Glu Val Ile Glu
    290                 295                 300

Ile Asn Glu Ala Phe Ser Ala Gln Val Val Ala Cys Gln Gln Ala Leu
305                 310                 315                 320

Asn Ile Ser Asn Thr Gln Leu Asn Ile Trp Gly Gly Ala Leu Ala Ser
                325                 330                 335

Gly His Pro Tyr Gly Ala Ser Gly Ala Gln Leu Val Thr Arg Leu Phe
            340                 345                 350

Tyr Met Phe Asp Lys Glu Thr Met Ile Ala Ser Met Gly Ile Gly Gly
            355                 360                 365

Gly Leu Gly Asn Ala Ala Leu Phe Thr Arg Phe
    370                 375

<210> SEQ ID NO 41
<211> LENGTH: 473
<212> TYPE: PRT
<213> ORGANISM: Artificial Sequence
<220> FEATURE:
<223> OTHER INFORMATION: Synthetic

<400> SEQUENCE: 41

Met Thr Ile Pro Leu Ala Thr Ala Val Ala Asp Ile Glu Leu Pro Arg
1               5                   10                  15

Pro Lys Asp Val Gly Val Leu Gly Ile Glu Val Tyr Phe Pro Arg Arg
                20                  25                  30

Cys Val Ser Glu Ala Asp Leu Glu Val Phe Asp Gly Val Ser Thr Gly
            35                  40                  45

Lys Tyr Thr Ile Gly Leu Gly Gln Glu Tyr Met Ala Trp Pro Asp Asp
    50                  55                  60

Arg Glu Asp Ile Asn Ser Phe Ala Leu Asn Ala Val Ser Gly Leu Leu
65                  70                  75                  80

Glu Lys Tyr Asn Ile Asp Pro Lys Ser Ile Gly Arg Ile Asp Val Gly
                85                  90                  95

Thr Glu Thr Ile Ile Asp Lys Ser Lys Ser Val Lys Thr Thr Leu Met
            100                 105                 110

Asp Leu Phe Ala Glu Ala Gly Asn Tyr Asp Ile Glu Gly Ile Asp Ser
        115                 120                 125

Lys Asn Ala Cys Tyr Gly Gly Thr Ala Ala Leu Phe Asn Ala Ile Asn
    130                 135                 140

Trp Ile Glu Ser Ser Ser Trp Asp Gly Arg Asn Ala Ile Val Val Ser
145                 150                 155                 160

Gly Asp Ile Ala Val Tyr Ala Glu Gly Ala Ala Arg Pro Ala Gly Gly
                165                 170                 175

Ala Gly Ala Cys Ala Ile Leu Ile Gly Pro Asn Ala Pro Val Val Phe
            180                 185                 190
```

```
Glu Pro Val His Gly Thr Tyr Met Ala Asn Thr Tyr Asp Phe Tyr Lys
        195                 200                 205

Pro Asn Leu Ser Ser Glu Tyr Pro Glu Val Asp Gly Pro Val Ser Val
    210                 215                 220

Val Thr Tyr Val Ala Ala Leu Asp Ala Ala Tyr Thr Thr Phe Lys Glu
225                 230                 235                 240

Lys Phe Ala Lys Ala Ala Lys Arg Ala Gln Val Ala Gly Lys Glu Val
                245                 250                 255

Ser Ser Ala Thr Phe Ser Leu Glu Asp Leu Asp Tyr Ala Ile Phe His
                260                 265                 270

Ser Pro Tyr Gly Lys Gln Ala Val Lys Gly His Ala Arg Met Leu Tyr
                275                 280                 285

Asn Asp Phe Ile Thr Asn Pro Lys Asp Pro Arg Phe Ala Asn Val Pro
    290                 295                 300

Asn Pro Glu Ser Phe Ile Ser Gln Ser His Ala Gln Ser Leu Thr Asp
305                 310                 315                 320

Lys Asn Val Glu Lys Thr Phe Val Ala Leu Ser Lys Ala Ser Phe Ala
                325                 330                 335

Lys Lys Thr Asp Pro Gly Met Ala Cys Ser Lys Arg Leu Gly Asn Met
                340                 345                 350

Tyr Thr Ala Ser Leu Tyr Gly Cys Leu Ala Ser Leu Leu Gly Thr Val
                355                 360                 365

Glu Pro Ser Glu Leu Gly Gly Lys Arg Val Ser Leu Phe Ser Phe Gly
                370                 375                 380

Ser Gly Cys Ala Ala Thr Phe Phe Thr Ala Arg Ile Lys Gly Asp Thr
385                 390                 395                 400

Ser Glu Ile Lys Glu Lys Leu Lys Leu Lys Glu Arg Leu Ala Ala Met
                405                 410                 415

Thr Val Ala Pro Pro Glu Glu Phe Val Ala Ala Leu Ala Leu Arg Glu
                420                 425                 430

Lys Asn His Asn Ala Val Asp Phe Thr Pro Glu Gly Ser Val Asp Asn
                435                 440                 445

Ile Trp Pro Gly Ala Tyr Tyr Leu Glu His Val Asp Ser Lys Phe Arg
    450                 455                 460

Arg Lys Tyr Val Arg Ala Pro Val Ala
465                 470

<210> SEQ ID NO 42
<211> LENGTH: 508
<212> TYPE: PRT
<213> ORGANISM: Artificial Sequence
<220> FEATURE:
<223> OTHER INFORMATION: Synthetic

<400> SEQUENCE: 42

Met Gln Arg Leu Leu Thr Pro Val Arg Gln Val Leu Gln Val Lys Arg
1               5                   10                  15

Val Met Gln Glu Ala Ser Leu Leu Pro Ala Arg Leu Leu Pro Ala Ala
                20                  25                  30

His Pro Ser Phe Ser Thr Val Pro Ala Val Pro Leu Ala Lys Thr Asp
                35                  40                  45

Thr Trp Pro Lys Asp Val Gly Ile Leu Ala Met Glu Val Tyr Phe Pro
        50                  55                  60

Ala Gln Tyr Val Asp Gln Thr Glu Leu Glu Lys Phe Asn Lys Val Glu
65                  70                  75                  80
```

-continued

```
Ala Gly Arg Tyr Thr Val Gly Leu Gly Gln Thr Gln Met Gly Phe Cys
                85                  90                  95
Ser Val Gln Glu Asp Val Asn Ser Leu Cys Leu Thr Val Val Gln Gln
            100                 105                 110
Leu Met Glu Arg Thr Gln Leu Pro Trp Asp Ser Val Gly Arg Leu Glu
        115                 120                 125
Val Gly Thr Glu Thr Ile Ile Asp Lys Ser Lys Ala Val Lys Thr Val
130                 135                 140
Leu Met Glu Leu Phe Gln Asp Ser Gly Asn Thr Asp Ile Glu Gly Ile
145                 150                 155                 160
Asp Thr Thr Asn Ala Cys Tyr Gly Gly Thr Ala Ser Leu Phe Asn Ala
                165                 170                 175
Ala Asn Trp Met Glu Ser Ser Ser Trp Asp Gly Arg Tyr Ala Leu Val
            180                 185                 190
Val Cys Gly Asp Ile Ala Val Tyr Pro Ser Gly Asn Ala Arg Pro Thr
        195                 200                 205
Gly Gly Ala Gly Ala Val Ala Met Leu Val Gly Pro Glu Ala Pro Leu
210                 215                 220
Val Leu Glu Arg Gly Leu Arg Gly Thr His Met Glu Asn Val Tyr Asp
225                 230                 235                 240
Phe Tyr Lys Pro Asp Val Thr Ser Glu Tyr Pro Leu Val Asp Gly Lys
                245                 250                 255
Leu Ser Ile Gln Cys Tyr Leu Arg Ala Leu Asp Lys Cys Tyr Ala Phe
            260                 265                 270
Tyr Arg Gln Lys Ile Glu Lys Gln Trp Lys Gln Ala Gly Ile Asp Arg
        275                 280                 285
Pro Phe Thr Leu Asp Asp Val Gln Tyr Met Ile Phe His Thr Pro Phe
290                 295                 300
Cys Lys Leu Val Gln Lys Ser Leu Ala Arg Leu Met Phe Asn Asp Phe
305                 310                 315                 320
Leu Leu Ala Ser Gly Asp Thr Gln Thr Gly Ile Tyr Lys Gly Leu Glu
                325                 330                 335
Ala Phe Arg Gly Leu Lys Leu Glu Asp Thr Tyr Thr Asn Lys Asp Val
            340                 345                 350
Asp Lys Ala Phe Leu Lys Ala Ser Leu Asn Met Phe Asn Lys Lys Thr
        355                 360                 365
Lys Asn Ser Leu Tyr Leu Ser Thr Tyr Asn Gly Asn Met Tyr Thr Ser
370                 375                 380
Ser Leu Tyr Gly Cys Leu Ala Ser Leu Leu Ala His His Ser Ala Gln
385                 390                 395                 400
Asp Leu Ala Gly Ser Arg Ile Gly Ala Phe Ser Tyr Gly Ser Gly Leu
                405                 410                 415
Ala Ala Ser Phe Phe Ser Phe Arg Val Ser Gln Asp Ala Ser Pro Gly
            420                 425                 430
Ser Pro Leu Glu Lys Leu Val Ser Thr Ser Asp Leu Gln Lys Arg
        435                 440                 445
Leu Ala Ser Arg Lys Arg Val Ser Pro Glu Glu Phe Thr Glu Ile Met
450                 455                 460
Asn Gln Arg Glu Gln Tyr Tyr His Lys Met Asn Phe Ser Pro Pro Gly
465                 470                 475                 480
Asp Lys Asn Ser Leu Phe Pro Gly Thr Trp Tyr Leu Glu Arg Val Asp
                485                 490                 495
```

Glu Leu Tyr Arg Arg Lys Tyr Ala Arg Arg Pro Val
            500                 505

<210> SEQ ID NO 43
<211> LENGTH: 462
<212> TYPE: PRT
<213> ORGANISM: Artificial Sequence
<220> FEATURE:
<223> OTHER INFORMATION: Synthetic

<400> SEQUENCE: 43

Met Ala Ser Gln Pro Lys Asn Val Gly Ile Leu Ala Met Glu Ile Tyr
1               5                   10                  15

Phe Pro Pro Thr Cys Leu Gln Gln Glu Val Leu Glu Ala His Asp Gly
            20                  25                  30

Ala Ser Lys Gly Lys Tyr Thr Ile Gly Leu Gly Gln Asp Cys Met Gly
        35                  40                  45

Phe Cys Thr Glu Val Glu Asp Val Ile Ser Met Ser Leu Thr Ala Val
50                  55                  60

Thr Ser Leu Pro Glu Lys Tyr Ala Ile Asp Pro Lys Gln Ile Gly Arg
65                  70                  75                  80

Leu Glu Val Gly Ser Glu Thr Val Ile Asp Lys Ser Lys Ser Ile Lys
                85                  90                  95

Thr Phe Leu Met Gln Ile Phe Glu Lys His Gly Asn Thr Asp Ile Glu
            100                 105                 110

Gly Val Asp Ser Thr Asn Ala Cys Tyr Gly Gly Thr Ala Ala Leu Phe
        115                 120                 125

Asn Cys Val Asn Trp Val Glu Ser Ser Trp Asp Gly Arg Tyr Gly
130                 135                 140

Leu Val Val Cys Thr Asp Ser Ala Val Tyr Ala Glu Gly Pro Ala Arg
145                 150                 155                 160

Pro Thr Gly Gly Ala Ala Ile Ala Met Leu Val Gly Pro Asp Ala
                165                 170                 175

Pro Ile Val Phe Glu Ser Lys Ile Arg Ala Ser His Met Ser His Ala
            180                 185                 190

Tyr Asp Phe Tyr Lys Pro Ile Leu Asp Ser Glu Tyr Pro Val Val Asp
        195                 200                 205

Gly Lys Leu Ser Gln Thr Cys Tyr Leu Met Ala Leu Asp Ser Cys Tyr
210                 215                 220

Lys Ser Leu Cys Asn Lys Tyr Glu Lys Leu Glu Gly Lys Gln Phe Ser
225                 230                 235                 240

Met Ala Asp Ala Ala Tyr Phe Val Phe His Ser Pro Tyr Asn Lys Leu
                245                 250                 255

Val Gln Lys Ser Phe Gly Arg Leu Leu Phe Asn Asp Phe Leu Arg Asn
            260                 265                 270

Ala Ser Ser Val Asp Glu Ser Ala Lys Gln Ile Leu Ala Pro Phe Glu
        275                 280                 285

Ser Leu Ala Gly Asp Glu Ser Tyr Gln Ser Arg Asp Leu Glu Lys Ala
290                 295                 300

Ser Gln Gln Val Ala Lys Pro Phe Tyr Asp Glu Lys Val Gln Pro Thr
305                 310                 315                 320

Thr Leu Ile Pro Lys Gln Val Gly Asn Met Tyr Thr Ala Ser Leu Tyr
                325                 330                 335

Ala Ala Phe Ala Ser Leu Ile His Asn Lys His Asn Thr Leu Ala Gly
            340                 345                 350

```
Gln Arg Val Ile Val Phe Ser Tyr Gly Ser Gly Leu Thr Ala Thr Met
            355                 360                 365

Phe Ser Leu Lys Phe Asn Glu Gly Gln His Pro Phe Ser Leu Ser Asn
    370                 375                 380

Ile Ala Ser Val Met Asn Val Ser Glu Lys Leu Lys Ser Arg His Glu
385                 390                 395                 400

Phe Thr Pro Glu Lys Phe Val Glu Ile Met Lys Leu Met Glu His Arg
                405                 410                 415

Tyr Gly Ala Lys Asp Phe Val Thr Ser Lys Asp Cys Ser Leu Leu Ala
            420                 425                 430

Pro Gly Thr Tyr Tyr Leu Thr Glu Val Asp Ser Lys Tyr Arg Arg Phe
            435                 440                 445

Tyr Ala Gln Lys Ala Pro Glu His Gly Leu Val Asn Gly His
    450                 455                 460

<210> SEQ ID NO 44
<211> LENGTH: 501
<212> TYPE: PRT
<213> ORGANISM: Artificial Sequence
<220> FEATURE:
<223> OTHER INFORMATION: Synthetic

<400> SEQUENCE: 44

Met Met Arg Asn Thr Cys Leu Ser Leu Ala Gly Val Ser Gly Met Ala
1               5                   10                  15

Val Tyr Ala Pro His Cys Arg Val Asp Leu Glu Gln Trp Cys Lys Trp
            20                  25                  30

Thr Gly Asn Ser Trp Asp Lys Val Ser Ser Val Val Gly Gln Ser Phe
        35                  40                  45

Arg Ile Thr Ser His Asn Glu Asn Ala Tyr Thr Met Ala Ala Asn Ala
    50                  55                  60

Val Leu Arg Leu Ile Val Asn Asn Ile Asp Pro Thr Lys Ile Gly
65                  70                  75                  80

Phe Leu Gly Leu Gly Thr Glu Ser Ser Ser Asp Asn Ser Ala Gly Ala
                85                  90                  95

Ile Ile Val Lys Gly Met Val Asp Lys Gly Leu Arg Ala Met Asn Met
            100                 105                 110

Pro Ala Met Ser Arg His Cys Glu Val Pro Glu Phe Lys His Ala Cys
        115                 120                 125

Leu Ala Gly Val Tyr Ala Met Glu Ser Ala Thr Arg Phe Val Asn Ala
    130                 135                 140

Asp Gly Lys Asp Arg Met Ala Ile Ala Val Ala Ser Asp Ile Ala Glu
145                 150                 155                 160

Tyr Ala Leu Gly Ser Thr Gly Glu Gln Thr Gln Gly Ala Gly Ala Thr
                165                 170                 175

Ala Met Val Leu Glu His Asp Pro Lys Leu Phe Glu Val Gln Leu Gln
            180                 185                 190

His Ser Gly Ser Ala Ser Asp Tyr Arg Gly Pro Asp Phe Arg Lys Pro
        195                 200                 205

His Arg Arg His Phe Met Asn Leu Glu Glu Tyr Thr Lys Ser Ser Ala
    210                 215                 220

Asn Gly Lys Met Ala Asp Phe Pro Val Phe Ser Gly Pro Tyr Ser Thr
225                 230                 235                 240

Leu Val Tyr Gln Glu Glu Val Thr Val Ala Val Glu His Met Leu Glu
                245                 250                 255
```

Arg Leu Gln Gln Ser Pro Gly Lys Tyr Tyr Asp Asp Val Thr Ala Leu
                260                 265                 270

Phe Phe His Arg Pro Tyr Asn Met Met Pro Ile Gln Ala Met Ser Phe
            275                 280                 285

Leu Tyr Ala Arg Gly Leu Ala Arg Ala Thr Ser Glu Glu His Lys Ala
        290                 295                 300

His Phe Ala Glu Leu Cys Lys Gln Gly Lys Ala Asp Pro Ala Ala Val
305                 310                 315                 320

Val Lys Glu Leu Asp Val Asn Pro His Tyr Phe Gln Gln Ile Glu Ser
                325                 330                 335

Gly Gly Glu Pro Lys Asp Ala Phe Pro Ala Thr Gly Lys Val Ala Lys
            340                 345                 350

Val Leu Arg Lys Asp Lys Lys Phe Ile Asp Leu Leu Glu Lys Lys Met
        355                 360                 365

Ser Met Gly Ser Pro Ala Met Gly Asn Phe Gly Asn Leu Tyr Thr Ala
        370                 375                 380

Ser Leu Pro Cys Trp Leu Ala Ala Gly Phe Glu Glu Ala Tyr Thr Arg
385                 390                 395                 400

Lys Leu Asp Ile Thr Gly Lys Pro Met Val Met Val Gly Tyr Gly Ser
                405                 410                 415

Gly Asp Ala Ser Met Ser Ile Pro Ile Leu Pro Val Pro Gly Trp Glu
            420                 425                 430

Asn Ala Ala Asn Ile Asn Val Ser Lys Ala Leu Glu Asn Pro Val
            435                 440                 445

Asn Leu Asp Lys Ala Gln Tyr Glu Ala Leu His Thr Gly Ala Glu Lys
        450                 455                 460

Asn Asp Leu Ala Lys Asp Arg Arg Lys Met Glu Phe Val Ile Asp Arg
465                 470                 475                 480

Leu Gly Asn Arg Asn Glu Ala Ala Phe Gln Asp Val Gly Ile Glu Tyr
                485                 490                 495

Tyr Arg Tyr Ile Gln
            500

<210> SEQ ID NO 45
<211> LENGTH: 388
<212> TYPE: PRT
<213> ORGANISM: Artificial Sequence
<220> FEATURE:
<223> OTHER INFORMATION: Synthetic

<400> SEQUENCE: 45

Met Thr Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Glu Met Ala Val Ser Pro Val Asn
        35                  40                  45

Gln Asp Ile Val Ser Met Gly Ala Asn Ala Ala Lys Asp Ile Ile Thr
    50                  55                  60

Asp Glu Asp Lys Lys Ile Gly Met Val Ile Val Ala Thr Glu Ser
65                  70                  75                  80

Ala Val Asp Ala Ala Lys Ala Ala Ala Val Gln Ile His Asn Leu Leu
                85                  90                  95

Gly Ile Gln Pro Phe Ala Arg Cys Phe Glu Met Lys Glu Ala Cys Tyr
            100                 105                 110

```
Ala Ala Thr Pro Ala Ile Gln Leu Ala Lys Asp Tyr Leu Ala Thr Arg
            115                 120                 125

Pro Asn Glu Lys Val Leu Val Ile Ala Thr Asp Thr Ala Arg Tyr Gly
        130                 135                 140

Leu Asn Ser Gly Gly Glu Pro Thr Gln Gly Ala Gly Ala Val Ala Met
145                 150                 155                 160

Val Ile Ala His Asn Pro Ser Ile Leu Ala Leu Asn Glu Asp Ala Val
                165                 170                 175

Ala Tyr Thr Glu Asp Val Tyr Asp Phe Trp Arg Pro Thr Gly His Lys
            180                 185                 190

Tyr Pro Leu Val Asp Gly Ala Leu Ser Lys Asp Ala Tyr Ile Arg Ser
        195                 200                 205

Phe Gln Gln Ser Trp Asn Glu Tyr Ala Lys Arg Gln Gly Lys Ser Leu
    210                 215                 220

Ala Asp Phe Ala Ser Leu Cys Phe His Val Pro Phe Thr Lys Met Gly
225                 230                 235                 240

Lys Lys Ala Leu Glu Ser Ile Ile Asp Asn Ala Asp Glu Thr Thr Gln
                245                 250                 255

Glu Arg Leu Arg Ser Gly Tyr Glu Asp Ala Val Asp Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Asn Arg Asp Leu Gln Ala Gly Glu Thr Ile Gly Leu Phe Ser
    290                 295                 300

Tyr Gly Ser Gly Ser Val Gly Glu Phe Tyr Ser Ala Thr Leu Val Glu
305                 310                 315                 320

Gly Tyr Lys Asp His Leu Asp Gln Ala Ala His Lys Ala Leu Leu Asn
                325                 330                 335

Asn Arg Thr Glu Val Ser Val Asp Ala Tyr Glu Thr Phe Phe Lys Arg
            340                 345                 350

Phe Asp Asp Val Glu Phe Asp Glu Glu Gln Asp Ala Val His Glu Asp
        355                 360                 365

Arg His Ile Phe Tyr Leu Ser Asn Ile Glu Asn Asn Val Arg Glu Tyr
    370                 375                 380

His Arg Pro Glu
385

<210> SEQ ID NO 46
<211> LENGTH: 1200
<212> TYPE: PRT
<213> ORGANISM: Artificial Sequence
<220> FEATURE:
<223> OTHER INFORMATION: Synthetic

<400> SEQUENCE: 46

Met Arg Ala Val Leu Arg Leu Leu Ser Thr His Thr Val Phe Ser Pro
1               5                   10                  15

Ile Glu Thr Ile Val Ser Val Phe Val Leu Ala Thr Leu Ala Tyr Phe
                20                  25                  30

His Ile Leu Ser Gly Ile Lys His Ser Ser Phe Phe Ala Ser Ser His
            35                  40                  45

Pro Pro Ala Ile Arg Pro Ala Phe Ala His Leu Thr Asn Gly Glu Trp
        50                  55                  60

Val Ala Val Ser Gln His Asp Trp Thr Glu Ala Trp Lys His Pro Gly
65                  70                  75                  80
```

```
Gly Ser Leu Asp Ala Leu Glu Leu Gln Gln Val Val Phe Thr Leu Asp
                85                  90                  95

Asp Lys Thr Gln Pro Ser Ala Val Leu Asp Ala Ser Ala Ile Ser Gln
            100                 105                 110

His Leu Val Ser Asn Val Pro Ala Leu Ser Gly Lys Ala Tyr Ser Ser
        115                 120                 125

Leu Cys His His Pro Asn Val Ser Gly Thr Ser Cys Phe Thr Ser Val
    130                 135                 140

Ser Gly Pro Gly Ala Ser Pro Ile Leu Thr Leu Ser Phe Lys Pro Gly
145                 150                 155                 160

Thr Arg Asp Asp Trp Leu Gly Ser Leu Arg Lys Glu Lys Thr Ile Thr
                165                 170                 175

Leu Asp Gly Val Lys Tyr Asp Val Gly Ala Gly Lys Arg Gln Glu Ser
            180                 185                 190

Ile Gly Asp Met Glu Ser Ser Lys Trp Val Ala Tyr Ala Leu Ser Ala
        195                 200                 205

Leu Val Leu Arg Phe Trp Glu Leu Thr Lys Ala Asp Ser Leu Asp Ile
    210                 215                 220

Leu Val Val Leu Thr Gly Tyr Ile Leu Met His Val Thr Phe Met Arg
225                 230                 235                 240

Leu Phe Leu Ala Ser Arg Ala Leu Gly Ser Asn Phe Trp Leu Ser Ala
                245                 250                 255

Gly Ile Phe Ser Ser Ala Thr Ile Ser Phe Leu Phe Thr Leu Pro Met
            260                 265                 270

Cys Arg Ser Met Asp Ile Pro Leu Asp Pro Ile Ala Leu Thr Glu Ala
        275                 280                 285

Leu Pro Phe Leu Val Cys Thr Val Gly Phe Asp Lys Pro Leu Arg Leu
    290                 295                 300

Ala Arg Ala Val Met Ala His Pro Asn Ile Leu Lys Pro Gln Asp Asp
305                 310                 315                 320

Gly Arg Met Lys Ala Ala Gly Asp Val Ile Leu Glu Ala Leu Asp Arg
                325                 330                 335

Val Gly Asn Met Ile Leu Arg Asp Tyr Ala Leu Glu Ile Ala Val Leu
            340                 345                 350

Phe Val Gly Val Asn Ser Arg Val Gly Gly Leu Lys Glu Phe Cys Ala
        355                 360                 365

Val Ala Ala Ala Leu Leu Ala Met Asp Arg Leu Met Thr Phe Thr Leu
    370                 375                 380

Tyr Thr Ala Val Leu Thr Ile Met Val Glu Val Arg Arg Ile Lys Lys
385                 390                 395                 400

Val Arg Asp Met Thr Lys Ala Arg Ser Arg Ser Ser Ile Thr Ala
                405                 410                 415

Val Thr Ala Asn Gly Thr Ala Ile Arg Gly Val Leu Ser Arg Lys Ser
            420                 425                 430

Ser Lys Gln Ser Val Thr Glu Pro Glu Thr Thr Lys Asn Leu Arg Gln
        435                 440                 445

Arg Ala Thr Asp Ser Ala Ile Gly Val Lys Gly Ser Leu Leu Lys Asp
    450                 455                 460

Gly Gly Arg Leu Gln Glu Ala Glu Glu Asn Pro Met Ala Arg Leu Lys
465                 470                 475                 480

Leu Leu Leu Ile Ala Ser Phe Leu Thr Leu His Ile Leu Asn Phe Cys
                485                 490                 495

Thr Thr Leu Thr Ser Ala Thr Ala Asn Ala Arg His Gln Arg His Pro
```

-continued

```
                500                 505                 510
Phe Arg Thr Val Gln Glu Val Val Pro Ile Pro Arg Val Asp Ile Thr
            515                 520                 525
Thr Pro Ala Ile Ala Asn Ile Leu Ser His Leu Ala Val Ala Gln Glu
        530                 535                 540
Pro Met Phe Thr Val Val Gly Ser Glu Pro Ile Glu Leu Leu Val Lys
545                 550                 555                 560
Val Ala Ala Pro Val Tyr Val His Ala Leu Pro Leu Ala Pro Ala Leu
                565                 570                 575
Arg Ala Ser Asn Thr Asn Thr Gly Glu Ala Ile Glu Asn Phe Met Ser
            580                 585                 590
Ser Trp Ser Ser Leu Val Gly Asp Pro Val Val Ser Lys Trp Ile Val
        595                 600                 605
Ala Leu Leu Ala Val Ser Val Ala Leu Asn Gly Tyr Leu Leu Lys Gly
        610                 615                 620
Ile Ala Ala Gly Ser Gly Leu Ala Ala Met Arg Ala Val Arg Ser Gln
625                 630                 635                 640
Gly Val Arg Phe Arg Ser Arg Ala Arg Ser Ile Val Lys Ile Ser Asp
                645                 650                 655
Glu Pro Glu Pro Glu Pro Glu His Ser Ile Asp Pro Ala Pro Val Val
                660                 665                 670
Phe Phe Ala Ser Ala Ala Pro Ala Val Glu Ala Pro Ala Pro Ala Pro
            675                 680                 685
Ala Pro Glu Pro Glu Pro Pro Val Asn Arg Pro Pro Leu Thr Ile
        690                 695                 700
Phe Ser Arg Pro Leu Asn Leu Glu Thr Val Asp Lys Lys Leu Gln Asp
705                 710                 715                 720
Ala Leu Pro Ile Arg Ser Pro Pro Val Glu Pro Ile Thr Pro Glu
                725                 730                 735
Ser Arg Glu Val Glu Pro Thr Gln Val Glu Val Arg Ser Leu Ala Glu
            740                 745                 750
Cys Val Asp Val Phe Glu Asn Gly Pro Arg Pro Val Ser Val Ala Leu
        755                 760                 765
Lys Thr Leu Asn Asp Glu Glu Val Ile Leu Leu Cys Gln Thr Gly Lys
        770                 775                 780
Ile Ala Pro Tyr Ala Leu Val Lys Met Leu Ala Asp Phe Asp Arg Ala
785                 790                 795                 800
Val Arg Val Arg Arg Ala Leu Ile Ser Arg Ala Ser Arg Thr Lys Thr
                805                 810                 815
Leu Glu Asn Ser Leu Val Pro Met Lys Asp Tyr Asp Tyr Ala Arg Val
            820                 825                 830
Met Gly Ala Cys Cys Glu Asn Val Ile Gly Tyr Met Pro Leu Pro Leu
        835                 840                 845
Gly Ile Ala Gly Pro Leu Lys Ile Asp Gly Leu Met Tyr Pro Ile Pro
        850                 855                 860
Met Ala Thr Ala Glu Gly Thr Leu Val Ala Ser Thr Ser Arg Gly Cys
865                 870                 875                 880
Lys Ala Leu Asn Ala Gly Gly Val Thr Thr Val Leu Thr Ala Asp
                885                 890                 895
Gly Met Thr Arg Gly Pro Ala Ile Asp Phe Pro Ser Ile Val Arg Ala
            900                 905                 910
Ala Glu Ala Lys Ala Phe Ile Glu Ser Glu Asp Gly Tyr Ala Thr Ile
        915                 920                 925
```

```
Arg Glu Ala Phe Glu Ser Thr Ser Arg Phe Ala Lys Leu Gln Lys Ile
    930                 935                 940

Lys Cys Ala Leu Ala Gly Arg Thr Leu Phe Val Arg Phe Ala Thr Arg
945                 950                 955                 960

Thr Gly Asp Ala Met Gly Met Asn Met Ile Ser Lys Ala Thr Glu Lys
                965                 970                 975

Ala Leu Asp Val Leu Ser His Glu Phe Pro Glu Met Val Val Leu Ala
            980                 985                 990

Leu Ser Gly Asn Tyr Cys Thr Asp Lys Lys Pro Ala Ala Ile Ser Trp
        995                 1000                1005

Ile Glu Gly Arg Gly Lys Ser Ile Val Ala Glu Ala Val Ile Pro
    1010                1015                1020

Gly Lys Val Val Lys Ser Val Leu Lys Thr Thr Val Glu Ser Leu
    1025                1030                1035

Cys Asn Val Asn Thr Lys Lys Asn Leu Ile Gly Ser Ala Met Ala
    1040                1045                1050

Gly Ser Val Gly Gly Phe Asn Ala His Ala Ala Asn Ile Leu Thr
    1055                1060                1065

Ala Val Phe Leu Ala Thr Gly Gln Asp Pro Ala Gln Asn Val Glu
    1070                1075                1080

Ser Ser Asn Cys Met Thr Leu Met Glu Pro Thr Asn Gly Gly Glu
    1085                1090                1095

Asp Leu Leu Met Thr Ile Ser Met Pro Cys Ile Glu Val Gly Thr
    1100                1105                1110

Val Gly Gly Gly Thr Ile Leu Glu Pro Gln Gly Ala Val Leu Asp
    1115                1120                1125

Leu Leu Gly Val Arg Gly Ala His Pro Thr Asn Pro Gly Gln Asn
    1130                1135                1140

Ala Gln Gln Leu Ala Arg Ile Ile Ala Ser Ala Val Met Ala Gly
    1145                1150                1155

Glu Leu Ser Leu Ile Ser Ala Leu Ala Ala Gly His Leu Val Arg
    1160                1165                1170

Ala His Leu Ala His Asn Arg Ser Gln Leu Asn Thr Pro Met Pro
    1175                1180                1185

Ser Arg Pro His Thr Pro Gly Pro Glu Asp Val Ser
    1190                1195                1200

<210> SEQ ID NO 47
<211> LENGTH: 888
<212> TYPE: PRT
<213> ORGANISM: Artificial Sequence
<220> FEATURE:
<223> OTHER INFORMATION: Synthetic

<400> SEQUENCE: 47

Met Leu Ser Arg Leu Phe Arg Met His Gly Leu Phe Val Ala Ser His
1               5                   10                  15

Pro Trp Glu Val Ile Val Gly Thr Val Thr Leu Thr Ile Cys Met Met
            20                  25                  30

Ser Met Asn Met Phe Thr Gly Asn Asn Lys Ile Cys Gly Trp Asn Tyr
        35                  40                  45

Glu Cys Pro Lys Leu Glu Glu Asp Val Leu Ser Ser Asp Ile Ile Ile
    50                  55                  60

Leu Thr Ile Thr Arg Cys Ile Ala Ile Leu Tyr Ile Tyr Phe Gln Phe
65                  70                  75                  80
```

-continued

```
Gln Asn Leu Arg Gln Leu Gly Ser Lys Tyr Ile Leu Gly Ile Ala Gly
             85                  90                  95
Leu Phe Thr Ile Phe Ser Ser Phe Val Phe Ser Thr Val Val Ile His
            100                 105                 110
Phe Leu Asp Lys Glu Leu Thr Gly Leu Asn Glu Ala Leu Pro Phe Phe
            115                 120                 125
Leu Leu Leu Val Asp Leu Ser Arg Ala Ser Ala Leu Ala Lys Phe Ala
130                 135                 140
Leu Ser Ser Asn Ser Gln Asp Glu Val Arg Glu Asn Ile Ala Arg Gly
145                 150                 155                 160
Met Ala Ile Leu Gly Pro Thr Phe Thr Leu Asp Ala Leu Val Glu Cys
                165                 170                 175
Leu Val Ile Gly Val Gly Thr Met Ser Gly Val Arg Gln Leu Glu Ile
                180                 185                 190
Met Cys Cys Phe Gly Cys Met Ser Val Leu Ala Asn Tyr Phe Val Phe
                195                 200                 205
Met Thr Phe Phe Pro Ala Cys Val Ser Leu Val Leu Glu Leu Ser Arg
            210                 215                 220
Glu Ser Arg Glu Gly Arg Pro Ile Trp Gln Leu Ser His Phe Ala Arg
225                 230                 235                 240
Val Leu Glu Glu Glu Asn Lys Pro Asn Pro Val Thr Gln Arg Val
                245                 250                 255
Lys Met Ile Met Ser Leu Gly Leu Val Leu Val His Ala His Ser Arg
                260                 265                 270
Trp Ile Ala Asp Pro Ser Pro Gln Asn Ser Thr Ala Asp Asn Ser Lys
                275                 280                 285
Val Ser Leu Gly Leu Asp Glu Asn Val Ser Lys Arg Ile Glu Pro Ser
290                 295                 300
Val Ser Leu Trp Gln Phe Tyr Leu Ser Lys Met Ile Ser Met Asp Ile
305                 310                 315                 320
Glu Gln Val Ile Thr Leu Ser Leu Ala Leu Leu Ala Val Lys Tyr
                325                 330                 335
Ile Phe Phe Glu Gln Ala Glu Thr Glu Ser Thr Leu Ser Leu Lys Asn
            340                 345                 350
Pro Ile Thr Ser Pro Val Val Thr Gln Lys Lys Ile Thr Asp Asp Cys
            355                 360                 365
Cys Arg Arg Asp Pro Val Leu Val Arg Asn Asp Gln Lys Phe His Ala
            370                 375                 380
Met Glu Glu Glu Thr Arg Lys Asn Arg Glu Arg Lys Val Glu Val Ile
385                 390                 395                 400
Lys Pro Leu Leu Ala Glu Asn Asp Thr Ser His Arg Ala Thr Phe Val
                405                 410                 415
Val Gly Asn Ser Ser Leu Leu Gly Thr Ser Leu Glu Leu Glu Thr Gln
                420                 425                 430
Glu Pro Glu Met Glu Leu Pro Val Glu Pro Arg Pro Asn Glu Glu Cys
            435                 440                 445
Leu Gln Ile Leu Glu Asn Ala Glu Lys Gly Ala Lys Phe Leu Ser Asp
            450                 455                 460
Ala Glu Ile Ile Gln Leu Val Asn Ala Lys His Ile Pro Ala Tyr Lys
465                 470                 475                 480
Leu Glu Thr Leu Met Glu Thr His Glu Arg Gly Val Ser Ile Arg Arg
                485                 490                 495
```

```
Gln Leu Leu Ser Lys Lys Leu Pro Glu Pro Ser Ser Leu Gln Tyr Leu
                500                 505                 510
Pro Tyr Arg Asp Tyr Asn Tyr Ser Leu Val Met Gly Ala Cys Cys Glu
            515                 520                 525
Asn Val Ile Gly Tyr Met Pro Ile Pro Val Gly Val Ala Gly Pro Leu
        530                 535                 540
Cys Leu Asp Gly Lys Glu Phe Gln Val Pro Met Ala Thr Thr Glu Gly
545                 550                 555                 560
Cys Leu Val Ala Ser Thr Asn Arg Gly Cys Arg Ala Ile Gly Leu Gly
                565                 570                 575
Gly Gly Ala Ser Ser Arg Val Leu Ala Asp Gly Met Thr Arg Gly Pro
            580                 585                 590
Val Val Arg Phe Pro Arg Ala Cys Asp Ser Ala Glu Val Lys Ala Trp
        595                 600                 605
Leu Glu Thr Pro Glu Gly Phe Thr Val Ile Lys Glu Ala Phe Asp Ser
610                 615                 620
Thr Ser Arg Val Ala Arg Leu Gln Lys Leu His Met Ser Val Ala Gly
625                 630                 635                 640
Arg Asn Leu Tyr Ile Arg Phe Gln Ser Arg Ser Gly Asp Ala Met Gly
                645                 650                 655
Met Asn Met Ile Ser Lys Gly Thr Glu Lys Ala Leu Ser Lys Leu Gln
            660                 665                 670
Glu Tyr Phe Pro Glu Met Gln Ile Leu Ala Val Ser Gly Asn Tyr Cys
        675                 680                 685
Thr Asp Lys Lys Pro Ala Ala Ile Asn Trp Ile Glu Gly Arg Gly Lys
690                 695                 700
Ser Val Val Cys Glu Ala Val Ile Pro Ala Lys Val Val Arg Glu Val
705                 710                 715                 720
Leu Lys Thr Thr Thr Glu Ala Met Ile Glu Val Asn Ile Asn Lys Asn
                725                 730                 735
Leu Val Gly Ser Ala Met Ala Gly Ser Ile Gly Gly Tyr Asn Ala His
            740                 745                 750
Ala Ala Asn Ile Val Thr Ala Ile Tyr Ile Ala Cys Gly Gln Asp Ala
        755                 760                 765
Ala Gln Asn Val Gly Ser Ser Asn Cys Ile Thr Leu Met Glu Ala Ser
770                 775                 780
Gly Pro Thr Asn Glu Asp Leu Tyr Ile Ser Cys Thr Met Pro Ser Ile
785                 790                 795                 800
Glu Ile Gly Thr Val Gly Gly Gly Thr Asn Leu Leu Pro Gln Gln Ala
                805                 810                 815
Cys Leu Gln Met Leu Gly Val Gln Gly Ala Cys Arg Asp Asn Pro Gly
            820                 825                 830
Glu Asn Ala Arg Gln Leu Ala Arg Ile Val Cys Gly Thr Val Met Ala
        835                 840                 845
Gly Glu Leu Ser Leu Met Ala Ala Leu Ala Ala Gly His Leu Val Arg
850                 855                 860
Ser His Met Ile His Asn Arg Ser Lys Ile Asn Leu Gln Asp Leu Gln
865                 870                 875                 880
Gly Thr Cys Thr Lys Lys Ala Ala
                885

<210> SEQ ID NO 48
<211> LENGTH: 567
<212> TYPE: PRT
```

<213> ORGANISM: Artificial Sequence
<220> FEATURE:
<223> OTHER INFORMATION: Synthetic

<400> SEQUENCE: 48

```
Met Asp Leu Arg Arg Lys Leu Pro Pro Lys Pro Pro Ser Ser Thr Thr
1               5                   10                  15

Thr Lys Gln Pro Ser His Arg Ser His Ser Pro Thr Pro Ile Pro Lys
            20                  25                  30

Ala Ser Asp Ala Leu Pro Leu Pro Leu Tyr Leu Thr Asn Thr Phe Phe
        35                  40                  45

Phe Thr Leu Phe Phe Ser Val Ala Tyr Tyr Leu Leu His Arg Trp Arg
    50                  55                  60

Asp Lys Ile Arg Ser Gly Thr Pro Leu His Val Val Thr Leu Thr Glu
65                  70                  75                  80

Leu Ser Ala Ile Val Leu Leu Ile Ala Ser Phe Ile Tyr Leu Leu Gly
                85                  90                  95

Phe Phe Gly Ile Asp Phe Val Gln Ser Phe Thr Ser Arg Glu Asn Glu
            100                 105                 110

Gln Leu Asn Asn Asp Asp His Asn Val Val Ser Thr Asn Asn Val Leu
        115                 120                 125

Ser Asp Arg Arg Leu Val Tyr Asp Tyr Gly Phe Asp Val Thr Gly Asp
    130                 135                 140

Asn Asp Asn Asp Asn Asp Asp Val Ile Val Lys Ser Val Val Ser
145                 150                 155                 160

Gly Glu Val Asn Ser Tyr Ser Leu Glu Ala Ser Leu Gly Asp Cys Tyr
                165                 170                 175

Arg Ala Ala Lys Ile Arg Lys Arg Ala Val Glu Arg Ile Val Gly Arg
            180                 185                 190

Glu Val Leu Gly Leu Gly Phe Glu Gly Phe Asp Tyr Glu Ser Ile Leu
        195                 200                 205

Gly Gln Cys Cys Glu Met Pro Ile Gly Tyr Val Gln Val Pro Val Gly
    210                 215                 220

Val Ala Gly Pro Leu Leu Leu Asn Gly Gly Glu Phe Met Val Pro Met
225                 230                 235                 240

Ala Thr Thr Glu Gly Cys Leu Val Ala Ser Thr Asn Arg Gly Cys Lys
                245                 250                 255

Ala Ile Cys Leu Ser Gly Gly Ala Thr Ala Ile Leu Leu Lys Asp Gly
            260                 265                 270

Met Thr Arg Ala Pro Val Val Arg Phe Ala Thr Ala Glu Arg Ala Ser
        275                 280                 285

Gln Leu Lys Phe Tyr Leu Glu Asp Gly Val Asn Phe Asp Thr Leu Ser
    290                 295                 300

Val Val Phe Asn Lys Ser Ser Arg Phe Ala Arg Leu Gln Asn Ile Gln
305                 310                 315                 320

Cys Ser Ile Ala Gly Lys Asn Leu Tyr Ile Arg Phe Thr Cys Ser Thr
                325                 330                 335

Gly Asp Ala Met Gly Met Asn Met Val Ser Lys Gly Val Gln Asn Val
            340                 345                 350

Leu Asp Phe Leu Gln Asn Asp Phe Pro Asp Met Asp Val Ile Gly Ile
        355                 360                 365

Ser Trp Lys Phe Cys Ser Asp Lys Lys Pro Thr Ala Val Asn Trp Ile
    370                 375                 380

Glu Gly Arg Gly Lys Ser Val Val Phe Gln Ala Val Ile Thr Lys Lys
```

```
                385                 390                 395                 400
Val Val Arg Lys Ser Ala Leu Asn Pro Gln Thr Cys Thr Cys Arg Thr
                    405                 410                 415

Leu Thr Cys Leu Arg Pro Leu Val Leu Leu Leu Val Leu Leu
                420                 425                 430

Val Asp Leu Met His Met Leu His Ile Val Ser Ala Val Phe Ile Ala
            435                 440                 445

Thr Gly Gln Asp Pro Ala Gln Asn Ile Glu Ser His Cys Ile Thr
        450                 455                 460

Met Met Glu Ala Val Asn Asn Gly Lys Asp Leu His Val Asn Val Thr
465                 470                 475                 480

Met Pro Ser Ile Glu Val Gly Thr Val Gly Gly Thr Gln Leu Ala
                485                 490                 495

Ser Gln Ser Ala Cys Leu Asn Leu Leu Gly Val Lys Gly Ala Cys Ile
                500                 505                 510

Glu Ser Pro Gly Ser Asn Ala Gln Leu Leu Ala Arg Ile Val Ala Gly
            515                 520                 525

Ser Val Leu Ala Gly Glu Leu Ser Leu Met Ser Ala Ile Ser Ala Gly
        530                 535                 540

Gln Leu Val Lys Ser His Met Lys Tyr Asn Arg Ser Ser Arg Asp Met
545                 550                 555                 560

Ser Ala Ile Ala Ser Lys Val
                565

<210> SEQ ID NO 49
<211> LENGTH: 435
<212> TYPE: PRT
<213> ORGANISM: Artificial Sequence
<220> FEATURE:
<223> OTHER INFORMATION: Synthetic

<400> SEQUENCE: 49

Met Phe Arg Arg Ala Ile Leu Leu Gly Cys Ser Ala Ala Lys Thr Pro
1               5                   10                  15

Trp Ser Glu Cys Ser Asn Ala Gln Leu Val Asp Ala Val Lys Ser Arg
            20                  25                  30

Lys Ile Ser Phe Tyr Gly Leu Glu Gln Ala Leu Glu Pro Asp Tyr Arg
        35                  40                  45

Arg Ala Ile Glu Val Arg Arg Glu Val Val Ser Glu Ile Ala Ser Gln
    50                  55                  60

Gln Pro Glu Ala Lys Lys Gln Ser Ala Leu His Thr Ile Pro Phe
65                  70                  75                  80

Glu Asn Tyr Asp Trp Asn Lys Val Val Gly Gln Asn Cys Glu Asn Ile
                85                  90                  95

Ile Gly Tyr Val Pro Ile Pro Leu Gly Val Ala Gly Pro Ile Leu Ile
            100                 105                 110

Asp Gly Lys Glu Tyr Pro Ile Pro Met Ala Thr Thr Glu Gly Ala Leu
        115                 120                 125

Val Ala Ser Thr His Arg Gly Ala Arg Ala Ile Thr Arg Ser Gly Gly
    130                 135                 140

Cys Lys Thr Leu Leu Leu Gly Glu Gly Met Thr Arg Ala Pro Val Val
145                 150                 155                 160

Glu Leu Pro Ser Leu Glu Glu Ala Gly Arg Leu His Lys Tyr Cys Asn
                165                 170                 175

Glu Asn Phe Leu Ser Leu Lys Glu Ala Phe Glu Ser Thr Thr Gln Tyr
```

```
            180                 185                 190
Gly Lys Leu Asn Ser Leu Lys Cys Val Leu Ala Gly Arg Lys Ala Tyr
            195                 200                 205
Leu Arg Phe Arg Ala Thr Thr Gly Asp Ala Met Gly Met Asn Met Ile
            210                 215                 220
Thr Lys Gly Val Asp Lys Ala Leu Ser Val Leu Gln Gln His Phe Pro
225                 230                 235                 240
Ser Met Glu Ile Leu Ala Leu Ser Gly Asn Tyr Cys Thr Asp Lys Lys
                245                 250                 255
Pro Ser Ala Val Asn Trp Ile Asp Gly Arg Gly Lys Ser Val Val Ala
            260                 265                 270
Glu Ala Thr Leu Leu Ala Asp Val Val Glu Asp Thr Leu Lys Cys Thr
            275                 280                 285
Val Asp Ser Leu Val Ser Leu Asn Ile Asp Lys Asn Leu Val Gly Ser
            290                 295                 300
Ala Met Ala Gly Ser Val Gly Gly Phe Asn Ala Gln Ala Ala Asn Ala
305                 310                 315                 320
Val Ala Ala Ile Phe Ile Ala Thr Gly Gln Asp Pro Ala Gln Val Val
                325                 330                 335
Glu Ser Ser Met Cys Ile Thr Thr Met Ser Lys Val Gly Asn Asp Leu
            340                 345                 350
Leu Ile Ser Val Thr Met Pro Ser Ile Glu Val Gly Val Val Gly Gly
            355                 360                 365
Gly Thr Gly Leu Ala Ala Gln Arg Gly Cys Leu Glu Leu Ile Gly Cys
            370                 375                 380
Gly Gly Pro Ser Lys Glu Ser Pro Gly Thr Asn Ala Gln Leu Leu Ser
385                 390                 395                 400
Arg Val Val Ala Ala Gly Val Leu Ser Ala Glu Leu Ser Leu Met Ser
                405                 410                 415
Gly Leu Ala Ala Gly His Leu Leu Ser Ala His Met Arg Leu Asn Arg
            420                 425                 430
Lys Lys Lys
        435

<210> SEQ ID NO 50
<211> LENGTH: 426
<212> TYPE: PRT
<213> ORGANISM: Artificial Sequence
<220> FEATURE:
<223> OTHER INFORMATION: Synthetic

<400> SEQUENCE: 50

Met Gln Ser Leu Asp Lys Asn Phe Arg His Leu Ser Arg Gln Gln Lys
1               5                   10                  15
Leu Gln Gln Leu Val Asp Lys Gln Trp Leu Ser Glu Gln Phe Asn
            20                  25                  30
Ile Leu Leu Asn His Pro Leu Ile Asp Glu Glu Val Ala Asn Ser Leu
            35                  40                  45
Ile Glu Asn Val Ile Ala Gln Gly Ala Leu Pro Val Gly Leu Leu Pro
        50                  55                  60
Asn Ile Ile Val Asp Asp Lys Ala Tyr Val Val Pro Met Met Val Glu
65                  70                  75                  80
Glu Pro Ser Val Val Ala Ala Ser Tyr Gly Ala Lys Leu Val Asn
                85                  90                  95
Gln Thr Gly Gly Phe Lys Thr Val Ser Ser Glu Arg Ile Met Ile Gly
```

```
            100                 105                 110
Gln Ile Val Phe Asp Gly Val Asp Thr Glu Lys Leu Ser Ala Asp
        115                 120                 125
Ile Lys Ala Leu Glu Lys Gln Ile His Gln Ile Ala Asp Glu Ala Tyr
        130                 135                 140
Pro Ser Ile Lys Ala Arg Gly Gly Gly Tyr Gln Arg Ile Ala Ile Asp
145                 150                 155                 160
Thr Phe Pro Glu Gln Gln Leu Leu Ser Leu Lys Val Phe Val Asp Thr
                165                 170                 175
Lys Asp Ala Met Gly Ala Asn Met Leu Asn Thr Ile Leu Glu Ala Ile
                180                 185                 190
Thr Ala Phe Leu Lys Asn Glu Phe Pro Gln Ser Asp Ile Leu Met Ser
                195                 200                 205
Ile Leu Ser Asn His Ala Thr Ala Ser Val Val Lys Val Gln Gly Glu
                210                 215                 220
Ile Asp Val Lys Asp Leu Ala Arg Gly Glu Arg Thr Gly Glu Val
225                 230                 235                 240
Ala Lys Arg Met Glu Arg Ala Ser Val Leu Ala Gln Val Asp Ile His
                245                 250                 255
Arg Ala Ala Thr His Asn Lys Gly Val Met Asn Gly Ile His Ala Val
                260                 265                 270
Val Leu Ala Thr Gly Asn Asp Thr Arg Gly Ala Glu Ala Ser Ala His
                275                 280                 285
Ala Tyr Ala Ser Lys Asp Gly Gln Tyr Arg Gly Ile Ala Thr Trp Arg
                290                 295                 300
Tyr Asp Gln Glu Arg Gln Arg Leu Ile Gly Thr Ile Glu Val Pro Met
305                 310                 315                 320
Thr Leu Ala Ile Val Gly Gly Gly Thr Lys Val Leu Pro Ile Ala Lys
                325                 330                 335
Ala Ser Leu Glu Leu Leu Asn Val Glu Ser Ala Gln Glu Leu Gly His
                340                 345                 350
Val Val Ala Ala Val Gly Leu Ala Gln Asn Phe Ala Ala Cys Arg Ala
                355                 360                 365
Leu Val Ser Glu Gly Ile Gln Gln Gly His Met Ser Leu Gln Tyr Lys
                370                 375                 380
Ser Leu Ala Ile Val Val Gly Ala Lys Gly Asp Glu Ile Ala Gln Val
385                 390                 395                 400
Ala Glu Ala Leu Lys Gln Glu Pro Arg Ala Asn Thr Gln Val Ala Glu
                405                 410                 415
Arg Ile Leu Gln Asp Leu Arg Ser Gln Gln
                420                 425

<210> SEQ ID NO 51
<211> LENGTH: 914
<212> TYPE: PRT
<213> ORGANISM: Artificial Sequence
<220> FEATURE:
<223> OTHER INFORMATION: Synthetic

<400> SEQUENCE: 51

Met Thr Pro Pro Lys Pro Leu Glu Thr Lys Gln Pro Leu His Asp Leu
1               5                   10                  15
Pro Thr Pro Gly Pro Glu Ser Pro Phe Arg Glu Arg Pro Tyr Arg
                20                  25                  30
Phe Ser Thr Leu Cys Ala Thr Val Asp Asn Pro Asp Met Lys Asp Gln
```

-continued

```
                35                  40                  45
Tyr Gly Ser Ser Ser Val Pro Ile Tyr Gln Thr Ala Thr Phe Lys Gly
 50                  55                  60

Val Gly Asn Glu Tyr Asp Tyr Thr Arg Ser Gly Asn Pro Thr Arg Ser
 65                  70                  75                  80

His Leu Gln His His Ile Ala Lys Ile Ser Ala Ala His Ala Phe
                 85                  90                  95

Thr Val Ser Ser Gly Met Ala Ala Leu Asp Val Ile Leu Arg Leu Leu
                100                 105                 110

Lys Pro Gly Asp Glu Val Ile Ala Gly Asp Leu Tyr Gly Gly Thr
            115                 120                 125

Asn Arg Leu Leu Thr Tyr Ile Arg Ser His Leu Gly Val Thr Val His
130                 135                 140

His Val Asp Thr Thr Asp Pro Thr Ser Leu His Lys Tyr Ile His Pro
145                 150                 155                 160

Thr Lys Thr Gly Met Val Leu Leu Glu Ser Pro Thr Asn Pro Leu Leu
                165                 170                 175

Lys Ile Ala Asp Leu Ala Thr Ile Ser Lys Asp Val Lys Glu Arg Ala
            180                 185                 190

Pro Asn Ala Ile Ile Val Val Asp Asn Thr Met Met Thr Ser Tyr Leu
195                 200                 205

Gln Arg Pro Leu Glu His Gly Ala Asp Ile Val Tyr Asp Ser Ala Thr
210                 215                 220

Lys Tyr Leu Ser Gly His His Asp Leu Met Ala Gly Val Val Thr Cys
225                 230                 235                 240

Asn Arg Asp Asp Ile Ala Gln Arg Leu Ala Phe Thr Ile Asn Ala Val
                245                 250                 255

Gly Asn Ala Leu Thr Pro Ile Asp Ser Phe Met Leu Leu Arg Gly Ile
            260                 265                 270

Lys Thr Leu Ala Ile Arg Met Asp Arg Gln Gln Thr Thr Ala Gln Leu
275                 280                 285

Val Ala Glu Tyr Leu Tyr Asn Leu Gly Phe Thr Val His Tyr Pro Gly
290                 295                 300

Leu Pro Ser His Pro Gly Arg Asp Val His Leu Arg Ile Ala Asp Gly
305                 310                 315                 320

Asn Gly Ala Val Leu Ser Phe Glu Thr Gly Asn Lys Glu Leu Ser Glu
                325                 330                 335

Arg Ile Val Ala Ala Thr Arg Leu Trp Gly Ile Ser Val Ser Phe Gly
            340                 345                 350

Cys Val Asn Ser Leu Ile Ser Met Pro Cys Val Met Ser His Ala Ser
355                 360                 365

Ile Asp Ala Ala Thr Arg Ala Arg Gly Leu Pro Glu Asp Leu Ile
370                 375                 380

Arg Leu Cys Val Gly Ile Glu Asp Pro His Asp Leu Leu Asp Asp Leu
385                 390                 395                 400

Glu His Ala Leu Leu Glu Ala Gly Ala Ile Glu Leu Asn Ala Ala Gln
                405                 410                 415

Asn Lys Phe Val Arg Ala Pro Pro Asp Ala Leu Ser Gln Ala Val
            420                 425                 430

His Asp Leu Asp Leu Asp Asp Gly Arg Asn Gln Leu Glu Trp Phe Val
435                 440                 445

Ser Ala Pro Gly Lys Val Ile Leu Phe Gly Glu His Ala Val Val His
450                 455                 460
```

-continued

```
Gly Val Thr Ala Ile Ala Ala Ser Val Asp Leu Arg Cys Tyr Gly Leu
465                 470                 475                 480

Thr Thr Pro Arg Thr Asp Asn Lys Leu Ser Ala His Phe Lys Asp Leu
                485                 490                 495

Gly Asn Phe Tyr His Glu Trp Asp Ile Asp Ser Leu Pro Trp Asp Ala
            500                 505                 510

Leu Thr Pro Ile Pro Pro Gly Glu Glu His Pro Glu Glu Leu Asp Gln
        515                 520                 525

Arg Leu Ile Glu Ala Leu Ser Gln Ser Val Leu Ala Glu Leu Gly Asp
    530                 535                 540

Glu Asn Lys Gln Ala Arg Ala Thr Leu Ala Phe Leu Tyr Leu Tyr
545                 550                 555                 560

Met Thr Leu Ala Arg Gly Gln His Arg Pro Ser Phe Asn Phe Thr Ala
                565                 570                 575

Arg Ala Thr Leu Pro Val Gly Ala Gly Leu Gly Ser Ser Ala Ser Phe
            580                 585                 590

Ser Ala Cys Ala Ala Thr Ala Leu Leu Leu His Arg Arg Ile Ser
        595                 600                 605

Val Pro Ala Lys Pro Ala Pro Ser Thr Glu Thr His Ile His Val Ser
610                 615                 620

His Glu Gly Arg Arg Ala Leu Pro Ala Ser Val Ala Glu Asp Val Asn
625                 630                 635                 640

Arg Trp Ala Phe Val Ala Glu Lys Ile Leu His Gly Asn Pro Ser Gly
                645                 650                 655

Val Asp Asn Ser Val Ala Val Phe Gly Ala Leu Ala Tyr Thr Arg
            660                 665                 670

Pro Gly Phe Gly Lys Lys Gly Gly Met Glu Gln Ile Gln Gly Phe Lys
        675                 680                 685

Ser Leu Lys Phe Leu Leu Thr Asn Ser Gln Val Pro Arg Asp Thr Lys
    690                 695                 700

Lys Leu Val Ala Gly Val Gly Glu Lys Lys Glu Asn Glu Pro Glu Leu
705                 710                 715                 720

Val Asn Gly Ile Leu Ala Ala Ile Gln Ser Ile Ser Asp Glu Ala Arg
                725                 730                 735

Arg Ala Leu Ala Asp Pro Glu Leu Ser Arg Asp Ala Leu Leu Ser Ala
            740                 745                 750

Leu Gln Glu Leu Ile Lys Glu Asn His Asp His Leu Val Thr Leu Gly
        755                 760                 765

Val Ser His Pro Ser Leu Glu Lys Ile Arg Glu Lys Thr Ser Glu Pro
    770                 775                 780

Tyr Gly Leu Lys Thr Lys Leu Thr Gly Ala Gly Gly Gly Gly Cys Ala
785                 790                 795                 800

Val Thr Leu Ile Pro Asp Asp Phe Lys Glu Glu Val Leu Asn Gly Leu
                805                 810                 815

Ile Asp Glu Leu Ile Arg Glu Gly Phe His Pro Tyr Leu Thr Ser Val
            820                 825                 830

Gly Gly Ser Gly Leu Gly Ile Leu Ser Pro Tyr Pro Glu His Arg Thr
        835                 840                 845

Arg Gly Ser Asp Pro Gln Pro Pro Arg Glu Asp Val Gly Gly Gly Gln
    850                 855                 860

Val Thr Pro Pro Asp Thr Pro Arg Ala Glu Ile Val Glu Arg His Thr
865                 870                 875                 880
```

```
Lys His Gly Val Thr Phe Asp Pro Leu Arg Pro Thr Phe Glu Thr Ala
                885                 890                 895

Ala Thr Thr Asp Ile Ser Asp Trp Ala Ser Ser Leu Gly Arg Trp Leu
        900                 905                 910

Tyr Val

<210> SEQ ID NO 52
<211> LENGTH: 396
<212> TYPE: PRT
<213> ORGANISM: Artificial Sequence
<220> FEATURE:
<223> OTHER INFORMATION: Synthetic

<400> SEQUENCE: 52

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ala
                20                  25                  30

Leu Asn Leu Arg Thr Phe Leu Arg Leu Gln Pro His Ser Asn Gly Arg
            35                  40                  45

Val Gly Leu Asn Leu Pro Asn Ile Gly Val Arg Arg Ala Trp Asp Val
50                  55                  60

Ala Ser Leu Gln Leu Leu Asp Thr Ser Phe Leu Gly His Gly Asp Ser
65                  70                  75                  80

Ala Ala Leu Thr Ala Lys His Val Glu Lys Leu Lys Glu Val Ala Gly
                85                  90                  95

Phe Pro Lys Asp Cys Val Asp Pro Glu His Leu Ala Val Leu Ala Phe
            100                 105                 110

Leu Tyr Leu Tyr Leu Ser Ile Cys Gln Ser Gln Arg Ala Leu Pro Ser
        115                 120                 125

Leu Asp Ile Thr Val Trp Ser Glu Leu Pro Thr Gly Ala Gly Leu Gly
130                 135                 140

Ser Ser Ala Ala Tyr Ser Val Cys Leu Ala Ala Ala Leu Leu Thr Ala
145                 150                 155                 160

Cys Glu Glu Ile Pro Asn Pro Leu Lys Asp Gly Glu Ala Ala Gly Arg
                165                 170                 175

Trp Thr Glu Glu Asn Leu Glu Leu Ile Asn Lys Trp Ala Phe Gln Gly
            180                 185                 190

Glu Arg Val Ile His Gly Asn Pro Ser Gly Val Asp Asn Ala Val Ser
        195                 200                 205

Thr Trp Gly Gly Ala Leu Arg Tyr Gln Gln Gly Lys Ile Ser Ser Leu
210                 215                 220

Lys Arg Pro Pro Val Leu Lys Ile Leu Leu Ile Asn Thr Lys Val Pro
225                 230                 235                 240

Arg Ser Thr Lys Val Leu Val Ala Asn Val Arg Ser Arg Leu Leu Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Ala Ala Ala Pro Thr Pro
        275                 280                 285

Glu His Tyr Leu Thr Leu Glu Glu Leu Ile Asp Met Asn Gln His His
        290                 295                 300

Leu Asn Ala Leu Gly Val Gly His Ala Ser Leu Asp Gln Leu Cys Gln
305                 310                 315                 320

Val Thr Thr Ala His Gly Leu His Ser Lys Leu Thr Gly Ala Gly Gly
```

```
                    325                 330                 335
Gly Gly Cys Gly Ile Thr Leu Leu Arg Pro Asp Val Glu Arg Pro Ala
            340                 345                 350

Val Glu Ala Thr Lys Arg Ala Leu Ser Gly Cys Gly Phe Asp Cys Trp
            355                 360                 365

Glu Thr Ser Val Gly Ala Pro Gly Val Ser Val His Thr Ala Ala Ser
    370                 375                 380

Leu Asp Ala Ser Val Gln Gln Gly Leu Asp Ser Leu
385                 390                 395

<210> SEQ ID NO 53
<211> LENGTH: 386
<212> TYPE: PRT
<213> ORGANISM: Artificial Sequence
<220> FEATURE:
<223> OTHER INFORMATION: Synthetic

<400> SEQUENCE: 53

Met Glu Val Lys Ala Arg Ala Pro Gly Lys Ile Ile Leu Ser Gly Glu
1               5                   10                  15

His Ala Val Val His Gly Ser Thr Ala Val Ala Ser Ile Asn Leu
            20                  25                  30

Tyr Thr Tyr Val Thr Leu Ser Phe Ala Thr Ala Glu Asn Asp Asp Ser
            35                  40                  45

Leu Lys Leu Gln Leu Lys Asp Leu Ala Leu Glu Phe Ser Trp Pro Ile
    50                  55                  60

Gly Arg Ile Arg Glu Ala Leu Ser Asn Leu Gly Ala Pro Ser Ser Ser
65                  70                  75                  80

Thr Arg Thr Ser Cys Ser Met Glu Ser Ile Lys Thr Ile Ser Ala Leu
                85                  90                  95

Val Glu Glu Glu Asn Ile Pro Glu Ala Lys Ile Ala Leu Thr Ser Gly
            100                 105                 110

Val Ser Ala Phe Leu Trp Leu Tyr Thr Ser Ile Gln Gly Phe Lys Pro
            115                 120                 125

Ala Thr Val Val Thr Ser Asp Leu Pro Leu Gly Ser Gly Leu Gly
    130                 135                 140

Ser Ser Ala Ala Phe Cys Val Ala Leu Ser Ala Ala Leu Leu Ala Phe
145                 150                 155                 160

Ser Asp Ser Val Asn Val Asp Thr Lys His Leu Gly Trp Ser Ile Phe
                165                 170                 175

Gly Glu Ser Asp Leu Glu Leu Leu Asn Lys Trp Ala Leu Glu Gly Glu
            180                 185                 190

Lys Ile Ile His Gly Lys Pro Ser Gly Ile Asp Asn Thr Val Ser Ala
    195                 200                 205

Tyr Gly Asn Met Ile Lys Phe Lys Ser Gly Asn Leu Thr Arg Ile Lys
    210                 215                 220

Ser Asn Met Pro Leu Lys Met Leu Val Thr Asn Thr Arg Val Gly Arg
225                 230                 235                 240

Asn Thr Lys Ala Leu Val Ala Gly Val Ser Glu Arg Thr Leu Arg His
                245                 250                 255

Pro Asn Ala Met Ser Phe Val Phe Asn Ala Val Asp Ser Ile Ser Asn
            260                 265                 270

Glu Leu Ala Asn Ile Ile Gln Ser Pro Ala Pro Asp Val Ser Ile
    275                 280                 285

Thr Glu Lys Glu Glu Lys Leu Glu Glu Leu Met Glu Met Asn Gln Gly
```

```
                290                 295                 300
Leu Leu Gln Cys Met Gly Val Ser His Ala Ser Ile Glu Thr Val Leu
305                 310                 315                 320

Arg Thr Thr Leu Lys Tyr Lys Leu Ala Ser Lys Leu Thr Gly Ala Gly
                325                 330                 335

Gly Gly Gly Cys Val Leu Thr Leu Leu Pro Thr Leu Leu Ser Gly Thr
            340                 345                 350

Val Val Asp Lys Ala Ile Ala Glu Leu Glu Ser Cys Gly Phe Gln Cys
            355                 360                 365

Leu Ile Ala Gly Ile Gly Gly Asn Gly Val Glu Phe Cys Phe Gly Gly
            370                 375                 380

Ser Ser
385

<210> SEQ ID NO 54
<211> LENGTH: 329
<212> TYPE: PRT
<213> ORGANISM: Artificial Sequence
<220> FEATURE:
<223> OTHER INFORMATION: Synthetic

<400> SEQUENCE: 54

Met His Val Ala Val Lys Asp Lys Thr Thr Arg His His Ile Gly Tyr
1               5                   10                  15

Gly Lys Val Ile Leu Phe Gly Glu His Phe Val Val Tyr Gly Ala Glu
                20                  25                  30

Ser Ile Val Ala Gly Ile Asn Glu Tyr Thr Thr Cys Glu Ile Ser Arg
            35                  40                  45

Leu Lys His Lys Pro Asn Val Val Glu Val Ile Asp Glu Arg Pro Ala
        50                  55                  60

Val Pro Gly Tyr Ile Lys Glu Lys Arg Glu Glu Gln Arg Val Ala His
65                  70                  75                  80

Gly Leu Val Leu Arg His Leu Asn Ile Asp Thr Ser Lys Asp Gly Leu
                85                  90                  95

Leu Val Lys Leu Gly Gly Pro Leu Val Pro Ser Ser Gly Ile Gly Ala
            100                 105                 110

Ser Ala Ser Asp Val Val Ser Leu Ser Arg Ala Leu Asn Glu Leu Tyr
        115                 120                 125

Ser Leu Asn Leu Ser Glu Glu Ala Val Asn Arg Ser Ala Tyr Ala Gly
    130                 135                 140

Glu Cys Gly Tyr His Gly Thr Pro Ser Gly Val Asp Asn Thr Ala Ala
145                 150                 155                 160

Thr Tyr Gly Gly Ile Ile Leu Phe Arg Arg Ala Leu Lys Lys Ser Val
                165                 170                 175

Phe Ser Arg Leu Ala Leu Gly Lys Thr Leu Ser Ile Ile Val Cys Ser
            180                 185                 190

Thr Gly Ile Thr Ala Ser Thr Thr Lys Val Val Ala Asp Val Ala Arg
        195                 200                 205

Leu Lys Ala Ala Gln Pro Ser Trp Phe Asp Asp Leu Phe Glu Gln Tyr
    210                 215                 220

Asn Ala Cys Val Arg Glu Ala Lys Lys Ala Leu Gln Ser Gly Asn Leu
225                 230                 235                 240

Arg Arg Val Gly Glu Leu Met Asn Ile Asn His Thr Leu Cys Gln Lys
                245                 250                 255

Leu Thr Val Ser Cys Pro Glu Leu Asp Ala Ile Ala Thr Cys Cys Arg
```

```
                      260                 265                 270
Thr Phe Gly Ala Leu Gly Ala Lys Met Ser Thr Gly Arg Gly Gly
                275                 280                 285
Leu Val Val Ala Leu Ala Ala Asn Thr Gln Glu Arg Asp Arg Ile Ala
            290                 295                 300
Lys Ala Val Arg Glu Gln Cys Lys Glu Ala Lys Phe Val Trp Arg Tyr
305                 310                 315                 320
Ser Val Gln Pro Gly Gly Ser Lys Leu
                325

<210> SEQ ID NO 55
<211> LENGTH: 306
<212> TYPE: PRT
<213> ORGANISM: Artificial Sequence
<220> FEATURE:
<223> OTHER INFORMATION: Synthetic

<400> SEQUENCE: 55

Met Thr Arg Lys Gly Tyr Gly Glu Ser Thr Gly Lys Ile Ile Leu Ile
1               5                   10                  15
Gly Glu His Ala Val Thr Phe Gly Glu Pro Ala Ile Ala Val Pro Phe
            20                  25                  30
Asn Ala Gly Lys Ile Lys Val Leu Ile Glu Ala Leu Glu Ser Gly Asn
        35                  40                  45
Tyr Ser Ser Ile Lys Ser Asp Val Tyr Asp Gly Met Leu Tyr Asp Ala
    50                  55                  60
Pro Asp His Leu Lys Ser Leu Val Asn Arg Phe Val Glu Leu Asn Asn
65                  70                  75                  80
Ile Thr Glu Pro Leu Ala Val Thr Ile Gln Thr Asn Leu Pro Pro Ser
                85                  90                  95
Arg Gly Leu Gly Ser Ser Ala Ala Val Ala Val Ala Phe Val Arg Ala
            100                 105                 110
Ser Tyr Asp Phe Leu Gly Lys Ser Leu Thr Lys Glu Glu Leu Ile Glu
        115                 120                 125
Lys Ala Asn Trp Ala Glu Gln Ile Ala His Gly Lys Pro Ser Gly Ile
    130                 135                 140
Asp Thr Gln Thr Ile Val Ser Gly Lys Pro Val Trp Phe Gln Lys Gly
145                 150                 155                 160
His Ala Glu Thr Leu Lys Thr Leu Ser Leu Asp Gly Tyr Met Val Val
                165                 170                 175
Ile Asp Thr Gly Val Lys Gly Ser Thr Arg Gln Ala Val Glu Asp Val
            180                 185                 190
His Lys Leu Cys Glu Asp Pro Gln Tyr Met Ser His Val Lys His Ile
        195                 200                 205
Gly Lys Leu Val Leu Arg Ala Ser Asp Val Ile Glu His His Asn Phe
    210                 215                 220
Glu Ala Leu Ala Asp Ile Phe Asn Glu Cys His Ala Asp Leu Lys Ala
225                 230                 235                 240
Leu Thr Val Ser His Asp Lys Ile Glu Gln Leu Met Lys Ile Gly Lys
                245                 250                 255
Glu Asn Gly Ala Ile Ala Gly Lys Leu Thr Gly Ala Gly Arg Gly Gly
            260                 265                 270
Ser Met Leu Leu Leu Ala Lys Asp Leu Pro Thr Ala Lys Asn Ile Val
        275                 280                 285
Lys Ala Val Glu Lys Ala Gly Ala Ala His Thr Trp Ile Glu Asn Leu
```

290                 295                 300
Gly Gly
305

<210> SEQ ID NO 56
<211> LENGTH: 491
<212> TYPE: PRT
<213> ORGANISM: Artificial Sequence
<220> FEATURE:
<223> OTHER INFORMATION: Synthetic

<400> SEQUENCE: 56

Met Val Arg Thr Thr Val Val Ser Ala Pro Gly Lys Val Leu Ile Ala
1               5                   10                  15

Gly Gly Tyr Leu Val Leu Asp Pro Ala Tyr Pro Gly Thr Val Val Ser
            20                  25                  30

Thr Ser Ser Arg Phe Tyr Thr Val Ile Gln Ser Gln Glu Leu Leu Ser
        35                  40                  45

Lys Asn Thr Ile Arg Val Arg Ser Pro Gln Phe Leu Glu Ala Thr Trp
50                  55                  60

Ser Tyr Ser Val Leu Phe Glu Pro Ala Val Ala Val Glu Ala Ser Pro
65                  70                  75                  80

Glu Asn Ser Ser Lys Asn Lys Phe Val His Leu Ala Leu Gln Lys Thr
                85                  90                  95

Ile Ala Leu Ala Val Glu Leu Arg Gly Ala Ala Gln Ile Gln Glu Ala
            100                 105                 110

Leu Thr His Gly Phe Asp Ile Ala Ile Val Gly Asp Asn Asp Phe Tyr
        115                 120                 125

Ser Gln Arg Ala Lys Leu Glu Ser Leu Gly Leu Pro Arg Thr Leu Asp
    130                 135                 140

Ser Leu Thr Glu Ile Thr Pro Phe Cys Ala Thr Glu Val His Leu Ser
145                 150                 155                 160

Asp Val His Lys Thr Gly Leu Gly Ser Ser Ala Ala Leu Ile Thr Ser
                165                 170                 175

Leu Thr Ser Ala Ile Leu Val His Leu Ser Val Ile Ser Glu Ser Ser
            180                 185                 190

Leu Ala Glu Asp Asp Ser Arg Asp Arg Arg Gln Ala His Asn Leu Ala
        195                 200                 205

Gln Tyr Val His Cys Leu Ala Gln Gly Lys Val Gly Ser Gly Phe Asp
    210                 215                 220

Val Ser Ala Ala Val Phe Gly Ser His Leu Tyr Ser Arg Phe Asp Pro
225                 230                 235                 240

Ala Val Ile Gln Asp Leu Met Ser Asp Ala Leu Pro Ser Gln Leu
                245                 250                 255

Pro Ser Val Leu Ser Pro Ser Asn Ala Ala Trp Asn Tyr Arg Ile Glu
            260                 265                 270

Pro Phe Lys Leu Pro Pro Leu Thr Arg Ile Val Leu Ala Asp Val Asp
        275                 280                 285

Ala Gly Ser Asp Thr Pro Ser Leu Val Gly Lys Val Leu Lys Trp Arg
    290                 295                 300

Lys Glu Asn Ser Thr Glu Ala Glu Ala Leu Trp Lys Asn Leu Asp Gln
305                 310                 315                 320

Gln Asn Gln Ser Leu Ala Gln Thr Leu Leu His Leu Gly Lys Leu Ala
                325                 330                 335

Glu Asp Asp Tyr Glu Asn Tyr Ala Ser Ala Val Lys Tyr Ile Cys Ser

```
                340                 345                 350
Leu Gln Pro Val Gln Gln Ile Leu Tyr Ser Pro Leu Arg Ser Asn Gln
            355                 360                 365

Ser Leu Gln His Ser Met Lys Pro Thr Ile Ser Ala Ile Arg Glu Lys
        370                 375                 380

Met Arg Glu Met Gly Asn Leu Ser Gly Val Pro Ile Glu Pro Ile Glu
385                 390                 395                 400

Gln Thr Thr Leu Leu Asp Ala Cys Ala Ser Gln Ala Gly Val Ile Gly
                405                 410                 415

Gly Gly Val Pro Gly Ala Gly Gly Tyr Asp Ala Ile Trp Leu Leu Val
            420                 425                 430

Cys Asp Pro Pro Ser Cys Ala Pro Asp Gln Ser Pro Leu Glu Arg Ile
        435                 440                 445

Glu His Leu Trp Ser His Tyr Glu Lys Leu Asp Val Ser Pro Leu Ser
    450                 455                 460

Ala Gln Glu Ser Thr Ala Lys Gly Val Arg Val Glu Ala Leu Asp Asp
465                 470                 475                 480

Ile Pro Gly Leu Lys Asn Ala Ile Ser Val Ser
                485                 490

<210> SEQ ID NO 57
<211> LENGTH: 192
<212> TYPE: PRT
<213> ORGANISM: Artificial Sequence
<220> FEATURE:
<223> OTHER INFORMATION: Synthetic

<400> SEQUENCE: 57

Met Ala Pro Leu Gly Gly Val Pro Gly Leu Val Leu Leu Phe Ser Gly
1               5                   10                  15

Lys Arg Lys Ser Gly Lys Asp Phe Val Thr Glu Ala Leu Gln Ser Arg
            20                  25                  30

Leu Gly Ala Asp Val Cys Ala Ile Leu Arg Leu Ser Gly Pro Leu Lys
        35                  40                  45

Glu Gln Tyr Ala Gln Glu His Gly Leu Asp Phe Gln Arg Leu Met Asp
    50                  55                  60

Ala Ser Thr Tyr Lys Glu Ala Tyr Arg Ser Asp Met Ile Arg Trp Gly
65                  70                  75                  80

Glu Glu Lys Arg Gln Ala Asp Pro Gly Phe Phe Cys Arg Lys Ile Val
                85                  90                  95

Glu Gly Val Cys Gln Pro Val Trp Leu Val Ser Asp Thr Arg Arg Val
            100                 105                 110

Ser Asp Ile Gln Trp Phe Gln Glu Ala Tyr Gly Ala Val Thr Gln Thr
        115                 120                 125

Val Arg Val Val Ala Thr Glu Glu Ser Arg Gln Gln Arg Gly Trp Val
    130                 135                 140

Phe Thr Pro Gly Val Asp Asp Ala Glu Ser Glu Cys Gly Leu Asp Asn
145                 150                 155                 160

Phe Arg Thr Phe Asp Trp Val Ile Glu Asn His Gly Asp Glu Gln His
                165                 170                 175

Leu Glu Glu Gln Leu Glu His Leu Ile Glu Phe Ile Arg Ser Arg Leu
            180                 185                 190

<210> SEQ ID NO 58
<211> LENGTH: 503
<212> TYPE: PRT
```

<213> ORGANISM: Artificial Sequence
<220> FEATURE:
<223> OTHER INFORMATION: Synthetic

<400> SEQUENCE: 58

```
Met Ala Val Val Ala Ser Ala Pro Gly Lys Val Leu Met Thr Gly Gly
1               5                   10                  15

Tyr Leu Ile Leu Glu Arg Pro Asn Ala Gly Ile Val Leu Ser Thr Asn
            20                  25                  30

Ala Arg Phe Tyr Ala Ile Val Lys Pro Ile Tyr Asp Glu Ile Lys Pro
        35                  40                  45

Asp Ser Trp Ala Trp Ala Trp Thr Asp Val Lys Leu Thr Ser Pro Gln
    50                  55                  60

Leu Ala Arg Glu Ser Leu Tyr Lys Leu Ser Leu Lys Asn Leu Ala Leu
65                  70                  75                  80

Gln Cys Val Ser Ser Ala Ser Arg Asn Pro Phe Val Glu Gln Ala
                85                  90                  95

Val Gln Phe Ala Val Ala Ala His Ala Thr Leu Asp Lys Asp Lys
                100                 105                 110

Lys Asn Val Leu Asn Lys Leu Leu Gln Gly Leu Asp Ile Thr Ile
                115                 120                 125

Leu Gly Thr Asn Asp Phe Tyr Ser Tyr Arg Asn Glu Ile Glu Ala Cys
130                 135                 140

Gly Leu Pro Leu Thr Pro Glu Ser Leu Ala Ala Leu Pro Ser Phe Ser
145                 150                 155                 160

Ser Ile Thr Phe Asn Val Glu Glu Ala Asn Gly Gln Asn Cys Lys Pro
                165                 170                 175

Glu Val Ala Lys Thr Gly Leu Gly Ser Ser Ala Ala Met Thr Thr Ala
                180                 185                 190

Val Val Ala Ala Leu Leu His His Leu Gly Leu Val Asp Leu Ser Ser
                195                 200                 205

Ser Cys Lys Glu Lys Lys Phe Ser Asp Leu Asp Leu Val His Ile Ile
            210                 215                 220

Ala Gln Thr Ala His Cys Ile Ala Gln Gly Lys Val Gly Ser Gly Phe
225                 230                 235                 240

Asp Val Ser Ser Ala Val Tyr Gly Ser His Arg Tyr Val Arg Phe Ser
                245                 250                 255

Pro Glu Val Leu Ser Ser Ala Gln Asp Ala Gly Lys Gly Ile Pro Leu
                260                 265                 270

Gln Glu Val Ile Ser Asn Ile Leu Lys Gly Lys Trp Asp His Glu Arg
            275                 280                 285

Thr Met Phe Ser Leu Pro Pro Leu Met Ser Leu Leu Gly Glu Pro
    290                 295                 300

Gly Thr Gly Gly Ser Ser Thr Pro Ser Met Val Gly Ala Leu Lys Lys
305                 310                 315                 320

Trp Gln Lys Ser Asp Thr Gln Lys Ser Gln Glu Thr Trp Arg Lys Leu
                325                 330                 335

Ser Glu Ala Asn Ser Ala Leu Glu Thr Gln Phe Asn Ile Leu Ser Lys
                340                 345                 350

Leu Ala Glu Glu His Trp Asp Ala Tyr Lys Cys Val Ile Asp Ser Cys
                355                 360                 365

Ser Thr Lys Asn Ser Glu Lys Trp Ile Glu Gln Ala Thr Glu Pro Ser
        370                 375                 380

Arg Glu Ala Val Val Lys Ala Leu Leu Gly Ser Arg Asn Ala Met Leu
```

```
            385                 390                 395                 400
        Gln Ile Arg Asn Tyr Met Arg Gln Met Gly Glu Ala Ala Gly Val Pro
                        405                 410                 415

Ile Glu Pro Glu Ser Gln Thr Arg Leu Leu Asp Thr Thr Met Asn Met
                        420                 425                 430

Asp Gly Val Leu Leu Ala Gly Val Pro Gly Ala Gly Phe Asp Ala
                        435                 440                 445

Val Phe Ala Val Thr Leu Gly Asp Ser Gly Thr Asn Val Ala Lys Ala
                    450                 455                 460

Trp Ser Ser Leu Asn Val Leu Ala Leu Leu Val Arg Glu Asp Pro Asn
        465                 470                 475                 480

Gly Val Leu Leu Glu Ser Gly Asp Pro Arg Thr Lys Glu Ile Thr Thr
                        485                 490                 495

Ala Val Phe Ala Val His Ile
                        500

<210> SEQ ID NO 59
<211> LENGTH: 471
<212> TYPE: PRT
<213> ORGANISM: Artificial Sequence
<220> FEATURE:
<223> OTHER INFORMATION: Synthetic

<400> SEQUENCE: 59

Met Val Val Ala Ser Cys Pro Gly Lys Val Leu Ile Leu Gly Gly Tyr
1               5                   10                  15

Leu Ile Val Glu Glu Pro Asn Val Gly Ile Ser Val Gly Thr Thr Ala
                20                  25                  30

Arg Phe Val Thr Arg Val Ala Ser Trp Lys Lys Cys Ser Asp Gly Lys
            35                  40                  45

Cys Arg Val His Ile Val Ser Ser Gln Phe Asn Lys Glu Phe Thr Phe
        50                  55                  60

Glu Cys Ala Ala Glu Glu Asp Ser Asp Ser Thr Ile Lys Ile Val Gln
65                  70                  75                  80

Leu Glu Gly Ala Pro Ser Pro Phe Leu Phe Tyr Gly Ile Leu Tyr Ser
                85                  90                  95

Val Ala Gly Ala Leu Leu Phe Gly Gly Asp Ile Phe Arg Asp Val Thr
                100                 105                 110

Leu Glu Leu Leu Ala Asp Asn Asp Phe Tyr Ser Gln Arg Asn Tyr Leu
            115                 120                 125

Glu Ser Gln Gly Lys Pro Val Thr Ala Ala Asn Leu Arg Leu Ile Pro
        130                 135                 140

Arg Tyr Thr Pro Leu Leu Gly Glu Val Ser Lys Thr Gly Leu Gly Ser
145                 150                 155                 160

Ser Ala Ala Met Thr Thr Ser Val Val Ala Cys Leu Leu Gln Leu Tyr
                165                 170                 175

Val Phe Asp Ser Lys Lys Asn Asn Ala Thr Glu Ser Val Glu Arg Ala
                180                 185                 190

Pro Glu Leu Pro Leu Arg Leu Glu Asp Val Thr Glu Phe Ile His Arg
            195                 200                 205

Ile Ser Gln Val Ala His Cys Val Ala Gln Gly Lys Val Gly Ser Gly
        210                 215                 220

Phe Asp Val Tyr Thr Ala Thr Phe Gly Thr Cys Val Tyr Arg Arg Phe
225                 230                 235                 240

Ser Ala Arg Val Leu Glu Lys Leu Val Lys Gly Asn Glu Pro Pro Lys
```

```
                    245                 250                 255
Arg Val Thr Ile Pro Leu Leu Arg Glu Cys Val Glu Thr Asp Glu Val
            260                 265                 270
Trp Val Gln Arg Ile Pro Phe Arg Leu Pro Thr Gly Leu Gln Leu Leu
            275                 280                 285
Leu Gly Asp Val His Lys Gly Thr Glu Thr Pro Gly Met Val Ser
            290                 295                 300
Lys Val Met Ser Trp Arg Arg Ser Val Thr Thr Asp Pro Asn Ser Leu
305                 310                 315                 320
Trp Glu Arg Leu Arg Met Ser Asn Glu Lys Tyr Val Glu Ala Leu Gln
                325                 330                 335
Gly Leu Ile Lys Gln Ser Gln Glu Ala Pro Val Ala Tyr Thr Glu Ala
            340                 345                 350
Val Lys Asn Leu Lys Ser Val Val Leu Ala Lys His Asn Pro Ser Thr
            355                 360                 365
Glu Ala Glu Arg Leu Trp Val Glu Ala Ala Ser Val Ala Ser Thr Ser
            370                 375                 380
Arg Arg Tyr Leu Arg Glu Met Gly Glu Ala Ala Gln Val Gln Ile Glu
385                 390                 395                 400
Pro Pro Glu Leu Thr Ser Leu Leu Asp Ala Thr Cys Ser Ile Pro Gly
                405                 410                 415
Val Phe Ala Val Gly Cys Pro Gly Ala Gly Tyr Asp Ala Val Phe
            420                 425                 430
Ala Leu Val Leu Gly Glu Glu Val Cys Ser Ala Val Glu Arg Phe Trp
            435                 440                 445
Glu Cys Tyr Asn Asp Leu Gln Val Cys Pro Leu Leu Val Arg Gly Asp
            450                 455                 460
Ala Asn Gly Leu Val Leu Asp
465                 470

<210> SEQ ID NO 60
<211> LENGTH: 358
<212> TYPE: PRT
<213> ORGANISM: Artificial Sequence
<220> FEATURE:
<223> OTHER INFORMATION: Synthetic

<400> SEQUENCE: 60

Met Ile Gln Val Lys Ala Pro Gly Lys Leu Tyr Ile Ala Gly Glu Tyr
1               5                   10                  15
Ala Val Thr Glu Pro Gly Tyr Lys Ser Val Leu Ile Ala Leu Asp Arg
            20                  25                  30
Phe Val Thr Ala Thr Ile Glu Glu Ala Asp Gln Tyr Lys Gly Thr Ile
            35                  40                  45
His Ser Lys Ala Leu His His Asn Pro Val Thr Phe Ser Arg Asp Glu
        50                  55                  60
Asp Ser Ile Val Ile Ser Asp Pro His Ala Ala Lys Gln Leu Asn Tyr
65                  70                  75                  80
Val Val Thr Ala Ile Glu Ile Phe Glu Gln Tyr Ala Lys Ser Cys Asp
                85                  90                  95
Ile Ala Met Lys His Phe His Leu Thr Ile Asp Ser Asn Leu Asp Asp
            100                 105                 110
Ser Asn Gly His Lys Tyr Gly Leu Gly Ser Ser Ala Ala Val Leu Val
            115                 120                 125
Ser Val Ile Lys Val Leu Asn Glu Phe Tyr Asp Met Lys Leu Ser Asn
```

```
            130                 135                 140
Leu Tyr Ile Tyr Lys Leu Ala Val Ile Ala Asn Met Lys Leu Gln Ser
145                 150                 155                 160

Leu Ser Ser Cys Gly Asp Ile Ala Val Ser Val Tyr Ser Gly Trp Leu
                165                 170                 175

Ala Tyr Ser Thr Phe Asp His Glu Trp Val Lys His Gln Ile Glu Asp
                180                 185                 190

Thr Thr Val Glu Glu Val Leu Ile Lys Asn Trp Pro Gly Leu His Ile
                195                 200                 205

Glu Pro Leu Gln Ala Pro Glu Asn Met Glu Val Leu Ile Gly Trp Thr
210                 215                 220

Gly Ser Pro Ala Ser Ser Pro His Phe Val Ser Glu Val Lys Arg Leu
225                 230                 235                 240

Lys Ser Asp Pro Ser Phe Tyr Gly Asp Phe Leu Glu Asp Ser His Arg
                245                 250                 255

Cys Val Glu Lys Leu Ile His Ala Phe Lys Thr Asn Asn Ile Lys Gly
                260                 265                 270

Val Gln Lys Met Val Arg Gln Asn Arg Thr Ile Ile Gln Arg Met Asp
                275                 280                 285

Lys Glu Ala Thr Val Asp Ile Glu Thr Glu Lys Leu Lys Tyr Leu Cys
290                 295                 300

Asp Ile Ala Glu Lys Tyr His Gly Ala Ser Lys Thr Ser Gly Ala Gly
305                 310                 315                 320

Gly Gly Asp Cys Gly Ile Thr Ile Asn Lys Asp Val Asp Lys Glu
                325                 330                 335

Lys Ile Tyr Asp Glu Trp Thr Lys His Gly Ile Lys Pro Leu Lys Phe
                340                 345                 350

Asn Ile Tyr His Gly Gln
                355

<210> SEQ ID NO 61
<211> LENGTH: 415
<212> TYPE: PRT
<213> ORGANISM: Artificial Sequence
<220> FEATURE:
<223> OTHER INFORMATION: Synthetic

<400> SEQUENCE: 61

Met Ser Glu Pro Ile Tyr Glu Ala Thr Ala Ser Ala Pro Val Asn Ile
1               5                   10                  15

Ala Val Ile Lys Tyr Trp Gly Lys Arg Asp Thr Ser Leu Ile Leu Pro
                20                  25                  30

Thr Asn Ser Ser Leu Ser Val Thr Leu Ser Gln Asp His Leu Arg Ser
                35                  40                  45

Thr Thr Thr Ser Arg Ala Ser Ser Phe Asp Lys Asp Arg Leu Trp
                50                  55                  60

Leu Asn Gly Gln Glu Asp Val Ile Lys Pro Gly Ser Arg Leu Glu Thr
65                  70                  75                  80

Cys Ile Arg Glu Met Lys Lys Leu Arg Lys Glu Leu Val Glu Asp Lys
                85                  90                  95

Asp Ala Asn Ala Pro Lys Leu Ser Thr Leu Pro Val His Ile Ala Ser
                100                 105                 110

Tyr Asn Asn Phe Pro Thr Ala Ala Gly Leu Ala Ser Ser Ala Ser Gly
                115                 120                 125

Phe Ala Ala Leu Val Ser Ser Leu Ala His Leu Tyr Thr Leu Thr Pro
```

```
                 130                 135                 140
Pro Leu Thr Ser Pro Ser Thr Leu Ser Leu Ile Ala Arg Gln Gly Ser
145                 150                 155                 160

Gly Ser Ala Cys Arg Ser Leu Phe Gly Gly Phe Val Ala Trp Glu Met
                165                 170                 175

Gly Ser Thr Pro Thr Gly Thr Asp Ser Leu Ala Val Gln Ile Ala Asp
            180                 185                 190

Glu Ala His Trp Pro Glu Met His Ala Leu Ile Cys Val Val Ser Asp
        195                 200                 205

Asp Lys Lys Gly Thr Ser Thr Ala Gly Met Gln Arg Thr Val Glu
    210                 215                 220

Thr Ser Thr Leu Leu Gln His Arg Ile Lys Asp Val Val Pro Arg Arg
225                 230                 235                 240

Met Asp Glu Met Ile Arg Ala Ile Lys Glu Lys Asp Phe Asp Ser Phe
                245                 250                 255

Ala Arg Ile Thr Met Ala Asp Ser Asn Ser Phe His Ala Val Ala Leu
            260                 265                 270

Asp Thr Glu Pro Pro Ile Phe Tyr Met Asn Asp Val Ser Arg Ala Ile
        275                 280                 285

Ile Ala Leu Ile Val Glu Leu Asn Arg Val Ser Leu Glu Lys Gly Glu
    290                 295                 300

Gly Tyr Lys Ala Ala Tyr Thr Tyr Asp Ala Gly Pro Asn Ala Val Ile
305                 310                 315                 320

Tyr Thr Leu Asp Lys Asn Val Lys Glu Val Ile Gln Leu Ile Val Lys
                325                 330                 335

Tyr Phe Pro Gln Lys Ala Gly Glu Phe Lys Asp Asn Leu Gln Val Leu
            340                 345                 350

Gly Gly Gly Val Ala Asp Ile Asn Gln Val Ala Gln Val Pro Glu Gly
        355                 360                 365

Phe Asn Glu Lys Val Ala Val Val Arg Glu Val Gly Ala Val Lys Gly
    370                 375                 380

Leu Ile His Thr Lys Val Gly Asp Gly Pro Arg Arg Leu Gly Asp Glu
385                 390                 395                 400

Glu Ser Leu Leu Gly Lys Asp Gly Phe Pro Lys Thr Leu Val Ala
                405                 410                 415

<210> SEQ ID NO 62
<211> LENGTH: 400
<212> TYPE: PRT
<213> ORGANISM: Artificial Sequence
<220> FEATURE:
<223> OTHER INFORMATION: Synthetic

<400> SEQUENCE: 62

Met Ala Ser Glu Lys Pro Ile Val Val Thr Cys Thr Ala Pro Val
1               5                   10                  15

Asn Ile Ala Val Val Lys Tyr Trp Gly Lys Arg Asp Glu Glu Leu Ile
                20                  25                  30

Leu Pro Ile Asn Ser Ser Leu Ser Val Thr Leu His Gln Asp Gln Leu
            35                  40                  45

Lys Thr Thr Thr Thr Ala Ala Ile Ser Arg Asp Phe Thr Glu Asp Arg
        50                  55                  60

Ile Trp Leu Asn Gly Arg Glu Glu Asp Met Gly His Pro Arg Leu Gln
65                  70                  75                  80

Ala Cys Leu Arg Glu Ile Arg Arg Leu Ala Arg Lys Arg Arg Ser Asp
```

```
                    85                  90                  95
Gly His Glu Asp Pro Leu Pro Leu Ser Leu Ser Tyr Lys Val His Val
            100                 105                 110

Ala Ser Glu Asn Asn Phe Pro Thr Ala Ala Gly Leu Ala Ser Ser Ala
        115                 120                 125

Ala Gly Tyr Ala Cys Leu Ala Tyr Thr Leu Ala Arg Val Tyr Gly Val
    130                 135                 140

Asp Ser Asp Leu Ser Glu Val Ala Arg Arg Gly Ser Gly Ser Ala Cys
145                 150                 155                 160

Arg Ser Leu Tyr Gly Gly Phe Val Glu Trp Gln Met Gly Glu Arg Pro
                165                 170                 175

Asp Gly Lys Asp Ser Val Ala Cys Gln Val Ala Pro Glu Ser His Trp
            180                 185                 190

Pro Glu Leu Arg Val Leu Ile Leu Val Val Ser Ala Glu Arg Lys Pro
        195                 200                 205

Met Gly Ser Thr Ala Gly Met Gln Thr Ser Val Glu Thr Ser Ala Leu
    210                 215                 220

Leu Lys Phe Arg Ala Glu Ala Leu Val Pro Pro Arg Met Ala Glu Met
225                 230                 235                 240

Thr Arg Cys Ile Arg Glu Arg Asn Phe Gln Ala Phe Gly Gln Leu Thr
                245                 250                 255

Met Lys Asp Ser Asn Gln Phe His Ala Thr Cys Leu Asp Thr Phe Pro
            260                 265                 270

Pro Ile Ser Tyr Leu Ser Asp Thr Ser Arg Arg Ile Ile Gln Leu Val
        275                 280                 285

His Arg Phe Asn Ala His His Gly Gln Thr Lys Val Ala Tyr Thr Phe
    290                 295                 300

Asp Ala Gly Pro Asn Ala Val Val Phe Thr Leu Asp Asp Thr Val Ala
305                 310                 315                 320

Glu Phe Val Ala Ala Val Arg His Ser Phe Pro Pro Glu Ser Asn Gly
                325                 330                 335

Asp Lys Phe Leu Lys Gly Leu Pro Val Glu Pro Val Leu Leu Ser Asp
            340                 345                 350

Glu Leu Lys Ala Val Leu Gly Met Asp Pro Val Pro Gly Ser Ile Arg
        355                 360                 365

Tyr Ile Ile Ala Thr Gln Val Gly Pro Gly Pro Gln Val Leu Asp Asp
    370                 375                 380

Pro Gly Ala His Leu Leu Gly Pro Asp Gly Leu Pro Lys Pro Ala Ala
385                 390                 395                 400

<210> SEQ ID NO 63
<211> LENGTH: 430
<212> TYPE: PRT
<213> ORGANISM: Artificial Sequence
<220> FEATURE:
<223> OTHER INFORMATION: Synthetic

<400> SEQUENCE: 63

Met Ser Gly Glu Gln Arg Glu Leu Asn Ser Trp Val Phe Met Val Thr
1               5                   10                  15

Ala Arg Ala Pro Thr Asn Ile Ala Val Ile Lys Tyr Trp Gly Lys Arg
            20                  25                  30

Asp Glu Lys Leu Ile Leu Pro Ile Asn Asp Ser Ile Ser Val Thr Leu
        35                  40                  45

Asp Pro Asp His Leu Ser Ala Thr Thr Thr Val Ala Val Ser Pro Ser
```

```
                    50                  55                  60
Phe Ser Ser Asp Arg Met Trp Leu Asn Gly Lys Glu Val Ser Leu Gly
 65                  70                  75                  80

Gly Glu Arg Tyr Gln Asn Cys Leu Arg Glu Ile Arg Ser Arg Gly Arg
                 85                  90                  95

Asp Val Val Asp Glu Lys Ser Gly Thr Leu Ile Lys Lys Glu Asp Trp
            100                 105                 110

Gln Thr Leu His Leu His Ile Ala Ser His Asn Asn Phe Pro Thr Ala
        115                 120                 125

Ala Gly Leu Ala Ser Ser Ala Ala Gly Phe Ala Cys Leu Val Tyr Ala
    130                 135                 140

Leu Ala Lys Leu Met Asp Ile Glu Glu Arg Tyr Ala Gly Glu Leu Ser
145                 150                 155                 160

Ala Ile Ala Arg Gln Gly Ser Gly Ser Ala Cys Arg Ser Leu Tyr Gly
                165                 170                 175

Gly Phe Val Lys Trp Asp Met Gly Lys Glu Arg Asp Gly Ser Asp Ser
            180                 185                 190

Ile Ala Val Gln Leu Ala Thr Glu Glu His Trp Glu Glu Leu Val Ile
        195                 200                 205

Leu Val Ala Val Ser Ser Arg Gln Lys Glu Thr Ser Ser Thr Thr
    210                 215                 220

Gly Met Arg Glu Ser Val Glu Thr Ser Glu Leu Leu His His Arg Ala
225                 230                 235                 240

Gln Glu Val Val Pro Lys Arg Ile Val Gln Met Gln Glu Ala Ile Ala
                245                 250                 255

Asn His Asp Phe Ala Ser Phe Ala Arg Ile Thr Cys Val Asp Ser Asn
            260                 265                 270

Gln Phe His Ala Val Cys Leu Asp Ala Ser Pro Ile Phe Tyr Met
        275                 280                 285

Asn Asp Thr Ser His Arg Ile Ile Asn Cys Ile Glu Lys Trp Asn Arg
    290                 295                 300

Phe Glu Gly Thr Pro Gln Val Ser Tyr Thr Phe Asp Ala Gly Pro Asn
305                 310                 315                 320

Ala Val Ile Cys Ala Pro Ser Arg Lys Val Ala Gly Leu Leu Leu Gln
                325                 330                 335

Arg Leu Leu Tyr Tyr Phe Pro Pro Asp Ser Ser Lys Glu Leu Ser Ser
            340                 345                 350

Tyr Val Ile Gly Asp Thr Ser Ile Leu Gly Glu Ile Gly Leu Lys Ser
        355                 360                 365

Met Lys Asp Val Glu Ser Leu Ile Ala Pro Pro Glu Phe Arg Ser Gln
    370                 375                 380

Asn Ser Ser Ser Ile His Pro Gly Glu Val Asp Tyr Phe Ile Cys Thr
385                 390                 395                 400

Arg Pro Gly Lys Gly Pro Ile Ile Leu Arg Asn Glu Asp Gln Ala Phe
                405                 410                 415

Phe Asn Asn Lys Thr Gly Phe Pro Phe Arg Ile Ser Glu Thr
            420                 425                 430

<210> SEQ ID NO 64
<211> LENGTH: 382
<212> TYPE: PRT
<213> ORGANISM: Artificial Sequence
<220> FEATURE:
<223> OTHER INFORMATION: Synthetic
```

<400> SEQUENCE: 64

```
Met Ser Asp Gln Cys Val Thr Val Glu Ala Pro Ile Asn Ile Ala Phe
1               5                   10                  15

Ile Lys Tyr Trp Gly Lys Arg Glu Gly Glu Thr Leu Ile Leu Pro
            20                  25                  30

Thr Asn Asp Ser Phe Ser Ile Thr Leu Ser Ala Ser Pro Phe Arg Ser
            35                  40                  45

Lys Thr Ser Val Glu Leu Arg Asp Asp Ile Glu Thr Asp Thr Leu Arg
        50                  55                  60

Leu Asn Gly Thr Glu Val Asp Val Gly Lys Thr Pro Arg Val Gln Ser
65                  70                  75                  80

Met Leu Leu His Leu Arg Ser Thr Cys Pro Glu Asp Leu Lys Asn Lys
                85                  90                  95

Lys Val Asn Ile Val Ser Glu Asn Phe Pro Thr Ala Ala Gly Met
            100                 105                 110

Ala Ser Ser Ala Ser Gly Tyr Cys Ala Met Ser Ala Ala Leu Ile Arg
        115                 120                 125

Ala Phe Lys Ser Thr Thr Asn Val Ser Met Leu Ala Arg Leu Gly Ser
130                 135                 140

Gly Ser Ala Cys Arg Ser Ala Phe Gly Gly Phe Val Ile Trp Asn Lys
145                 150                 155                 160

Gly Glu Lys Pro Asp Gly Ser Asp Cys Val Ala Thr Gln Phe Val Asp
                165                 170                 175

Glu Thr His Trp Pro Glu Ile Gln Val Met Cys Ala Val Leu Lys Gly
            180                 185                 190

Ala Gln Lys Asp Val Ser Ser Thr Lys Gly Met Gln Gln Ser Leu Lys
        195                 200                 205

Thr Ser Pro Leu Met Lys Lys Arg Ile Ser Glu Thr Val Pro Glu Arg
210                 215                 220

Met Lys Ile Ala Ser Arg Ala Ile Lys Ala Arg Asp Phe Ala Thr Phe
225                 230                 235                 240

Ala Glu Ile Ala Met Leu Glu Ser Asp Asp Leu Gln Glu Ile Cys Ala
                245                 250                 255

Thr Thr Glu Pro Lys Ile Thr Tyr Ala Thr Glu Asp Ser Tyr Ala Met
            260                 265                 270

Ile Arg Leu Val Lys Ala Tyr Asn Ala Lys Lys Gly Arg Thr Ala Leu
        275                 280                 285

Ala Tyr Thr Phe Asp Ala Gly Ala Asn Cys Phe Leu Phe Val Leu Lys
290                 295                 300

Glu Asp Leu Pro Glu Ala Val Ala Met Leu Met Glu His Phe Pro Thr
305                 310                 315                 320

Pro Phe Glu Lys Phe Phe Phe Gly Asp Arg Glu Leu Leu Glu Lys Val
                325                 330                 335

Lys Val Val Ser Leu Pro Asp Glu Tyr Lys Lys Leu Ile Asp His Pro
            340                 345                 350

Lys Lys Pro Phe Glu Met Leu Leu Gln Ser Pro Val Gly Cys Gly Val
        355                 360                 365

Lys Tyr Leu Gly Pro Ser Glu Ser Leu Ile Pro Pro Arg Val
370                 375                 380
```

<210> SEQ ID NO 65
<211> LENGTH: 327
<212> TYPE: PRT
<213> ORGANISM: Artificial Sequence
<220> FEATURE:
<223> OTHER INFORMATION: Synthetic

<400> SEQUENCE: 65

Met Ile Lys Ser Gly Lys Ala Arg Ala His Thr Asn Ile Ala Leu Ile
1               5                   10                  15

Lys Tyr Trp Gly Lys Lys Asp Glu Ala Leu Ile Ile Pro Met Asn Asn
            20                  25                  30

Ser Ile Ser Val Thr Leu Glu Lys Phe Tyr Thr Glu Thr Lys Val Thr
        35                  40                  45

Phe Asn Asp Gln Leu Thr Gln Asp Gln Phe Trp Leu Asn Gly Glu Lys
    50                  55                  60

Val Ser Gly Lys Glu Leu Glu Lys Ile Ser Lys Tyr Met Asp Ile Val
65                  70                  75                  80

Arg Asn Arg Ala Gly Ile Asp Trp Tyr Ala Glu Ile Glu Ser Asp Asn
                85                  90                  95

Phe Val Pro Thr Ala Ala Gly Leu Ala Ser Ser Ala Ser Ala Tyr Ala
            100                 105                 110

Ala Leu Ala Ala Ala Cys Asn Gln Ala Leu Asp Leu Gln Leu Ser Asp
        115                 120                 125

Lys Asp Leu Ser Arg Leu Ala Arg Ile Gly Ser Gly Ser Ala Ser Arg
    130                 135                 140

Ser Ile Tyr Gly Gly Phe Ala Glu Trp Glu Lys Gly Tyr Asn Asp Glu
145                 150                 155                 160

Thr Ser Tyr Ala Val Pro Leu Glu Ser Asn His Phe Glu Asp Asp Leu
                165                 170                 175

Ala Met Ile Phe Val Val Ile Asn Gln His Ser Lys Lys Val Pro Ser
            180                 185                 190

Arg Tyr Gly Met Ser Leu Thr Arg Asn Thr Ser Arg Phe Tyr Gln Tyr
        195                 200                 205

Trp Leu Asp His Ile Asp Glu Asp Leu Ala Glu Ala Lys Ala Ala Ile
    210                 215                 220

Gln Asp Lys Asp Phe Lys Arg Leu Gly Glu Val Ile Glu Glu Asn Gly
225                 230                 235                 240

Leu Arg Met His Ala Thr Asn Leu Gly Ser Thr Pro Pro Phe Thr Tyr
                245                 250                 255

Leu Val Gln Glu Ser Tyr Asp Val Met Ala Leu Val His Glu Cys Arg
            260                 265                 270

Glu Ala Gly Tyr Pro Cys Tyr Phe Thr Met Asp Ala Gly Pro Asn Val
        275                 280                 285

Lys Ile Leu Val Glu Lys Lys Asn Lys Gln Gln Ile Ile Asp Lys Leu
    290                 295                 300

Leu Thr Gln Phe Asp Asn Asn Gln Ile Ile Asp Ser Asp Ile Ile Ala
305                 310                 315                 320

Thr Gly Ile Glu Ile Ile Glu
                325

<210> SEQ ID NO 66
<211> LENGTH: 227
<212> TYPE: PRT
<213> ORGANISM: Artificial Sequence
<220> FEATURE:
<223> OTHER INFORMATION: Synthetic

<400> SEQUENCE: 66

Met Ser Ser Gln Gln Glu Lys Lys Asp Tyr Asp Glu Glu Gln Leu Arg

```
            1               5                  10                 15
Leu Met Glu Glu Val Cys Ile Val Val Asp Glu Asn Asp Val Pro Leu
                    20                 25                 30

Arg Tyr Gly Thr Lys Lys Glu Cys His Leu Met Glu Asn Ile Asn Lys
                35                 40                 45

Gly Leu Leu His Arg Ala Phe Ser Met Phe Ile Phe Asp Glu Gln Asn
            50                 55                 60

Arg Leu Leu Leu Gln Gln Arg Ala Glu Glu Lys Ile Thr Phe Pro Ser
65                  70                 75                 80

Leu Trp Thr Asn Thr Cys Cys Ser His Pro Leu Asp Val Ala Gly Glu
                85                 90                 95

Arg Gly Asn Thr Leu Pro Glu Ala Val Glu Gly Val Lys Asn Ala Ala
                100                105                110

Gln Arg Lys Leu Phe His Glu Leu Gly Ile Gln Ala Lys Tyr Ile Pro
                115                120                125

Lys Asp Lys Phe Gln Phe Leu Thr Arg Ile His Tyr Leu Ala Pro Ser
            130                135                140

Thr Gly Ala Trp Gly Glu His Glu Ile Asp Tyr Ile Leu Phe Phe Lys
145                 150                155                160

Gly Lys Val Glu Leu Asp Ile Asn Pro Asn Glu Val Gln Ala Tyr Lys
                165                170                175

Tyr Val Thr Met Glu Glu Leu Lys Glu Met Phe Ser Asp Pro Gln Tyr
                180                185                190

Gly Phe Thr Pro Trp Phe Lys Leu Ile Cys Glu His Phe Met Phe Lys
                195                200                205

Trp Trp Gln Asp Val Asp His Ala Ser Lys Phe Gln Asp Thr Leu Ile
            210                215                220

His Arg Cys
225

<210> SEQ ID NO 67
<211> LENGTH: 287
<212> TYPE: PRT
<213> ORGANISM: Artificial Sequence
<220> FEATURE:
<223> OTHER INFORMATION: Synthetic

<400> SEQUENCE: 67

Met Trp Arg Ala Leu Ala Pro Ala Arg Ala Ile Gly Arg Ala Ala Ser
1               5                  10                 15

Gly Gly Gly Ala Arg Ile Gly Gly Gly Ala Arg Ala Leu Gly Arg Ser
                20                 25                 30

Leu Lys Asp Thr Pro Pro Ala Val Gln Pro Thr Val Asp Gly Ser Cys
            35                 40                 45

Leu Arg Phe Pro Gly Arg Gly Gly Trp Ala Ala Met Pro Glu Val
            50                 55                 60

Ser Thr Asp Asp Leu Asp Glu Arg Gln Val Gln Leu Met Ala Glu Met
65                  70                 75                 80

Cys Ile Leu Val Asp Glu Asn Asp Arg Ile Gly Ala Glu Thr Lys
                85                 90                 95

Lys Asn Cys His Leu Asn Glu Asn Ile Glu Arg Gly Leu Leu His Arg
                100                105                110

Ala Phe Ser Val Phe Leu Phe Asn Thr Glu Asn Lys Leu Leu Leu Gln
            115                120                125

Gln Arg Ser Asp Ala Lys Ile Thr Phe Pro Gly Cys Phe Thr Asn Thr
```

```
                  130                 135                 140
Cys Cys Ser His Pro Leu Ser Asn Pro Ser Glu Leu Glu Glu Asn Asp
145                 150                 155                 160

Ala Ile Gly Val Arg Arg Ala Ala Gln Arg Arg Leu Lys Ala Glu Leu
                165                 170                 175

Gly Ile Pro Met Glu Glu Val Pro Pro Glu Glu Ile Asn Tyr Leu Thr
            180                 185                 190

Arg Ile His Tyr Lys Ala Gln Ser Asp Ser Ile Trp Gly Glu His Glu
        195                 200                 205

Ile Asp Tyr Ile Leu Leu Val Lys Lys Asn Val Thr Leu Asn Pro Asp
    210                 215                 220

Pro Asn Glu Ile Lys Ser Tyr Cys Tyr Val Thr Lys Glu Glu Leu Glu
225                 230                 235                 240

Glu Leu Ile Gly Lys Ala His Gly Glu Ile Lys Ile Thr Pro Trp
                245                 250                 255

Phe Gln Ile Ile Ala Asp Thr Phe Leu Phe Lys Trp Trp Asp Asn Leu
                260                 265                 270

Asn Arg Leu Asn Leu Phe Val Asp His Glu Lys Ile His Arg Met
            275                 280                 285

<210> SEQ ID NO 68
<211> LENGTH: 284
<212> TYPE: PRT
<213> ORGANISM: Artificial Sequence
<220> FEATURE:
<223> OTHER INFORMATION: Synthetic

<400> SEQUENCE: 68

Met Ala Glu Thr Leu Val Ser Lys Cys Ser Ser Gln Phe Thr Lys Leu
1               5                   10                  15

Ser Ser Phe Ser Leu Thr Ser Ser Ser Asn Leu Tyr Gln Arg Gln
            20                  25                  30

Phe Val Thr Phe Lys Pro Arg Ser Ser Phe Ala Ala Ser Val Ser Ser
        35                  40                  45

Ser Thr Thr Ile Leu Thr Asp Ala Asp Ser Asn Met Asp Ala Val Gln
50                  55                  60

Arg Arg Leu Met Phe Glu Asp Glu Cys Ile Leu Val Asp Ala Asn Asp
65                  70                  75                  80

Ala Val Val Gly His Asp Thr Lys Tyr Asn Cys His Leu Met Glu Lys
                85                  90                  95

Ile Gln Ser Glu Asn Leu Leu His Arg Ala Phe Ser Val Phe Leu Phe
            100                 105                 110

Asn Ser Lys Tyr Glu Leu Leu Leu Gln Gln Arg Ser Ala Thr Lys Val
        115                 120                 125

Thr Phe Pro Leu Val Trp Thr Asn Thr Cys Cys Ser His Pro Leu Tyr
    130                 135                 140

Arg Glu Ser Glu Leu Ile Glu Glu Asn Tyr Leu Gly Val Arg Asn Ala
145                 150                 155                 160

Ala Gln Arg Lys Leu Leu Asp Glu Leu Gly Ile Pro Ser Asp Glu Leu
                165                 170                 175

Pro Val Asn Glu Phe Ile Pro Leu Gly Arg Ile Leu Tyr Lys Ala Pro
            180                 185                 190

Ser Asp Gly Lys Trp Gly Glu His Glu Leu Asp Tyr Leu Leu Phe Ile
        195                 200                 205

Val Arg Asp Val Ser Met Ala Pro Asn Pro Asp Glu Val Ala Glu Val
```

```
            210                 215                 220
Lys Tyr Val Asn Arg Glu Gln Leu Lys Glu Leu Val Met Lys Ala Asp
225                 230                 235                 240

Leu Gly Glu Glu Gly Leu Lys Leu Ser Pro Trp Phe Arg Ile Val Val
                245                 250                 255

Asp Asn Phe Leu Phe Lys Trp Trp Asp His Val Glu Asn Gly Ser Leu
                260                 265                 270

Leu Glu Ala Cys Asp Met Lys Thr Ile His Asn Leu
                275                 280

<210> SEQ ID NO 69
<211> LENGTH: 356
<212> TYPE: PRT
<213> ORGANISM: Artificial Sequence
<220> FEATURE:
<223> OTHER INFORMATION: Synthetic

<400> SEQUENCE: 69

Met Thr Gln Gly Ser Gly Phe Asn Lys Glu Asp Ile Val Arg Arg Arg
1               5                   10                  15

Lys Lys Asp His Ile Asp Ile Cys Leu His Lys Val Val Glu Pro Tyr
                20                  25                  30

Lys Asn Gly Pro Ser Ile Trp Glu Lys Tyr Lys Ile Pro Tyr Thr Ala
                35                  40                  45

Leu Pro Glu Ile Ser Met Gly Lys Ile Asp Thr Arg Cys Glu Phe Met
            50                  55                  60

Gly Trp Thr Leu Ser Phe Pro Leu Ile Ile Ser Ser Met Thr Gly Gly
65              70                  75                  80

Glu Glu His Gly Arg Ile Ile Asn Glu Asn Leu Ala Lys Ala Cys Glu
                85                  90                  95

Ala Glu Gly Ile Pro Phe Gly Leu Gly Ser Met Arg Ile Val Asn Arg
            100                 105                 110

Tyr Ala Val Ala Ile His Thr Phe Asp Val Lys Lys Phe Cys Pro Ser
            115                 120                 125

Val Pro Met Phe Ala Asn Ile Gly Leu Val Gln Leu Asn Tyr Gly Phe
130                 135                 140

Gly Val Lys Glu Val Asn Asn Leu Ile Lys Cys Val Asn Ala Asp Gly
145                 150                 155                 160

Leu Phe Ile His Leu Asn His Thr Gln Glu Ala Cys Gln Pro Glu Gly
                165                 170                 175

Asp Thr Asn Phe Glu Ser Leu Leu His Lys Leu Glu Glu Leu Leu Pro
            180                 185                 190

His Ile Lys Val Pro Val Ile Val Lys Gly Val Gly His Gly Ile Glu
        195                 200                 205

Lys Arg Ser Val Met Ala Leu Gln Arg Val Gly Val Lys Tyr Ile Asp
210                 215                 220

Val Ser Gly Cys Gly Gly Thr Ser Trp Ala Trp Ile Glu Gly Trp Arg
225                 230                 235                 240

His Pro Asp Leu Pro Asp Asp Gln Asn Leu Gly Tyr Ile Phe Arg Asp
                245                 250                 255

Val Gly Ile Thr Thr Asp Arg Ser Leu Gln Glu Cys Ala Pro Leu Thr
            260                 265                 270

Gln Ala Ser Asp Leu Arg Leu Ile Ala Gly Gly Ile Arg Thr Gly
            275                 280                 285

Leu Asp Ile Ala Lys Ser Leu Met Met Gly Ala Glu Cys Ala Thr Ala
```

```
                290                 295                 300
Ala Leu Pro Phe Leu Lys Ala Ala Leu Glu Ser Pro Glu Arg Val Arg
305                 310                 315                 320

Gly Val Ile Gln Arg Phe Lys Lys Glu Leu Ile Val Ala Met Phe Ala
                325                 330                 335

Cys Gly Ala Ser Thr Ile Glu Glu Leu Arg Lys Met Ser Leu Ser Val
                340                 345                 350

Ser Ser Ser Leu
            355

<210> SEQ ID NO 70
<211> LENGTH: 349
<212> TYPE: PRT
<213> ORGANISM: Artificial Sequence
<220> FEATURE:
<223> OTHER INFORMATION: Synthetic

<400> SEQUENCE: 70

Met Ser Asp Phe Gln Arg Glu Gln Arg Lys Asn Glu His Val Glu Ile
1               5                   10                  15

Ala Met Ala Gln Ser Asp Ala Met His Ser Asp Phe Asp Lys Met Arg
                20                  25                  30

Phe Val His His Ser Ile Pro Ser Ile Asn Val Asn Asp Ile Asp Leu
            35                  40                  45

Thr Ser Gln Thr Pro Asp Leu Thr Met Thr Tyr Pro Val Tyr Ile Asn
    50                  55                  60

Ala Met Thr Gly Gly Ser Glu Trp Thr Lys Asn Ile Asn Glu Lys Leu
65              70                  75                  80

Ala Val Val Ala Arg Glu Thr Gly Leu Ala Met Ala Val Gly Ser Thr
                85                  90                  95

His Ala Ala Leu Arg Asn Pro Arg Met Ala Glu Thr Phe Thr Ile Ala
            100                 105                 110

Arg Lys Met Asn Pro Glu Gly Met Ile Phe Ser Asn Val Gly Ala Asp
        115                 120                 125

Val Pro Val Glu Lys Ala Leu Glu Ala Val Glu Leu Leu Glu Ala Gln
130                 135                 140

Ala Leu Gln Ile His Val Asn Ser Pro Gln Glu Leu Val Met Pro Glu
145                 150                 155                 160

Gly Asn Arg Glu Phe Val Thr Trp Leu Asp Asn Ile Ala Ser Ile Val
                165                 170                 175

Ser Arg Val Ser Val Pro Val Ile Ile Lys Glu Val Gly Phe Gly Met
            180                 185                 190

Ser Lys Glu Leu Met His Asp Leu Gln Gln Ile Gly Val Lys Tyr Val
        195                 200                 205

Asp Val Ser Gly Lys Gly Gly Thr Asn Phe Val Asp Ile Glu Asn Glu
210                 215                 220

Arg Arg Ala Asn Lys Asp Met Asp Tyr Leu Ser Ser Trp Gly Gln Ser
225                 230                 235                 240

Thr Val Glu Ser Leu Leu Glu Thr Thr Ala Tyr Gln Ser Glu Ile Ser
                245                 250                 255

Val Phe Ala Ser Gly Gly Leu Arg Thr Pro Leu Asp Ala Ile Lys Ser
            260                 265                 270

Leu Ala Leu Gly Ala Lys Ala Thr Gly Met Ser Arg Pro Phe Leu Asn
        275                 280                 285

Gln Val Glu Asn Asn Gly Ile Ala His Thr Val Ala Tyr Val Glu Ser
```

```
            290                 295                 300
Phe Ile Glu His Met Lys Ser Ile Met Thr Met Leu Asp Ala Lys Asn
305                 310                 315                 320

Ile Asp Asp Leu Thr Gln Lys Gln Ile Val Phe Ser Pro Glu Ile Leu
                325                 330                 335

Ser Trp Ile Glu Gln Arg Asn Leu Asn Ile His Arg Gly
                340                 345
```

<210> SEQ ID NO 71
<211> LENGTH: 1131
<212> TYPE: DNA
<213> ORGANISM: Artificial Sequence
<220> FEATURE:
<223> OTHER INFORMATION: Synthetic

<400> SEQUENCE: 71

| | | | | | |
|---|---|---|---|---|---|
| atggattacg | cgaacatcct | cacagcaatt | ccactcgagt | ttactcctca | ggatgatatc | 60 |
| gtgctccttg | aaccgtatca | ctacctagga | agaaccctg | aaaagaaat | tcgatcacaa | 120 |
| ctcatcgagg | ctttcaacta | ttggttggat | gtcaagaagg | aggatctcga | ggtcatccag | 180 |
| aacgttgttg | gcatgctaca | taccgctagc | ttattaatgg | acgatgtgga | ggattcatcg | 240 |
| gtcctcaggc | gtgggtcgcc | tgtggcccat | ctaatttacg | ggattccgca | gacaataaac | 300 |
| actgcaaact | acgtctactt | tctggcttat | caagagatct | tcaagcttcg | cccaacaccg | 360 |
| atacccatgc | ctgtaattcc | tccttcatct | gcttcgcttc | aatcatccgt | ctcctctgca | 420 |
| tcctcctcct | cctcggcctc | gtctgaaaac | gggggcacgt | caactcctaa | ttcgcagatt | 480 |
| ccgttctcga | agatacgta | tcttgataaa | gtgatcacag | acgagatgct | ttccctccat | 540 |
| agagggcaag | gcctggagct | attctggaga | gatagtctga | cgtgtcctag | cgaagaggaa | 600 |
| tatgtgaaaa | tggttcttgg | aaagacggga | ggtttgttcc | gtatagcggt | cagattgatg | 660 |
| atggcaaagt | cagaatgtga | catagacttt | gtccagcttg | tcaacttgat | ctcaatatac | 720 |
| ttccagatca | gggatgacta | tatgaacctt | cagtcttctg | agtatgccca | ataataagaat | 780 |
| tttgcagagg | acctcacaga | aggaaaaattc | agttttccca | ctatccactc | gattcatgcc | 840 |
| aacccctcat | cgagactcgt | catcaatacg | ttgcagaaga | aatcgacctc | tcctgagatc | 900 |
| cttcaccact | gtgtaaacta | catgcgcaca | gaaacccact | cattcgaata | tactcaggaa | 960 |
| gtcctcaaca | ccttgtcagg | tgcactcgag | agagaactag | gaaggcttca | aggagagttc | 1020 |
| gcagaagcta | actcaaagat | tgatcttgga | gacgtagagt | cggaaggaag | aacggggaag | 1080 |
| aacgtcaaat | tggaagcgat | cctgaaaaag | ctagccgata | tccctctgtg | a | 1131 |

<210> SEQ ID NO 72
<211> LENGTH: 2022
<212> TYPE: DNA
<213> ORGANISM: Artificial Sequence
<220> FEATURE:
<223> OTHER INFORMATION: Synthetic

<400> SEQUENCE: 72

| | | | | | |
|---|---|---|---|---|---|
| atgacggctc | tcgcatatta | ccagatccat | ctgatctata | ctctcccaat | tcttggtctt | 60 |
| ctcggcctgc | tcacttcccc | gatttttgaca | aaatttgaca | tctacaaaat | atcgatcctc | 120 |
| gtatttattg | cgtttagtgc | aaccacacca | tgggactcat | ggatcatcag | aaatggcgca | 180 |
| tggacatatc | catcagcgga | gagtggccaa | ggcgtgtttg | gaacgtttct | agatgttcca | 240 |
| tatgaagagt | acgctttctt | tgtcattcaa | accgtaatca | ccggcttggt | ctacgtcttg | 300 |

```
gcaactaggc accttctccc atctctcgcg cttcccaaga ctagatcgtc cgcccttcct    360
ctcgcgctca aggcgctcat ccctctgccc attatctacc tatttaccgc tcaccccagc    420
ccatcgcccg acccgctcgt gacagatcac tacttctaca tgcgggcact ctccttactc    480
atcaccccac ctaccatgct cttggcagca ttatcaggcg aatatgcttt cgattggaaa    540
agtggccgag caaagtcaac tattgcagca atcatgatcc cgacggtgta tctgatttgg    600
gtagattatg ttgctgtcgg tcaagactct tggtcgatca acgatgagaa gattgtaggg    660
tggaggcttg gaggtgtact acccattgag gaagctatgt tcttcttact gacgaatcta    720
atgattgttc tgggtctgtc tgcctgcgat catactcagg ccctatacct gctacacggt    780
cgaactattt atggcaacaa aaagatgcca tcttcatttc ccctcattac accgcctgtg    840
ctctccctgt tttttagcag ccgaccatac tcttctcagc caaaacgtga cttggaactg    900
gcagtcaagt tgttggagga aaagagccgg agcttttttg ttgcctcggc tggatttcct    960
agcgaagtta gggagaggct ggttggacta tacgcattct gccgggtgac tgatgatctt   1020
atcgactctc ctgaagtatc ttccaacccg catgccacaa ttgacatggt ctccgatttt   1080
cttaccctac tatttgggcc cccgctacac ccttcgcaac ctgacaagat ccttttcttcg  1140 cctttacttc ctccttcgca cccttcccga cccacgggaa tgtatcccct cccgcctcct   1200
ccttcgctct cgcctgccga gctcgttcaa ttccttaccg aaagggttcc cgttcaatac   1260
catttcgcct tcaggttgct cgctaagttg caagggctga tccctcgata cccactcgac   1320
gaactcctta gaggatacac cactgatctt atctttccct tatcgacaga ggcagtccag   1380
gctcggaaga cgcctatcga gaccacagct gacttgctgg actatggtct atgtgtagca   1440
ggctcagtcg ccgagctatt ggtctatgtc tcttgggcaa gtgcaccaag tcaggtccct   1500
gccaccatag aagaaagaga agctgtgtta gtggcaagcc gagagatggg aactgccctt   1560
cagttggtga acattgctag ggacattaaa ggggacgcaa cagaagggag attttaccta   1620
ccactctcat tctttggtct tcgggatgaa tcaaagcttg cgatcccgac tgattggacg   1680
gaacctcggc tcaagatttt cgacaaactc ctcagtctat ctccttcgtc cacattacca   1740
tcttcaaacg cctcagaaag cttccggttc gaatggaaga cgtactcgct tccattagtc   1800
gcctacgcag aggatcttgc caaacattct tataagggaa ttgaccgact tcctaccgag   1860
gttcaagcgg gaatgcgagc ggcttgcgcg agctacctac tgatcggccg agagatcaaa   1920
gtcgtttgga aggagacgt cggagagaga aggacagttg ccggatggag gagagtacgg    1980
aaagtcttga gtgtggtcat gagcggatgg gaagggcagt aa                      2022
```

<210> SEQ ID NO 73
<211> LENGTH: 1788
<212> TYPE: DNA
<213> ORGANISM: Artificial Sequence
<220> FEATURE:
<223> OTHER INFORMATION: Synthetic

<400> SEQUENCE: 73

```
atggctgaga ctcagagacc acgaagcgcc attatcgttg gcgcaggagc aggcggtatc     60
gccgtcgcgg cccgtctggc caaagccgga gtagacgtca cagttctcga aaagaacgac    120
ttcacaggag gccgctgcag tctcatccac acaaaagctg gctaccgctt cgaccaaggt    180
ccctcactcc tcctcctacc gggtctcttc cgcgagacct ttgaagattt aggcaccact    240
ctcgagcagg aagatgtcga gctcctccaa tgtttcccca actacaacat ctggttctcc    300
gacggcaagc gcttctcgcc caccaccgac aacgccacca tgaaggtcga gatcgaaaag    360
```

```
tgggaaggcc ccgacggctt ccgccgctac ctctcgtggc tcgccgaggg ccaccaacac    420
tacgagacca gcttgcgaca cgttctgcac cgcaacttca agtccatcct cgagctggcg    480
gacccccgcc ttgtcgtcac gttgctcatg gctcttcacc ccttcgagag catctggcac    540
cgcgccgggc gttacttcaa gacggatcgc atgcagcgcg tctttacttt tgcgaccatg    600
tacatgggca tgagcccgtt cgatgcgccg gcgacgtaca gtctgcttca atactcggag    660
ttggccgagg gtatctggta tccccgcgga ggcttccaca aggtgttgga cgctttggtc    720
aaaattggag agaggatggg cgtcaagtac agactcaaca cgggcgtgtc ccaggttctc    780
acggacgagg cgaagaacgg aaagaagcca aaggctacgg tgtccagct tgagaacggc    840
gaggtgctga acgccgatct ggtggtggtt aacgccgact tggtatatac gtacaacaac    900
ctcctgccga aggagatcgg gggcatcaag aagtatgcga acaaactcaa caaccgcaag    960
gcgtcgtgca gttctatttc ttttactgg agtttgtcgg gtatggccaa agagttggag   1020
acgcacaata tcttttttggc ggaggagtac aaggagtcct tgacgctat ctttgagagg   1080
caggccctgc ctgatgatcc cagcttctac atccacgtcc cctcccgcgt tgacccctcg   1140
gccgccctc ccgaccgcga cgccgtcatc gccctcgtcc ccgttggcca ccttctccaa   1200
aacggccaac cagagctcga ctggcctact ctcgtctcca agcccgtgc cggcgttctg   1260
gccaccatcc aagcccgtac cggcctgtcc ctgtcccccc ttatcaccga gaaatcgtc   1320
aacacccctt acacctggga gaccaagttc aacctcagca agggcgccat cctcggtttg   1380
gcccacgact tcttcaacgt gctggccttc cgcccgcgca ccaaagccca aggcatggat   1440
aacgcctact tgtcggcgc tagcacccat ccgggaaccg gcgtgccgat tgtccttgca   1500
ggtgccaaga tcactgccga gcagattctt gaggagacgt ttcctaagaa cacaaaggtg   1560
ccgtggacga cgaacgagga gaggaacagt gagcggatga ggaaggagat ggatgagaag   1620
attacggagg aggggattat tatgaggagt aacagcagta agccgggcag gagggggagt   1680
gatgcttttg agggcgccat ggaggtggtt aatctcttgt cgcagagggc gttcccttg    1740
ttggtggcgt tgatgggggt gctgtatttc ttgctatttg tgaggtag                1788
```

<210> SEQ ID NO 74
<211> LENGTH: 376
<212> TYPE: PRT
<213> ORGANISM: Artificial Sequence
<220> FEATURE:
<223> OTHER INFORMATION: Synthetic

<400> SEQUENCE: 74

```
Met Asp Tyr Ala Asn Ile Leu Thr Ala Ile Pro Leu Glu Phe Thr Pro
1               5                   10                  15

Gln Asp Asp Ile Val Leu Leu Glu Pro Tyr His Tyr Leu Gly Lys Asn
            20                  25                  30

Pro Gly Lys Glu Ile Arg Ser Gln Leu Ile Glu Ala Phe Asn Tyr Trp
        35                  40                  45

Leu Asp Val Lys Lys Glu Asp Leu Glu Val Ile Gln Asn Val Val Gly
    50                  55                  60

Met Leu His Thr Ala Ser Leu Leu Met Asp Asp Val Glu Asp Ser Ser
65                  70                  75                  80

Val Leu Arg Arg Gly Ser Pro Val Ala His Leu Ile Tyr Gly Ile Pro
                85                  90                  95

Gln Thr Ile Asn Thr Ala Asn Tyr Val Tyr Phe Leu Ala Tyr Gln Glu
            100                 105                 110
```

```
Ile Phe Lys Leu Arg Pro Thr Pro Ile Pro Met Pro Val Ile Pro Pro
            115                 120                 125

Ser Ser Ala Ser Leu Gln Ser Ser Val Ser Ser Ala Ser Ser Ser Ser
        130                 135                 140

Ser Ala Ser Ser Glu Asn Gly Gly Thr Ser Thr Pro Asn Ser Gln Ile
145                 150                 155                 160

Pro Phe Ser Lys Asp Thr Tyr Leu Asp Lys Val Ile Thr Asp Glu Met
                165                 170                 175

Leu Ser Leu His Arg Gly Gln Gly Leu Glu Leu Phe Trp Arg Asp Ser
            180                 185                 190

Leu Thr Cys Pro Ser Glu Glu Tyr Val Lys Met Val Leu Gly Lys
            195                 200                 205

Thr Gly Gly Leu Phe Arg Ile Ala Val Arg Leu Met Met Ala Lys Ser
        210                 215                 220

Glu Cys Asp Ile Asp Phe Val Gln Leu Val Asn Leu Ile Ser Ile Tyr
225                 230                 235                 240

Phe Gln Ile Arg Asp Asp Tyr Met Asn Leu Gln Ser Ser Glu Tyr Ala
                245                 250                 255

His Asn Lys Asn Phe Ala Glu Asp Leu Thr Glu Gly Lys Phe Ser Phe
            260                 265                 270

Pro Thr Ile His Ser Ile His Ala Asn Pro Ser Ser Arg Leu Val Ile
        275                 280                 285

Asn Thr Leu Gln Lys Lys Ser Thr Ser Pro Glu Ile Leu His His Cys
290                 295                 300

Val Asn Tyr Met Arg Thr Glu Thr His Ser Phe Glu Tyr Thr Gln Glu
305                 310                 315                 320

Val Leu Asn Thr Leu Ser Gly Ala Leu Glu Arg Glu Leu Gly Arg Leu
                325                 330                 335

Gln Gly Glu Phe Ala Glu Ala Asn Ser Lys Ile Asp Leu Gly Asp Val
            340                 345                 350

Glu Ser Glu Gly Arg Thr Gly Lys Asn Val Lys Leu Glu Ala Ile Leu
        355                 360                 365

Lys Lys Leu Ala Asp Ile Pro Leu
370                 375

<210> SEQ ID NO 75
<211> LENGTH: 673
<212> TYPE: PRT
<213> ORGANISM: Artificial Sequence
<220> FEATURE:
<223> OTHER INFORMATION: Synthetic

<400> SEQUENCE: 75

Met Thr Ala Leu Ala Tyr Tyr Gln Ile His Leu Ile Tyr Thr Leu Pro
1               5                   10                  15

Ile Leu Gly Leu Leu Gly Leu Leu Thr Ser Pro Ile Leu Thr Lys Phe
            20                  25                  30

Asp Ile Tyr Lys Ile Ser Ile Leu Val Phe Ile Ala Phe Ser Ala Thr
        35                  40                  45

Thr Pro Trp Asp Ser Trp Ile Ile Arg Asn Gly Ala Trp Thr Tyr Pro
    50                  55                  60

Ser Ala Glu Ser Gly Gln Gly Val Phe Gly Thr Phe Leu Asp Val Pro
65              70                  75                  80

Tyr Glu Glu Tyr Ala Phe Phe Val Ile Gln Thr Val Ile Thr Gly Leu
                85                  90                  95
```

```
Val Tyr Val Leu Ala Thr Arg His Leu Leu Pro Ser Leu Ala Leu Pro
            100                 105                 110

Lys Thr Arg Ser Ser Ala Leu Ser Leu Ala Leu Lys Ala Leu Ile Pro
            115                 120                 125

Leu Pro Ile Ile Tyr Leu Phe Thr Ala His Pro Ser Pro Ser Pro Asp
            130                 135                 140

Pro Leu Val Thr Asp His Tyr Phe Tyr Met Arg Ala Leu Ser Leu Leu
145                 150                 155                 160

Ile Thr Pro Pro Thr Met Leu Leu Ala Leu Ser Gly Glu Tyr Ala
                165                 170                 175

Phe Asp Trp Lys Ser Gly Arg Ala Lys Ser Thr Ile Ala Ala Ile Met
            180                 185                 190

Ile Pro Thr Val Tyr Leu Ile Trp Val Asp Tyr Val Ala Val Gly Gln
            195                 200                 205

Asp Ser Trp Ser Ile Asn Asp Glu Lys Ile Val Gly Trp Arg Leu Gly
            210                 215                 220

Gly Val Leu Pro Ile Glu Glu Ala Met Phe Phe Leu Leu Thr Asn Leu
225                 230                 235                 240

Met Ile Val Leu Gly Leu Ser Ala Cys Asp His Thr Gln Ala Leu Tyr
                245                 250                 255

Leu Leu His Gly Arg Thr Ile Tyr Gly Asn Lys Lys Met Pro Ser Ser
            260                 265                 270

Phe Pro Leu Ile Thr Pro Pro Val Leu Ser Leu Phe Phe Ser Ser Arg
            275                 280                 285

Pro Tyr Ser Ser Gln Pro Lys Arg Asp Leu Glu Leu Ala Val Lys Leu
            290                 295                 300

Leu Glu Glu Lys Ser Arg Ser Phe Phe Val Ala Ser Ala Gly Phe Pro
305                 310                 315                 320

Ser Glu Val Arg Glu Arg Leu Val Gly Leu Tyr Ala Phe Cys Arg Val
                325                 330                 335

Thr Asp Asp Leu Ile Asp Ser Pro Glu Val Ser Ser Asn Pro His Ala
            340                 345                 350

Thr Ile Asp Met Val Ser Asp Phe Leu Thr Leu Leu Phe Gly Pro Pro
            355                 360                 365

Leu His Pro Ser Gln Pro Asp Lys Ile Leu Ser Ser Pro Leu Leu Pro
            370                 375                 380

Pro Ser His Pro Ser Arg Pro Thr Gly Met Tyr Pro Leu Pro Pro Pro
385                 390                 395                 400

Pro Ser Leu Ser Pro Ala Glu Leu Val Gln Phe Leu Thr Glu Arg Val
                405                 410                 415

Pro Val Gln Tyr His Phe Ala Phe Arg Leu Leu Ala Lys Leu Gln Gly
            420                 425                 430

Leu Ile Pro Arg Tyr Pro Leu Asp Glu Leu Leu Arg Gly Tyr Thr Thr
            435                 440                 445

Asp Leu Ile Phe Pro Leu Ser Thr Glu Ala Val Gln Ala Arg Lys Thr
            450                 455                 460

Pro Ile Glu Thr Thr Ala Asp Leu Leu Asp Tyr Gly Leu Cys Val Ala
465                 470                 475                 480

Gly Ser Val Ala Glu Leu Leu Val Tyr Val Ser Trp Ala Ser Ala Pro
                485                 490                 495

Ser Gln Val Pro Ala Thr Ile Glu Glu Arg Glu Ala Val Leu Val Ala
            500                 505                 510
```

```
Ser Arg Glu Met Gly Thr Ala Leu Gln Leu Val Asn Ile Ala Arg Asp
        515                 520                 525

Ile Lys Gly Asp Ala Thr Glu Gly Arg Phe Tyr Leu Pro Leu Ser Phe
    530                 535                 540

Phe Gly Leu Arg Asp Glu Ser Lys Leu Ala Ile Pro Thr Asp Trp Thr
545                 550                 555                 560

Glu Pro Arg Pro Gln Asp Phe Asp Lys Leu Leu Ser Leu Ser Pro Ser
                565                 570                 575

Ser Thr Leu Pro Ser Ser Asn Ala Ser Glu Ser Phe Arg Phe Glu Trp
                580                 585                 590

Lys Thr Tyr Ser Leu Pro Leu Val Ala Tyr Ala Glu Asp Leu Ala Lys
            595                 600                 605

His Ser Tyr Lys Gly Ile Asp Arg Leu Pro Thr Glu Val Gln Ala Gly
        610                 615                 620

Met Arg Ala Ala Cys Ala Ser Tyr Leu Leu Ile Gly Arg Glu Ile Lys
625                 630                 635                 640

Val Val Trp Lys Gly Asp Val Gly Glu Arg Arg Thr Val Ala Gly Trp
                645                 650                 655

Arg Arg Val Arg Lys Val Leu Ser Val Val Met Ser Gly Trp Glu Gly
                660                 665                 670

Gln
```

<210> SEQ ID NO 76
<211> LENGTH: 595
<212> TYPE: PRT
<213> ORGANISM: Artificial Sequence
<220> FEATURE:
<223> OTHER INFORMATION: Synthetic

<400> SEQUENCE: 76

```
Met Ala Glu Thr Gln Arg Pro Arg Ser Ala Ile Ile Val Gly Ala Gly
1               5                   10                  15

Ala Gly Gly Ile Ala Val Ala Ala Arg Leu Ala Lys Ala Gly Val Asp
            20                  25                  30

Val Thr Val Leu Glu Lys Asn Asp Phe Thr Gly Gly Arg Cys Ser Leu
        35                  40                  45

Ile His Thr Lys Ala Gly Tyr Arg Phe Asp Gln Gly Pro Ser Leu Leu
    50                  55                  60

Leu Leu Pro Gly Leu Phe Arg Glu Thr Phe Glu Asp Leu Gly Thr Thr
65                  70                  75                  80

Leu Glu Gln Glu Asp Val Glu Leu Leu Gln Cys Phe Pro Asn Tyr Asn
                85                  90                  95

Ile Trp Phe Ser Asp Gly Lys Arg Phe Ser Pro Thr Thr Asp Asn Ala
            100                 105                 110

Thr Met Lys Val Glu Ile Glu Lys Trp Glu Gly Pro Asp Gly Phe Arg
        115                 120                 125

Arg Tyr Leu Ser Trp Leu Ala Glu Gly His Gln His Tyr Glu Thr Ser
    130                 135                 140

Leu Arg His Val Leu His Arg Asn Phe Lys Ser Ile Leu Glu Leu Ala
145                 150                 155                 160

Asp Pro Arg Leu Val Val Thr Leu Leu Met Ala Leu His Pro Phe Glu
                165                 170                 175

Ser Ile Trp His Arg Ala Gly Arg Tyr Phe Lys Thr Asp Arg Met Gln
            180                 185                 190

Arg Val Phe Thr Phe Ala Thr Met Tyr Met Gly Met Ser Pro Phe Asp
```

```
                195                 200                 205
Ala Pro Ala Thr Tyr Ser Leu Leu Gln Tyr Ser Glu Leu Ala Glu Gly
        210                 215                 220

Ile Trp Tyr Pro Arg Gly Gly Phe His Lys Val Leu Asp Ala Leu Val
225                 230                 235                 240

Lys Ile Gly Glu Arg Met Gly Val Lys Tyr Arg Leu Asn Thr Gly Val
            245                 250                 255

Ser Gln Val Leu Thr Asp Gly Gly Lys Asn Gly Lys Lys Pro Lys Ala
        260                 265                 270

Thr Gly Val Gln Leu Glu Asn Gly Glu Val Leu Asn Ala Asp Leu Val
    275                 280                 285

Val Val Asn Ala Asp Leu Val Tyr Thr Tyr Asn Asn Leu Leu Pro Lys
290                 295                 300

Glu Ile Gly Gly Ile Lys Lys Tyr Ala Asn Lys Leu Asn Asn Arg Lys
305                 310                 315                 320

Ala Ser Cys Ser Ser Ile Ser Phe Tyr Trp Ser Leu Ser Gly Met Ala
            325                 330                 335

Lys Glu Leu Glu Thr His Asn Ile Phe Leu Ala Glu Glu Tyr Lys Glu
        340                 345                 350

Ser Phe Asp Ala Ile Phe Glu Arg Gln Ala Leu Pro Asp Asp Pro Ser
    355                 360                 365

Phe Tyr Ile His Val Pro Ser Arg Val Asp Pro Ser Ala Ala Pro Pro
370                 375                 380

Asp Arg Asp Ala Val Ile Ala Leu Val Pro Val Gly His Leu Leu Gln
385                 390                 395                 400

Asn Gly Gln Pro Glu Leu Asp Trp Pro Thr Leu Val Ser Lys Ala Arg
            405                 410                 415

Ala Gly Val Leu Ala Thr Ile Gln Ala Arg Thr Gly Leu Ser Leu Ser
        420                 425                 430

Pro Leu Ile Thr Glu Glu Ile Val Asn Thr Pro Tyr Thr Trp Glu Thr
    435                 440                 445

Lys Phe Asn Leu Ser Lys Gly Ala Ile Leu Gly Leu Ala His Asp Phe
450                 455                 460

Phe Asn Val Leu Ala Phe Arg Pro Arg Thr Lys Ala Gln Gly Met Asp
465                 470                 475                 480

Asn Ala Tyr Phe Val Gly Ala Ser Thr His Pro Gly Thr Gly Val Pro
            485                 490                 495

Ile Val Leu Ala Gly Ala Lys Ile Thr Ala Glu Gln Ile Leu Glu Glu
        500                 505                 510

Thr Phe Pro Lys Asn Thr Lys Val Pro Trp Thr Thr Asn Glu Glu Arg
    515                 520                 525

Asn Ser Glu Arg Met Arg Lys Glu Met Asp Glu Lys Ile Thr Glu Glu
530                 535                 540

Gly Ile Ile Met Arg Ser Asn Ser Ser Lys Pro Gly Arg Arg Gly Ser
545                 550                 555                 560

Asp Ala Phe Glu Gly Ala Met Glu Val Val Asn Leu Leu Ser Gln Arg
            565                 570                 575

Ala Phe Pro Leu Leu Val Ala Leu Met Gly Val Leu Tyr Phe Leu Leu
        580                 585                 590

Phe Val Arg
    595

<210> SEQ ID NO 77
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 77
ggcgcgccgc ggccgcagct                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gcggccgcgg cgcgccaatt                                               20

<210> SEQ ID NO 79
<211> LENGTH: 33
<212> TYPE: DNA
<213> ORGANISM: Artificial Sequence
<220> FEATURE:
<223> OTHER INFORMATION: Synthetic

<400> SEQUENCE: 79
aaaaggcgcg ccatatgttc atgtatgtat ctg                                33

<210> SEQ ID NO 80
<211> LENGTH: 35
<212> TYPE: DNA
<213> ORGANISM: Artificial Sequence
<220> FEATURE:
<223> OTHER INFORMATION: Synthetic

<400> SEQUENCE: 80
aaaaggcgcg cctttatgtg atgattgatt gattg                              35

<210> SEQ ID NO 81
<211> LENGTH: 69
<212> TYPE: DNA
<213> ORGANISM: Artificial Sequence
<220> FEATURE:
<223> OTHER INFORMATION: Synthetic

<400> SEQUENCE: 81
gacaggggca agaataaga gcacagaaga agagaaaaga cgaaggcggc cgcataggcc    60
actagtgga                                                          69

<210> SEQ ID NO 82
<211> LENGTH: 66
<212> TYPE: DNA
<213> ORGANISM: Artificial Sequence
<220> FEATURE:
<223> OTHER INFORMATION: Synthetic

<400> SEQUENCE: 82
cttcatctcg accggatgca atgccaattc taatagcttt cccatttatg tgatgattga    60
ttgatt                                                             66

<210> SEQ ID NO 83
<211> LENGTH: 20
<212> TYPE: DNA
<213> ORGANISM: Artificial Sequence
```

<220> FEATURE:
<223> OTHER INFORMATION: Synthetic

<400> SEQUENCE: 83
ggcgcgccgc ggccgcagct                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
gcggccgcgg cgcgccaatt                                          20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
ggcgcgccgc ggccgcagct                                          20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
gcggccgcgg cgcgccaatt                                          20

<210> SEQ ID NO 87
<211> LENGTH: 33
<212> TYPE: DNA
<213> ORGANISM: Artificial Sequence
<220> FEATURE:
<223> OTHER INFORMATION: Synthetic

<400> SEQUENCE: 87
aaaaggcgcg ccatatgttc atgtatgtat ctg                           33

<210> SEQ ID NO 88
<211> LENGTH: 35
<212> TYPE: DNA
<213> ORGANISM: Artificial Sequence
<220> FEATURE:
<223> OTHER INFORMATION: Synthetic

<400> SEQUENCE: 88
aaaaggcgcg cctttatgtg atgattgatt gattg                         35

<210> SEQ ID NO 89
<211> LENGTH: 69
<212> TYPE: DNA
<213> ORGANISM: Artificial Sequence
<220> FEATURE:
<223> OTHER INFORMATION: Synthetic

<400> SEQUENCE: 89
tgtcaaatta cctaaaaaat ggccgagagc cgcaaagggg aggtcgcggc cgcataggcc    60

```
actagtgga                                                                 69

<210> SEQ ID NO 90
<211> LENGTH: 66
<212> TYPE: DNA
<213> ORGANISM: Artificial Sequence
<220> FEATURE:
<223> OTHER INFORMATION: Synthetic

<400> SEQUENCE: 90
accacgaaca atgggtctct tgatggcaga acgtgcagac agcatttatg tgatgattga         60
ttgatt                                                                    66
```

METHOD OF PRODUCING ISOPRENOID COMPOUNDS IN YEAST

CROSS REFERENCE TO RELATED APPLICATIONS

This application is a U.S. national stage application under 35 U.S.C. §371 of International Application Number PCT/US2011/037337, filed 20 May, 2011, which claims the benefit of priority from U.S. provisional application Ser. No. 61/346,853, filed 20 May 2010, which is hereby incorporated by reference in its entirety. All patent and non-patent references cited in the application are also hereby incorporated by reference in their entirety.

FIELD OF THE INVENTION

An improved method for production of one or more the pathway enzymes and synthesis of an isoprenoid or isoprenoid precursor is described. Improved biosynthesis of terpenoid molecules derived from prenyl phosphates is described, and more particularly, methods for biosynthesizing terpenoids are further described, as well as to nucleic acid sequences, enzymes, expression vectors, and transformed host cells for carrying out such methods.

BACKGROUND OF THE INVENTION

Isoprenoid compounds (also known as terpenoid compounds) comprise the most numerous and structurally diverse family of natural products. In this family, terpenoids isolated from plants and other natural sources are used as commercial flavor and fragrance compounds as well as antimalarial and anticancer drugs. A majority of the terpenoid compounds in use today are natural products or their derivatives. One example of isoprenoid compounds are carotenoids, which are a structurally diverse class of pigments derived from isoprenoid pathway intermediate products.

The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural-product from a native source is limited by the availability of the native source; and synthetic or semi-synthetic production of natural products can suffer from low yield and/or high cost. Such production problems and limited availability of the natural source can restrict the commercial and clinical development of such products.

The biosynthesis of isoprenoid natural products in engineered microbes could tap the unrealized commercial and therapeutic potential of these natural resources and yield less expensive and more widely available fine chemicals and pharmaceuticals. A major obstacle to high level terpenoid biosynthesis is the production of terpene precursors. Previous studies have shown that, when expressed in E. coli, the mevalonate pathway provides for production of isopentenyl pyrophosphate (IPP), which can be isomerized and polymerized into isoprenoids and terpenes of commercial value. Further, it has been shown that the expression of mevalonate-producing enzymes can inhibit cell growth and limit the productivity of microbial cultures.

Extraction and purification methods usually provide a low yield of the desired isoprenoid, as biological materials typically contain only small quantities of these compounds. Unfortunately, the difficulty involved in obtaining relatively large amounts of isoprenoids has limited their practical use. The lack of readily available methods by which to obtain certain isoprenoids has slowed down the progression of drug candidates through clinical trials.

Thus, it would be of significant value to terpenoid biosynthesis via the mevalonate pathway to find ways of increasing the availability of prenyl phosphate.

SUMMARY OF THE INVENTION

Genetically modified host cells and their use for boosting production of isoprenoid compounds are provided. Enhanced yeast host cell comprises one or more heterologous enzymes. Methods for increasing prenyl phosphate availability for terpenoid biosynthesis is described.

Increasing prenyl phosphate availability for terpenoid biosynthesis can be significantly increased as disclosed. In one embodiment, prenyl phosphate availability for terpenoid biosynthesis is increased by two alternative and additive strategies.

In one aspect, a method of increasing the prenyl phosphate (PPP) pool in *Saccharomyces cerevisiae* (yeast) for the purpose of higher isoprenoid flux is provided.

In another aspect, recombinant yeast host cells having the capability for significantly increased production of PPP are provided.

In another aspect, heterologous mevalonate pathway genes that result in a higher prenyl phosphate production are described. In a another aspect, acetyl-CoA production is increased in the yeast cell. In a another aspect, these approaches are combined in order to provide synergistic increases in production of isoprenoid compounds.

In one embodiment, a yeast cell is provided, comprising MEV-1 (SEQ ID. NO:1), MEV-6 (SEQ ID. NO:6), MEV-15 (SEQ ID. NO:15), MEV-18 (SEQ ID. NO:18), MEV-21 (SEQ ID. NO:21), and/or MEV-33 (SEQ ID. NO:33). In another embodiment, the yeast cell comprises the heterologous enzyme ATP-citrate lyase.

In one embodiment, methods for producing at least one carotenoid in a greater amount than an unaltered yeast naturally produces are provided. In one embodiment, the carotenoid is β-carotene. In another embodiment, β-carotene is produced in an amount of at least 150 mg/gram dry weight.

In another aspect, methods for improving isoprenoid compound flux via the mevalonate pathway are provided.

In another aspect, a method of producing isoprenoid compounds in a yeast cell is described, the method comprising cultivating a yeast cell in a suitable medium where the yeast cell is capable of growing, the yeast cell comprising a heterologous nucleotide sequence encoding a product involved in the biosynthesis pathway leading to an isoprenoid compound.

In another aspect, a method for preparing a yeast host cell with increased synthesis of isoprenoid compounds relative to an unaltered yeast cell is described, the method comprising introducing a heterologous nucleotide sequence encoding a product involved in the biosynthesis pathway leading to an isoprenoid compound into a yeast host cell.

In another aspect, a yeast host cell is described comprising a heterologous nucleotide sequence encoding a product involved in the biosynthesis pathway leading to an isoprenoid compound.

In another aspect, a method of producing isoprenoid compounds in a yeast cell is described, the method comprising cultivating a yeast cell in a suitable medium where the yeast cell is capable of growing, the yeast cell comprising a heterologous nucleotide sequence encoding an ATP-citrate lyase enzyme.

In another aspect, a method for preparing a yeast host cell with increased synthesis of isoprenoid compounds relative to an unaltered yeast cell is described, the method comprising introducing a heterologous nucleotide sequence encoding an ATP-citrate lyase enzyme into a yeast host cell.

In another aspect, a yeast host cell is described comprising a heterologous nucleotide sequence encoding an ATP-citrate lyase enzyme.

In another aspect, a method of producing isoprenoid compounds in a yeast cell is described, the method comprising cultivating a yeast cell in a suitable medium where the yeast cell is capable of growing, the yeast cell comprising:
  a heterologous nucleotide sequence encoding a product involved in the biosynthesis pathway leading to an isoprenoid compound; and,
  a heterologous nucleotide sequence encoding an ATP-citrate lyase enzyme.

In another aspect, a method for preparing a yeast host cell with increased synthesis of isoprenoid compounds relative to an unaltered yeast cell is described, the method comprising:
  introducing a heterologous nucleotide sequence encoding a product involved in the biosynthesis pathway leading to an isoprenoid compound into the yeast host cell; and
  introducing a heterologous nucleotide sequence encoding an ATP-citrate lyase enzyme into the yeast host cell.

In another aspect, a yeast host cell is described comprising a heterologous nucleotide sequence encoding a product involved in the biosynthesis pathway leading to an isoprenoid compound and a heterologous nucleotide sequence encoding an ATP-citrate lyase enzyme.

In another aspect, a method for preparing a yeast host cell with increased synthesis of isoprenoid compounds relative to an unaltered yeast cell is described, the method comprising up- or down-regulating one or more genes involved in a biosynthesis pathway leading to an isoprenoid compound. In one embodiment, the genes of the method are selected from nucleotides encoding one or more of SEQ ID. NOs. 1-35. In another embodiment, the method further comprises introducing a heterologous nucleotide sequence encoding an ATP-citrate lyase enzyme into a yeast host cell.

In another aspect, the method described further comprises recovering an isoprenoid compound.

In another aspect, the method is described wherein the isoprenoid compound produced is a carotenoid. In one embodiment, the method produces a carotenoid which is selected from the group consisting of β-carotene, antheraxanthin, adonirubin, adonixanthin, astaxanthin, canthaxanthin, capsorubrin, β-cryptoxanthin, α-carotene, β,ψ-carotene, Δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids.

In another aspect, a yeast host cell is described wherein the isoprenoid compound produced by the cell is a carotenoid. In one embodiment, the yeast host cell produces a carotenoid which is selected from the group consisting of β-carotene, antheraxanthin, adonirubin, adonixanthin, astaxanthin, canthaxanthin, capsorubrin, β-cryptoxanthin, α-carotene, β,ψ-carotene, Δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids.

In one embodiment, the carotenoid produced is β-carotene. In one embodiment, the amount of carotenoid produced by the recombinant yeast cell is at least about 150 mg/g DW. In one embodiment, the carotenoid is β-carotene and is produced in a recoverable amount of at least about 150 mg/g DW. In one embodiment, the recombinant yeast cell has the ability to produce at least one carotenoid in a greater amount than an unaltered yeast naturally produces.

In another aspect, a yeast host cell is described wherein the nucleotide sequence encoding a product involved in the biosynthesis pathway comprises one or more of SEQ ID. NOs. 1-35. In one embodiment, the yeast host cell comprises nucleotides according to one or more of MEV-1 (SEQ ID. NO. 1), MEV-6 (SEQ ID. NO. 6), MEV-15 (SEQ ID. NO. 15), MEV-18 (SEQ ID. NO. 18), MEV-21 (SEQ ID. NO. 21), or MEV-23 (SEQ ID. NO. 23).

In one embodiment, the yeast cell, comprises MEV-1, MEV-6, MEV-15, MEV-18, MEV-21 and MEV-33.

In another aspect, a method is described, wherein the nucleotide sequence encoding a product involved in the biosynthesis pathway comprises one or more of SEQ ID. NOs. 1-35. In one embodiment, the method comprises nucleotides according to one or more of MEV-1 (SEQ ID. NO. 1), MEV-6 (SEQ ID. NO. 6), MEV-15 (SEQ ID. NO. 15), MEV-18 (SEQ ID. NO. 18), MEV-21 (SEQ ID. NO. 21), or MEV-23 (SEQ ID. NO. 23).

In another aspect, the method is described wherein the heterologous nucleotide sequence encoding an ATP-citrate lyase enzyme is from either *Chlamydomonas rheinhardtii* or *Yarrowia lipolytica*. In one embodiment, the method further comprises expressing in the yeast host cell a heterologous ATP-citrate lyase.

In another aspect, a yeast host cell is described which comprises the heterologous nucleotide sequence encoding an ATP-citrate lyase enzyme is from either *Chlamydomonas rheinhardtii* or *Yarrowia lipolytica*.

In one aspect, an enhanced yeast host cell is provided for producing an isoprenoid molecule via the mevalonate pathway, the yeast host cell comprising one or more heterologous enzyme selected from the group consisting of the enzymes shown in Table 1 and a heterologous ATP-citrate lyase, wherein culturing the transformed host cell in a suitable medium provides for increased acetyl-CoA production.

In another aspect, a recombinant yeast host cell is provided for production of a carotenoid product, the host cell comprising one or more enzymes selected from the group consisting of the enzymes of Table 3 and a heterologous ACL enzyme.

In one embodiment, the recombinant yeast cell comprises one or more of heterologous genes encoding one or more enzymes selected from the group consisting of the enzymes disclosed in Table 2 or Table 3.

In another aspect, a method for improving isoprenoid compound flux via the mevalonate pathway is described, comprising transforming a yeast host cell with one or more heterologous genes selected from the group consisting of the genes shown in Table 1 and a heterologous ACL gene.

In another aspect, a method is described, wherein the one or more heterologous genes are selected from the enzymes shown in Table 2.

In another aspect, a method for increasing the mevalonate pathway flux of a carotenoid compound is described, comprising expressing in a yeast host cell one or more of the enyzymes selected from the group consisting of the enzymes shown in Table 2 and a heterologous ATP-citrate lyase.

In another aspect, a yeast host cell is described, wherein the cell further comprises reduced inherent ACO1 and/or ERG9 expression relative to an unaltered yeast cell.

In another aspect, a method is described, wherein the cell further comprises reduced inherent ACO1 and/or ERG9 expression relative to an unaltered yeast cell. In one embodiment, the yeast host cell comprises reduced inherent ACO1 expression.

In another aspect, a yeast host cell is described, wherein the cell further comprises a heterologous CUP1 gene promoter. In one embodiment, the yeast host cell comprises a CUP1 gene promoter. In one embodiment, the method further comprises the step of substituting an ERG9 gene promoter with a CUP1 gene promoter. In one embodiment, the method further comprises the step of substituting an ACO1 gene promoter with a CUP1 gene promoter.

In another aspect, a yeast host cell is described, wherein the yeast host cell produces at least about 25 fold more isoprenoid compound relative to an unaltered yeast cell.

In another aspect, a method is described, wherein the yeast host cell produces at least about 25 fold more isoprenoid compound relative to an unaltered yeast cell. In one embodiment, a transformed host cell overproduces an isoprenoid or isoprenoid precursor by up to at least about 25 fold, as compared to a control host cell that is not transformed with the one or more heterologous nucleic acid.

In one embodiment, the isoprenoid or isoprenoid precursor is synthesized in a recoverable amount of at least about 150 mg/g DW.

In another aspect, a yeast host cell is described, wherein the isoprenoid compound is produced in a recoverable amount of at least about 150 mg/g dry weight (DW).

In another aspect, a method is described wherein the isoprenoid compound is produced in a recoverable amount of at least about 150 mg/g dry weight (DW).

BRIEF DESCRIPTION OF THE DRAWINGS

The following detailed description of the embodiments can be best understood when read in conjunction with the following drawings.

DEFINITIONS

Figure 1:
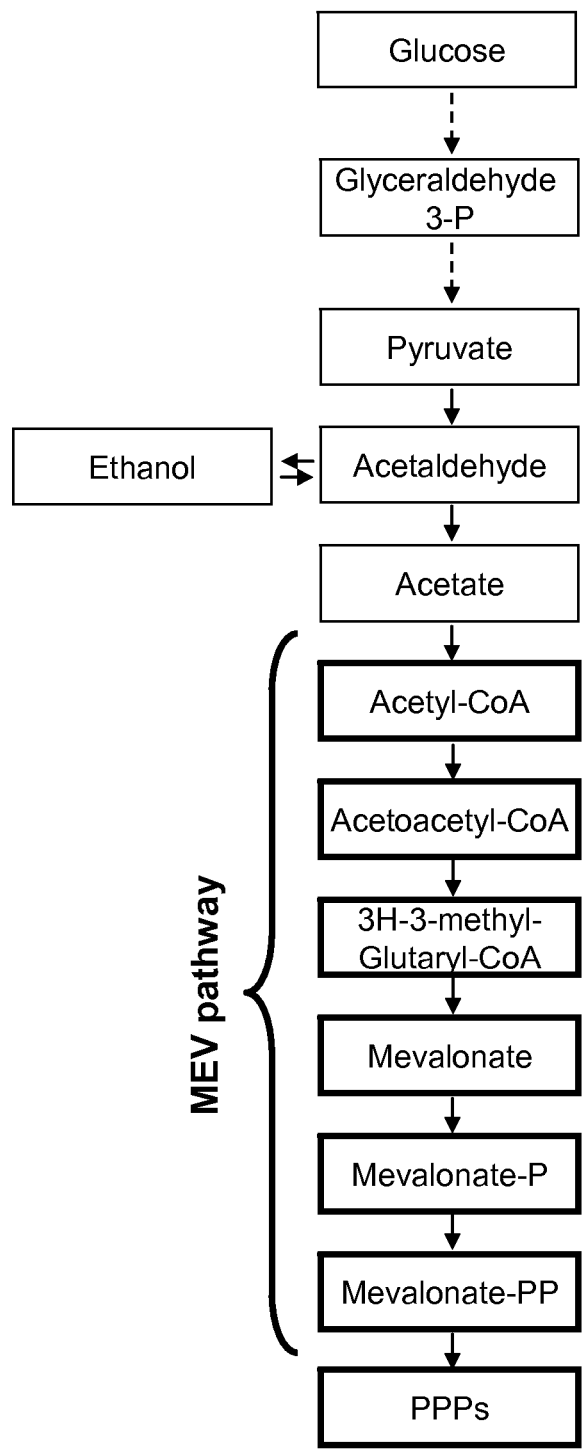
FIG. 1 shows the yeast cytosolic "mevalonate (MEV) pathway" in which cytosolic acetyl-CoA is converted to isopentenyl pyrophosphate in a 6-step process via consumption of ATP and NADPH, one of two known pathways for production of prenyl phosphates (PPP).

Unless defined otherwise, all technical and scientific terms used herein have the same meaning as is commonly understood by one of skill in the art to which this invention belongs.

As used herein, growth under selective conditions, means growth of a cell under conditions that require expression of a selectable marker for survival.

By a controllable promoter is meant a promoter, which can be controlled through external manipulations such as addition or removal of a compound from the surroundings of the cell, change of physical conditions, etc.

An independently controllable promoter may be induced/repressed substantially without affecting the induction/repression of other promoters according to the invention. The induction/repression of an independently controllable promoter may affect native promoters in the host cells.

Coordinated expression refers to the expression of a sub-set of genes which are induced or repressed by the same external stimulus.

Isoprenoid compound: The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g. C5, C10, C15, C20, C25, C30 and C40). Irregular isoprenoids and polyterpenes have been reported, and are also included in the definition of "isoprenoid." Isoprenoid compounds include, but are not limited to, carotenoids, monoterpenes, sesquiterpenes, triterpenes, polyterpenes, and diterpenes.

Biosynthesis pathway: The term "biosynthesis pathway" refers to a sequence of transformations of one molecule into another in a cell. In one embodiment, the biosynthesis pathway is a metabolic pathway. In another embodiment, the biosynthesis pathway is the mevalonate pathway. In another embodiment, the biosynthesis pathway is an isoprenoid pathway. Isoprenoid pathway is understood to refer to a metabolic pathway that either produces or utilizes the five-carbon metabolite isopentyl pyrophosphate (IPP). Two different pathways can produce the common isoprenoid precursor IPP, the "mevalonate pathway" and the "non-mevalonate pathway". The term "biosynthesis pathway" is sufficiently general to encompass both of these types of pathway, and can encompass any metabolic pathway.

Mevalonate pathway: The term "mevalonate pathway" or "MEV pathway" is used herein to refer to the biosynthesis pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate.

Heterologous nucleotide: The term "heterologous nucleotide," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant.

Product involved in the biosynthesis pathway: The term "product involved in the biosynthesis pathway" refers to any biological or organic material that is involved in a biosynthesis pathway. As a non-limiting example, "product involved in the biosynthesis pathway" can refer to the isoprenoid precursors or intermediates involved in the mevolonate pathway, such as but not limited to acetyl-CoA C-acetyltransferase, 3-hydroxy-3-methylglutaryl-CoA synthase, 3-hydroxy-3-methylglutaryl-coenzyme A reductase, mevalonate kinase, phosphomevalonate kinase, diphosphomevalonate decarboxylase and the isopentenyl diphosphate: dimethylallyl diphosphate isomerase. In one embodiment, the product is an enzyme. "Product involved in the biosynthesis pathway" further includes enzymes that act on isoprenoid intermediates prior to production of prenyl phosphates (PPP), IPP (isopentenyl pyrophosphate), DMAPP (dimethylallyl pyrophosphate), FPP (farnesyl pyrophosphate), GPP (geranyl pyrophosphate) and GGPP (geranylgeranyl pyrophosphate). In one embodiment, the product is a polypeptide. However the product may also for example be a RNA molecule affecting the expression of a gene. The product may be directly involved in the biosynthesis pathway or indirectly via other precursors or intermediates.

Yeast host cell: As used herein, the "yeast host cell" is a yeast or fungal cell that is altered according to the described methods. In one embodiment, the cell is altered genetically.

Restriction site: The term "restriction site", as used herein, is abbreviated by RSn (n=1,2,3, etc) is used to designate a nucleotide sequence comprising a restriction site. A restriction site is defined by a recognition sequence and a cleavage site. The cleavage site may be located within or outside the recognition sequence. The abbreviation "rs$_1$" or "rs$_2$" is used to designate the two ends of a restriction site after cleavage. The sequence "rs$_1$-rs$_2$" together designate a complete restriction site.

The cleavage site of a restriction site may leave a double stranded polynucleotide sequence with either blunt or sticky ends. Thus, "rs$_1$" or "rs$_2$" may designate either a blunt or a sticky end.

In the notation used throughout the present invention, formula like:

RS1-RS2-SP--PR--X-TR--SP--RS2-RS1 should be interpreted to mean that the individual sequences follow in the order specified. This does not exclude that part of the recognition sequence of e.g. RS2 overlap with the spacer sequence, but it is a strict requirement that all the items except RS1 and RS1' are functional and remain functional after cleavage and re-assemblage. Furthermore the formulae do not exclude the possibility of having additional sequences inserted between the listed items. For example introns can be inserted as described in the invention below and further spacer sequences can be inserted between RS1 and RS2 and between TR and RS2. Important is that the sequences remain functional. Furthermore, when reference is made to the size of the restriction site and/or to specific bases within it, only the bases in the recognition sequence are referred to.

Gene regulation: The term "gene regulation" or "gene expression" refers to the processes that cells use to regulate the way that the information in genes is turned into gene products. Gene regulation may occur in any of the following stages of gene expression: transcription, post-transcriptional modification, RNA transport, translation, mRNA degradation, or post-translational modifications, among others. A gene's regulation may be modified by several ways as is well-known in the art. Any step of the gene's expression may be modified. In one embodiment, the gene regulation of a cell can be modified such that the gene is expressed differently as compared to the unaltered cell. For example, gene expression may be altered up or down by modifying gene regulation. In one embodiment, this modification changes the quantity or quality of the gene product produced. In one non-limiting example, the promoter of the gene is modified to alter gene regulation, but it should be understood that the definition is not limited to any particular mechanism of regulation of gene expression.

Expression State: The term "expression state" is a state in any specific tissue of any individual organism at any one time. Any change in conditions leading to changes in gene expression leads to another expression state. Different expression states are found in different individuals, in different species but they may also be found in different organs in the same species or individual, and in different tissue types in the same species or individual. Different expression states may also be obtained in the same organ or tissue in any one species or individual by exposing the tissues or organs to different environmental conditions comprising but not limited to changes in age, disease, infection, drought, humidity, salinity, exposure to xenobiotics, physiological effectors, temperature, pressure, pH, light, gaseous environment, chemicals such as toxins.

Artificial Chromosome: As used herein, an "artificial chromosome" (AC) is a piece of DNA that can stably replicate and segregate alongside endogenous chromosomes. For eukaryotes the artificial chromosome may also be described as a nucleotide sequence of substantial length comprising a functional centromer, functional telomeres, and at least one autonomous replicating sequence. It has the capacity to accommodate and express heterologous genes inserted therein. It is referred to as a mammalian artificial chromosome (MAC) when it contains an active mammalian centromere. Plant artificial chromosome and insect artificial chromosome (BUGAC) refer to chromosomes that include plant and insect centromers, respectively. A human artificial chromosome (HAC) refers to a chromosome that includes human centromeres, AVACs refer to avian artificial chromosomes. A yeast artificial chromosome (YAC) refers to chromosomes are functional in yeast, such as chromosomes that include a yeast centromere.

As used herein, stable maintenance of chromosomes occurs when at least about 85%, preferably 90%, more preferably 95% of the cells retain the chromosome. Stability is measured in the presence of a selective agent. Preferably these chromosomes are also maintained in the absence of a selective agent. Stable chromosomes also retain their structure during cell culturing, suffering neither intrachromosomal nor interchromosomal rearrangements.

Other terms used herein are defined throughout the specification.

DETAILED DESCRIPTION

All publications, patents and patent applications cited herein are hereby expressly incorporated by reference for all purposes. A detailed discussion of entry vectors, YAC construction, host cells, and transformation of host cells can be found in WO 02/059290, published Aug. 1, 2002; WO 02/059297, published Aug. 1, 2002; WO 2004/016791, published Feb. 26, 2004; WO 03/062419, published Jul. 31, 2003; and WO 02/059296, published Aug. 1, 2002 all of which are hereby incorporated by reference in their entirety.

Increasing prenyl phosphate availability for isoprenoid/terpenoid biosynthesis is one aspect of the provided disclosure. Attaining high yields of terpenoids/isoprenoids in any organism depends on attaining high yields of the prenyl phosphates (PPP), IPP (isopentenyl pyrophosphate), DMAPP (dimethylallyl pyrophosphate), FPP (farnesyl pyrophosphate), GPP (geranyl pyrophosphate) and GGPP (geranylgeranyl pyrophosphate).

Yeast is a convenient production organism, because its genetics is well-known and widely described, also because it is easy to work with and has "Generally Recognized As Safe" (GRAS) status. Reported productivities of terpenoids in yeast are modest however, ranging from 25 μg/l of the diterpenoid taxadien-5α-ol (DeJong et al., 2005, Biotechnol. Bioeng. 93: 212) to 153 mg/l of the sesquiterpenoid amorphadiene (Ro et al., 2006, Nature 440: 940).

Yeast has a cytosolic MEV pathway for the biosynthesis of prenyl phosphates (see FIG. 1). In this pathway, cytosolic acetyl-CoA is converted to IPP in a 6-step process under the consumption of ATP and NADPH. IPP can isomerise to DMAPP, these can combine to form GPP, GPP can combine with IPP to form FPP, and finally GGPP can be formed from IPP and FPP. The MEV pathway is one of the two known biosyntheses for prenyl phosphate production in fungi such as yeast. In Saccharomyces cerevisiae, however, the MEV pathway is heavily regulated, thus reducing the suitability of this yeast strain to produce large quantities of isoprenoids. One problem is the low amounts of synthesis of the enzyme acetyl-CoA. Acetyl-CoA is biosynthesized in the cytoplasm, but the rather low concentrations limit the amount of PPP that can be produced by the MEV pathway. Because most fungi produce somewhat modest amounts of acetyl-CoA, the challenge in the biosynthesis of terpenoid molecules in yeast is attaining adequate levels of acetyl-CoA in the cytosol, thus presenting significant limitations to prenyl phosphate production and terpenoid biosynthesis via the mevalonate pathway. Only oleaginous fungi have high cytosolic acetyl-CoA concentrations, but none of these are amenable to advanced molecular biology. Non-oleaginous fungi and yeast produce cytosolic acetyl-CoA through the "pyruvate dehydrogenase by-pass" in which pyruvate is converted to acetyl-CoA through the intermediates acetaldehyde and acetate. To date, no studies have proven effective in increasing the production of acetyl-CoA in S. cerevisiae. One study tested over-expression of non-regulated bacterial acetyl-CoA enzyme in yeast, but only attained a 4-fold increase in activity of this enzyme, even with concomitant over-expression of yeast aldehyde reductase (Shiba et al. (2007, Metabolic Engineering 9: 160).

Another significant problem for S. cerevisiae commercial production of terpenoids via the MEV pathway is the activity of cellular prenyl phosphate, which converts prenyl phosphate to ergosterol. Prenyl phosphates are made from acetyl-CoA by the MEV pathway. Paradise et al. (2008, Biotechnol Bioeng. 100: 371) showed that by decreasing the enzymatic activity for the first step from IPP towards ergosterol by 80%, and combining with two modifications of the mevalonate biosynthesis pathway, a 20-fold increase in production of an FPP-dependent sesquiterpenoid was seen. However, for terpenoid biosynthesis, such prenyl phosphate production levels are too low to attain commercial production in yeast of any interesting terpenoid molecule.

Introducing Mevalonate Pathway Gene Analogs

In one aspect, a novel combination of heterologous gene analogs are provided for increased PPP production via the mevalonate pathway. A recombinant yeast host cell is also provided comprising one or more heterologous enzymes for increased PPP production via the mevalonate pathway. The expression of these gene analogs increase PPP production by overriding the native regulation mechanisms working on the inherent yeast mevalonate pathway enzymes, surprisingly providing for about five times higher production relative to the wild-type yeast cell.

In one embodiment, improved conversion of acetyl-CoA to PPP in yeast is achieved by simultaneously expressing five taxonomically diverse functional analogs of each of the six Saccharomyces cerevisiae mevalonate pathway enzymes: acetyl-CoA C-acetyltransferase, 3-hydroxy-3-methylglutaryl-CoA synthase, 3-hydroxy-3-methylglutaryl-coenzyme A reductase, mevalonate kinase, phosphomevalonate kinase, diphosphomevalonate decarboxylase and the isopentenyl diphosphate:dimethylallyl diphosphate isomerase. In certain embodiments, these gene analogs come from other yeast strains. See Table 1 for a list of non-limiting examples of the MEV enzyme gene analogs. DNA sequences of the optimized MEV gene analogs can be found in Table 6. Protein sequences of the optimized MEV analogs can be found in Table 7.

TABLE 1

Examples of the MEV enzyme gene analogs and corresponding plasmids pMEV-1 to pMEV-35

| Accession # | Organism | Enzyme | Size (nt) | Gene Name | Construct |
| --- | --- | --- | --- | --- | --- |
| NM_001022609 | Schizosaccharomyces pombe | Acetyl-CoA C-acetyltransferase | 1188 | MEV-1 | pMEV-1 |
| NM_001046075 | Bos taurus | Acetyl-CoA C-acetyltransferase | 1269 | MEV-2 | pMEV-2 |
| X78116 | Saxa knacker | Acetyl-CoA C-acetyltransferase | 1221 | MEV-3 | pMEV-3 |

TABLE 1-continued

Examples of the MEV enzyme gene analogs and corresponding plasmids pMEV-1 to pMEV-35

| Accession # | Organism | Enzyme | Size (nt) | Gene Name | Construct |
|---|---|---|---|---|---|
| XM_001467423 | *Leishmania infantum* | Acetyl-CoA C-acetyltransferase | 1323 | MEV-4 | pMEV-4 |
| CAI80214 | *Staphylococcus aureus* | Acetyl-CoA C-acetyltransferase | 1140 | MEV-5 | pMEV-5 |
| XM_001831228 | *Coprinopsis cinerea* | 3-hydroxy-3-methylglutaryl-CoA synthase | 1422 | MEV-6 | pMEV-6 |
| NM_001045883 | *Bos taurus* | 3-hydroxy-3-methylglutaryl-CoA synthase | 1527 | MEV-7 | pMEV-7 |
| EF636813 | *Nicotiana hybrid* | 3-hydroxy-3-methylglutaryl-CoA synthase | 1389 | MEV-8 | pMEV-8 |
| XM_001683677 | *Leishmania major* | 3-hydroxy-3-methylglutaryl-CoA synthase | 1506 | MEV-9 | pMEV-9 |
| YP_001443120 | *Staphylococcus aureus* | 3-hydroxy-3-methylglutaryl-CoA synthase | 1167 | MEV-10 | pMEV-10 |
| EU263989 | *Ganoderma lucidum* | 3-Hydroxy-3-methylglutaryl-coenzyme A reductase | 3681 | MEV-11 | pMEV-11 |
| BC153262 | *Bos taurus* | 3-Hydroxy-3-methylglutaryl-coenzyme A reductase | 2667 | MEV-12 | pMEV-12 |
| AAD47596 | *Artemisia annua* | 3-Hydroxy-3-methylglutaryl-coenzyme A reductase | 1704 | MEV-13 | pMEV-13 |
| AAB62280 | *Trypanosoma cruzi* | 3-Hydroxy-3-methylglutaryl-coenzyme A reductase | 1308 | MEV-14 | pMEV-14 |
| CAG41604 | *Staphylococcus aureus* | 3-Hydroxy-3-methylglutaryl-coenzyme A reductase | 1281 | MEV-15 | pMEV-15 |
| XP_001836355 | *Coprinopsis cinerea* | Mevalonate kinase | 2745 | MEV-16 | pMEV-16 |
| BC104540 | *Bos taurus* | Mevalonate kinase | 1191 | MEV-17 | pMEV-17 |
| AB294693 | *Hevea brasiliensis* | Mevalonate kinase | 1161 | MEV-18 | pMEV-18 |
| AAX69523 | *Trypanosoma brucei* | Mevalonate kinase | 990 | MEV-19 | pMEV-19 |
| YP_001315773 | *Staphylococcus aureus* | Mevalonate kinase | 921 | MEV-20 | pMEV-20 |
| XP_001877360 | *Laccaria bicolor* | Phosphomevalonate kinase | 1476 | MEV-21 | pMEV-21 |
| BC112509 | *Bos taurus* | Phosphomevalonate kinase | 579 | MEV-22 | pMEV-22 |
| AF429385 | *Hevea brasiliensis* | Phosphomevalonate kinase | 1512 | MEV-23 | pMEV-23 |
| XP_803822 | *Trypanosoma brucei* | Phosphomevalonate kinase | 1416 | MEV-24 | pMEV-24 |
| YP_001315775 | *Staphylococcus aureus* | Phosphomevalonate kinase | 1077 | MEV-25 | pMEV-25 |
| XP_001830848 | *Coprinopsis cinerea* | Diphosphomevalonate decarboxylase | 1248 | MEV-26 | pMEV-26 |
| NM_001075424 | *Bos taurus* | Diphosphomevalonate decarboxylase | 1203 | MEV-27 | pMEV-27 |
| AY757921 | *Ginkgo biloba* | Diphosphomevalonate decarboxylase | 1293 | MEV-28 | pMEV-28 |
| XP_827840 | *Trypanosom brucei* | Diphosphomevalonate decarboxylase | 1149 | MEV-29 | pMEV-29 |
| ABR51487 | *Staphylococcus aureus* | Diphosphomevalonate decarboxylase | 984 | MEV-30 | pMEV-30 |
| SPU21154 | *Schizosaccharomyces pombe* | Isopentenyl diphosphate: dimethylallyl diphosphate isomerase | 684 | MEV-31 | pMEV-31 |
| NM_001075659 | *Bos taurus* | Isopentenyl diphosphate: dimethylallyl diphosphate isomerase | 864 | MEV-32 | pMEV-32 |
| DQ666334 | *Artemisia annua* | Isopentenyl diphosphate: dimethylallyl diphosphate isomerase | 855 | MEV-33 | pMEV-33 |
| AJ866772 | *Trypanosoma cruzi* | Isopentenyl diphosphate: dimethylallyl diphosphate isomerase | 1071 | MEV-34 | pMEV-34 |
| BAB21468 | *Staphylococcus aureus* | Isopentenyl diphosphate: dimethylallyl diphosphate isomerase | 1050 | MEV-35 | pMEV-35 |

As described herein, the steps of obtaining a transformed host cell containing an evolvable artificial chromosome may be performed, starting with the entry vector.

Origin of Expressible Nucleotide Sequences

The expressible nucleotide sequences that can be inserted into the vectors, concatemers, and cells encompass any type of nucleotide such as RNA, DNA. Such a nucleotide sequence could be obtained e.g. from cDNA, which by its nature is expressible. But it is also possible to use sequences of genomic DNA, coding for specific genes. Preferably, the expressible nucleotide sequences correspond to full length genes such as substantially full length cDNA, but nucleotide sequences coding for shorter peptides than the original full length mRNAs may also be used. Shorter peptides may still retain the catalytic activity similar to that of the native proteins.

Another way to obtain expressible nucleotide sequences is through chemical synthesis of nucleotide sequences coding for known peptide or protein sequences. Thus the expressible DNA sequences does not have to be a naturally occurring sequence, although it may be preferable for practical purposes to primarily use naturally occurring nucleotide sequences. Whether the DNA is single or double stranded will depend on the vector system used.

In most cases the orientation with respect to the promoter of an expressible nucleotide sequence will be such that the coding strand is transcribed into a proper mRNA. It is however conceivable that the sequence may be reversed generating an antisense transcript in order to block expression of a specific gene.

Cassettes

An important aspect of the invention concerns a cassette of nucleotides in a highly ordered sequence, the cassette having the general formula in 5' to 3' direction:

[RS1--RS2--SP--PR--CS-TR--SP--RS2'-RS1']

wherein RS1 and RS1' denote restriction sites, RS2 and RS2' denote restriction sites different from RS1 and RS1', SP individually denotes a spacer sequence of at least two nucleotides, PR denotes a promoter, CS denotes a cloning site, and TR denotes a terminator.

It is an advantage to have two different restriction sites flanking both sides of the expression construct. By treating the primary vectors with restriction enzymes cleaving both restriction sites, the expression construct and the primary vector will be left with two non-compatible ends. This facilitates a concatenation process, since the empty vectors do not participate in the concatenation of expression constructs.

In certain embodiments, the cassettes are linear. These linear cassettes are often cloned into entry vectors, as described.

Restriction Sites

In principle, any restriction site, for which a restriction enzyme is known can be used. These include the restriction enzymes generally known and used in the field of molecular biology such as those described in Sambrook, Fritsch, Maniatis, "A laboratory Manual", 2nd edition. Cold Spring Harbor Laboratory Press, 1989.

The restriction site recognition sequences preferably are of a substantial length, so that the likelihood of occurrence of an identical restriction site within the cloned oligonucleotide is minimized. Thus the first restriction site may comprise at least 6 bases, but more preferably the recognition sequence comprises at least 7 or 8 bases. Restriction sites having 7 or more non N bases in the recognition sequence are generally known as "rare restriction sites". However, the recognition sequence may also be at least 10 bases, such as at least 15 bases, for example at least 16 bases, such as at least 17 bases, for example at least 18 bases, such as at least 18 bases, for example at least 19 bases, for example at least 20 bases, such as at least 21 bases, for example at least 22 bases, such as at least 23 bases, for example at least 25 bases, such as at least 30 bases, for example at least 35 bases, such as at least 40 bases, for example at least 45 bases, such as at least 50 bases.

Preferably the first restriction site RS1 and RS1' is recognized by a restriction enzyme generating blunt ends of the double stranded nucleotide sequences. By generating blunt ends at this site, the risk that the vector participates in a subsequent concatenation is greatly reduced. The first restriction site may also give rise to sticky ends, but these are then preferably non-compatible with the sticky ends resulting from the second restriction site, RS2 and RS2' and with the sticky ends in the AC.

According to one embodiment, the second restriction site, RS2 and RS2' comprises a rare restriction site. Thus, the longer the recognition sequence of the rare restriction site the more rare it is and the less likely is it that the restriction enzyme recognizing it will cleave the nucleotide sequence at other undesired positions.

The rare restriction site may furthermore serve as a PCR priming site. Thereby it is possible to copy the cassettes via PCR techniques and thus indirectly "excise" the cassettes from a vector.

Spacer Sequence

The spacer sequence located between the RS2 and the PR sequence is preferably a non-transcribed spacer sequence. The purpose of the spacer sequence(s) is to minimize recombination between different concatemers present in the same cell or between cassettes present in the same concatemer, but it may also serve the purpose of making the nucleotide sequences in the cassettes more "host" like. A further purpose of the spacer sequence is to reduce the occurrence of hairpin formation between adjacent palindromic sequences, which may occur when cassettes are assembled head to head or tail to tail. Spacer sequences may also be convenient for introducing short conserved nucleotide sequences that may serve e.g. as PCR primer sites or as target for hybridization to e.g. nucleic acid or PNA or LNA probes allowing affinity purification of cassettes.

The cassette may also optionally comprise another spacer sequence of at least two nucleotides between TR and RS2. When cassettes are cut out from a vector and concatenated into concatemers of cassettes, the spacer sequences together ensure that there is a certain distance between two successive identical promoter and/or terminator sequences. This distance may comprise at least 50 bases, such as at least 60 bases, for example at least 75 bases, such as at least 100 bases, for example at least 150 bases, such as at least 200 bases, for example at least 250 bases, such as at least 300 bases, for example at least 400 bases, for example at least 500 bases, such as at least 750 bases, for example at least 1000 bases, such as at least 1100 bases, for example at least 1200 bases, such as at least 1300 bases, for example at least 1400 bases, such as at least 1500 bases, for example at least 1600 bases, such as at least 1700 bases, for example at least 1800 bases, such as at least 1900 bases, for example at least 2000 bases, such as at least 2100 bases, for example at least 2200 bases, such as at least 2300 bases, for example at least 2400 bases, such as at least 2500 bases, for example at least 2600 bases, such as at least 2700 bases, for example at least 2800 bases, such as at least 2900 bases, for example at least 3000 bases, such as at least 3200 bases, for example at least 3500 bases, such as at least 3800 bases, for example at least 4000 bases, such as at least 4500 bases, for example at least 5000 bases, such as at least 6000 bases.

The number of the nucleotides between the spacer located 5' to the PR sequence and the one located 3' to the TR sequence may be any. However, it may be advantageous to ensure that at least one of the spacer sequences comprises between 100 and 2500 bases, preferably between 200 and 2300 bases, more preferably between 300 and 2100 bases, such as between 400 and 1900 bases, more preferably between 500 and 1700 bases, such as between 600 and 1500 bases, more preferably between 700 and 1400 bases.

If the intended host cell is yeast, the spacers present in a concatemer should comprise a combination of a few ARSes with varying lambda phage DNA fragments.

Preferred examples of spacer sequences include but are not limited to: A phage DNA, prokaryotic genomic DNA such as *E. coli* genomic DNA, ARSes.

Promoters

A promoter is a DNA sequence to which RNA polymerase binds and initiates transcription. The promoter determines the polarity of the transcript by specifying which strand will be transcribed.

Bacterial promoters normally consist of −35 and −10 (relative to the transcriptional start) consensus sequences which are bound by a specific sigma factor and RNA polymerase.

Eukaryotic promoters are more complex. Most promoters utilized in expression vectors are transcribed by RNA polymerase II. General transcription factors (GTFs) first bind specific sequences near the transcriptional start and then recruit the binding of RNA polymerase II. In addition to these minimal promoter elements, small sequence elements are recognized specifically by modular DNA-binding/transactivating proteins (e.g. AP-1, SP-1) which regulate the activity of a given promoter.

Viral promoters may serve the same function as bacterial and eukaryotic promoters. Upon viral infection of their host, viral promoters direct transcription either by using host transcriptional machinery or by supplying virally encoded enzymes to substitute part of the host machinery. Viral promoters are recognised by the transcriptional machinery of a large number of host organisms and are therefore often used in cloning and expression vectors.

Promoters may furthermore comprise regulatory elements, which are DNA sequence elements which act in conjunction with promoters and bind either repressors (e.g., lacO/LAC Iq repressor system in *E. coli*) or inducers (e.g., gal1/GAL4 inducer system in yeast). In either case, transcription is virtually "shut off" until the promoter is derepressed or induced, at which point transcription is "turned-on". The choice of promoter in the cassette is primarily dependent on the host organism into which the cassette is intended to be inserted. An important requirement to this end is that the promoter should preferably be capable of functioning in the host cell, in which the expressible nucleotide sequence is to be expressed.

In one embodiment, the promoter is an externally controllable promoter, such as an inducible promoter and/or a repressible promoter. The promoter may be either controllable (repressible/inducible) by chemicals such as the absence/presence of chemical inducers, e.g. metabolites, substrates, metals, hormones, sugars. The promoter may likewise be controllable by certain physical parameters such as temperature, pH, redox status, growth stage, developmental stage, or the promoter may be inducible/repressible by a synthetic inducer/repressor such as the gal inducer.

In order to avoid unintentional interference with the gene regulation systems of the host cell, and in order to improve controllability of the coordinated gene expression the promoter is preferably a synthetic promoter. Suitable promoters are described in U.S. Pat. No. 5,798,227, U.S. Pat. No. 5,667,986. Principles for designing suitable synthetic eukaryotic promoters are disclosed in U.S. Pat. No. 5,559,027, U.S. Pat. No. 5,877,018 or U.S. Pat. No. 6,072,050.

Synthetic inducible eukaryotic promoters for the regulation of transcription of a gene may achieve improved levels of protein expression and lower basal levels of gene expression. Such promoters preferably contain at least two different classes of regulatory elements, usually by modification of a native promoter containing one of the inducible elements by inserting the other of the inducible elements. For example, additional metal responsive elements) and/or glucocorticoid responsive elements (GREs) may be provided to native promoters. Additionally, one or more constitutive elements may be functionally disabled to provide the lower basal levels of gene expression.

Non-limiting examples of promoters include those promoters being induced and/or repressed by any factor selected from the group comprising carbohydrates, e.g. galactose; low inorganic phosphase levels; temperature, e.g. low or high temperature shift; metals or metal ions, e.g. copper ions; hormones, e.g. dihydrotestosterone; deoxycorticosterone; heat shock (e.g. 39.degree. C.); methanol; redox-status; growth stage, e.g. developmental stage; synthetic inducers, e.g. gal inducer. Examples of such promoters include ADH 1, PGK 1, GAP 491, TPI, PYK, ENO, PMA 1, PHO5, GAL 1, GAL 2, GAL 10, MET25, ADH2, MEL 1, CUP 1, HSE, AOX, MOX, SV40, CaMV, Opaque-2, GRE, ARE, PGK/ARE hybrid, CYC/GRE hybrid, TPI/α2 operator, AOX 1, MOX A.

In one embodiment, the promoter is selected from hybrid promoters such as PGK/ARE hybrid, CYC/GRE hybrid or from synthetic promoters. Such promoters can be controlled without interfering too much with the regulation of native genes in the expression host.

In one embodiment, the promoter is a methionine dependent promoter. In another embodiment, the promoter is the MET25 promoter, which is repressed when cells are grown in the presence of methionine. In another embodiment, the promoter is MET2. In another embodiment, the promoter is MET14. These MET promoters have previously been found to exhibit expression patterns in S. cerevisiae similar to the native MET25 promoter.

Yeast Promoters

In the following, examples of known yeast promoters that may be used in conjunction are described. The examples are by no way limiting and only serve to indicate to the skilled practitioner how to select or design promoters that are useful.

Although numerous transcriptional promoters which are functional in yeasts have been described in the literature, only some of them have proved effective for the production of polypeptides by the recombinant route. There may be mentioned in particular the promoters of the PGK genes (3-phosphoglycerate kinase, TDH genes encoding GAPDH (Glyceraldehyde phosphate dehydrogenase), TEF1 genes (Elongation factor 1), MF-alpha-1 (alpha sex pheromone precursor) which are considered as strong constitutive promoters or alternatively the regulatable promoter CYCI which is repressed in the presence of glucose or PHO5 which can be regulated by thiamine. However, for reasons which are often unexplained, they do not always allow the effective expression of the genes which they control. In this context, it is always advantageous to be able to have new promoters in order to generate new effective host/vector systems. Furthermore, having a choice of effective promoters in a given cell also makes it possible to envisage the production of multiple proteins in this same cell (for example several enzymes of the same metabolic chain) while avoiding the problems of recombination between homologous sequences.

In general, a promoter region is situated in the 5' region of the genes and comprises all the elements allowing the transcription of a DNA fragment placed under their control, in particular:

(1) a promoter region comprising the TATA box and the site of initiation of transcription, which determines the position of the site of initiation as well as the basal level of transcription. In *Saccharomyces cerevisiae*, the length of the minimal promoter region is relatively variable. Indeed, the exact location of the TATA box varies from one gene to another and may be situated from −40 to −120 nucleotides upstream of the site of the initiation (Chen and Struhl, 1985, EMBO J., 4, 3273-3280)

(2) sequences situated upstream of the TATA box (immediately upstream up to several hundreds of nucleotides) which make it possible to ensure an effective level of transcription either constitutively (relatively constant level of transcription all along the cell cycle, regardless of the conditions of culture) or in a regulatable manner (activation of transcription in the presence of an activator and/or repression in the presence of a repressor). These sequences, may be of several types: activator, inhibitor, enhancer, inducer, repressor and may respond to cellular factors or varied culture conditions.

Examples of such promoters are the ZZA1 and ZZA2 promoters disclosed in U.S. Pat. No. 5,641,661, the EF1-α protein promoter and the ribosomal protein S7 gene promoter disclosed in WO 97/44470, the COX 4 promoter and two unknown promoters disclosed in U.S. Pat. No. 5,952,195. Other useful promoters include the HSP150 promoter disclosed in WO 98/54339 and the SV40 and RSV promoters disclosed in U.S. Pat. No. 4,870,013 as well as the PyK and GAPDH promoters disclosed in EP 0 329 203 A1.

In one embodiment, the promoter is the inducible CUP1 promoter, which has a very low basal activity in the absence of copper ions.

Synthetic Yeast Promoters

Use of synthetic promoters may be employed. Synthetic promoters are often constructed by combining the minimal promoter region of one gene with the upstream regulating sequences of another gene. Enhanced promoter control may be obtained by modifying specific sequences in the upstream regulating sequences, e.g. through substitution or deletion or through inserting multiple copies of specific regulating sequences. One advantage of using synthetic promoters is that they may be controlled without interfering too much with the native promoters of the host cell.

One such synthetic yeast promoter comprises promoters or promoter elements of two different yeast-derived genes, yeast killer toxin leader peptide, and amino terminus of IL-1 β. (WO 98/54339).

Another example of a yeast synthetic promoter is disclosed in U.S. Pat. No. 5,436,136 (Hinnen et al), which concerns a yeast hybrid promoter including a 5' upstream promoter element comprising upstream activation site(s) of the yeast PHO5 gene and a 3' downstream promoter element of the yeast GAPDH gene starting at nucleotide −300 to −180 and ending at nucleotide −1 of the GAPDH gene.

Another example of a yeast synthetic promoter is disclosed in U.S. Pat. No. 5,089,398 (Rosenberg et al). This disclosure describes a promoter with the general formula—

(P.R.(2)-P.R.(1))— wherein:

P.R.(1) is the promoter region proximal to the coding sequence and having the transcription initiation site, the RNA polymerase binding site, and including the TATA box, the CAAT sequence, as well as translational regulatory signals, e.g., capping sequence, as appropriate;

P.R.(2) is the promoter region joined to the 5'-end of P.R.(1) associated with enhancing the efficiency of transcription of the RNA polymerase binding region.

In U.S. Pat. No. 4,945,046 (Horii et al) discloses a further example of how to design a synthetic yeast promoter. This specific promoter comprises promoter elements derived both from yeast and from a mammal. The hybrid promoter consists essentially of *Saccharomyces cerevisiae* PHO5 or GAP-DH promoter from which the upstream activation site (UAS) has been deleted and replaced by the early enhancer region derived from SV40 virus.

Cloning Site

The cloning site in the cassette in the primary vector should be designed so that any nucleotide sequence can be cloned into it.

The cloning site in the cassette preferably allows directional cloning. Hereby is ensured that transcription in a host cell is performed from the coding strand in the intended direction and that the translated peptide is identical to the peptide for which the original nucleotide sequence codes.

However according to some embodiments it may be advantageous to insert the sequence in opposite direction. According to these embodiments, so-called antisense constructs may be inserted which prevent functional expression of specific genes involved in specific pathways. Thereby it may become possible to divert metabolic intermediates from a prevalent pathway to another less dominant pathway.

The cloning site in the cassette may comprise multiple cloning sites, generally known as MCS or polylinker sites, which is a synthetic DNA sequence encoding a series of restriction endonuclease recognition sites. These sites are engineered for convenient cloning of DNA into a vector at a specific position and for directional cloning of the insert.

Cloning of cDNA does not have to involve the use of restriction enzymes. Other alternative systems include but are not limited to the Creator™ Cre-loxP system from Clontech, which uses recombination and loxP sites, or use of Lambda attachment sites (att-λ), such as the Gateway™ system from Life Technologies. Both of these systems are directional.

Terminator

The role of the terminator sequence is to limit transcription to the length of the coding sequence. An optimal terminator sequence is thus one, which is capable of performing this act in the host cell.

In prokaryotes, sequences known as transcriptional terminators signal the RNA polymerase to release the DNA template and stop transcription of the nascent RNA.

In eukaryotes, RNA molecules are transcribed well beyond the end of the mature mRNA molecule. New transcripts are enzymatically cleaved and modified by the addition of a long sequence of adenylic acid residues known as the poly-A tail. A polyadenylation consensus sequence is located about 10 to 30 bases upstream from the actual cleavage site.

Preferred examples of yeast derived terminator sequences include, but are not limited to: ADN1, CYC1, GPD, ADH1 alcohol dehydrogenase.

Intron

Optionally, the cassette in the vector comprises an intron sequence, which may be located 5' or 3' to the expressible nucleotide sequence. The design and layout of introns is well known in the art. The choice of intron design largely depends on the intended host cell, in which the expressible nucleotide sequence is eventually to be expressed. The effects of having intron sequence in the expression cassettes are those generally associated with intron sequences.

Examples of yeast introns can be found in the literature and in specific databases such as Ares Lab Yeast Intron Database (Version 2.1) as updated on 15 Apr. 2000. Earlier versions of the database as well as extracts of the database have been published in: "Genome-wide bioinformatic and molecular analysis of introns in *Saccharomyces cerevisiae*." by Spingola M, Grate L, Haussler D, Ares M Jr. (RNA February 1999; 5(2):221-34) and "Test of intron predictions reveals novel splice sites, alternatively spliced mRNAs and new introns in meiotically regulated genes of yeast." by Davis C A, Grate L, Spingola M, Ares M Jr, (Nucleic Acids Res Apr. 15, 2000; 28(8):1700-6).

Primary Vectors (Entry Vectors)

The term "Entry Vector" is meant a vector for storing and amplifying cDNA or other expressible nucleotide sequences using the cassettes. The primary vectors are preferably able to propagate in *E. coli* or any other suitable standard host cell. It should preferably be amplifiable and amenable to standard normalization and enrichment procedures.

The primary vector may be of any type of DNA that has the basic requirements of a) being able to replicate itself in at least one suitable host organism and b) allows insertion of foreign DNA which is then replicated together with the vector and c) preferably allows selection of vector molecules that contain insertions of said foreign DNA. In a preferred embodiment the vector is able to replicate in standard hosts like yeasts, and bacteria and it should preferably have a high copy number per host cell. It is also preferred that the vector in addition to a host specific origin of replication, contains an origin of replication for a single stranded virus, such as e.g. the f1 origin for filamentous phages. This will allow the production of single stranded nucleic acid which may be useful for normalization and enrichment procedures of cloned sequences. A vast number of cloning vectors have been described which are commonly used and references may be given to e.g. Sambrook, J; Fritsch, E. F; and Maniatis T. (1989) Molecular Cloning: A laboratory manual. Cold Spring Harbor Laboratory Press, USA, Netherlands Culture Collection of Bacteria (www.cbs.knaw.nl/NCCB/collection.htm) or Department of Microbial Genetics, National Institute of Genetics, Yata 1111 Mishima Shizuoka 411-8540, Japan (www.shigen.nig.ac.jp/cvector/cvector.html). A few type-examples that are the parents of many popular derivatives are M13 mp 10, pUC18, λ gt 10, and pYAC4. Examples of primary vectors include but are not limited to M13K07, pBR322, pUC18, pUC19, pUC118, pUC119, pSP64, pSP65, pGEM-3, pGEM-3Z, pGEM-3Zf(−), pGEM4, pGEM-4Z, TrAN13, pBluescript II, CHARON 4A, λ.sup.+, CHARON 21A, CHARON 32, CHARON 33, CHARON 34, CHARON 35, CHARON 40, EMBL3A, λ2001, λDASH, λFIX, λgt10, λgt11, λgt18, λgt20, λgt22, λORF8, λZAP/R, pJB8, c2RB, pcos1EMBL.

Methods for cloning of cDNA or genomic DNA into a vector are well known in the art. Reference may be given to J. Sambrook, E. F. Fritsch, T. Maniatis: Molecular Cloning, A Laboratory Manual (2nd edition, Cold Spring Harbor Laboratory Press, 1989).

Nucleotide Library (Entry Library)

Methods as well as suitable vectors and host cells for constructing and maintaining a library of nucleotide sequences in a cell are well known in the art. The primary requirement for the library is that it should be possible to store and amplify in it a number of primary vectors (constructs), the vectors (constructs) comprising expressible nucleotide sequences from at least one expression state and wherein at least two vectors (constructs) are different.

One specific example of such a library is the well-known and widely employed cDNA libraries. The advantage of the cDNA library is mainly that it contains only DNA sequences corresponding to transcribed messenger RNA in a cell. Suitable methods are also present to purify the isolated mRNA or the synthesized cDNA so that only substantially full-length cDNA is cloned into the library.

Methods for optimization of the process to yield substantially full length cDNA may comprise size selection, e.g. electrophoresis, chromatography, precipitation or may comprise ways of increasing the likelihood of getting full length cDNAs, e.g. the SMART™ method (Clonetech) or the CapTrap™ method (Stratagene).

Preferably the method for making the nucleotide library comprises obtaining a substantially full length cDNA population comprising a normalised representation of cDNA species. More preferably a substantially full length cDNA population comprises a normalised representation of cDNA species characteristic of a given expression state.

Normalization reduces the redundancy of clones representing abundant mRNA species and increases the relative representation of clones from rare mRNA species.

Methods for normalisation of cDNA libraries are well known in the art. Reference may be given to suitable protocols for normalisation such as those described in U.S. Pat. No. 5,763,239 (DIVERSA) and WO 95/08647 and WO 95/11986. and Bonaldo, Lennon, Soares, Genome Research 1996, 6:791-806; Ali, Holloway, Taylor, Plant Mol Biol Reporter, 2000, 18:123-132.

Enrichment methods are used to isolate clones representing mRNA which are characteristic of a particular expression state. A number of variations of the method broadly termed as subtractive hybrisation are known in the art. Reference may be given to Sive, John, Nucleic Acid Res, 1988, 16:10937; Diatchenko, Lau, Campbell et al, PNAS, 1996, 93:6025-6030; Caminci, Shibata, Hayatsu, Genome Res, 2000, 10:1617-30, Bonaldo, Lennon, Soares, Genome Research 1996, 6:791-806; Ali, Holloway, Taylor, Plant Mol Biol Reporter, 2000, 18:123-132. For example, enrichment may be achieved by doing additional rounds of hybridization similar to normalization procedures, using e.g. cDNA from a library of abundant clones or simply a library representing the uninduced state as a driver against a tester library from the induced state. Alternatively mRNA or PCR amplified cDNA derived from the expression state of choice can be used to subtract common sequences from a tester library. The choice of driver and tester population will depend on the nature of target expressible nucleotide sequences in each particular experiment.

In the library an expressible nucleotide sequence coding for one peptide is preferably found in different but similar vectors under the control of different promoters. Preferably the library comprises at least three primary vectors with an expressible nucleotide sequence coding for the same peptide under the control of three different promoters. More preferably the library comprises at least four primary vectors with an expressible nucleotide sequence coding for the same peptide under the control of four different promoters. More preferably the library comprises at least five primary vectors with an expressible nucleotide sequence coding for the same peptide under the control of five different promoters, such as comprises at least six primary vectors with an expressible nucleotide sequence coding for the same peptide under the control of six different promoters, for example comprises at least seven primary vectors with an expressible nucleotide sequence coding for the same peptide under the control of seven different promoters, for example comprises at least eight primary vectors with an expressible nucleotide sequence coding for the same peptide under the control of eight different promoters, such as comprises at least nine primary vectors with an expressible nucleotide sequence coding for the same peptide under the control of nine different promoters, for example comprises at least ten primary vectors with an expressible nucleotide sequence coding for the same peptide under the control of ten different promoters.

The expressible nucleotide sequence coding for the same peptide preferably comprises essentially the same nucleotide sequence, more preferably the same nucleotide sequence.

By having a library with what may be termed one gene under the control of a number of different promoters in different vectors, it is possible to construct from the nucleotide library an array of combinations of genes and promoters. Preferably, one library comprises a complete or substantially complete combination such as a two dimensional array of genes and promoters, wherein substantially all genes are found under the control of substantially all of a selected number of promoters.

According to another embodiment, the nucleotide library comprises combinations of expressible nucleotide sequences combined in different vectors with different spacer sequences and/or different intron sequences. Thus any one expressible nucleotide sequence may be combined in a two, three, four or five dimensional array with different promoters and/or different spacers and/or different introns and/or different terminators. The two, three, four or five dimensional array may be complete or incomplete, since not all combinations will have to be present.

The library may suitably be maintained in a host cell comprising prokaryotic cells or eukaryotic cells. Preferred prokaryotic host organisms may include but are not limited to *Escherichia coli, Bacillus subtilis, Streptomyces lividans, Streptomyces coelicolor Pseudomonas aeruginosa, Myxococcus xanthus*.

Yeast species such as *Saccharomyces cerevisiae* (budding yeast), *Schizosaccharomyces pombe* (fission yeast), *Pichia pastoris*, and *Hansenula polymorpha* (methylotropic yeasts) may also be used. *Filamentous ascomycetes*, such as *Neurospora crassa* and *Aspergillus nidulans* may also be used. Plant cells such as those derived from *Nicotiana* and *Arabidopsis* are preferred. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York, Freeman & Co. 1990).

Concatemers

In certain embodiments, the analog genes of the MEV pathway are inserted into expression cassettes together with regulatory sequences including one or more promoters, then liberated to produce concatemers. In some embodiments, each concatemer contains between 20 and 25 of these gene cassettes.

A concatemer is a series of linked units. In the present context a concatemer is used to denote a number of serially linked nucleotide cassettes, wherein at least two of the serially linked nucleotide units comprises a cassette having the basic structure: [rs$_2$-SP-PR-X-TR-SP-rs$_1$]
wherein
rs$_1$ and rs$_2$ together denote a restriction site,
SP individually denotes a spacer of at least two nucleotide bases,
PR denotes a promoter, capable of functioning in a cell,
X denotes an expressible nucleotide sequence,
TR denotes a terminator, and
SP individually denotes a spacer of at least two nucleotide bases.

Optionally the cassettes comprise an intron sequence between the promoter and the expressible nucleotide sequence and/or between the terminator and the expressible sequence.

The expressible nucleotide sequence in the cassettes of the concatemer may comprise a DNA sequence selected from the group comprising cDNA and genomic DNA.

According to one aspect, a concatemer comprises cassettes with expressible nucleotide from different expression states, so that non-naturally occurring combinations or non-native combinations of expressible nucleotide sequences are obtained. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

For example, the expressible nucleotide sequences may originate from eukaryotic organisms such as mammals such as humans, mice or whale, from reptiles such as snakes crocodiles or turtles, from tunicates such as sea squirts, from lepidoptera such as butterflies and moths, from coelenterates such as jellyfish, anenomes, or corals, from fish such as bony and cartilaginous fish, from plants such as dicots, e.g. coffee, oak or monocots such as grasses, lilies, and orchids; from lower plants such as algae and gingko, from higher fungi such as terrestrial fruiting fungi, from marine actinomycetes. The expressible nucleotide sequences may also originate from protozoans such as malaria or trypanosomes, or from prokaryotes such as *E. coli* or archaebacteria.

Furthermore, the expressible nucleotide sequences may originate from one or more expression states from the following non-limiting list of species and genera: Bacteria *Streptomyces, Micromonospora, Norcadia, Actinomadura, Actinoplanes, Streptosporangium, Microbispora, Kitasatosporiam, Azobacterium, Rhizobium, Achromobacterium, Enterobacterium, Brucella, Micrococcus, Lactobacillus, Bacillus* (B.t. toxins), *Clostridium* (toxins), *Brevibacterium, Pseudomonas, Aerobacter, Vibrio, Halobacterium, Mycoplasma, Cytophaga, Myxococcus* Fungi *Amanita muscaria* (fly agaric, ibotenic acid, muscimol), *Psilocybe* (psilocybin) *Physarium, Fuligo, Mucor, Phytophtora, Rhizopus, Aspergillus, Penicillium* (penicillin), *Coprinus, Phanerochaete, Acremonium* (Cephalosporin), *Trochoderma, Helminthosporium, Fusarium, Alternaria, Myrothecium, Saccharomyces* Algae *Digenea simplex* (kainic acid, antihelminthic), *Laminaria anqustata* (laminine, hypotensive) Lichens *Usnea fasciata* (vulpinicacid, antimicrobial; usnic acid, antitumor) Higher *Artemisia* (artemisinin), *Coleus* (forskolin), *Desmodium* (K channel agonist), Plants *Catharanthus* (Vince alkaloids), *Digitalis* (cardiac glycosides), *Podophyllum* (podophyllotoxin), *Taxus* (taxol), *Cephalotaxus* (homoharringtonine), *Camptotheca* (Camptothecin), *Camellia sinensis* (Tea), *Cannabis indica, Cannabis sativa* (Hemp), *Erythroxylum coca* (Coca), *Lophosphora williamsii* (Peyote *Myristica fragrans* (Nutmeg), *Nicotiana, Papaver somniferum* (Opium Poppy), *Phalaris arundinacea* (Reed canary grass) Protozoa *Ptychodiscus brevis;* Dinoflagellates (brevitoxin, cardiovascular) Sponges *Microciona prolifera* (ectyonin, antimicrobial) *Cryptotethya cryta* (D-arabino furanosides) *Coelenterata* Portuguese Man o War & other jellyfish and medusoid toxins. Corals *Pseudoterogonia* species (Pseudoteracins, anti-inflammatory), *Erythropodium* (erythrolides, anti-inflammatory) Aschelminths Nematode secretory compounds *Molluscs Conus* toxins, sea slug toxins, cephalopod neurotransmitters, squid inks *Annelida Lumbriconereis heteropa* (nereistoxin, insecticidal) *Arachnids Dolomedes* ("fishing spider" venoms) *Crustacea Xenobalanus* (skin adhesives) Insects *Epilachna* (mexican bean beetle alkaloids) *Spinunculida Bonellia viridis* (bonellin, neuroactive) *Bryozoans Bugula neritina* (bryostatins, anti-cancer) *Echinoderms Crinoid* chemistry *Tunicates Trididemnum solidum* (didemnin, anti-tumor and anti-viral; *Ecteinascidia turbinata ecteinascidins*, anti-tumor) *Vertebrates Eptatretus stoutii* (eptatretin, cardioactive), *Trachinus draco* (proteinaceous toxins, reduce blood pressure, respiration and reduce heart rate). Dendrobatid frogs (batrachotoxins, pumiliotoxins, histrionicotoxins, and other polyamines); Snake venom toxins; *Orinthorhynohus anatinus* (duck-billed platypus venom), modified carotenoids, retinoids and steroids; Avians: histrionicotoxins, modified carotenoids, retinoids and steroids.

According to one embodiment, the concatemer comprises at least a first cassette and a second cassette, said first cassette being different from said second cassette. More preferably, the concatemer comprises cassettes, wherein substantially all cassettes are different. The difference between the cassettes may arise from differences between promoters, and/or expressible nucleotide sequences, and/or spacers, and/or terminators, and/or introns.

The number of cassettes in a single concatemer is largely determined by the host species into which the concatemer is eventually to be inserted and the vector through which the insertion is carried out The concatemer thus may comprise at least 10 cassettes, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000 cassettes.

Once the concatemer has been assembled or concatenated it may be ligated into a suitable vector. Such a vector may advantageously comprise an artificial chromosome. The basic requirements for a functional artificial chromosome have been described in U.S. Pat. No. 4,464,472, the contents of which is hereby incorporated by reference. An artificial chromosome or a functional minichromosome, as it may also be termed must comprise a DNA sequence capable of replication and stable mitotic maintenance in a host cell comprising a DNA segment coding for centromere-like activity during mitosis of said host and a DNA sequence coding for a replication site recognized by said host.

In certain embodiments, the analog genes of the MEV pathway are synthesized into expression Yeast Artificial Chromosome (eYACS).

Suitable artificial chromosomes include a Yeast Artificial Chromosome (YAC) (see e.g. Murray et al, Nature 305:189-193; or U.S. Pat. No. 4,464,472), a mega Yeast Artificial Chromosome (mega YAC), a Bacterial Artificial Chromosome (BAC), a mouse artificial chromosome, a Mammalian Artificial Chromosome (MAC) (see e.g. U.S. Pat. No. 6,133,503 or U.S. Pat. No. 6,077,697), an Insect Artificial Chromosome (BUGAC), an Avian Artificial Chromosome (AVAC), a Bacteriophage Artificial Chromosome, a Baculovirus Artificial Chromosome, a plant artificial chromosome (U.S. Pat. No. 5,270,201), a BIBAC vector (U.S. Pat. No. 5,977,439) or a Human Artificial Chromosome (HAC).

The artificial chromosome is preferably so large that the host cell perceives it as a "real" chromosome and maintains it and transmits it as a chromosome. For yeast and other suitable host species, this will often correspond approximately to the size of the smallest native chromosome in the species. For *Saccharomyces*, the smallest chromosome has a size of 225 Kb.

MACs may be used to construct artificial chromosomes from other species, such as insect and fish species. The artificial chromosomes preferably are fully functional stable chromosomes. Two types of artificial chromosomes may be used. One type, referred to as SATACs [satellite artificial chromosomes] are stable heterochromatic chromosomes, and the other type are minichromosomes based on amplification of euchromatin.

Mammalian artificial chromosomes provide extra-genomic specific integration sites for introduction of genes encoding proteins of interest and permit megabase size DNA integration, such as integration of concatemers.

According to another embodiment, the concatemer may be integrated into the host chromosomes or cloned into other types of vectors, such as a plasmid vector, a phage vector, a viral vector or a cosmid vector.

A preferable artificial chromosome vector is one that is capable of being conditionally amplified in the host cell, e.g. in yeast. The amplification preferably is at least a 10 fold amplification. Furthermore, it is advantageous that the cloning site of the artificial chromosome vector can be modified to comprise the same restriction site as the one bordering the cassettes described above, i.e. RS2 and/or RS2'.

Concatenation

Cassettes to be concatenated are normally excised from a vector either by digestion with restriction enzymes or by PCR. After excision the cassettes may be separated from the vector through size fractionation such as gel filtration or through tagging of known sequences in the cassettes. The isolated cassettes may then be joined together either through interaction between sticky ends or through ligation of blunt ends.

Single-stranded compatible ends may be created by digestion with restriction enzymes. For concatenation a preferred enzyme for excising the cassettes would be a rare cutter, i.e. an enzyme that recognizes a sequence of 7 or more nucleotides. Examples of enzymes that cut very rarely are the meganucleases, many of which are intron encoded, like e.g. I-Ceu I, I-Sce I, I-Ppo I, and PI-Psp I. Other preferred enzymes recognize a sequence of 8 nucleotides like e.g. Asc I, AsiS I, CciN I, CspB I, Fse I, MchA I, Not I, Pac I, Sbf I, Sda I, Sgf I, SgrA I, Sse232 I, and Sse8387 I, all of which create single stranded, palindromic compatible ends.

Other preferred rare cutters, which may also be used to control orientation of individual cassettes in the concatemer are enzymes that recognize non-palindromic sequences like e.g. Aar I, Sap I, Sfi I, Sdi I, and Vpa (see WO 02059297, Example 6 for others).

Alternatively, cassettes can be prepared by the addition of restriction sites to the ends, e.g. by PCR or ligation to linkers (short synthetic dsDNA molecules). Restriction enzymes are continuously being isolated and characterized and it is anticipated that many of such novel enzymes can be used to generate single-stranded compatible ends as described.

It is conceivable that single stranded compatible ends can be made by cleaving the vector with synthetic cutters. Thus, a reactive chemical group that will normally be able to cleave DNA unspecifically can cut at specific positions when coupled to another molecule that recognizes and binds to specific sequences. Examples of molecules that recognize specific dsDNA sequences are DNA, PNA, LNA, phosphothioates, peptides, and amides. See e.g. Armitage, B.(1998) Chem. Rev. 98: 1171-1200, who describes photocleavage using e.g. anthraquinone and UV light; Dervan P. B. & Burli R. W. (1999) Curr. Opin. Chem. Biol. 3: 688-93 describes the specific binding of polyamides to DNA; Nielsen, P. E. (2001) Curr. Opin. Biotechnol. 12: 16-20 describes the specific binding of PNA to DNA, and Chemical Reviews special thematic issue: RNA/DNA Cleavage (1998) vol. 98 (3) Bashkin J. K. (ed.) ACS publications, describes several examples of chemical DNA cleavers. Other rare cutters can be found in WO 02059297, particularly at Example 6.

Single-stranded compatible ends may also be created by using e.g. PCR primers including dUTP and then treating the PCR product with Uracil-DNA glycosylase (Ref: U.S. Pat. No. 5,035,996) to degrade part of the primer. Alternatively, compatible ends can be created by tailing both the vector and insert with complimentary nucleotides using Terminal Transferase (Chang, L M S, Bollum T J (1971) J Biol Chem 246:909).

It is also conceivable that recombination can be used to generate concatemers, e.g. through the modification of techniques like the Creator™ system (Clontech) which uses the Cre-loxP mechanism (Sauer B 1993 Methods Enzymol 225:890-900) to directionally join DNA molecules by recombination or like the Gateway™ system (Life Technologies, U.S. Pat. No. 5,888,732) using lambda aft attachment sites for directional recombination (Landy A 1989, Ann Rev Biochem 58:913). It is envisaged that also lambda cos site dependent systems can be developed to allow concatenation.

More preferably the cassettes may be concatenated without an intervening purification step through excision from a vector with two restriction enzymes, one leaving sticky ends on the cassettes and the other one leaving blunt ends in the vectors. This is the preferred method for concatenation of cassettes from vectors having the basic structure of [RS1-RS2-SP-PR--X-TR--SP--RS2'-RS1'].

An alternative way of producing concatemers free of vector sequences would be to PCR amplify the cassettes from a single-stranded primary vector. The PCR product must include the restriction sites RS2 and RS2' which are subsequently cleaved by its cognate enzyme(s). Concatenation can then be performed using the digested PCR product, essentially without interference from the single stranded primary vector template or the small double stranded fragments, which have been cut from the ends.

Preferably concatenation further comprises
starting from a primary vector [RS1-RS2-SP-PR--X-TR--SP--RS2'-RS1'-],
wherein X denotes an expressible nucleotide sequence,
RS1 and RS1' denote restriction sites,
RS2 and RS2' denote restriction sites different from RS1 and RS1', SP individually denotes a spacer sequence of at least two nucleotides, PR denotes a promoter, TR denotes a terminator, i) cutting the primary vector with the aid of at least one restriction enzyme specific for RS2 and RS2' obtaining cassettes having the general formula [rs$_2$-SP--PR--X-TR--SP-rs$_1$] wherein rs$_1$ and rs$_2$ together denote a functional restriction site RS2 or RS2', ii) assembling the cut out cassettes through interaction between rs$_1$ and rs$_2$.

In this way at least 10 cassettes can be concatenated, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000.

In some embodiments, the vector arms are artificial chromosome vector arms.

Stopper fragments may be added to the concatenation solution, the stopper fragments each having a RS2 or RS2' in one end and a non-complementary overhang or a blunt end in the other end. The ratio of stopper fragments to cassettes can likewise control the maximum size of the concatemer.

The complete sequence of steps to be taken when starting with the isolation of mRNA until inserting into an entry vector may include the following steps i) isolating mRNA from an expression state;

ii) obtaining substantially full length cDNA corresponding to the mRNA sequences, iii) inserting the substantially full length cDNA into a cloning site in a cassette in a primary vector, said cassette being of the general formula in 5' to 3' direction:

[RS1-RS2-SP--PR--CS-TR--SP--RS2'-RS1']

wherein CS denotes a cloning site.

In preparation of the concatemer, genes may be isolated from different entry libraries to provide the desired selection of genes. Accordingly, concatenation may further comprise selection of vectors having expressible nucleotide sequences from at least two different expression states, such as from two different species. The two different species may be from two different classes, such as from two different divisions, more preferably from two different sub-kingdoms, such as from two different kingdoms.

As an alternative to including vector arms in the concatenation reaction it is possible to ligate the concatemer into an artificial chromosome selected from the group comprising yeast artificial chromosome, mega yeast artificial chromosome, bacterial artificial chromosome, mouse artificial chromosome, human artificial chromosome.

Preferably at least one inserted concatemer further comprises a selectable marker. The marker(s) are conveniently not included in the concatemer as such but rather in an artificial chromosome vector, into which the concatemer is inserted. Selectable markers generally provide a means to select, for growth, only those cells which contain a vector. Such markers are of two types: drug resistance and auxotrophy. A drug resistance marker enables cells to grow in the presence of an otherwise toxic compound. Auxotrophic markers allow cells to grow in media lacking an essential component by enabling cells to synthesize the essential component (usually an amino acid).

Illustrative and non-limiting examples of common compounds for which selectable markers are available with a brief description of their mode of action follow:

Prokaryotic

Ampicillin: interferes with a terminal reaction in bacterial cell wall synthesis. The resistance gene (bla) encodes beta-lactamase which cleaves the beta-lactam ring of the antibiotic thus detoxifying it.

Tetracycline: prevents bacterial protein synthesis by binding to the 30S ribosomal subunit. The resistance gene (tet) specifies a protein that modifies the bacterial membrane and prevents accumulation of the antibiotic in the cell.

Kanamycin: binds to the 70S ribosomes and causes misreading of messenger RNA. The resistant gene (npth) modifies the antibiotic and prevents interaction with the ribosome.

Streptomycin: binds to the 30S ribosomal subunit, causing misreading of messenger RNA. The resistance gene (Sm) modifies the antibiotic and prevents interaction with the ribosome.

Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.

Eukaryotic

Hygromycin: a aminocyclitol that inhibits protein synthesis by disrupting ribosome translocation and promoting mistranslation. The resistance gene (hph) detoxifies hygromycin-B-phosphorylation.

Nourseothricin: the dihydrogensulphate of the weakly basic antibiotic nourseothricin, consisting of the components streptothricin F, E and D. Resistance is based on monoacetylation of β-amino groups of the β-lysyl moiety of the streptothricin molecules.

Histidinol: cytotoxic to mammalian cells by inhibiting histidyl-tRNA synthesis in histidine free media. The resistance gene (hisD) product inactivates histidinol toxicity by converting it to the essential amino acid, histidine.

Neomycin (G418): blocks protein synthesis by interfering with ribosomal functions. The resistance gene ADH encodes amino glycoside phosphotransferase which detoxifies G418.

Uracil: Laboratory yeast strains carrying a mutated gene which encodes orotidine-5'-phosphate decarboxylase, an enzyme essential for uracil biosynthesis, are unable to grow in the absence of exogenous uracil. A copy of the wild-type gene (ura4+, *S. pombe* or URA3 *S. cerevisiae*) carried on the vector will complement this defect in transformed cells.

Adenosine: Laboratory strains carrying a deficiency in adenosine synthesis may be complemented by a vector carrying the wild type gene, ADE 2.

Amino acids: Vectors carrying the wild-type genes for LEU2, TRP1, HIS3 or LYS2 may be used to complement strains of yeast deficient in these genes.

Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.

Transgenic Cells

In one aspect, the concatemers comprising the multitude of cassettes are introduced into a host cell, in which the concatemers can be maintained and the expressible nucleotide sequences can be expressed in a co-ordinated way. The cassettes comprised in the concatemers may be isolated from the host cell and re-assembled due to their uniform structure with—preferably—concatemer restriction sites between the cassettes.

The host cells selected for this purpose are preferably cultivable under standard laboratory conditions using standard culture conditions, such as standard media and protocols. Preferably the host cells comprise a substantially stable cell line, in which the concatemers can be maintained for generations of cell division. Standard techniques for transformation of the host cells and in particular methods for insertion of artificial chromosomes into the host cells are known.

Standard medium includes any media that can support cell growth, including but not limited to Synthetic Complete medium (SC), Hartwell's complete (HC) medium, (PDA) or potato dextrose broth, Wallerstein Laboratories nutrient (WLN) agar, yeast peptone dextrose agar (YPD), and yeast mould agar or broth (YM).

In one embodiment, the host cells are capable of undergoing meiosis to perform sexual recombination. It is also advantageous that meiosis is controllable through external manipulations of the cell culture. One especially advantageous host cell type is one where the cells can be manipulated through external manipulations into different mating types.

The genome of a number of species have already been sequenced more or less completely and the sequences can be found in databases. The list of species for which the whole genome has been sequenced increases constantly. Preferably the host cell is selected from the group of species, for which the whole genome or essentially the whole genome has been sequenced. The host cell should preferably be selected from a species that is well described in the literature with respect to genetics, metabolism, physiology such as model organism used for genomics research.

In one embodiment, the host organism should be conditionally deficient in the abilities to undergo homologous recombination. The host organism should preferably have a codon usage similar to that of the donor organisms. Furthermore, in the case of genomic DNA, if eukaryotic donor organisms are used, it is preferable that the host organism has the ability to process the donor messenger RNA properly, e.g., splice out introns.

The host cells can be bacterial, archaebacteria, or eukaryotic and can constitute a homogeneous cell line or mixed culture. Suitable cells include the bacterial and eukaryotic cell lines commonly used in genetic engineering and protein expression.

Example prokaryotic host organisms may include but are not limited to *Escherichia coli, Bacillus subtilis, B licehniformis, B. cereus, Streptomyces lividans, Streptomyces coelicolor, Pseudomonas aeruginosa, Myxococcus xanthus. Rhodococcus, Streptomycetes, Actinomycetes, Corynebacteria, Bacillus, Pseudomonas, Salmonella*, and *Erwinia*. The complete genome sequences of *E. coli* and *Bacillus subtilis* are described by Blattner et al., Science 277, 1454-1462 (1997); Kunst et al., Nature 390, 249-256 (1997)).

Example eukaryotic host organisms are mammals, fish, insects, plants, algae and fungi.

Examples of mammalian cells include those from, e.g., monkey, mouse, rat, hamster, primate, and human, both cell lines and primary cultures. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York. Freeman & Co. 1990), and stem cells, including embryonic stem cells and hemopoietic stem cells, zygotes, fibroblasts, lymphocytes, kidney, liver, muscle, and skin cells.

Examples of insect cells include baculo lepidoptera.

Examples of plant cells include maize, rice, wheat, cotton, soybean, and sugarcane. Plant cells such as those derived from *Nicotiana* and *Arabidopsis* are preferred Examples of fungi include *penicillium, aspergillus*, such as *Aspergillus nidulans, podospora, neurospora*, such as *Neurospora crassa, saccharomyces*, such as *Saccharomyces cerevisiae* (budding yeast), *Schizosaccharomyces*, such as *Schizosaccharomyces pombe* (fission yeast), *Pichia* spp, such as *Pichia pastoris*, and *Hansenula polymorpha* (methylotropic yeasts).

In one embodiment the host cell is a yeast cell, and an illustrative and not limiting list of suitable yeast host cells comprise: baker's yeast, *Kluyveromyces marxianus, K. lactis, Candida utilis, Phaffia rhodozyma, Saccharomyces boulardii, Pichia pastoris, Hansenula polymorpha, Yarrowia lipolytica, Candida paraffinica, Schwanniomyces castellii, Pichia stipitis, Candida shehatae, Rhodotorula glutinis, Lipomyces lipofer, Cryptococcos curvatus, Candida* spp. (e.g. *C. palmioleophila), Yarrowia lipolytica, Candida guilliermondii, Candida, Rhodotorula* spp., *Saccharomycopsis* spp., *Aureobasidium pullulans, Candida brumptii, Candida hydrocarbofumarica, Torulopsis, Candida tropicalis, Saccharomyces cerevisiae, Rhodotorula rubra, Candida flayeri, Eremothecium ashbyii, Pichia* spp., *Pichia pastoris, Kluyveromyces, Hansenula, Kloeckera, Pichia, Pachysolen* spp., or *Torulopsis bornbicola*.

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are *E. coli*, lactobacilli, Streptomycetes, Actinomycetes, *Saccharomyces* and filamentous fungi.

In any one host cell it is possible to make all sorts of combinations of expressible nucleotide sequences from all possible sources. Furthermore, it is possible to make combinations of promoters and/or spacers and/or introns and/or terminators in combination with one and the same expressible nucleotide sequence.

Thus in any one cell there may be expressible nucleotide sequences from two different expression states. Furthermore, these two different expression states may be from one species or advantageously from two different species. Any one host cell may also comprise expressible nucleotide sequences from at least three species, such as from at least four, five, six, seven, eight, nine or ten species, or from more than 15 species such as from more than 20 species, for example from more than 30, 40 or 50 species, such as from more than 100 different species, for example from more than 300 different species, such as form more than 500 different species, for example from more than 1000 different species, thereby obtaining combinations of large numbers of expressible nucleotide sequences from a large number of species. In this way potentially unlimited numbers of combinations of expressible nucleotide sequences can be combined across different expression states. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

Any two of these species may be from two different classes, such as from two different divisions, more preferably from two different sub-kingdoms, such as from two different kingdoms. Thus expressible nucleotide sequences may be combined from a eukaryote and a prokaryote into one and the same cell.

According to another embodiment, the expressible nucleotide sequences may be from one and the same expression state. The products of these sequences may interact with the products of the genes in the host cell and form new enzyme combinations leading to novel biochemical pathways. Furthermore, by putting the expressible nucleotide sequences under the control of a number of promoters it becomes possible to switch on and off groups of genes in a co-ordinated manner. By doing this with expressible nucleotide sequences from only one expression states, novel combinations of genes are also expressed.

The number of concatemers in one single cell may be at least one concatemer per cell, preferably at least 2 concatemers per cell, more preferably 3 per cell, such as 4 per cell, more preferably 5 per cell, such as at least 5 per cell, for example at least 6 per cell, such as 7, 8, 9 or 10 per cell, for example more than 10 per cell. As described above, each concatemer may preferably comprise up to 1000 cassettes, and it is envisages that one concatemer may comprise up to 2000 cassettes. By inserting up to 10 concatemers into one single cell, this cell may thus be enriched with up to 20,000 heterologous expressible genes, which under suitable conditions may be turned on and off by regulation of the regulatable promoters.

Often it is more preferable to provide cells having anywhere between 10 and 1000 heterologous genes, such as 20-900 heterologous genes, for example 30 to 800 heterologous genes, such as 40 to 700 heterologous genes, for example 50 to 600 heterologous genes, such as from 60 to 300 heterologous genes or from 100 to 400 heterologous genes which are inserted as 2 to 4 artificial chromosomes each containing one concatemer of genes. The genes may advantageously be located on 1 to 10 such as from 2 to 5 different concatemers in the cells. Each concatemer may advantageously comprise from 10 to 1000 genes, such as from 10 to 750 genes, such as from 10 to 500 genes, such as from 10 to 200 genes, such as from 20 to 100 genes, for example from 30 to 60 genes, or from 50 to 100 genes.

The concatemers may be inserted into the host cells according to any known transformation technique, preferably according to such transformation techniques that ensure stable and not transient transformation of the host cell. The concatemers may thus be inserted as an artificial chromosome which is replicated by the cells as they divide or they may be inserted into the chromosomes of the host cell. The concatemer may also be inserted in the form of a plasmid such as a plasmid vector, a phage vector, a viral vector, a cosmid vector, that is replicated by the cells as they divide. Any combination of the three insertion methods is also possible. One or more concatemers may thus be integrated into the chromosome(s) of the host cell and one or more concatemers may be inserted as plasmids or artificial chromosomes. One or more concatemers may be inserted as artificial chromosomes and one or more may be inserted into the same cell via a plasmid.

Measurement of Metabolic Pathway Outputs

In seeking to evolve metabolic pathways that produce molecules with defined pharmaceutical, industrial, nutritional properties one must have a method of selecting for the desired properties.

Each cell in a cell population, given that it is genetically different from other cells, has an intrinsic variability that can potentially express itself in one or more ways. Here, the term "output" shall be taken to mean a property of the cell that is consequent to the expression of one or more expression cassettes, and/or the expression of a metabolic pathway encoded by the individual cassettes. Optionally the property may be consequent to both the expression of one or more expression cassettes and the expression of a certain set of host genes.

Outputs can be measured according to various different criteria. These criteria may be directly or indirectly linked to the functional or structural properties that are being optimized. Alternatively they may be inversely linked to functional or structural properties that are not desired.

In one embodiment, the output of the metabolic pathway is production of a carotenoid. Carotenoids refer to a structurally diverse class of pigments derived from isoprenoid pathway intermediates. In one embodiment, the carotenoid is β-carotene. Other carotenoids include but are not limited to: antheraxanthin, adonirubin, adonixanthin, astaxanthin, canthaxanthin, capsorubrin, β-cryptoxanthin, α-carotene, β-carotene, β,ψ-carotene, Δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

In another embodiment, a yeast cell is provided that produces β-carotene from PPP.

In one aspect, a yeast cell is capable of converting PPPs into β-carotene. The three genes responsible for converting PPP to β-carotene were introduced into a yeast cell and integrated into the genome using recombination. The three genes encode enzymes geranylgeranyl pyrophosphate synthase, phytoene synthase, β-carotene synthase, ζ-carotene synthase and δ-carotene desaturase. Two of these enzymes are bifunctional. In another embodiment, these three genes are integrated into the yeast genome.

In addition to commercial production, β-carotene can be used as a screening tool, for it produces an orange pigment when expressed. For a detailed description of this screening technique, see T. Lotan, FEBS Letters, 1995, 364:125-128, which is hereby incorporated by reference. For further details on the methods and experimental conditions, see PCT application no. WO 03/062419, Example 7, hereby incorporated by reference.

β-carotene can be measured several ways. In certain embodiments, β-carotene is measured by visual inspection. LC-MS analysis is used to measure it. In other embodiments, β-carotene is measured using liquid chromatography-coupled mass spectrometry (LC-MS), or any other analytical method known in the art.

Modification of the MEV Pathway

Occasionally, the metabolic outputs must be controlled such that the desired output can be more accurately measured. At times, certain modifications of the metabolic pathway must be made to ensure precise measurements.

In one aspect, a yeast strain is created which blocks the conversion of cellular PPP into ergosterol. The enzyme encoded by ERG9, squalene synthase, joins two farnesyl pyrophosphate moieties to form squalene in the sterol biosynthesis pathway. This enzyme is the first in a pathway that under normal circumstances in the yeast cell turns most of the cellular PPP units into ergosterol. Although yeast needs ergosterol for growing, it can manage with very little ergosterol. Removing ERG9 expression ensures a low ergosterol production, and provides for most of the PPP availability for terpenoid biosynthesis.

In one embodiment, the yeast host cell comprises reduced inherent ERG9 expression relative to an unaltered yeast cell. In certain embodiments, the inherent ERG9 expression is reduced by 5, 10, 15, 20, 25, 30, 35, 40, 45, 50, 55, 60, 65, 70, 75, 80, 85, 90, 95 percent or more. In other embodiments, the ERG9 expression is reduced to the lowest level that maintains host cell viability.

In one non-limiting embodiment, a yeast strain is prepared by substituting the inherent promoter of the ERG9 gene with an inducible promoter. In one embodiment, the inducible promoter is the CUP1 promoter, which has a very low basal activity in the absence of copper ions. In one embodiment, this substitution is made using recombination. In another embodiment, any promoter with low basal activity is substituted for the ERG9 promoter.

Despite the fact that down-regulating the ERG9 step in ergosterol production in the mevalonate pathway in yeast results in an increased PPP pool inside the yeast, the rate-limiting step is still the amount of acetyl CoA in the yeast cytosol available for conversion to PPP.

In another aspect, PPP production is increased by producing increased levels of acetyl-CoA. Production of PPP from acetyl-CoA in the mevalonate pathway is dependent upon the available amount of acetyl-CoA in the cytosol. Due to limited conversion of acetyl-CoA to PPP and a limited total amount of acetyl-CoA in the yeast cytosol, there is a limit to the size of the PPP pool.

Figure 2A:
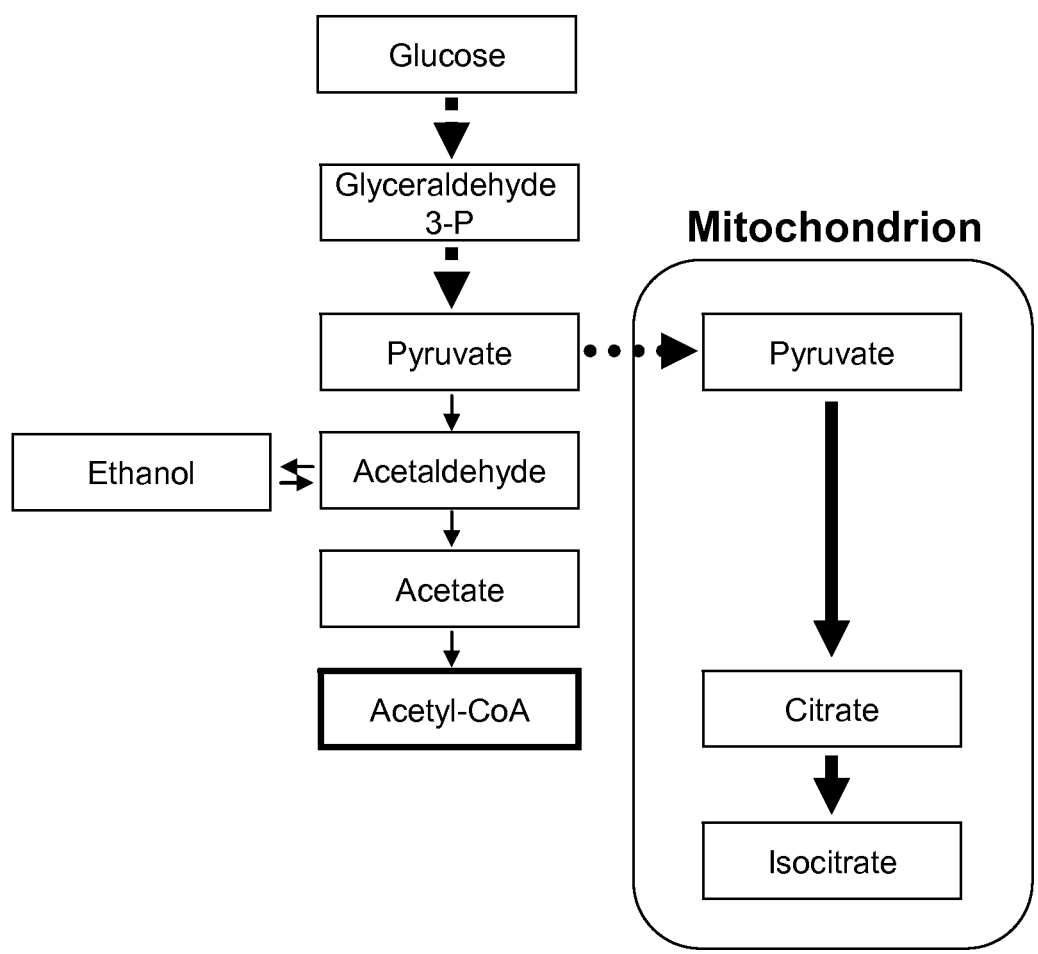
FIG. 2 shows, in (a) conversion of some pyruvate to acetyl-CoA for use in the mitochondrion in the citric acid cycle and not available for acetyl-CoA formation in the yeast cytosol; and (b) the effect of partially blocking this conversion.

FIG. 2(a) shows the pathway of conversion of some pyruvate to citrate for use in the mitochondrion in the citric acid cycle. Since the pyruvate moves to the mitochondrion, it and not available for acetyl-CoA formation in the yeast cytosol. Mitochondrial citrate is turned into isocitrate by the aconitase enzyme which is part of the TCA cycle in all organisms. Aconitase is encoded by the ACO1 gene in yeast. An inherent yeast carboxylic acid shuttle (encoded by the CTP1 gene) ensures that excess citrate that is not converted into isocitrate is transferred from the mitochondrion to the cytosol.

In one embodiment, the availability of acetyl-CoA for PPP production is improved by shunting some of the citrate being produced in the yeast mitochondrion into the yeast cytosol. In this embodiment, mitochondrial aconitase activity is down-regulated.

In one embodiment, the yeast host cell comprises reduced inherent ACO1 expression relative to an unaltered yeast cell. In certain embodiments, the inherent ACO1 expression is reduced by 5, 10, 15, 20, 25, 30, 35, 40, 45, 50, 55, 60, 65, 70, 75, 80, 85, 90, 95 percent or more. In other embodiments, the ACO1 expression is reduced to the lowest level that maintains host cell viability.

In order to increase the concentration of acetyl-CoA, substituting the inherent promoter of the S. cerevisiae aconitase gene ACO1 with a CUP1 promoter, the cytosolic concentration of citrate is increased. The CUP1 promoter has very low activity in the absence of added copper ions. Use of the CUP1 promoter in place of the inherent promoter of the S. cerevisiae aconitase gene ACO1, ensures a lower than usual activity of aconitase. Lower aconitase results in build-up of unusually high concentrations of citrate inside the mitochondrion. An inherent yeast carboxylic acid shuttle encoded by the CTP1 gene ensures that excess citrate is transferred from the mitochondrion to the cytosol. In another embodiment, any promoter with low basal activity is substituted for the ACO1 promoter.

Figure 2B:
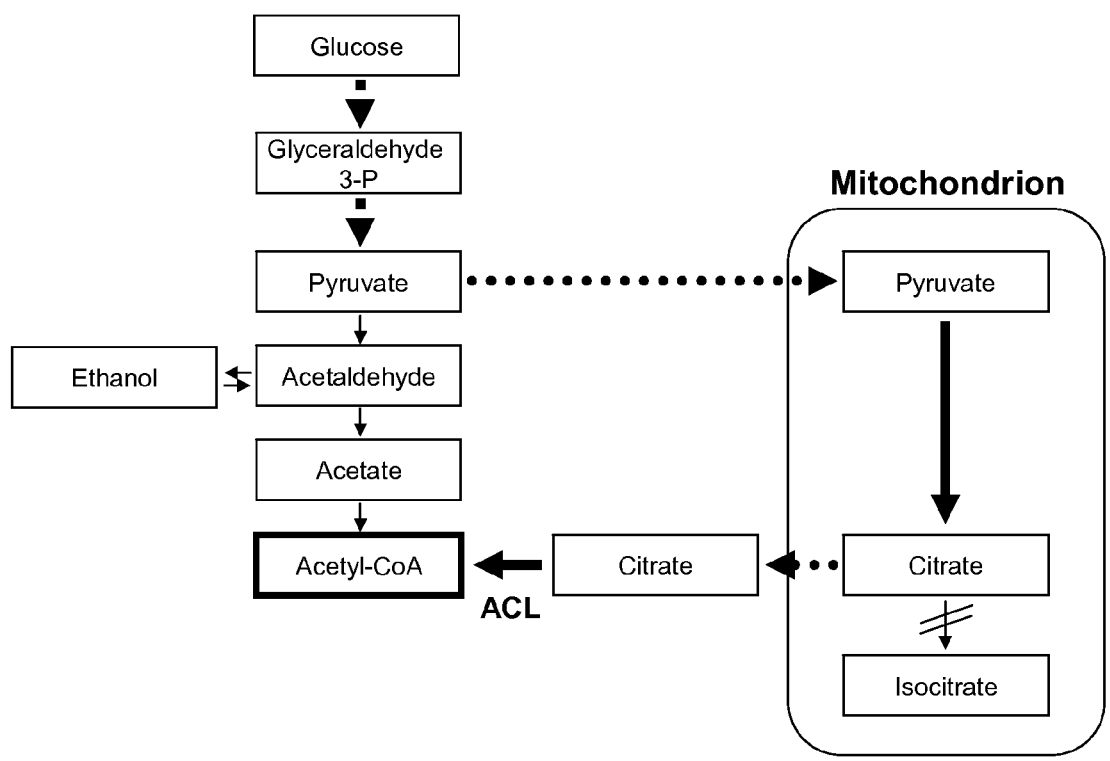

FIG. 2(b) shows the result of partially blocking citrate conversion to isocitrate, resulting in an increase in the mitochondrial concentration of citrate. In one aspect, this blocking is accomplished by reducing gene expression of the aconitase enzyme. Because of the carboxylic acid shuttle encoded by the CTP1 gene residing in the mitochondrial membrane, the citrate concentrations in the mitochondrion and cytosol will "equilibrate", resulting in increased cytosolic concentration of citrate.

In another embodiment of the invention, the availability of acetyl-CoA for PPP production was improved by increasing the rate of conversion of citrate to acetyl-CoA in the yeast cytosol. In one embodiment, the enzyme ATP citrate lyase (ACL) is introduced into a host cell. ACL functions by converting citrate into acetyl-GoA and oxaloacetate with the consumption of ATP and CoA. ACL does not exist in S. cerevisiae. In this embodiment, expression of a heterologous non-yeast ATP-citrate lyase (ACL) enzyme is produced in the yeast cytosol. To create gene expression vectors which can express ACL in S. cerevisiae, vectors containing optimized versions of the Chlamydomonas rheinhardtii ACL subunits 1 and 2 or the Yarrowia lipolytica ACL subunits 1 and 2 from a methionine-repressible promoter (yeast MET25), are created using high copy number plasmid vectors (see Table 2).

TABLE 2

Gene expression vectors of the *Chlamydomonas rheinhardtii* ACL subunits 1 and 2 or the *Yarrowia lipolytica* ACL subunits 1 and 2 from a methionine-repressible promoter (yeast MET25).

| Accession # | Organism | Enzyme | Size (nt) | Gene Name | Construct |
|---|---|---|---|---|---|
| XP_503231 | Yarrowia lipolytica | ATP-citrate lyase subunit 2 | 1494 | ACL-1 | pACL-1 |
| XM_504787 | Yarrowia lipolytica | ATP-citrate lyase subunit 1 | 1953 | ACL-2 | pACL-2 |
| XM_001700848 | Chlamydomonas reinhardtii | ATP-citrate lyase subunit 1 | 1308 | ACL-3 | pACL-3 |
| XM_001701903 | Chlamydomonas reinhardtii | ATP-citrate lyase subunit 2 | 1605 | ACL-4 | pACL-4 |

In one embodiment, the increased amount of citrate in the mitochondrion results in increased amounts of citrate in the yeast cytosol. The ACL enzyme converted the citrate to Acetyl-CoA, which led to a further several times higher β-carotene production than is seen in the absence of this modification.

In another embodiment, the availability of acetyl-CoA for PPP production was improved by both shunting some of the citrate being produced in the yeast mitochondrion into the yeast cytosol and increasing the rate of conversion of citrate to acetyl-CoA in the yeast cytosol. In this embodiment, availability of acetyl-CoA for PPP production was improved by shunting some of the citrate being produced in the yeast mitochondrion, into the yeast cytosol, by first down-regulating mitochondrial aconitase activity (turns citrate into isocitrate), and then expressing non-yeast ACL (ATP-citrate lyase) enzyme in the yeast cytosol. The increased amount of citrate in the mitochondrion results in increased amounts of citrate in the yeast cytosol. The ATP-citrate lyase (ACL) enzyme converts the more citrate to more acetyl-CoA. This acetyl-CoA is used by the mevalonate pathway to make increased amounts of PPPs.

In another aspect, the MEV analog concatemers and the ACL subunit genes are introduced into the yeast cells containing the modified MEV pathway. The new yeast strain that combines the heterologous mevalonate pathway genes and the ACL subunit genes produces significantly more β-carotene than any of the other yeast strains. Approximately 150 m/gDW (yeast cell Dry weight) can be obtained, representing an increase of about 25-fold with the combined strategy.

EXAMPLES

The Examples that follow are illustrative of specific embodiments, and various uses thereof. They are set forth for explanatory purposes only, and are not to be taken as limiting.

Example 1

Alleviating Metabolic Bottlenecks in Mevalonate (MEV) Pathway for Prenyl Phosphate Production (PPP)

In *Saccharomyces cerevisiae* the mevalonate pathway is heavily regulated, for example, at the level of the enzyme 3-Hydroxy-3-methylglutaryl-coenzyme A reductase. The following example assesses whether the MEV enzymes from other organisms are regulated differently from the yeast MEV enzymes, and therefore that a higher flux could be obtained in yeast with some of these heterologous enzymes. For the six steps of the mevalonate pathway (see FIG. 1), the use of several combinations of these gene analogs turned up PPP production by overriding the native regulation mechanisms working on the inherent yeast MEV pathway enzymes, providing for about five times higher production.

For further details on the methods and experimental conditions, see PCT application no. WO 03/062419, Example 7, hereby incorporated by reference.

Host Strains

All cloning in *E. coli* is performed with XL10 Gold (Stratagene). Yeast strains are trp1 derivatives of *S. cerevisiae* BY4741 (MAT a, his3Δ1, leu2Δ0, ade8Δ0, trp1:: kanMX4, ura3Δ0, arg4Δ0), and BY4742 (MAT a, his3Δ1, leu2Δ0, lys2Δ0, trp1::kanMX4, ura3Δ0, arg4Δ0).

Cloning of Entry Vectors

A large number of genes are tested using our proprietary genetic chemistry technology (see Table 1, showing 35 genes from those analogs). Five taxonomically diverse gene analogs of the yeast MEV pathway are sourced by yeast codon optimized synthesis (DNA 2.0 Inc™) (www.dna20.com). For details on the optimization, see U.S. Pat. No. 7,561,972 and U.S. Pat. No. 7,561,973. DNA sequences of the 35 optimized genes can be found in Table 6. All steps of the MEV pathway are covered from acetyl-CoA to the prenyl phosphates for several different terpenoid molecules. The corresponding amino acid sequences for the optimized MEV gene variants are listed in Table 7.

For ease of handling, all 35 genes are first cloned in *E. coli* vectors having yeast expression cassettes containing i) a yeast promoter, ii) the gene of interest, and iii) a yeast transcription termination signal. To reduce the number of repeated sequences in the final YAC expression vectors and, hence, limit the chance of spontaneous homologous recombination, a mix of Entry Vectors can be used, containing all possible combinations of different promoters and different transcription terminators, all deriving from yeast species other than *S. cerevisiae*.

The set of diverse Entry Vectors are constructed such that every gene is controlled by its own methionine-repressible gene promoter (MET2, MET25 or MET14), inserted between BglII and HindIII sites. The insertion of genes behind promoters is done in a random fashion by ligating each gene with a pool of prepared vectors having either MET2, MET25 or MET14 promoters. The plasmids, named pMEV-1 to pMEV-35, are shown in Table 1.

Preparation of eYACs

For further details on the methods and experimental conditions, see PCT application no. WO 02/059297, Example 1, hereby incorporated by reference.

In order to produce functional expression Yeast Artificial Chromosome (eYACS), each of which contains between 20 and 25 expression cassettes, the expression cassettes are liberated from the Entry Vectors by restriction digestion using AscI and SrfI. DNA in the amount of 30 to 200 μg is prepared from each of the cassette-containing Entry Vectors and the cassettes are then randomly concatenated into YACs by ligation with T4 ligase in a 3 hour reaction. The success of the concatenation reaction is assessed by the viscosity of the reaction mixture, since concatenated DNA is highly viscous.

DNA fragments ("arms") containing a centromere, two telomeres and the LEU2 and TRP1 selection markers are added to the end of the concatenated expression cassettes, thereby creating functional eYACs. Arms for preparing YACs can be obtained from vectors based on pYAC4 (Sigma) in which the URA3 auxotrophic marker gene on the short arm is exchanged for the HIS3 or the LEU2 marker gene. In addition, an oligo containing an Asc I restriction site is inserted into the unique EcoR I site of pYAC4. Into this new Asc I site a DNA fragment is cloned containing the A-tag and the K-tag, separated by an Mlu I site. After digestion with Mlu I and Bam H III the digested YAC plasmids are used without purification.

Creating Yeast Strain ERG-1

A yeast strain for testing is prepared by substituting the inherent promoter of the ERG9 gene with a CUP1 promoter. This promoter has a very low basal activity in the absence of copper ions. The enzyme encoded by ERG9 is the first in a pathway that under normal circumstances turns most of the cellular PPP units into ergosterol. Although, yeast needs ergosterol for growing, it can manage with very little ergosterol. Lowering ERG9 expression ensures a low ergosterol production, and provides for most of the PPP availability for terpenoid biosynthesis.

To create the new yeast strain, we first prepare a basic vector: pUC19 plasmid DNA is restriction digested with EcoRI+HindIII, then ligated to a DNA fragment made by annealing two oligonucleotide primers having the following sequence: 5'-GGCGCGCCGCGGCCGCAGCT-3' (SEQ ID. NO. 77) and 5'-GCGGCCGCGGCGCGCCAATT-3' (SEQ ID. NO. 78) (thus introducing NotI and AscI restriction sites between destroyed EcoRI and HindIII sites). Next, the 423 bp promoter region residing immediately upstream (5') of the CUP1 open reading frame is amplified by PCR using Taq polymerase, *S. cerevisiae* genomic DNA as template and the oligonucleotide primers CUP1_F (5'-AAAAGGCGCGC-CATATGTTCATGTATGTATCTG-3') (SEQ ID. NO. 79) and CUP1_R 5'-AAAAGGCGCGCCTTTATGTGATGATT-GATTGATTG). (SEQ ID. NO. 80). The resulting PCR fragment is then restriction digested to release an AscI fragment, which is inserted into the modified pUC19 vector as described. The orientation of the fragment is identified by restriction analysis and a clone is selected with the promoter 3'-end pointing away from the NotI site of the vector. In the resulting plasmid, the NotI-contained NatMX selection marker fragment from pAG25 is inserted into the NotI site, and a clone with the TEF1 terminator part pointed away from the CUP1 promoter fragment selected.

Oligonucleotide primers ERG9_FII 5'-GACA-GGGGCAAAGAATAAGAGCACAGAA GAAGA-GAAAAGACGAAGGCGGCCGCATAGGC-CACTAGTGGA-3') (SEQ ID. NO. 81) and ERG9_R_CUP 1 (5'-CTTCATCTCGACCGGATGCAATGCCAAT-TCTAATAGCTTTCCCATT TATGTGATGATTGATT-GATT-3') (SEQ ID. NO. 82), covering the whole NatMX-CUP1 promoter fragment, are used to PCR amplify (using Taq polymerase) a gene substitution fragment. These primers contain a 45 nucleotide sequence at their 3'-end which is homologous to various sequences of the native ERG9 promoter, substituting the ERG9 ORF-nearest 45 bp of the ERG9 promoter with the NatMX-CUP1 promoter fragment.

This PCR fragment is transformed into a trp1-derivative of yeast strain BY4742 (described in Naesby et al., 2009, Microbial Cell Factories 8:45) and nourseothricin-resistant clones are selected. The common lithium acetate protocol is used for transformation. Five resistant clones are PCR analysed and confirmed to contain the CUP1 promoter rather than their native ERG9 gene promoter. One of these yeast strains, named ERG-1, is selected for future experiments.

Creating Yeast Strain CAR-1

A yeast strain is needed for the purpose of monitoring the cellular PPP availability. The strain CAR-1 can be created to monitor PPP availability by converting PPPs into the colored compound β-carotene for visual selection.

To create the CAR-1 strain, genes CAR-1 (SEQ. ID. NO. 71), CAR-2 (SEQ. ID. NO. 72), and CAR-3 (SEQ. ID. NO. 73) (the genes encoding the enzymes geranylgeranyl pyrophosphate synthase, phytoene synthase, β-carotene synthase, ζ-carotene synthase and δ-carotene desaturase, see Table 3) are first fused to the constitutively expressed GPD1 promoter, as follows: The 3 complete open reading frame of the CAR genes are PCR amplified using cDNA from either *Xanthophyllomyces dendrorhous* or *Neurospora crassa* as template and 21 nt oligonucleotide primers corresponding to the 5'-most and 3'-most sequence of the open reading frame. The 5'-most oligonucleotide primer is prolonged at its 5'-end with 35 nts corresponding to the 35 nts present immediately upstream of the yeast GPD1 open reading frame in yeast. The 500 bp of the yeast GPD1 promoter is PCR amplified in a similar fashion, using yeast genomic DNA as template oligonucleotide primers corresponding to the 21 nucleotide sequence immediately upstream of the GPD1 open reading frame, and to the 21 nucleotide sequence from 500 bp upstream to 479 bp upstream of the GPD1 open reading frame. Three different types of primer are used for the primer corresponding to the 21 nucleotide sequence immediately upstream of the GPD1 open reading frame, each at its 5'-end prolonged with 35 nts corresponding to the first 35 nts of either CAR-1, CAR-2 or CAR-3. The two corresponding PCR fragments are used as templates in a sequence overlap extension PCR gene amplification in a reaction also containing oligonucleotide primers corresponding to the 5'-terminus of the GPD1 promoter PCR fragment and to the 3'-terminus of the CAR genes open reading frames. The GPD1 homologous primer is prolonged at its 5'-end with sequence corresponding to an AscI restriction site and then 4 A's (5'-most). All the three 3-terminus CAR primers are prolonged at their 5' end with sequence corresponding to an AscI site, then 4 A's (5'-most). The resulting fragments (3 different) consist of the CAR-1, CAR-2 and CAR-3 genes, all fused at their 5' end to the 500 nt large GPD1 promoter.

These fragments are restricted by enzyme AscI, then ligated into linearized integration vectors pCAR-Int-1, pCAR-Int-2 or pCAR-Int-3, which were prepared in the following way: pUC19 plasmid DNA was restriction digested with EcoRI+HindIII then ligated to a DNA fragment made by annealing two oligonucleotide primers having the following sequence: 5'-GGCGCGCCGCGGCCGCA-GCT-3' (SEQ ID. NO. 83) and 5'-GCGGCCGCGGCGCGC-CAATT-3' (SEQ ID. NO. 84) (thus introducing NotI and AscI restriction sites between destroyed EcoRI and HindIII sites). In this vector we insert the selection markers *Schizosaccharomyces pombe* his5 (complements *S. cerevisiae* his3), HphMX (giving hygromycin B resistance) or *K. lactis* URA3 (complements *S. cerevisiae* ura3) from the commercial vectors pUG27, pAG32 and pUG72, liberated by NotI restriction digestion of these plasmids, resulting in integration vectors pCAR-Int-1, pCAR-Int-2 and pCAR-Int-3. The GPD1 promoter CAR gene fusion fragments described above are inserted in the AscI sites of pCAR-Int-1, pCAR-

TABLE 3

Enzymes required for production of β-carotene from PPP in yeast strain CAR-1.

| Accession # | Organism | Enzyme | Size (nt) | Gene Name | Construct |
|---|---|---|---|---|---|
| DQ012943 | *Xanthophyllomyces dendrorhous* | Geranylgeranyl pyrophosphate synthase | 909 | CAR-1 | pCAR-1 |
| AY177204 | *Xanthophyllomyces dendrorhous* | Phytoene synthase & β-carotene synthase | 2022 | CAR-2 | pCAR-2 |
| M57465 | *Neurospora crassa* | ζ-carotene synthase & δ-carotene desaturase | 1701 | CAR-3 | pCAR-3 |

Int-2 or pCAR-Int-3, resulting in the construction of plasmids pCAR-1, pCAR-2 and pCAR-3. In all of these three plasmids there is a unique SbfI site in the GPD1 promoter region. The integration plasmids pCAR-1, pCAR-2 and pCAR-3 are all linearized by restriction digestion with SbfI, and the linearized plasmids used for transformation of yeast strain ERG-1, one at a time. The linearization directs homologous recombination to the GPD1 promoter region. The common lithium acetate protocol is used for transformation.

This linearized gene expression plasmids can then be integrated into particular locations in the yeast genome using homologous recombination. After transformation with pCAR-1 integrants are selected on growth medium without histidine and correct insertion of the expression plasmids is ensured by PCR analysis of the resulting transformants (using Taq polymerase). The yeast strain containing the correct insertion of the pCAR-1 expression cassette is selected and named CAR-1a. This strain is used for transformation with linearized pCAR-2 and the resulting integrant called CAR-1b. This strain is used for transformation with linearized pCAR-3 and the resulting verified strain called CAR-1. This strain now contains integrated genes constitutively expressing all genes necessary for β-carotene production.

eYAC β-Carotene Screening and Results

For further details on the methods and experimental conditions, see PCT application no. WO 03/062419, Example 7, hereby incorporated by reference.

The eYACs containing the heterologous MEV genes are transformed into transformation-competent spheroplasts of yeast strain CAR-1 by zymolyase digestion of the yeast cell wall, followed by treatment with a CaCl$_2$/PEG buffer, making the spheroplasts permeable to large molecules such as eYACs. After transformation, the yeast spheroplasts are embedded in a "noble agar" based solid growth medium, in which regeneration of the cell wall can take place. Colonies typically appear 4-8 days after inoculation. The regeneration medium lacks the amino acids leucine and tryptophan, thus can select for the presence of double-armed eYACs in the yeast cells. Approximately 5,000 transformants are usually obtained.

The transformants are visually inspected for orange color formation due to β-carotene production. One hundred of the transformants having the highest β-carotene production are selected and analyzed for actual production of β-carotene using Liquid Chromatography-coupled Mass Spectrometry with Triple Quadropole (LC-MS). For eYAC gene content, real-time PCR is used to assess actual gene content as well as copy number of individual genes. Each transformant is re-streaked and tested for yeast strain markers and the genetic presence of both arms of the eYAC, i.e. the LEU2 and TRP1 markers. If the transformant has the correct genotype, the transformant is given a CEY designation number.

For β-carotene production assessment, 48 CEYs are grown in 50 ml of Synthetic Complete medium (SC) in 100 ml Erlenmeyer flasks, without methionine, so as to induce gene expression from the eYACs, and without tryptophan, leucine and histidine, so as to counter-select for loss of eYACs. The cultures have a start density corresponding to an OD600 of 0.25, and they are inoculated for 48 hours at 30 C, with slow shaking (150 rpm). After 24 hours, 1 ml supernatant from each culture is collected and subjected to LC-MS analysis for the presence of β-carotene. Culture supernatants are centrifuged, and 100 μl supernatant is mixed thoroughly with the same volume of 100% methanol (to precipitate macromolecules), and the mixture centrifuged. 40 μl of the supernatant is analyzed.

When compared to the yeast strain CAR-1, many of the analyzed CEYs show a 100-500% increase in β-carotene production. Table 4 shows an exemplary combination of heterologous MEV genes increasing PPP units which resulted in a β-carotene production of 34 mg/gDW (yeast cell Dry weight), an approximately 5-fold increase in production using this approach to optimize the MEV pathway.

Thus, these assays identify combinations of non-S. cerevisiae MEV genes that are able to provide the cell with significantly increased levels of PPP units, as judged by these yeast strains' capability to produce significantly increased levels of β-carotene.

Table 4 shows an exemplary combination of heterologous MEV genes increasing PPP units which produce β-carotene at 34 mg/gDW (yeast cell Dry weight). Yeast strains containing MEV-1 (SEQ ID. NO:1), MEV-6 (SEQ ID. NO:6), MEV-15 (SEQ ID. NO:15), MEV-18 (SEQ ID. NO:18), MEV-21 (SEQ ID. N):21), and MEV-33 (SEQ ID. NO:33) produce approximately 5-fold increase in production from the mevalonate pathway.

TABLE 4

Examples of heterologous MEV genes that produced significant increase in production from the mevalonate pathway.

| Accession # | Organism | Enzyme | Size (nt) | Gene Name |
|---|---|---|---|---|
| NM_001022609 | Schizosaccharomyces pombe | Acetyl-CoA C-acetyltransferase | 1188 | MEV-1 |
| XM_001831228 | Coprinopsis cinerea | 3-hydroxy-3-methylglutaryl-CoA synthase | 1422 | MEV-6 |
| CAG41604 | Staphylococcus aureus | 3-Hydroxy-3-methylglutaryl-coenzyme A reductase | 1281 | MEV-15 |
| AB294693 | Hevea brasiliensis | Mevalonate kinase | 1161 | MEV-18 |
| XP_001877360 | Laccaria bicolor | Phosphomevalonate kinase | 1476 | MEV-21 |
| NM_001075424 | Bos taurus | Diphosphomevalonate decarboxylase | 1203 | MEV-27 |
| DQ666334 | Artemisia annua | Isopentenyl diphosphate: dimethylallyl diphosphate isomerase | 855 | MEV-33 |

Example 2

Increasing Cytosolic Acetyl-CoA Content

If maximal flux from acetyl-CoA to PPP is obtained from the MEV pathway, the limiting component of MEV production is the concentration of cytosolic acetyl-CoA. Increasing the concentration of cytosolic acetyl-CoA should increase the production of the MEV pathway. Acetyl-CoA is biosynthesized in the cytoplasm, but the rather low concentrations limit the amount of PPP that can be produced by the MEV pathway. The enzyme ATP citrate lyase (ACL), which does not exist in S. cerevisiae, will turn citrate into acetyl-CoA and oxaloacetate with the consumption of ATP and CoA. This example shows that heterologous ACL can be used in S. cerevisiae to increase production of acetyl-CoA in the cytosol of S. cerevisiae (see FIGS. 2 (a) and (b)). This example demonstrates that expression of the heterogeneous enzyme ACL (ATP-citrate lyase) will increase cytosolic citrate, which will thus be converted to acetyl-CoA. The increased amount of acetyl-CoA can then be used to form prenyl phosphate via the mevalonate pathway.

Host Strains

All cloning in E. coli is performed with XL10 Gold (Stratagene). Yeast strains are S. cerevisiae trp1 derivatives of BY4741 (MAT a, his3Δ1, leu2Δ0, ade8Δ0, trp1::kanMX4, ura3Δ0, arg4Δ0), and BY4742 (MAT a, his3Δ1, leu2Δ0, lys2Δ0, trp1::kanMX4, ura3Δ0, arg4Δ0).

Preparation of Expression Vectors

To increase the cytosolic concentration of citrate, endogenous acotinase expression in yeast must be reduced. To reduce acotinase expression, the inherent promoter of the S. cerevisiae aconitase gene ACO1 is substituted with a CUP1 promoter. This promoter has very low activity in the absence of added copper ions, which will reduce expression of aconitase and therefore buildup of unusually high concentrations of citrate inside the mitochondrion.

To create the new yeast strain, we prepare a basic vector: pUC19 plasmid DNA is restriction digested with EcoRI+HindIII, then ligated to a DNA fragment made by annealing two oligonucleotide primers having the following sequence: 5'-GGCGCGCCGCGGCCGCAGCT-3' (SEQ ID. NO. 85) and 5'-GCGGCCGCGGCGCGCCAATT-3' (SEQ. ID. NO. 86) (thus introducing NotI and AscI restriction sites between destroyed EcoRI and HindIII sites). Now the 423 bp promoter region residing immediately upstream (5') of the CUP1 open reading frame is amplified by PCR using Taq polymerase, S. cerevisiae genomic DNA as template and the oligonucleotide primers CUP1_F (5'-AAAAGGCGCGCCATATGTTCATGTATGTATCTG-3') (SEQ ID. NO. 87) and CUP1_R25'-AAAAGGCGCGCCTTTATGTGATGATTGATTGATTG) (SEQ ID. NO. 88). The resulting PCR fragment is then restriction digested to release an AscI fragment, which is inserted into the modified pUC19 vector just described. The orientation of the fragment is identified by restriction analysis and a clone is selected with the promoter 3'-end pointing away from the NotI site of the vector. In the resulting plasmid the NotI-contained KanMX selection marker fragment from pUG6 is inserted into the NotI site, and a clone with the TEF1 terminator part pointed away from the CUP1 promoter fragment selected. Oligonucleotide primers ACO1_F-II 5'-TGTCAAATTAC-CTAAAAAATGGCCGAGAGCCG CAAAAGGGAG-GTCGCGGCCGCAT AGGCCACTAGTGGA-3') (SEQ ID. NO. 89) and ACO1_R_CUP1 (5'-ACCAC-GAACAATGGGTCTCTTGATGGCAGAACGTGCA-GACAGCA TTTATGTGATGATTGATTGATT-3') (SEQ ID. NO. 90) covering the whole KanMX-CUP1 promoter fragment, are used to PCR amplify (using Taq polymerase) a gene substitution fragment. These primers contain a 45 nucleotide sequence at their 3'-end which is homologous to various sequences of the native ACO1 promoter, substituting the ACO1 ORF-nearest 355 bp of the ACO1 promoter with the KanMX-CUP1 promoter fragment.

This PCR fragment is transformed into yeast strain CAR-1 (described in Example 1 above) and G418-resistant clones are selected. The common lithium acetate protocol is used for transformation. Five resistant clones are PCR analysed and confirmed to contain the CUP1 promoter rather than their native ACO1 gene promoter. One of these yeast strains, named ACO-1 (see Table 5), is selected for future experiments.

TABLE 5

Modified genome characteristics of the yeast strains used in these Examples. (−) denotes lack of natural or functional expression of gene or pathway in question, (+) denotes natural or functional expression of gene or pathway in question.

| Yeast Strain | Erg9 | Aco1 | β-carotene |
|---|---|---|---|
| ERG-1 | (−) | (+) | (−) |
| CAR-1 | (−) | (+) | (+) |
| ACO-1 | (−) | (−) | (+) |

Acetyl-CoA Quantity Screening

To create gene expression vectors which can express ACL in S. cerevisiae, vectors containing optimized versions of the Chlamydomonas rheinhardtii ACL subunits 1 and 2 or the Yarrowia lipolytica ACL subunits 1 and 2 from a methionine-repressible promoter (yeast MET25), are created using high copy number plasmid vectors (see Table 2).

If the heterogeneous enzyme ATP-citrate lyase (ACL) is expressed in ACO-1, the increased cytosolic citrate will be converted to acetyl-CoA. The increased amount of acetyl-CoA can then be used to form PPP via the MEV pathway. The pACL-1, -2, -3 and -4 expression plasmids were made in the following way: First the S. cerevisiae ARG4 gene is PCR amplified from genomic S. cerevisiae DNA, using oligonucleotide primers corresponding to the nucleotides from 500 to 480 bp upstream of the ARG4 ORF (forward primer) and from 480 to 500 bp downstream of the ARG4 ORF (downstream primer). Each primer has at their 5'-ends 4 A's followed by an AscI site. The resulting PCR fragment is restriction digested with AscI and inserted in AscI-digested plasmid pYC240 (see Olesen et al., 2001, Yeast 16:1035), resulting in plasmid pYC240-ARG4. In a similar fashion the S. cerevisiae LYS2 gene (including 50 bp upstream and downstream of the LYS2 ORF) is PCR amplified, also with AscI-containing oligonucleotide primers. The AscI-digested PCR fragment was inserted in AscI-digested pYC240, resulting in plasmid pYC240-LYS2. GPD1 promoter controlled ACL-1 to −4 was obtained by PCR amplification of the S. cerevisiae GPD1 promoter, PCR amplification of the full ORFs of ACL-1 to −4, and sequence overlap extension similar to the procedure with the CAR genes described in Example 1 above. However, here the PacI restriction sites are incorporated into the sequence overlap extension oligonucleotide primers, resulting in 4 fusion fragments: GPD1 promoter-ACL-1, GPD1 promoter-ACL-2, GPD1 promoter-ACL-3 and GPD1 promoter-ACL-4, each of them containing at their termini PacI restriction sites. Now the GPD1 promoter-ACL-1 and GPD1 promoter-ACL-4 fragments are restriction digested with PacI and inserted in PacI digested pYC240-ARG4 plasmid, and GPD1 promoter-ACL-2 and GPD1 promoter-ACL-3 fragments are restriction digested with PacI and inserted into PacI digested pYC240-LYS2, creating expression plasmids pACL-1, -2, -3 and -4.

The ACL expression plasmids pACL1-4, which contain expression cassettes for both ACL sub-units, are introduced into both the ACO-1 and CAR-1 yeast strains using the common lithium acetate transformation protocol. The plasmids were introduced in the following combinations: pACL-1+pACL-2, pACL-1+pACL-3, pACL-4+pACL-2 and pACL-4+pACL-3. The presence of the plasmids in the transformed yeast strains was ensured by selection of growth medium without the 2 amino acids arginine and lysine.

The transformed ACO-1 and CAR-1 strains are incubated in growth medium without methionine (so as to initiate expression of the ACL genes) and without copper ions (so as to keep expression from ERG9 and/or ACO1 down-regulated), and β-carotene production is assayed as a measure for acetyl-CoA production. A non-transformed CAR-1 yeast strain, which does not express ACL, is also grown as a negative control. The yeast strains are grown in Synthetic Complete medium (SC) in 100 ml Erlenmeyer flasks. The yeast are grown for 48 hours at 30 degrees C., with slow shaking (150 rpm), with a start density corresponding to an OD600 of 0.25. A 1 ml culture supernatant is centrifuged, and 100 ml supernatant is mixed thoroughly with the same volume of 100% methanol to precipitate macromolecules, followed by mixture centrifugation. 40 µl of the supernatant is analyzed by LC-MS for content of β-carotene.

The transformed ACO-1 strain, which expresses ACL, produces significantly more β-carotene than both the transformed CAR-1 strain and the untransformed CAR-1 strain. As an example β-carotene is produced at a surprisingly high concentration of 38 mg/g DW (yeast cell Dry weight) by strain ACO-1 expressing ACL gene combination ACL-1+ACL-2, an approximately 5-fold increase in production as compared to the CAR-1 strain. This example shows that eliminating endogenous aconitase expression and introducing exogenous ACL in yeast will produce significantly more PPP.

Example 3

Enhancing PPP Production by Both Alleviating Metabolic Bottlenecks in PPP Production and Increasing the Cytosolic Acetyl-CoA Content Since both alleviating metabolic bottlenecks in PPP production in Example 1 and increasing the cytosolic Acetyl-CoA content in Example 2 can produce increased amounts of PPP, it was hypothesized that combining both modifications into a single yeast cell could produce an even greater effect.

Host Strains

All cloning in E. coli is performed with XL10 Gold (Stratagene). Yeast strains are S. cerevisiae BY4741 (MAT a, his3Δ1, leu2Δ0, ade8Δ0, trp1::kanMX4, ura3Δ0, arg4Δ0), and BY4742 (MAT a, his3Δ1, leu2Δ0, lys2 Δ0, trp1::kanMX4, ura3Δ0, arg4Δ0).

Dual Transformation Screening

New eYACs are produced containing the genes MEV-1, MEV-6, MEV-15, MEV-18, MEV-21 and MEV-33 (see Table 4) in a manner as described in Example 1. These eYACs are co-transformed with the plasmids pACL-1 and pACL-2 (described in Example 2) into the ACO-1 yeast strain. The transformed ACO-1 yeast strain containing both eYAC and pACL plasmids is grown at 50 ml volume in Synthetic Complete medium (SC) in 100 ml Erlenmeyer flasks, without methionine, so as to induce gene expression from the eYACs, without tryptophan, leucine and histidine, so as to counter-select for loss of eYACs, and without arginine and lysine, so as to select for the ACL gene expressing plasmids. A 1 ml culture supernatant is centrifuged, and 100 ml supernatant is mixed thoroughly with the same volume of 100% methanol to precipitate macromolecules, followed by mixture centrifugation. As controls, the yeast strains producing the most β-carotene from Example 1 and 2 are also tested as well. 40 µl of the supernatant was analyzed by LC-MS for content of β-carotene.

The new ACO-1 strain that combines the heterologous mevalonate pathway genes (Example 1) and the ACL subunit genes (Example 2) produces significantly more β-carotene than any of the other yeast strains. Approximately 150 m/gDW (yeast cell Dry weight) is obtained, representing an increase of about 25-fold when the approaches described in Examples 1 and 2 are combined.

TABLE 6

DNA Sequences of Optimized Mevalonate Pathway Gene Analogs

| SEQ ID NO: | Optimized Gene | DNA Sequence |
|---|---|---|
| 1 | MEV-1 | ATGGTCAACACTGAAGTTTACATCGTATCTGCTGTTAGAACACCTATGGGGTCATTTGGTG GCTCTTTCGCTTCATTGCCAGCTACTAAACTGGGCTCTATCGCAATCAAAGGGGCACTTGA ACGTGTCAATATCAAGCCTTCTGATGTAGATGAGGTTTTCATGGGAAATGTGGTTTCCGCT AACCTAGGACAAAACCCAGCTAGACAATGCGCCTTGGGTGCAGGATTACCAAGATCAATT GTTTGTACCACAGTAAACAAGGTTTGTGCCTCTGGCATGAAGGCCACTATCTTGGGTGCC CAGACTATTATGACTGGTAATGCTGAAATTGTAGTTGCTGGTGGGACAGAATCAATGAGTA ACGCCCCTTACTATGCTCCTAAAAACAGATTCGGTGCTAAGTACGGTAATGTTGAATTAGT CGATGGCCTGTTGAGAGACGGCTTGTCCGACGCCTATGACGGCTTACCAATGGGTAATGC AGCTGAACTATGTGCTGAAGAGCACTCCATCGATAGAGCATCTCAAGATGCCTTTGCTATC TCTTCATACAAGAGAGCTCAAAATGCTCAAGCAACAAAAGCCTTCGAACAAGAGATAGTCC CAGTCGAAGTGCCAGTTGGAAGAGGGAAGCCAAACAAACTTGTTACAGAAGATGAGGAGC CTAAAAACTTAAACGAAGATAAGCTGAAGAGTGTTAGAGCTGTCTTTAAGTCAAACGGAAC AGTTACTGCCGCTAATGCCTCTACACTAAATGATGGTGCATCTGCTTTAGTATTGATGTCA GCAGCAAAGGTTAAGGAACTGGGTTTGAAGCCTTTGGCAAAGATAATAGGCTGGGCGAG GCAGCTCAAGATCCAGAAAGATTCACTACAAGTCCTTCCCTTGCTATTCCAAAGGCCCTAA AACATGCAGGTATTGAAGCATCCCAGGTAGATTACTATGAGATTAATGAGGCATTCTCTGT TGTCGCAGTGGCCAATACCAAAATCCTAGGTCTTGACCCAGAAAGAGTGAACATAAACGG CGGTGGTGTCGCTATGGGTCATCCTTTAGGATCTTCAGGATCAAGGATCATCTGTACTTTG GCCTACATTTTAGCACAAAAAGATGCTAAGATTGGTGTCGCTGCAGTGTGCAACGGAGGA GGTGGGGCTTCTTCTATCGTTATAGAAAGAGTATAA |
| 2 | MEV-2 | ATGCCAGTTTTGGCTGCACTACTTAGAAGAGGTCCTTTATTGCAAAGGAGGGTACAGGAAA TTAGATATGCTGAAAGATCCTACGTTAGTAAGCCAACACTGAATGAGGTAGTTATAGTCTC AGCAATTAGAACTCCAATTGGCTCCTTCTTGGGTTCTTTATCATCACTACCTGCTACCAAAT TGGGGTCCATTGCCATACAAGGCGCTATCGAAAAGGCTGGTATACCTAAGGAGGAAGTAA AAGAGGCCTACATGGGAAACGTTCTGCAAGGTGGAGAAGGGCAAGCCCCTACAAGACAA GCTGTGTTGGGTGCTGGCTTACCAATATCTACACCATGCACTACAATCAATAAGGTGTGTG CTTCTGGTATGAAGGCTATCATGATGGCATCTCAAAATCTGATGTGTGGCCACCAAGATGT TATGGTTGCTGGTGGTATGGAATCTATGTCTAATGTTCCTTATGTCATGAATAGAGGAGCC |

TABLE 6-continued

DNA Sequences of Optimized Mevalonate Pathway Gene Analogs

| SEQ ID. NO: | Optimized Gene | DNA Sequence |
|---|---|---|
| | | ACACCATATGGCGGTGTAAAACTTGAGGATCTGATCGTGAAGGACGGATTAACTGATGTCT<br>ACAACAAAATTCATATGGGGAACTGTGCAGAAAACACTGCCAAAAAGTTGAACATTACAAG<br>AGAGGAACAAGATACCTACGCCTTAAACAGTTACACAAGATCTAAAGCCGCTTGGGAAGC<br>TGGTAGATTCGGTAATGAGGTGGTTCCAGTGACAATTACTGTAAAGGGCAAACCTGATGTT<br>GTCGTGAAGGAAGATGAGGAATACAAGAGGGTCGACTTTTCCAAGATCCCAAAACTAAAG<br>ACGGTGTTCCAAAGAGAAAACGGCACGGTTACAGCCGCCAATGCTTCTACTTTGAATGAC<br>GGTGCAGCCGCTGTTGTCTTGATGACGGCTGACGCCGCTAAGAGATTAAACGTCAAACCT<br>TTAGCTAGAATTGCAGCTTTTGCTGATGCCGCTGTTGAACCAATCGATTTCCCACTTGCAC<br>CTGCATACGCCGTACCTAAAGTCTTGAAAGACGCAGGGTTGAAAAGGAAGATATAACCAT<br>GTGGGAAGTAAACGAGGCCTTTTCTGTTGTAGTTCTAGCTAACATCAAAATGTTAGAAATG<br>GATCCCACAAAAGGTTAACATTAATGGTGGTGCCGTCTCATTGGGCCATCCAATAGGAATGA<br>GTGGAGCCAGAATTGTGGTACATCTAGCCCACGCTTTGAAACAGGGTGAATATGGACTTG<br>CCTCAATTTGCAATGGTGGAGGAGGGGCAAGTGCCATGCTAATCCAGAAATTGTAA |
| 3 | MEV-3 | ATGGCCCATTCCGCTGATTCATCTGACAACCCAAGAGATGTTTGCATCGTAGGCGTGGCT<br>AGAACCCCAATGGGTGGTTTCTTAGGGTCACTTTCATCTTTGCCAGCCACTAAATTGGGCT<br>CCTTGGCCATTACAGCTGCATTGAAAAGAGAGATGTTAACTAGACTGTGGAGTAAGGAGG<br>TCGTTTTCGGTAATGTTTTAAGTGCTAATCTGGGTCAAGCCCCTGCCAGGCAGGCTGCCC<br>TGGGCGCTGGTATAAGTAACAGTGTCATCTGTACAACAGTAAACAAAGTGTGTGCCTCCG<br>GCATGAAAGCTGTTATGATAGCCGCTCAAAGTATCCAATTAGGTATAAACGATGTCGTAGT<br>GGCCGGTGGCATGGAATCCATGTCTAATACTCCAAAGTATCTTGCTGAAGCCAGAAAAGG<br>GTCTAGATTTGGCCACGACTCATTGGTAGACGGCATGCTGAAGGACGGACTATGGGATGT<br>TTACAATGATTGTGGTATGGGTTCATGCGCCGAACTGTGCGCAGAGAAGTTTGAAATCACA<br>AGAGAACAACAAGATGATTATGCAGTACAATCTTTTGAAAGAGGAATCGCTGCCCAGGAGT<br>CTGGTGCATTCACATGGGAAATTGTTCCAGTGGAAGTTTCTGGTGGAAGAGGTAGACCTT<br>CAACAATTGTAGATAAAGACGAAGGGTTAGGGAAATTCGATGCCGCCAAGTTAAGGAAGT<br>TGAGGCCTTCCTTTAAAGAGAACGGTGGAACGGTCACAGCCGGGAACGCATCTTCCATCT<br>CCGATGGTGCAGCTGCTATCGTTCTAGTGTCAGGAGAAAAGGCCTTGCAACTAGGGTTGC<br>AAGTGTTAGCTAAGGTTAAGGGGTACGGAGATGCCGCTCAGGAACCAGAGTTCTTCACGA<br>CCGCACCAGCTCTTGCTATTCCAAAAGCTATTGCACCTAATTCACCTTACTCTGAATCCTAT<br>CAAGTTGATTACTATGAGATTAACGAAGCCTTTGCTGTCGTCGCTTTAGCTAACCAAAAGTT<br>ATTGGGAATTTCACCTGAAAAAGTGAACGTGAATGGCGGAGCCGTTTCTCTAGGTCATCCT<br>CTAGGTTGCTCTGGCGCTAGAATTCTTATAACTTTGCTTGGCATTCTGAAAAAGAGAAACG<br>GAAAGTACGGTGTAGGAGGAGTCTGTAATGGAGGTGGTGGTGCTTCTGCATTGGTTTTGG<br>AAGTTGTCTAA |
| 4 | MEV-4 | ATGCATTCTACCAGACATATCTTAAGACAAAGGGCCGTCCTAGTTACAGGCGCTAGAACAC<br>CATTCGTGAAATCATTTGGGGCTCTTATGAAAGCAGATACCTTGGAATTGGCATCAGCATC<br>AGTCGCTGGGTTGCTGAACAAGACCTCACTGGACCCTAGAGATATCGATCATATCGTTTG<br>GGGTAATGTTGTACTTCAAGGATCAGCTCATAACTGCGCCAGAGAAATAGTTATCGACCTT<br>AACATGCCTAAAAAGATCATCGGTAATTTGACATCTATGGCCTGTGCTTCAGGCTTATCTTC<br>TTTGTCACAAGCCTGTATGCTAATAGAGGGTGGTCATGCCGATGTCGTCATTGCTGGCGG<br>TTCTGATTCAGTCTCCAACACTGAAGTGCCTTTGCCAAGATCCGTCACTTACGGTCTAATG<br>ATGGCCAAAGGAAGGGTGTTATGGGCTTCTTTAAGGAAGCAGGATACAACCCATTCAAA<br>TGGTTTCCAGGCGGTATTGCTTTAACCGAACGTAGTACAGGAAAAACTATGGGTTGGCAT<br>GGAGACTTAATTGCTGAGTTAAACTCTATATCTAGAGATGACCAGGAAGCCCTGGCTGTG<br>GCTTCTCATGCAAATGCTGCTAGAGCAGAAAAAGCTGGGTACTTTAAGGAGGAAATTGTAC<br>CTGTGACAATCGACAAAAAGGGCAAAAAGACTGAAGTAACATGTGATGATGTTATGCAAAG<br>AGATACAGAAAAGATGAAGGCCAAGATGCCATCATTGAAGCCTGTTTTCAGAAAAGAGGG<br>AGGTACAATAACAGCAGCCACTTCCAGTACTCTGACTGATGGTGGCTCTGCAATGTTGGTT<br>ATGTCAGAGGAAAAGGCCAAAAAGTTGGGTTATCCAACTGATGTCTGCGTGAAGTCTTGG<br>TATTTCAGTGGTATCGATCCTTACCCACAACTTTTGTTAGCACCAGTTCTAGGTTGGGGTC<br>CAGCTTTGAAAAAGGCCGGATTAACCCCTAAAGATATCGATTTGTACGAAATTCACGAAGC<br>ATTTGCTGCACAAGTTCTAGCCACAATTAAGTGTTTGAAGTCTCAGGAATTCTTCGATAGGT<br>ACGCTAACGGTGCAAAGCCAGTATTAACTGAGGATATTGATCTTTCTAAACTAAATGTTAAT<br>GGCGGTTCCTTAGCACTTGGCCACCCATTCGCCGCTACAGGAGGTAGAATCGTAATCTCT<br>CTAGCAAATGAGTTGAGAAGATCCGGAAAGAGACACGGGCTGGTCAGTATTTGTGCAGCT<br>GGAGGGTTAGGCGGAGTAGCTATACTTGAGCATACAGCAAGTAAGTAA |
| 5 | MEV-5 | ATGAACCAAGCAGTCATCGTTGCTGCCAAGAGAAACAGCTTTCGGAAAGTACGGTGGCACA<br>CTAAAACACATCGAGCCAGAGCAACTGTTAAAGCCACTTTTCCAACATTTCAAGGAGAAAT<br>ATCCAGAGGTTATATCCAAGATTGATGATGTTGTTAGGGAATGTTGTAGGTAACGGAGG<br>CAACATCGCCAGAAAGGCTCTGCTTGAAGCTGGCCTGAAAGACAGTATTCCAGGTGTTAC<br>AATTGATAGACAATGCGGTAGTGGTTTAGAATCTGTCCAGTATAGTTGTAGAATGATACAG<br>GCCGGAGCCGGCAAAGTCTACATTGCTGGTGGTGTTGAGTCTACGTCCAGAGCTCCTTGG<br>AAGATCAAAAGACCTCATTCTGTCTACGAAACAGCTTTACCAGAATTCTATGAAAGAGCTTC<br>ATTTGCCCCTGAGATGTCCGATCCTTCAATGATTCAAGGTGCCGAAAATGCAGCTAAAATG<br>TACGACGTATCAAGAGAATTGCAAGATGAATTTGCCTACAGATCTCACCAGCTTACGGCAG<br>AAAATGTCAAAAATGGTAATATCTCTCAAGGAGAATCTTCCAATTACAGTTAAGGGAGAAATC<br>TTTAACACTGACGAATCACTAAAAAGTCATATACCTAAGGATAACTTCGGGAGGTTTAAACC<br>AGTAATCAAGGCGGTACTGTGACCGCAGCCAACTCTTGTATGAAAAATGATGGTGCCGT<br>CCTGTTGTTGATTATGGAAAAGACATGGCCTACGAATTAGATTTTGAACACGGGCTGTTG<br>TTCAAGGATGGAGTAACTGTGGGAGTGGACTCTAATTTCCCTGGTATTGCCCAGTACCA<br>GCTATCTCTAAATTTGTTGAAGAGAAACCAATTGACTATCGAAAACATTGAAGTCATTGAGAT |

TABLE 6-continued

DNA Sequences of Optimized Mevalonate Pathway Gene Analogs

| SEQ ID. NO: | Optimized Gene | DNA Sequence |
|---|---|---|
| | | AAACGAAGCCTTCTCAGCACAAGTTGTGGCCTGTCAACAGGCCTTGAACATCTCAAACACT<br>CAATTGAACATATGGGGAGGAGCTCTAGCCTCTGGGCATCCTTACGGAGCTTCCGGTGCT<br>CAACTAGTGACCAGATTGTTCTATATGTTTGATAAGGAAACAATGATAGCTTCCATGGGAAT<br>TGGCGGTGGCTTAGGTAATGCTGCTTTATTCACAAGGTTCTAA |
| 6 | MEV-6 | ATGACTATCCCTTTGGCCACAGCTGTTGCAGATATTGAATTACCAAGACCAAAGGATGTTG<br>GCGTTTTGGGTATCGAAGTATACTTTCCTAGGAGATGTGTTTCAGAAGCCGACCTGGAAGT<br>GTTCGATGGCGTTTCCACAGGAAAGTACACTATTGGACTGGGTCAGGAATACATGGCATG<br>GCCTGATGACCGTGAAGATATCAATTCTTTTGCCCTTAACGCTGTATCTGGTCTGTTGGAA<br>AAGTACAACATTGATCCAAAATCAATTGGCAGAATCGATGTAGGCACAGAAACTATCATTG<br>ATAAGTCAAAATCTGTTAAAACAACACTGATGGATCTTTTCGCAGAAGCTGGAAACTACGA<br>TATCGAAGGTATTGACAGTAAAAACGCTTGTTACGGAGGTACTGCTGCCTTGTTCAATGCA<br>ATCAATTGGATAGAGTCCTCTTCTTGGGACGGTAGAAACGCTATAGTTGTATCCGGAGATA<br>TAGCTGTCTACGCCGAAGGTGCTGCAAGACCAGCAGGTGGTGCAGGGGCTTGTGCAATC<br>TTAATCGGACCAAATGCTCCAGTTGTCTTTGAACCAGTGCATGGTACCTACATGGCTAACA<br>CATATGACTTCTACAAGCCAAATTTGTCATCAGAGTATCCAGAGGTTGATGGCCCAGTGAG<br>TGTCGTCACATATGTCGCCGCTCTTGATGCCGCATATACTACTTTCAAGGAAAAGTTCGCT<br>AAAGCTGCAAAGAGAGCTCAAGTTGCTGGAAAGGAAGTAAGTTCTGCAACTTTCTCTTTAG<br>AGGATTTGGATTATGCCATTTTTCACTCCCCTTATGGTAAACAAGCAGTCAAGGGGCATGC<br>TAGAATGTTATACAACGATTTCATCACTAATCCTAAAGATCCTAGATTCGCCAACGTTCCAA<br>ATCCAGAGTCCTTCATATCACAATCACATGCACAATCTTTGACTGACAAAAACGTTGAAAAG<br>ACTTTCGTGGCACTAAGTAAAGCATCTTTTGCTAAAAAGACAGATCCTGGGATGGCATGCT<br>CAAAGAGACTAGGGAACATGTACACAGCATCTCTATACGGTTGTTTGGCATCATTGTTAGG<br>TACTGTTGAACCATCCGAGTTAGGCGGTAAGAGAGTTTCTTTGTTTTCTTTTGGCTCAGGG<br>TGCGCTGCTACATTCTTCACCGCCAGGATTAAAGGCGACACCAGTGAGATAAAGGAAAAG<br>TTAAAGCTAAAGGAAAGACTAGCTGCTATGACAGTTGCCCCTCCTGAAGAGTTCGTGGCT<br>GCCTTGGCCTTGAGAGAGAAAAATCATAACGCAGTAGATTTTACCCCAGAAGGATCTGTG<br>GATAACATCTGGCCAGGTGCTTACTACCTTGAGCACGTAGATTCTAAGTTTCGTAGAAAAT<br>ACGTCAGAGCCCCTGTTGCATAA |
| 7 | MEV-7 | ATGCAAAGATTATTGACACCAGTCAGACAGGTACTTCAAGTTAAGAGGGTTATGCAGGAAG<br>CCAGTCTTTTACCAGCTAGACTTTTGCCAGCTGCACACCCTTCTTTCTCAACAGTTCCAGC<br>TGTACCACTTGCAAAGACTGACACATGGCCAAAGGACGTCGGCATACTGGCAATGGAGGT<br>TTACTTTCCAGCCCAGTACGTGGATCAAACTGAACTTGAAAAGTTCAATAAGGTAGAAGCA<br>GGTAGATACACCGTAGGTTTGGGTCAAACACAAATGGGATTTTGTAGTGTTCAAGAGGATG<br>TAAAATTCACTATGCTTAACTGTGGTTCAACAATTGATGGAGAGAACCCAACTGCCATGGGA<br>TTCCGTGGGCAGATTAGAAGTTGGCACAGAAACAATCATTGATAAGTCTAAAGCAGTTAAG<br>ACAGTGTTAATGGAACTATTTCAGGATTCTGGTAATACAGATATCGAAGGTATCGATACTAC<br>AAACGCCTGTTATGGAGGAACAGCTTCATTGTTTAACGCAGCAAACTGGATGGAATCTTCA<br>TCTTGGGATGGTAGATACGCTTTGGTAGTATGCGGAGATATCGCTGTCTATCCTTCAGGTA<br>ACGCAAGACCAACAGGCGGTGCTGGGGCTGTCGCAATGTTGGTTGGTCCAGAAGCTCCA<br>TTAGTTTTAGAAAGAGGTTTGAGGGGTACACACATGGAAAATGTTTATGACTTCTATAAACC<br>TGATGTCACTTCTGAATACCCTTTAGTCGACGGAAAACTTTCCATTCAATGTTACCTAAGAG<br>CCCTTGATAAATGTTACGCATTCTACAGACAAAAGATTGAAAAGCAATGGAAGCAAGCCGG<br>AATTGATAGACCTTTCACCTTAGATGATGTTCAATACATGATCTTCCATACTCCATTCTGTA<br>AGTTGGTTCAAAAGTCCTTAGCTAGATTGATGTTTAATGATTTCTTGCTAGCATCTGGCGAT<br>ACTCAAACCGGAATATACAAAGGCTTAGAGGCTTTCAGAGGTCTTAAACTGGAGGACACCT<br>ACACTAATAAGGATGTAGATAAGGCCTTTCTGAAGGCTTCTCTGAATATGTTCAACAAAAA<br>GACTAAAAACTCTCTTTACTTGTCCACATATAACGAAACATGTACACTAGTTCTCTGTACG<br>GTTGCTTAGCCTCCCCTATTAGCTCATCATTCAGCTCAGGATTTGGCTGGGTCTAGAATAGG<br>TGCTTTTTCATACGGCTCAGGCCTAGCAGCAAGTTTCTTTTCCTTCCGTGTTAGTCAAGAT<br>GCCTCTCCAGGGTCCCCTCTGGAAAAGTTAGTCTCATCTACTTCTGACTTGCAGAAAAGAC<br>TAGCCAGTAGAAAACGTGTTTCTCCTGAGGAATTCACAGAGATTATGAATCAAAGAGAGCA<br>GTATTACCATAAGATGAACTTCTCACCACCAGGTGACAAAAACTCATTGTTTCCTGGGAGA<br>TGGTATTTGGAAAGAGTCGATGAGTTGTACAGAAGGAAATATGCCCGTAGACCAGTTTAA |
| 8 | MEV-8 | ATGGCTTCTCAACCTAAAAACGTTGGTATCTTGGCAATGGAAATATATTTTCCTCCTACCTG<br>TCTGCAACAGGAAGTGTTAGAAGCTCACGATGGTGCATCTAAAGGTAAATACACTATTGGT<br>CTGGGTCAAGATTGTATGGGCTTTTGTACAGAAGTCGAGGATGTAATATCTATGTCCTTGA<br>CTGCTGTTACATCATTGCCTGAGAAGTACGCCATTGATCCAAAGCAAATAGGGAGACTTGA<br>GGTTGGCTCCGAAACGGTTATTGATAAATCCAAGAGTATTAAGACGTTTTTGATGCAGATC<br>TTTGAAAAACATGGTAATACCGATATAGAAGGTGTAGACTCAACAAATGCCTGTTATGGAG<br>GAACTGCCGCCTTGTTCAACTGCGTGAACTGGGTTGAATCTTCTTCCTGGGATGGAAGAT<br>ACGGCCTTGTAGTCTGTACAGATAGTGCCGTGTATGCCGAAGGGCCAGCCAGACCAACA<br>GGAGGTGCTGCTGCCATAGCAATGCTAGTGGGCCCTGACGCTCCTATTGTTTTCGAGAGT<br>AAAAATCAGAGCCTCACATATGTCTCATGCTTATGACTTCTATAAACCTATCTTAGATTCCGA<br>ATACCCAGTGGTCGATGGGAAGTATCTCAGACATGTTATTTGATGGCTTTGGATTCTTGT<br>TACAAAAGTCTATGCAATAAGTACGAAAAACTGGAGGGGAAGCAGTTCTCCATGGCTGAC<br>GCTGCATACTTTGTCTTTCATTCTCCATACAACAAATTAGTGCAAAAATCATTTGTAGACT<br>GTTGTTCAATGACTTCCTTAGGAACGCCTCTTCTGTAGATGAATCAGCAAAGCAAATCTTA<br>GCTCCTTTCGAGTCTTTGGCCGGAGACGAATCTTACCAATCTAGAGATTTGGAAAAGGCCT<br>CCCAACAGGTTGCTAAGCCATTCTATGATGAGAAAGTTCAACCAACAACTCTAATTCCTAA<br>ACAAGTAGGGTAACATGTATACCGCCAGTCTGTACGCTGCCTTTGCTTCATTGATCCACAAT<br>AAGCATAATACACTGGCAGGTCAAAGAGTGATTGTTTTCAGTTACGGTTCCGGACTAACAG |

TABLE 6-continued

DNA Sequences of Optimized Mevalonate Pathway Gene Analogs

| SEQ ID. NO: | Optimized Gene | DNA Sequence |
|---|---|---|
| | | CAACAATGTTCTCTTTGAAGTTCAACGAAGGACAACATCCATTTTCTTTGAGTAACATTGCT<br>TCAGTCATGAATGTTTCAGAGAAGCTAAAATCAAGGCATGAGTTCACTCCAGAAAAGTTCG<br>TAGAGATTATGAAGTTAATGGAACACAGATATGGCGCCAAGGATTTTGTTACTTCTAAGGA<br>CTGCTCCTTATTGGCACCAGGGACTTACTACCTTACGGAAGTCGATTCAAAATACAGAAGA<br>TTCTACGCTCAAAAAGCCCCAGAACACGGATTAGTTAATGGCCACTAA |
| 9 | MEV-9 | ATGATGAGAAACACATGTTTATCTTTGGCTGGAGTTTCAGGTATGGCAGTTTACGCACCTC<br>ATTGCAGAGTCGATTTGGAACAATGGTGTAAGTGGACTGGGAACTCCTGGGATAAAGTCT<br>CTAGTGTTGTCGGTCAGAGTTTTAGAATCACCTCCCACAACGAAATGCCTACACAATGGC<br>TGCCAATGCTGTGTTGAGACTAATCGTTAACAACAATATTGATCCTACCAAAATAGGGTTC<br>CTGGGATTAGGCACTGAATCAAGTTCCGATAACTCTGCCGGTGCCATAATCGTAAAAGGTA<br>TGGTTGACAAAGGCTTGAGAGCTATGAATATGCCTGCTATGTCAAGACATTGTGAGGTTCC<br>TGAATTCAAGCACGCTTGTTTAGCAGGTGTGTATGCAATGGAGTCAGCAACAAGATTTGTC<br>AACGCAGATGGCAAGGACAGAATGGCAATAGCCGTGGCCTCTGATATAGCTGAGTACGCC<br>CTAGGCTCAACTGGGGAACAGACTCAAGGTGCCGGTGCAACTGCAATGGTCCTTGAACAT<br>GACCCTAAGCTGTTTGAAGTACAATTACAACATTCAGGGTCTGCCTCCGACTACAGAGGAC<br>CAGATTTTAGAAAACCACACCGTAGACATTTCATGAATTTGGAGGAATACACCAAATCTTCC<br>GCTAATGGTAAGATGGCTGATTTCCCAGTCTTTAGTGGACCTTATTCTACTTTAGTATATCA<br>GGAAGAGGTTACAGTAGCTGTCGAACACATGCTAGAAAGATTGCAACAATCTCCTGGTAAA<br>TACTACGATGATGTTACAGCATTATTCTTCCATCGTCCATACAACATGATGCCAATCCAAGC<br>CATGAGTTTCTTATATGCTAGAGGATTAGCAAGAGCTACATCTGAAGAGCACAAGGCACAT<br>TTCGCTGAATTGTGTAAGCAGGGCAAGGCCGATCCAGCAGCTGTTGTTAAGGAATTAGAT<br>GTTAATCCACATTACTTCCAACAAATCGAATCAGGAGGAGAACCAAAGGATGCATTCCCAG<br>CCACTGGCAAAGTAGCTAAGGTGTTGAGAAAGGACAAAAAGTTTATTGATCTACTAGAGAA<br>AAAGATGTCTATGGGTTCCCCAGCAATGGGAAACTTCGGCAATCTGTATACTGCTTCTCTA<br>CCTTGTTGGCTTGCAGCTGGTTTCGAGGAAGCATACACAAGGAAGTTAGATATTACAGGTA<br>AGCCAATGGTTATGTGGGTTTACGGGTCAGGTGATGCTTCAATGTCTATTCCAATTTTGCC<br>AGTACCAGGATGGGAAAACGCCGCTGCTAATATCAACGTATCAAAGGCCTTGGAAAATCC<br>TGTTAACCTTGATAAAGCTCAATACGAAGCATTGCATACAGGTGCTGAGAAAAACGACCTT<br>GCTAAGGATCGTAGAAAGATGGAGTTCGTTATCGATAGGCTTGGCAATAGAAACGAAGCT<br>GCATTTCAAGATGTTGGCATTGAGTATTACAGATACATCCAATAA |
| 10 | MEV-10 | ATGACAATCGGTATTGATAAGATAAACTTCTATGTTCCAAAATACTATGTTGATATGGCAAA<br>GTTAGCTGAGGCCAGGCAAGTAGATCCTAACAAATTTCTAATTGGCATTGGACAGACTGAG<br>ATGGCAGTCAGTCCTGTTAATCAAGATATCGTCTCTATGGGTGCTAATGCAGCTAAAGACA<br>TCATCACCGATGAGGACAAGAAGAAAATCGGTATGGTTATAGTTGCCACAGAATCTGCAGT<br>TGATGCCGCAAAGGCTGCTGCTGTCCAAATTCATAACCTGTTAGGTATACAACCATTCGCC<br>AGATGTTTCGAGATGAAAGAGGCCTGCTACGCCGCTACTCCTGCCATCCAATTGGCTAAG<br>GATTACTTAGCAACAAGACCAAACGAAAAGGTTTTGGTAATAGCTACAGATACTGCTAGAT<br>ATGGGTTGAATTCTGGAGGTGAACCAACACAGGGAGCCGGTGCTGTTGCAATGGTGATCG<br>CTCACAATCCATCAATTTTGGCTTTGAATGAGGATGCAGTGGCTTACACTGAGGACGTTTA<br>CGACTTCTGGCGTCCAACTGGTCATAAGTACCCTTTGGTAGACGGCGCACTTTCAAAAGAT<br>GCTTACATTAGATCATTCCAACAATCCTGGAACGAATACGCTAAGAGACAAGGCAAATCTC<br>TAGCTGACTTCGCCAGTTTATGTTTTCATGTACCTTTTACTAAGATGGGCAAAAAGGCCCTA<br>GAATCCATTATCGATAACGCAGATGAAACCACACAGGAAAGGCTAAGATCTGGTTACGAG<br>GATGCAGTAGATTACAACAGATACGTCGGGAACATCTACACAGGATCCTTATACTTATCTC<br>TTATTTCACTTCTGGAAAACAGAGATCTGCAAGCAGGTGAAACAATCGGTTTGTTCTCATAT<br>GGATCTGGTTCTGTCGGGGAATTCTATTCAGCAACACTTGTTGAAGGATACAAAGATCATC<br>TGGATCAAGCTGCTCACAAGGCCTTATTGAATAACAGAACTGAAGTGAGTGTTGATGCATA<br>TGAAACATTTTTCAAAAGATTCGATGATGTTGAATTTGATGAAGAGCAAGACGCAGTTCATG<br>AGGATAGACACATATTCTACTTGTCCAATATAGAAAACAATGTCAGAGAATATCATCGTCCA<br>GAATAA |
| 11 | MEV-11 | ATGAGAGCTGTCCTTAGATTGTTATCAACACATACTGTTTTCTCTCCTATTGAAACAATTGT<br>ATCTGTTTTCGTGTTAGCTACATTAGCTTACTTCCACATCTTGTCCGGAATCAAGCACTCAA<br>GTTTCTTTGCATCTTCTCATCCTCCTGCTATCAGACCTGCTTTTGCACATCTGACCAACGG<br>GGAATGGGTTGCCGTCTCCCAACATGATTGGACTGAAGCATGGAAGCATCCTGGCGGTTC<br>ACTTGATGCATTAGAACTTCAACAAGTAGTTTTCACTTTAGATGACAAGACTCAACCATCTG<br>CTGTGCTAGATGCATCCGCAATTAGTCAGCACTTAGTTTCCAATGTTCCTGCATTATCTGG<br>AAAAGCCTACTCTTCATTGTGCCACCATCCAAATGTATCAGGCACCTCCTGTTTTACATCA<br>GTTTCTGGTCCAGGAGCTTCACCAATCTTGACACTGAGTTTTAAGCCTGGAACTAGAGACG<br>ATTGGTTAGGATCATTAAGGAAGGAGAAAACTATCACACTAGATGGGGTTAAGTACGACGT<br>TGGAGCCGGAAAAAGACAAGAGTCAATCGCGATATGGAATCATCTAAGTGGGTTGCTTA<br>TGCATTATCAGCTTTGGTACTTAGATTTGGGAATTAACAAAGGCAGATTCCTTAGATATAC<br>TAGTGGTTCTAACTGGGTACATCCTAATGCACGTAACATTCATGAGATTGTTCTTGGCATC<br>CAGAGCACTTGGCAGTAACTTTTGGTTATCAGCTGGCATATTCTCCTCCGCAACAATTTCT<br>TTCCTATTCACTTTACCAATGTGTAGATCTATGGATATTCCACTTGATCCAATTGCCTTGAC<br>AGAAGCCCTGCCATTCTTGGTGTGTACCGTAGGTTTGACAAACCACTTAGATTGGCAAGA<br>GCTGTGATGGCTCATCCTAATATCCTTAAACCTCAAGATGATGATTGAGAGCTGCC<br>GAGATGTCATTCTTGAGGCACTGGACAGAGTTGGTAACATGATATTGAGAGATTACGCTTT<br>AGAGATCGCAGTTCTATTCGTTGGCGTTAACTCCAGAGTTGGCGGTCTTAAGGAATTTTGT<br>GCTGTAGCTGCAGCATTACTTGCTATGGACAGATTAATGACATTCACACTTTATACAGCAG<br>TGTTAACCATCATGGTTGAGGTAAGGCGTATCAAAAAGGTCAGAGATATGACTAAGGCTAG<br>ATCTAGAAGTTCTTCTATTACCGCCGTTACAGCCAACGGCACCGCCATAAGAGGCGTTTTG |

TABLE 6-continued

DNA Sequences of Optimized Mevalonate Pathway Gene Analogs

| SEQ ID. NO: | Optimized Gene | DNA Sequence |
|---|---|---|
| | | AGTAGAAAATCTTCAAAACAATCTGTGACAGAACCAGAGACAACTAAAAACCTAAGACAAA<br>GAGCCACTGATTCAGCCATCGGTGTTAAGGGTTCATTGCTGAAAGATGGAGGCAGATTGC<br>AGGAAGCCGAGGAGAATCCAATGGCAAGATTAAAGCTATTGTTAATCGCTTCCTTCTTAAC<br>ACTACACATCTTGAACTTTTGTACTACTTTGACTTCAGCCACAGCTAACGCAAGACATCAAA<br>GACATCCTTTTAGAACCGTTCAAGAGGTAGTACCAATTCCTAGAGTTGACATTACTACCCC<br>AGCCATAGCCAATATCTTGTCTCATCTAGCTGTGTGGCTCAGGAACCTATGTTCACTGTTGTT<br>GGCAGTGAACCTATCGAACTTCTTGTTAAAGTCGCTGCTCCAGTCTACGTCCATGCTCTAC<br>CATTGGCCCCTGCTTTAAGAGCTTCAAACACTAATACTGGAGAAGCTATTGAAAACTTTAT<br>GAGTTCATGGTCTAGTCTGGTAGGTGACCCAGTTGTTAGTAAGTGGATCGTAGCATTGCTA<br>GCTGTCTCTGTTGCATTGAATGGATACTTGTTAAAGGGTATAGCCGCAGGTTCCGGGTTG<br>GCTGCCATGAGAGCTGTTAGATCTCAAGGTGTTCGTTTCAGATCTAGAGCTAGAAGTATCG<br>TAAAGATATCTGATGAACCTGAGCCAGAGCCAGAACACTCTATCGACCCAGCACCAGTAG<br>TGTTCTTCGCTTCCGCAGCACCAGCTGTAGAGGCCCTGCTCCAGCTCCTGCACCTGAAC<br>CAGAACCACCAGTCAACAGACCACCACCATTGACTATTTTCTCAAGACCACTGAACTTAGA<br>AACAGTGGACAAAAAGTTACAAGATGCTCTGCCAATAAGATCCCCACCACCTGTTGAACCA<br>ATCACTCCAGAATCTAGAGAAGTGGAACCAACCCAAGTAGAAGTAAGATCTCTAGCTGAAT<br>GTGTGGATGTGTTCGAGAATGGGCCAAGACCAGTCTCAGTGGCTTTAAAGACTCTGAATG<br>ATGAGGAAGTTATCCTGCTTTGCCAAACAGGTAAGATAGCTCCATATGCATTGGTTAAGAT<br>GTTGGCTGATTTCGATAGGGCCGTACGTGTCAGAAGAGCACTTATTAGTAGAGCTTCACG<br>TACAAAAACTTTAGAAAACTCACTGGTTCCTATGAAAGATTATGATTACGCCAGAGTCATGG<br>GTGCCTGTTGTGAAAACGTTATCGGATACATGCCATTACCACTAGGGATTGCAGGTCCATT<br>GAAGATTGATGGCTTGATGTATCCTATACCAATGGCAACCGCAGAAGGTACCTTGGTTGCA<br>TCTACTTCTAGGGGCTGTAAGGCCTTAAATGCTGGTGGAGGGGTCACAACTGTCTTGACA<br>GCAGATGGCATGACAAGAGGGCCAGCTATAGACTTTCCTTCCATCGTCAGAGCTGCAGAG<br>GCTAAGGCCTTCATTGAATCAGAAGATGGATACGCTACAATCAGGGAGGCTTTCGAGTCT<br>ACTTCTAGATTTGCCAAGTTGCAAAAGATCAAGTGTGCACTAGCTGGTCGTACTCTTTTTGT<br>CAGATTTGCTACTAGAACAGGAGATGCCATGGGTATGAACATGATTTCTAAGGCTACCGAA<br>AAGGCACTTGATGTCCTGAGTCACGAGTTCCCTGAAATGGTCGTCCTTGCTTTGTCTGGTA<br>ACTACTGCACAGACAAAAAGCCTGCAGCTATTTCATGGATCGAAGGTAGGGGAAAATCTAT<br>TGTAGCAGAAGCAGTTATTCCTGGTAAGGTCGTTAAGTCAGTCCTGAAAACAACAGTCGAG<br>TCTCTTTGCAATGTCAACACTAAGAAAAACCTGATTGGTTCAGCCATGGCAGGTTCTGTTG<br>GTGGTTTCAACGCTCATGCCGCCAACATCCTAACAGCTGTGTTCCTAGCCACAGGTCAGG<br>ATCCTGCTCAAAATGTCGAATCTTCTAATTGCATGACTTTAATGGAACCAACAAACGGCGG<br>TGAGGATTGCTAATGACAATTTCAATGCCATGTATAGAGGTAGGAACCGTTGGTGGAGG<br>GACAATTCTGGAACCACAAGGTGCAGTTTTGGATTTGTTGGGCGTTAGAGGGGCTCACCC<br>TACTAATCCTGGTCAAAACGCTCAACAGTTAGCCAGAATTATCGCATCAGCTGTAATGCCA<br>GGCGAATTGTCTTTGATAAGTGCCTTAGCCGCAGGTCATTTGGTTAGAGCTCATCTTGCCC<br>ACAATCGTTCTCAATTGAATACACCAATGCCATCCAGACCACATACTCCTGGCCCTGAGGA<br>TGTCTCACATGTGCAGCAGCTACCTACACCATCTGCATCTGATGATAAAGGTGTTACAGCT<br>CAAGGTTACGTTGTCGAAGCAAAATAA |
| 12 | MEV-12 | ATGTTATCAAGATTGTTCAGAATGCATGGTCTATTTGTTGCTTCTCACCCTTGGGAAGTAAT<br>AGTTGGTACTGTAACATTAACGATCTGTATGATGTCTATGAACATGTTTACCGGAAACAACA<br>AGATTTGTGGTTGGAATTATGAGTGTCCTAAGCTGGAAGAGGATGTGTTGAGTTCAGACAT<br>CATCATACTTACTATAACAAGATGCATTGCAATATTGTATATCTACTTCCAATTTCAAAACCT<br>TAGACAATTGGGTAGTAAATACATCCTAGGCATCGCCGGATTGTTCACTATTTTCTCTAGTT<br>TTGTTTTCTCAACCGTCGTTATTCACTTTTTGGACAAAGAGTTAACTGGTTTGAACGAAGCT<br>CTACCATTCTTCTTGCTGCTGGTAGATTTGTCCAGAGCTTCCGCTTTAGCTAAATTCGCTCT<br>GTCCTCTAATTCTCAAGATGAAGTTAGAGAGAATATAGCAAGGGGAATGGCCATACTTGGA<br>CCTACTTTCACACTTGATGCCCTTGTCGAATGTTTGGTTATTGGGGTTGGCACAATGTCCG<br>GCGTTAGACAGTTAGAAATCATGTGTTGTTTTGGCTGTATGAGTGTCTTGGCTAACTACTTT<br>GTCTTTATGACATTCTTTTCCAGCTTGCGTTTCTTTGGTATTGGAGCTGTCAAGAGAATCAAG<br>AGAAGGCAGACCAATATGGCAACTATCACATTTCGCCAGAGTGTTAGAAGAGGAGGAAAA<br>CAAACCTAATCCTGTCACACAGAGAGTGAAAATGATCATGTCTTTGGGTTTAGTCCTAGTG<br>CATGCTCATTCTAGATGGATCGCAGATCCATCCCCTCAGAATTCTACAGCTGATAACTCTA<br>AAGTTAGTTTAGGTTTAGATGAAAATGTAAGTAAGAGGATTGAACCTTCCGTGTCTTTGTG<br>GCAATTCTACTTATCAAAAATGATTTCCATGGATATTGAACAAGTGATAACGTTGTCTTTGG<br>CTTTATTGTTAGCCGTTAAGTACATTTTCTTTGAGCAAGCCGAAACGGAATCTACATTATCA<br>CTGAAAAACCCAATTACATCCCCAGTCGTTACCCAGAAAAAGATAACTGATGATTGCTGTA<br>GAAGAGATCCAGTGTTGGTCAGGAATGATCAAAAGTTCCACGCCATGGAGGAGGAAACTA<br>GGAAAAACAGAGAAAGGAAAGTTGAAGTTATCAAGCCTCTATTAGCAGAAAATGACACTTC<br>ACATAGGGCCACTTTCGTTGTCGGCAATTCATCTCTTTTAGGTACGTCATTGGAGCTGGAA<br>ACACAGGAACCAGAAATGGAACTACCAGTTGAACCAAGACCAAATGAGGAATGTTTGCAA<br>ATACTAGAGAACGCTGAAAAGGGAGCCAAGTTCCTATCTGATGCCGAGATTATCCAGCTG<br>GTCAATGCCAAGCACATTCCTGCCTACAAGTTGGAAACCCTTATGGAGACACATGAGAGA<br>GGTGTGTCTATTAGGAGACAATTACTATCTAAAAAGTTACCTGAACCAAGTTCCCTACAATA<br>CCTGCCTTATAGAGATTACAATTACTCCTTGGTAATGGGAGCTTGTTGTGAAAATGTCATTG<br>GGTACATGCCAATTCCAGTGGGTGTCGCCGGTCCACTATGTTTGGACGGTAAGGAATTTC<br>AAGTACCTATGGCAACGACTGAAGGCTGCTTAGTTGCATCTACAAACAGAGGTTGTAGAG<br>CCATTGGATTAGGTGGCGGTGCTTCTTCAAGAGTCTTGGCTGACGTATGACTAGAGGTC<br>CTGTTGTGAGATTTCCTAGGGCCTGTGACTCTGCAGAAGTTAAGGCTTGGTTGGAAACTC<br>CAGAAGGTTTCACCGTAATCAAAGAGGCCTTTGATTCCACATCAAGGGTGGCCAGATTACA<br>AAAACTACACATGTCTGTCGCTGGGAGAAATCTGTATATCAGATTTCAATCCAGATCCGGC<br>GACGCAATGGGTATGAATATGATTTCAAAAGGGACAGAAAAGGCTTTGTCAAAGCTGCAG |

TABLE 6-continued

DNA Sequences of Optimized Mevalonate Pathway Gene Analogs

| SEQ ID. NO: | Optimized Gene | DNA Sequence |
|---|---|---|
| | | GAGTATTTCCCAGAGATGCAAATCTTGGCCGTATCTGGCAACTATTGCACAGACAAAAAGC<br>CTGCCGCCATCAACTGGATTGAAGGAAGAGGCAAATCTGTGGTTTGTGAAGCTGTAATTC<br>CAGCCAAAGTTGTTAGAGAAGTGTTAAAGACCACAACAGAAGCTATGATTGAAGTAAACAT<br>AAACAAAAACTTAGTAGGGTCTGCCATGGCTGGTTCAATTGGAGGATACAACGCTCATGCT<br>GCCAATATTGTAACCGCTATCTACATCGCATGTGGACAAGATGCTGCCCAAAATGTCGGTT<br>CCTCAAATTGCATCACATTGATGGAAGCATCTGGCCCTACAAACGAGGATTTGTATATCAG<br>TTGCACAATGCCATCTATAGAAATAGGGACTGTGGGAGGAGGAACTAACTTACTTCCACAG<br>CAAGCCTGCTTACAAATGCTGGGTGTACAAGGAGCCTGTAGAGATAATCCAGGGGAGAAC<br>GCTAGACAACTTGCCAGAATTGTTTGTGGGACAGTTATGGCTGGTGAACTTAGTCTAATGG<br>CAGCTTTGGCTGCTGGGCACCTGGTGAGATCTCATATGATTCATAATAGAAGTAAGATTAA<br>CCTTCAAGATTTGCAAGGTACGTGTACGAAAAAGGCTGCCTAA |
| 13 | MEV-13 | ATGGATTTGAGAAGGAAATTACCACCTAAGCCTCCATCTTCAACAACAACAAAAACAGCCAA<br>GTCATAGGTCCCATTCTCCTACGCCAATTCCAAAGGCTTCAGATGCATTGCCTCTTCCATT<br>GTACCTGACCAATACGTTTTTCTTCACTCTTTTCTTTTCCGTAGCATATTACCTGTTGCATA<br>GGTGGAGAGACAAGATTAGATCCGGAACACCTTTACACGTTGTGACACTGACTGAACTAT<br>CCGCAATTGTACTGCTGATTGCTTCCTTCATCTATCTTTTAGGCTTTTTCGGTATTGATTTT<br>GTGCAATCTTTCACATCAAGAGAAAATGAGCAACTAAACAACGATGATCACAACGTCGTGT<br>CAACAAACAATGTTTTATCTGATAGAAGGTTAGTTTACGACTATGGATTCGATGTGACAGG<br>AGACAACGATAACGATAATGATGACGATGTTATTGTGAAAAGTGTCGTTTCTGGGGAAGTT<br>AATTCTTATAGTTTGGAGGCTTCCCTAGGAGATTGTTACAGAGCCGCAAAGATTAGAAAGA<br>GAGCCGTCGAGAGAATTGTCGGGAGAGAAGTATTAGGCTTGGGTTTCGAGGGATTTGATT<br>ATGAATCTATCCTGGGGCAATGTTGTGAAATGCCTATCGGGTACGTCCAAGTGCCAGTAG<br>GTGTCGCTGGACCTTTATTGTTAAATGGTGGGGAATTCATGGTTCCAATGGCTACAACTGA<br>AGGCTGTCTTGTAGCTTCCACTAATAGAGGTTGTAAAGCCATATGCTTATCAGGTGGTGCC<br>ACTGCCATATTGCTAAAGATGGTATGACAAGAGCCCCAGTAGTGAGATTCGCCACAGCT<br>GAGAGAGCTTCACAACTAAAGTTTTACTTGGAAGATGGTGTCAATTTCGATACATTGTCGT<br>TGTCTTTAACAAAAGTTCAAGATTTGCCAGATTGCAAAACATCCAATGCTCAATTGCCGGTA<br>AAAACTTGTACATTAGGTTTACTTGCTCCACAGGCGACGCCATGGGTATGAACATGGTTTC<br>AAAAGGAGTACAAAATGTATTAGACTTTTTACAAAATGATTTTCCTGATATGGACGTAATTG<br>GGATCTCTTGGAAGTTCTGCTCTGACAAAAAGCCAACAGCTGTCAACTGGATTGAGGGCA<br>GAGGAAAGTCTGTCGTTTTCCAGGCCGTAATTACCAAAAAGGTGGTTAGAAAGTCTGCACT<br>GAACCCTCAAACTTGCACATGTAGAACTTTGACCTGTTTAAGACCATTATTGGTTCTGCTAC<br>TTCTGGTTTTGCTAGTGGACTTAATGCATATGCTTCATATCGTGTCTGCCGTGTTCATCGCT<br>ACCGGTCAAGATCCAGCTCAGAATATCGAATCTAGTCACTGTATCACTATGATGGAGGCTG<br>TCAACAATGGTAAGGATTTGCACGTTAATGTTACGATGCCATCTATAGAAGTTGGCACGT<br>GGGAGGTGGCACTCAGCTAGCCTCTCAATCAGCCTGTTTGAACTTGCTTGGTGTAAAGGG<br>TGCCTGTATAGAATCCCCAGGATCAAACGCCCAGTTGTTAGCTAGAATCGTTGCTGGTTCT<br>GTTCTGGCAGGCGAATTAAGTTTGATGTCAGCTATAAGTGCTGGGCAACTAGTTAAATCTC<br>ATATGAAATACAATAGGTCTAGTAGAGATATGTCAGCAATAGCTTCTAAGGTCTAA |
| 14 | MEV-14 | ATGTTTAGAAGAGCTATACTGTTAGGATGCTCTGCTGCCAAGCACCATGGTCTGAGTGTT<br>CTAACGCTCAATTAGTTGATGCAGTTAAGTCTAGAAAGATCTCATTCTACGGTCTTGAACAA<br>GCCTTGGAACCAGATTATAGAAGGGCTATCGAAGTAAGGAGGAGAGGTTGTCTCTGAAATC<br>GCCTCACAACAGCCAGAAGCAAAAAGAAGCAATCCGCATTGCACACAATACCATTTGAG<br>AATTATGATTGGAATAAGGTCGTTGGCCAAAACTGTGAAAACATTATTGGATACGTCCCAA<br>TACCACTGGGCGTTGCTGGCCCTATTTTGATTGATGGTAAAGAGTACCCAATACCAATGGC<br>TACAACAGAAGGCGCTTTGGTCGCTAGTACTCATAGAGGTGCTAGAGCTATTACAAGATCC<br>GGAGGTTGTAAGACATTGTTATTAGGTGAAGGTATGACAAGAGCACCAGTGGTTGAATTG<br>CCTTCATTAGAGGAAGCTGGGCGTTTGCACAAGTACTGTAATGAGAACTTCTTATCTTTAA<br>AGGAAGCATTTGAATCAACTACCCAATATGGAAAACTTAATTCTTTAAAGTGCGTACTAGCT<br>GGTAGAAAAGCATACCTTAGATTCAGAGCCACTACAGGCGATGCTATGGGCATGAACATG<br>ATAACAAAGGGTGTAGACAAAGCACTGTCTGTTCTACAGCAACATTTCCCTTCAATGGAAA<br>TCCTAGCCCTAAGTGGTAATTACTGTACCGACAAAAAGCCATCTGCTGTAAATTGGATTGA<br>TGGCAGAGGTAAATCAGTGGTTGCAGAAGCCACTTTATTGGCTGATGTTGTCGAAGATACT<br>CTGAAATGTACAGTCGATTCTTTGGTATCCTTGAATATCGACAAAAACCTTGTTGGGTCAG<br>CTATGGCTGGTTCTGTTGGAGGTTTTAACGCCCAGGCTGCAAACGCTGTGGCAGCCATTT<br>TCATTGCAACCGGTCAAGATCCTGCTCAAGTGGTAGAAAGTTCAATGTGTATCACTACAAT<br>GTCCAAGGTAGGTAACGATCTATTGATCTCTGTGACCATGCCTTCTATCGAGGTCGGGGT<br>CGTGGGAGGAGGGACTGGTCTTGCTGCCCAAAGAGGATGCTTAGAGTTAATAGGGTGCG<br>GAGGCCCATCTAAGGAGTCTCCTGGTACTAATGCCCAACTTCTAAGTAGAGTTGTTGCAG<br>CTGGCGTTTTATCAGCCGAACTTTCCTTGATGTCCGGACTGGCAGCAGGTCATCTATTGTC<br>AGCACATATGAGATTGAACAGAAAGAAGAAATAA |
| 15 | MEV-15 | ATGCAATCCCTGGACAAAAACTTTAGACACTTATCAAGACAACAGAAGTTACAACAGCTAG<br>TTGATAAACAATGGCTATCAGAGGAACAATTCAATATTCTACTTAACCACCCACTTATTGAT<br>GAAGAGGTAGCAAACTCATTGATAGAAAATGTCATCGCACAGGGCGCACTGCCTGTTGGT<br>TTACTACCAAATATCATCGTTGATGACAAAGCATACGTCGTGCCTATGATGGTGGAAGAGC<br>CATCTGTTGTTGCCGCTGCTTCATACGGCGCTAAATTGGTGAACCAAACAGGTGGTTTCAA<br>AACCGTGTCCTCAGAACGTATCATGATAGGTCAAATAGTATTTGATGGAGTCGATGATACC<br>GAGAAACTGTCTGCAGATATCAAGGCTCTTGAAAAACAAATCCATCAGATTGCAGATGAGG<br>CTTACCCTTCTATTAAGGCCAGAGGTGGAGGCTATCAAAGGATCGCCATCGATACATTCCC<br>AGAACAACAGTTGCTTTCATTGAAGGTTTTCGTTGACTAAGGATGCTATGGGCGCTAAT<br>ATGTTAAACACAATCCTAGAAGCAATCACAGCCTTTTTGAAAAACGAATTCCCACAATCTGA |

TABLE 6-continued

DNA Sequences of Optimized Mevalonate Pathway Gene Analogs

| SEQ ID. NO: | Optimized Gene | DNA Sequence |
|---|---|---|
| | | TATCTTGATGTCTATCCTTTCCAACCACGCAACAGCCAGTGTTGTCAAGGTCCAGGGTGAA<br>ATAGACGTTAAGGATTTGGCAAGAGGAGAACGTACTGGAGAAGAGGTCGCTAAGAGAATG<br>GAAAGAGCATCTGTGTTAGCTCAAGTGGACATTCATAGAGCAGCAACACACAATAAGGGT<br>GTTATGAATGGCATTCATGCTGTAGTCTTGGCTACAGGTAATGATACTAGAGGTGCAGAAG<br>CCTCTGCTCACGCTTACGCTTCCAAAGACGGTCAATATAGAGGGATAGCTACATGGAGAT<br>ACGATCAAGAGAGACAAAGGTTAATAGGAACTATAGAAGTTCCAATGACTCTGGCCATTGT<br>TGGTGGCGGTACCAAGGTACTGCCTATTGCTAAGGCCTCTTTAGAACTGTTAAACGTAGAA<br>AGTGCCCAAGAGTTGGGACATGTTGTCGCTGCCGTTGGACTAGCTCAAAACTTCGCTGCA<br>TGTAGAGCTTTGGTTTCCGAAGGTATTCAACAAGGGCATATGTCTTTGCAATACAAGTCTTT<br>AGCCATCGTAGTCGGGGCTAAGGGCGATGAAATTGCTCAGGTAGCCGAAGCACTAAAGC<br>AAGAGCCAAGAGCAAACACTCAAGTTGCAGAGAGAATTTTGCAAGATTTGAGAAGTCAACA<br>ATAA |
| 16 | MEV-16 | ATGACACCACCTAAACCATTGGAAACTAAGCAACCTTTACATGATCTGCCTACACCTGGAC<br>CAGAAAGTCCTTTCAGAGAGAGAAGGCCATACAGATTCTCTACCTTATGTGCTACCGTAGA<br>TAATCCAGACATGAAAGATCAATACGGTAGTTCTTCCGTGCCAATATACCAAACTGCTACA<br>TTCAAAGGTGTAGGGAACGAGTATGATTATACTAGATCCGGTAATCCTACAAGGTCACATT<br>TGCAGCATCATATTGCAAAATCTCCTCTGCAGCACATGCTTTTACTGTTTCTTCAGGTATG<br>GCCGCTCTGGACGTCATCTTAAGACTACTGAAACCTGGGGATGAGGTGATTGCTGGAGAT<br>GATCTTTACGGCGGAACAAATAGACTTTTAACTTACATTAGATCCCACCTTGGTGTAACTGT<br>CCACCATGTCGATACAACAGATCCAACATCTCTGCATAAGTACATTCATCCAACGAAAACT<br>GGGATGGTTTTACTTGAATCACCAACAAACCCATTATTGAAGATAGCAGATCTTGCTACAAT<br>ATCAAAGGATGTTAAAGAGAGAGCCCCAAACGCCATCATCGTTGTTGACAATACAATGATG<br>ACCTCTTATTTGCAAAGACCACTGGAACATGGTGCCGATATCGTGTATGATTCTGCCACAA<br>AATACTTATCTGGACACCACGATTTGATGGCCGGAGTTGTCACTTGTAATAGAGACGATAT<br>TGCCCAAAGATTGGCTTTCACTATCAACGCCGTGGGCAATGCTTTAACGCCAATTGATTCA<br>TTCATGTTGTTGAGGGGCATTAAGACATTAGCCATCAGAATGGATAGACAGCAAACCACAG<br>CCCAATTGGTGGCAGAATACTTATACAATCTAGGTTTTACAGTTCACTATCCAGGTCTACCT<br>TCACATCCTGGCAGAGACGTACACCTGAGGATAGCTGACGGAAATGGGGCTGTCTTGTCT<br>TTCGAAACAGGTAACAAGGAACTGTCTGAAAGGATTGTCGCAGCCACGAGACTGTGGGGA<br>ATTAGTGTCTCCTTCGGGTGCGTTAATTCATTGATATCTATGCCTTGCGTTATGTCCCATGC<br>CAGTATCGACGCCGCTACAAGAGCCGCCAGAGGACTGCCAGAAGATCTTATTAGATTGTG<br>TGTAGGTATTGAGGATCCACACGACTTATTGGACGATCTAGAACACGCTCTACTAGAAGCT<br>GGCGCAATTGAATTGAATGCTGCCCAAAACAAGTTTGTAAGGGCTCCTGATCCAGACGCC<br>TTATCTCAAGCTGTTCATGATCTAGATTTGGATGACGGTAGAAACCAGCTTGAATGGTTTG<br>TTTCTGCACCTGGCAAGGTGATTTTGTTTGGCGAACACGCCGTTGTACATGGTGTAACTGC<br>TATTGCCGCCTCAGTGGATCTAAGATGTTATGGTCTAACGACGCCTAGAACAGATAACAAA<br>CTGTCCGCTCACTTCAAAGACTTAGGAAATTTCTACCATGAATGGGATATTGATTCCTTACC<br>TTGGGATGCCTTGACTCCTATTCCACCAGGTGAGGAACATCCTGAGGAATTAGACCAGAG<br>ATTGATTGAAGCCTTATCACAAAGTGTTCTGGCTGAGCTGGGAGATGAGAACAAACAAGCT<br>AGAGCTGCCACTCTTGCATTCTTATATCTATACATGACCCTGGCCAGAGGTCAACATAGAC<br>CATCCTTTAACTTCACAGCCAGAGCAACATTACCAGTGGGCGCTGGACTAGGCAGTTCTG<br>CCTCCTTCTCTGCTTGCGCAGCTACAGCTTTGTTATTGCTGCATAGGAGGATCAGTGTCCC<br>TGCAAAGCCTGCTCCATCTACGAAACACACATCCATGTCTCTCATGAAGGCAGAAGGGC<br>TCTACCAGCCAGTGTAGCCGAGGATGTGAATAGGTGGGCTTTTGTCGCCGAAAAGATTTT<br>GCACGGGAATCCTAGTGGAGTCGATAACAGTGTTGCCGTATTCGGTGGTGCTTTGGCCTA<br>TACAAGACCTGGGTTTGGCAAAAAGGGAGGGATGGAACAAATCCAGGGTTTTAAGTCCTT<br>GAAATTCTTGTTGACTAACTCTCAAGTTCCTAGAGATACTAAAAAGCTAGTGGCTGGGGTG<br>GGTGAGAAAAAGGAAAACGAGCCAGAATTGGTCAACGGTATATTGGCTGCAATACAATCT<br>ATCTCCGATGAGGCTAGAAGAGCCTTGGCAGACCCAGAATTATCTAGAGATGCCTTGTTG<br>TCTGCTCTACAAGAGCTTATCAAGGAAAACCATGACCACTTAGTGACATTGGGAGTATCAC<br>ACCCATCTCTGGAAAAGATTAGAGAAAAGACTTCAGAACCTTACGGCTTAAAGACCAAACT<br>TACAGGTGCAGGTGGTGGTGGCTGTGCTGTCACGCTGATACCTGATGATTTCAAAGAGGA<br>AGTTCTTAATGGTTTGATCGACGAATTGATCAGAGAAGGTTTTCACCCATACTTAACTTCTG<br>TTGGTGGATCAGGTCTAGGGATATTGTCACCATATCCAGAACACAGAACCAGAGGTTCTG<br>ACCCTCAGCCACCTAGAGAAGATGTAGGAGGAGGCCAAGTTACACCTCCTGATACTCCTA<br>GAGCCGAGATAGTTGAAAGACATACGAAGCATGGAGTTACTTTTGATCCATTAAGACCAAC<br>CTTCGAGACAGCTGCCACGACTGATATTTCAGATTGGGCTTCATCCTTAGGGAGATGGCTT<br>TACGTGTAA |
| 17 | MEV-17 | ATGTTGTCAGAAGTGCTGTTAGTCTCTGCTCCAGGTAAGGTTATTCTGCATGGTGAGCATG<br>CCGTGGTCCATGGTAAAGTCGCCCTGGCCGTTGCTCTAAACCTGAGAACTTTCTTGAGATT<br>ACAACCACACTCAAATGGTCGTGTTGGGTTAAACTTGCCTAACATTGGTGTTAGAAGAGCA<br>TGGGATGTGGCTTCTTTGCAACTTCTTGATACATCATTCTTGGGCCATGGCGATTCCGCAG<br>CTCTTACTGCAAAGCATGTTGAAAAGCTAAAGGAAGTAGCTGGTTTTCCTAAGGACTGTGT<br>AGATCCAGAACACTTAGCTGTGTTAGCATTCCTTTATCTATACTTGTCCATTTGCCAATCTC<br>AAAGAGCCTTGCCATCTCTGGATATCACAGTCTGGTCTGAATTGCCTACTGGCGCTGGCC<br>TTGGTTCTAGTGCCGCCTACTCAGTCTGTTTGGCAGCCGCATTGTTAACCGCTTGCGAAG<br>AGATCCCAAACCCATTGAAAGATGGAGAAGCTGCCGGTAGATGGCAGAGAGGAAAATCTAG<br>AGTTAATCAACAAATGGGCATTCCAAGGCGAAAGAGTAATTCATGGAAATCCATCAGGCGT<br>GGACAATGCCGTTAGTACTTGGGGTGGTGCTCTAAGATATCAACAGGGAAAGATTAGTTCT<br>CTTAAAAGACCACCAGTTTTGAAGATCTTATTGATAAACACAAAGGTTCCTAGATCCACAAA<br>GGTCCTAGTTGCAAATGTTAGATCAAGACTGCTGAAATTTCCAGAAATTGTAGCCCCACTT<br>TTGACCTCTATCGATGCCATAAGTTTGGAATGTGAAAGGGTCTTAGGCGAAATGGCAGCT |

TABLE 6-continued

DNA Sequences of Optimized Mevalonate Pathway Gene Analogs

| SEQ ID. NO: | Optimized Gene | DNA Sequence |
|---|---|---|
| | | GCACCTACACCAGAGCATTACTTAACATTGGAGGAGCTGATCGATATGAATCAACACCACT<br>TGAACGCTTTGGGTGTCGGACATGCTTCATTAGACCAATTATGTCAGGTAACCACTGCTCA<br>TGGTTTACACTCCAAGTTGACAGGAGCAGGTGGAGGAGGTTGTGGGATAACACTGTTAAG<br>ACCAGATGTTGAAAGGCCTGCAGTGGAAGCTACTAAACGTGCTTTATCAGGCTGTGGTTTT<br>GATTGCTGGGAGACTTCTGTTGGGGCACCTGGAGTTTCTGTCCACACTGCTGCTTCCCTT<br>GATGCATCTGTACAACAGGGTCTAGACTCATTGTAA |
| 18 | MEV-18 | ATGGAAGTTAAGGCTAGAGCTCCTGGTAAGATCATATTGAGTGGCGAACATGCCGTAGTG<br>CACGGGTCAACAGCTGTCGCCGCTTCCATCAACTTGTACACTTATGTCACGTTGTCCTTCG<br>CCACTGCTGAAAACGATGATTCATTGAAATTACAGTTAAAAGATCTGGCCCTGGAATTCTC<br>ATGGCCAATTGGGAGAATAAGAGAGGCCTTGTCTAATCTGGGCGCTCCTTCTTCTTCAACT<br>AGAACCAGTTGTTCTATGGAATCCATTAAGACTATCTCTGCTTTAGTCGAGGAGGAGAACA<br>TACCAGAAGCTAAGATTGCCTTAACTTCTGGGGTATCTGCCTTCCTATGGTTATACACCTC<br>TATCCAAGGATTCAAACCAGCCACTGTAGTGGTTACATCTGACTTACCATTGGGTTCCGGC<br>CTTGGTTCTTCAGCAGCTTTTTGTGTCGCCCTTTCTGCTGCATTGCTAGCTTTTTCAGACAG<br>TGTAAATGTCGATACAAAACATTTGGGATGGTCAATTTTCGGTGAATCCGACTTGGAACTA<br>CTGAACAAATGGGCCTTGGAAGGCGAGAAGATCATTCACGGTAAGCCTTCTGGTATCGAT<br>AATACCGTTTCAGCCTATGGTAACATGATTAAGTTCAAATCTGGTAATTTGACAAGGATAAA<br>GTCCAACATGCCATTAAAGATGTTAGTAACAAACACCAGAGTCGGCAGGAATACAAAAGCC<br>TTGGTTGCTGGCGTTTCTGAGAGAACATTGAGACATCCTAATGCTATGTCCTTTGTGTTTAA<br>CGCTGTGGATAGTATTAGTAACGAACTAGCTAACATTATACAGAGTCCTGCTCCTGATGAC<br>GTTAGTATTACAGAAAAAGAGGAAAAACTGGAGGAACTGATGGAGATGAATCAAGGTTTAC<br>TTCAATGTATGGGCGTGTCCCATGCATCAATCGAAACGGTTTTGAGAACAACTTTAAAGTA<br>CAAACTTGCCAGTAAGTTGACTGGGGCAGGAGGTGGTGGATGCGTTCTTACGCTGCTTCC<br>AACACTACTATCTGGAACAGTGGTTGATAAGGCTATCGCCGAATTAGAATCTTGCGGATTT<br>CAATGTTTGATAGCAGGCATTGGTGGAAATGGTGTAGAATTCTGTTTCGGTGGGTCCTCTT<br>AA |
| 19 | MEV-19 | ATGCACGTTGCTGTGAAGGATAAAACAACTAGACATCATATTGGTTACGGCAAAGTTATCC<br>TATTTGGGGAACACTTCGTCGTGTACGGTGCCGAGTCAATTGTAGCCGGCATTAACGAAT<br>ATACTACGTGCGAGATTAGTAGACTGAAACATAAACCAAATGTCGTGGAAGTTATAGACGA<br>AAGACCTGCCGTTCCAGGGTATATCAAAGAGAAGAGGGAAGAGCAAAGAGTGGCCCACG<br>GTTTGGTTTTGAGACACTTAAACATAGACACCTCCAAGGATGGTTTACTAGTCAAATTAGGT<br>GGCCCTTTGGTCCCATCTTCTGGGATTGGTGCTTCAGCTTCTGATGTAGTATCATTGTCCA<br>GAGCTTTAAACGAGCTATATTCCTTGAACTTGAGTGAGGAAGCTGTGAACAGATCTGCTTA<br>CGCCGGAGAATGCGGATATCACGGAACACCTTCTGGTGTTGATAACACAGCTGCAACTTA<br>CGGTGGCATAATTCTATTCAGAAGAGCCTTGAAAAAGTCTGTTTTCTCAAGGCTTGCCCTA<br>GGTAAGACCCTGTCAATTATCGTTTGTAGTACTGGAATAACTGCATCAACAACAAAAGTCG<br>TGGCTGATGTTGCTAGGCTGAAGGCAGCCCAACCTTCTTGGTTTGATGACTTATTCGAACA<br>GTACAATGCTTGTGTAAGAGAAGCCAAAAAGGCTTTACAATCCGGAAATCTTAGAAGAGTT<br>GGTGAACTGATGAATATCAATCATCGTTATGTCAAAAGTTGACAGTTTCCTGTCCAGAACT<br>TGATGCCATCGCTACTTGTTGTAGAACATTCGGAGCATTGGGCGCTAAGATGTCTGGTAC<br>GGGTAGAGGTGGGTTGGTGGTAGCCCTGGCCGCAAATACACAGGAAAGAGATAGAATTG<br>CTAAGGCTGTTAGAGAACAATGCAAGGAGGCAAAGTTTGTGTGGAGATACTCTGTACAAC<br>CAGGAGGCAGTAAACTTTAA |
| 20 | MEV-20 | ATGACTAGAAAGGGATACGGTGAATCTACAGGCAAAATCATTCTGATTGGGGAACATGCC<br>GTTACATTCGGTGAGCCTGCTATCGCCGTGCCATTCAATGCTGGCAAGATTAAGGTATTGA<br>TAGAAGCCTTAGAAAGTGGAAATTACTCTTCTATAAAGTCAGATGTCTATGATGGAATGTTG<br>TACGACGCCCCAGATCACCTGAAGTCATTAGTTAACAGATTTGTCGAGTTAAACAACATTA<br>CAGAACCTTTAGCCGTCACAATTCAAACAAACTTGCCACCTTCCAGAGGTTTGGGCTCTTC<br>TGCTGCCGTTGCTGTTGCTTTCGTTAGGGCCTCATACGACTTTCTGGGAAAATCTCTAACA<br>AAGGAGGAATTGATTGAAAAAGCAAACTGGGCTGAACAAATCGCTCATGGGAAACCATCC<br>GGGATCGATACTCAGACGATAGTTTCAGGTAAACCTGTTTGGTTCCAAAAGGGGCACGCT<br>GAAACCCTGAAAACTTTGTCCTTAGATGGTTATATGGTGGTAATCGATACAGGAGTGAAGG<br>GTAGTACTAGACAAGCAGTAGAAGATGTTCATAAACTATGCGAAGATCCTCAGTATATGTC<br>ACACGTCAAGCACATTGGCAAACTTGTGCTGAGAGCTTCTGATGTAATAGAACATCACAAT<br>TTTGAAGCCCTGGCTGACATCTTCAATGAGTGTCATGCTGACTTGAAAGCATTAACTGTCT<br>CCCATGATAAGATCGAACAACTTATGAAAATTGGAAAAGAGAATGGTGCCATTGCCGGAAA<br>GTTGACAGGCGCTGGGAGAGGAGGTTCTATGTTGTTGTTAGCCAAAGACCTACCAACTGC<br>CAAAAACATTGTAAAGGCAGTGGAGAAGGCAGGTGCTGCCCATACCTGGATTGAAAATCT<br>TGGTGGCTAA |
| 21 | MEV-21 | ATGGTCAGAACAACAGTAGTTTCTGCCCCAGGTAAGGTGCTAATTGCCGGAGGTTATCTG<br>GTATTAGACCCTGCCTACCCTGGCACAGTAGTCTCCACGAGTTCTAGATTTTACACAGTAA<br>TCCAATCTCAGGAGCTACTAAGTAAAAACACCATTAGAGTGAGATCCCCACAGTTTTTGGA<br>AGCAACATGGTCATACTCCGTACTGTTCGAGCCAGCTGTTGCTGTGGAGGCTTCTCCAGA<br>AAACTCTTCCAAAAACAAGTTTGTGCACTTAGCTCTGCAGAAAACAATAGCCTTGGCCGTC<br>GAACTGAGAGGAGCTGCCCAGATCCAGGAAGCCTTGACACATGGTTTCGATATTGCCATA<br>GTTGGGGACAATGATTTCTATTCTCAAAGAGCCAAGCTGGAATCCTTGGGTTTACCTAGAA<br>CTCTTGATTCTCTTACAGAAATTACACCTTTTTGCGCTACTGAAGTTCATTTGTCTGATGTG<br>CACAAGACTGGACTTGGATCATCAGCCGCCTTGATCACTTCTTTGACATCTGCTATACTAG<br>TACACCTATCTGTCATCTCAGAATCATCATTAGCCGAAGATGATTCCAGAGATAGGAGACA<br>AGCTCATAACTTGGCCCAATACGTGCATTGTTTGGCACAAGGTAAAGTTGGATCAGGCTTC |

TABLE 6-continued

DNA Sequences of Optimized Mevalonate Pathway Gene Analogs

| SEQ ID. NO: | Optimized Gene | DNA Sequence |
|---|---|---|
| | | GATGTAAGTGCTGCTGTTTTCGGTTCCCATCTTTACTCAAGGTTTGATCCAGCCGTCATCC<br>AGGACCTAATGTCAGATGACGCTTTACCATCTCAACTTCCTTCTGTGCTATCTCCATCTAAT<br>GCCGCTTGGAATTACAGAATTGAACCATTCAAATTACCACCATTGACTAGAATCGTTTTAGC<br>CGATGTTGATGCTGGGTCAGACACTCCTTCTCTGGTGGGCAAGGTATTGAAGTGGAGAAA<br>GGAAAATTCTACTGAAGCAGAGGCTTTGTGGAAAAACTTAGATCAACAAAACCAATCTTTG<br>GCACAAACCTTATTACATCTGGGCAAGTTGGCAGAGGACGATTATGAAAACTATGCTTCCG<br>CCGTCAAGTACATTTGTTCATTACAACCAGTTCAACAAATCTTGTATAGTCCTTTAAGGTCT<br>AATCAATCTCTTCAACACAGTATGAAACCAACAATTTCAGCAATCAGAGAGAAAATGAGAG<br>AGATGGGAATTTGAGTGGCGTGCCAATTGAACCAATTGAGCAAACAACACTGTTAGATG<br>CCTGTGCCAGTCAAGCTGGTGTTATTGGTGGTGGCGTTCCTGGGGCAGGTGGATACGAT<br>GCTATATGGTTGTTAGTGTGTGATCCTCCTAGTTGCGCTCCAGATCAATCTCCACTTGAAA<br>GGATTGAACATCTATGGTCCCACTACGAAAAGCTGGATGTCTCCCCTTTATCCGCTCAAGA<br>GTCTACGGCTAAGGGTGTCAGAGTTGAAGCTTGGACGACATACCTGGATTGAAAAATGC<br>AATTTCAGTAAGTTAA |
| 22 | MEV-22 | ATGGCTCCTCTAGGCGGTGTTCCAGGACTGGTGTTGTTATTCTCCGGTAAGAGAAAATCT<br>GGAAAGGATTTTGTTACAGAAGCACTGCAATCTAGATTAGGAGCCGATGTATGCGCAATCT<br>TGAGATTGTCAGGTCCACTGAAGGAACAGTACGCCCAGGAACATGGTCTTGACTTTCAAA<br>GGCTTATGGACGCTTCAACCTACAAAGAGGCTTACAGGTCTGATATGATCCGTTGGGGTG<br>AAGAGAAAAGACAAGCTGATCCAGGCTTTTTCTGTAGAAAGATTGTTGAAGGCGTCTGTCA<br>ACCTGTTTGGTTAGTAAGTGATACTAGAAGAGTGTCAGATATTCAATGGTTCCAAGAGGCC<br>TATGGTGCTGTCACACAAACAGTTAGAGTTGTCGCAACAGAAGAGTCTAGACAACAAAGA<br>GGGTGGGTGTTCACTCCAGGGGTTGATGACGCAGAATCCGAATGTGGTTAGATAACTTT<br>CGTACTTTCGATTGGGTTATAGAAATCACGGTGATGAGCAACACCTAGAAGAGCAGCTA<br>GAACATTTGATTGAATTCATCAGAAGTAGATTGTAA |
| 23 | MEV-23 | ATGGCCGTTGTCGCATCTGCTCCAGGAAAGGTATTGATGACAGGTGGTTACTTAATCTTAG<br>AAAGGCCAAACGCCGGTATCGTCTTATCTACGAATGCCAGATTCTATGCTATTGTTAAACC<br>AATCTATGACGAGATTAAGCCAGATTCCTGGGCCTGGGCTTGGACTGATGTAAAGTTGAC<br>ATCCCCACAACTAGCCAGAGAATCTTTATACAAGCTATCACTGAAAAATCTGGCTCTGCAA<br>TGTGTGTCCTCTTCTGCTTCTAGAAATCCATTCGTGGAACAAGCCGTTCAGTTCGCAGTAG<br>CCGCAGCTCACGCCACATTGGATAAGGACAAAAAGAACGTATTGAACAAACTACTATTACA<br>GGGATTGGACATTACCATTCTTGGTACAAATGATTCTACTCTTATAGAAATGAGATAGAGG<br>CTTGCGGGTTGCCACTTACACCAGAATCATTAGCAGCATTGCCATCATTTTCATCTATCAC<br>GTTCAACGTCGAGGAAGCCAATGGGCAAAATTGTAAGCCTGAAGTTGCTAAAACAGGTTTA<br>GGCTCATCCGCTGCTATGACAACTGCCGTCGTGGCAGCTTTATTGCACCATTTGGGTCTG<br>GTTGATCTGTCTAGTTCATGTAAAGAGAAAAAGTTCAGTGACTTAGATTTGGTCCATATCAT<br>CGCTCAAACAGCTCACTGTATTGCCCAAGGCAAGGTGGGTAGTGGTTTTGACGTTAGTAG<br>TGCTGTTTACGGATCTCATAGGTACGTCAGATTTTCCCCAGAAGTATTGTCCTCAGCACAA<br>GATGCTGGAAAGGGTATACCTTTGCAGGAAGTAATTTCTAACATTCTAAAGGGCAAATGGG<br>ATCATGAGAGAACTATGTTCTCATTGCCTCCTTTGATGTCTTTACTTCTGGGCGAACCTGG<br>AACTGGTGGTTCTTCAACCCCTTCTATGGTGGGAGCTTTGAAAAAGTGGCAAAAGTCAGAT<br>ACACAAAAGAGTCAGGAAACGTGGAGAAAGCTAAGTGAAGCCAACTCTGCCTTGGAAACT<br>CAATTCAACATATTGTCCAAACTGGCTGAAGAGCACTGGGATGCTTATAAGTGTGTCATTG<br>ACTCTTGCTCTACCAAAAACAGTGAAAAATGGATAGAACAGGCCACGGAGCCATCCAGAG<br>AAGCCGTCGTCAAAGCCTTATTAGGCTCTAGAAACGCCATGTTGCAAATAAGGAATTACAT<br>GAGACAAATGGGCGAGGCTGCTGGGGTGCCTATTGAACCAGAATCACAAACTAGACTTCT<br>TGATACAACCATGAATATGGATGGGGTTCTACTTGCAGGAGTGCCTGGTGCCGGAGGATT<br>TGACGCTGTTTTTGCCGTTACATTAGGGGATTCTGGTACAAATGTTGCTAAGGCATGGTCC<br>TCATTAAACGTTCTTGCATTGCTGGTAAGAGAAGATCCAAACGGTGTTCTATTGGAATCTG<br>GAGATCCTAGAACAAAAGAGATCACTACTGCCGTGTTTGCCGTTCATATTTAA |
| 24 | MEV-24 | ATGGTGGTCGCTTCTTGTCCAGGAAAGGTTTTGATTTTAGGTGGGTACTTAATTGTAGAGG<br>AACCAAACGTTGGTATTTCCGTCGGCACCACCGCTAGATTCGTAACTCGTGTTGCCTCTTG<br>GAAAAAGTGTTCAGATGGCAAATGTAGAGTTCATATCGTTAGTTCTCAATTCAATAGGAAT<br>TCACTTTTGAGTGTGCAGCTGAGGAAGATTCAGATTCAACCATTAAGATCGTCCAATTGGA<br>AGGAGCACCTTCACCTTTCTTATTCTACGGAATACTATATTCTGTAGCCGGAGCTCTGTTAT<br>TTGGTGGGATATCTTTAGGGATGTTACATTGGAATTGTTAGCAGATAATGACTTCTATTCT<br>CAGAGAAATTACCTAGAGTCTCAAGGTAAGCCTGTTACAGCTGCTAACTTAAGACTAATCC<br>CAAGATACACTCCACTTCTTGGTGAAGTAAGTAAGACAGGTTTAGGATCTTCCGCAGCCAT<br>GACTACAAGTGTTGTGGCTTGTTTGCTTCAACTATACGTGTTCGATTCCAAAAAAAACAAC<br>GCCACTGAGTCAGTTGAAAGAGCTCCTGAACTTCCACTTAGACTGGAAGATGTAACTGAAT<br>TCATTCATAGAATATCTCAAGTCGCACATTGCGTGGCTCAAGGCAAGGTGGGTTCAGGTTT<br>CGACGTCTACACTGCCACCTTTGGGACATGTGTTTACAGAAGATTCTCTGCTAGAGTGTTA<br>GAAAAGCTAGTTAAGGGAAATGAGCCACCAAAAAGAGTCACCATCCCATTGCTAAGAGAAT<br>GCGTTGAAACTGATGAGGTATGGGTTCAGAGAATACCATTCCGTTTGCCAACAGGTTTGCA<br>ACTGCTTCTAGGAGATGTACACAAAGGCGGTACAGAAACACCAGGCATGGTATCAAAGGT<br>TATGAGTTGGAGGAGATCTGTAACAACAGATCCAATTCCTTGTGGGAAAGATTGAGGATG<br>TCTAACGAAAAGTACGTGGAGGCATTGCAAGGTCTGATCAAGCAATCTCAGGAAGCTCCA<br>GTTGCCTATACTGAAGCTGTCAAAAACTTGAATCTGTTGTTTTGGCTAAGCACAACCCCAT<br>CAACAGAGGCTGAAAGACTTTGGGTAGAGGCAGCATCAGTCGCCTCTACATCAAGACGTT |

TABLE 6-continued

DNA Sequences of Optimized Mevalonate Pathway Gene Analogs

| SEQ ID. NO: | Optimized Gene | DNA Sequence |
|---|---|---|
| | | ACCTGAGAGAAATGGGCGAGGCTGCACAAGTTCAAATTGAACCACCTGAATTGACTTCTTT<br>ACTTGATGCCACTTGCAGTATTCCTGGTGTCTTTGCTGTAGGGTGTCCTGGAGCAGGTGG<br>GTACGACGCCGTTTTTGCATTAGTTCTAGGTGAAGAGGTCTGTTCCGCAGTTGAGAGATTT<br>TGGGAATGCTATAACGACTTACAAGTCTGTCCTTTGCTGGTGAGAGGCGATGCTAATGGAT<br>TGGTTTTAGATTAA |
| 25 | MEV-25 | ATGATTCAAGTTAAGGCTCCAGGAAAATTGTACATCGCAGGTGAATATGCTGTAACTGAAC<br>CAGGCTACAAATCTGTTTTGATTGCTTTGGACAGATTCGTCACAGCAACCATCGAGGAAGC<br>CGATCAATACAAGGGTACTATCCATTCAAAGGCTTTACATCATAATCCTGTAACTTTTTCTA<br>GGGACGAAGATTCCATTGTTATTTCTGATCCACACGCTGCAAAACAGTTGAACTACGTCGT<br>TACAGCTATCGAGATTTTCGAGCAATACGCTAAGTCTTGTGATATCGCCATGAAACATTTTC<br>ACCTTACCATCGATTCTAATTTGGATGATTCTAATGGACATAAGTACGGACTTGGTTCATCT<br>GCAGCTGTCTTAGTTTCCGTCATAAAGGTGTTAAACGAATTCTATGATATGAAACTGTCAAA<br>CCTATACATCTACAAACTTGCCGTTATTGCAAATATGAAGCTGCAATCCTTGTCATCATGTG<br>GGGACATTGCAGTTTCTGTGTATAGTGGGTGGTTAGCCTACTCCACTTTTGACCACGAATG<br>GGTCAAACATCAAATCGAAGATACTACAGTGGAGGAGGTACTGATCAAAAACTGGCCAGG<br>TTTGCATATTGAACCTCTTCAAGCCCCTGAAAACATGGAGGTGTTGATAGGTTGGACTGGC<br>TCTCCAGCTTCTTCACCACACTTTGTTTCTGAAGTTAAAAGACTAAAGTCAGATCCAAGTTT<br>CTACGGCGATTTCCTAGAAGATAGTCACAGATGCGTCGAAAAGTTAATACACGCATTCAAA<br>ACAAATAACATCAAAGGGGTTCAAAAGATGGTAAGACAAAATAGAACCATTATTCAGCGTA<br>TGGATAAAGAGGCCACAGTAGATATAGAAACTGAAAAGTTGAAGTACCTGTGTGACATTGC<br>TGAAAAGTATCATGGTGCTAGTAAGACATCAGGAGCAGGTGGAGGCGATTGCGGTATAAC<br>AATCATCAACAAAGACGTTGATAAGGAGAAAATCTACGATGAATGGACAAAGCATGGTATT<br>AAGCCTCTAAAGTTCAACATATATCATGGACAATAA |
| 26 | MEV-26 | ATGTCAGAGCCAATCTACGAAGCTACAGCATCTGCCCCTGTTAACATCGCTGTTATCAAGT<br>ACTGGGGCAAGAGAGACACTTCTCTAATCTTGCCTACAAACTCAAGTTTGTCTGTTACTCT<br>ATCCCAAGATCATCTTAGATCTACTACAACATCCAGAGCCTCATCTTCTTTCGATAAAGATA<br>GGTTATGGTTAAACGGTCAAGAGGATGTCATTAAACCTGGCTCTAGACTGGAAACTTGCAT<br>TAGAGAGATGAAAAAGTTGAGAAAGGAATTAGTGGAAGATAAGGATGCTAATGCACCTAAA<br>CTGTCAACATTGCCAGTTCATATTGCTTCTTACAATAACTTTCCTACCGCTGCAGGTTTGGC<br>TTCTTCCGCATCAGGATTCGCAGCACTAGTTTCATCTTTAGCACATCTATACACATTAACAC<br>CTCCATTGACCTCCCCAAGTACACTGTCTCTTATCGCTAGACAAGGATCAGGGAGTGCAT<br>GTAGATCTCTTTTCGGTGGCTTTGTTGCTTGGGAAATGGGATCAACTCCAACAGGAACCGA<br>TTCTTTAGCCGTCCAAATTGCCGATGAAGCTCATTGGCCAGAAATGCACGCACTTATCTGT<br>GTTGTTTCCGATGACAAAAAGGGCACATCTAGTACTGCTGGTATGCAAAGGACAGTCGAA<br>ACATCAACTTTGTTGCAACACAGAATTAAGGATGTTGTTCCAAGACGTATGGACGAAATGA<br>TTAGAGCTATTAAGGAAAAGGATTTTGATTCTTTCGCTAGAATAACTATGGCAGATTCAAAT<br>TCTTTTCATGCCGTAGCACTAGACACTGAGCCTCCAATATTCTACATGAATGATGTCTCCA<br>GAGCAATTATCGCACTGATAGTAGAGCTTAACAGAGTCTCCTTGGAGAAAGGAGAAGGTT<br>ATAAGGCAGCCTATACTTATGATGCCGGACCAAACGCCGTAATCTACACCTTGGACAAAAA<br>TGTAAAGGAAGTTATACAGTTAATAGTAAAGTACTTCCCTCAGAAAGCCGGTGAATTCAAG<br>GATAACCTGCAGGTATTGGGTGGTGGCGTGGCCGATATCAATCAAGTGGCTCAAGTGCCA<br>GAGGGATTCAACGAGAAGGTTGCCGTCGTGAGAGAAGTTGGCGCTGTGAAGGGGTTGAT<br>CCACACAAAAGTCGGTGACGGTCCACGTAGACTTGGTGATGAAGAGTCACTATTAGGTAA<br>GGATGGGTTTCCAAAAACCTTAGTTGCTTAA |
| 27 | MEV-27 | ATGGCATCAGAGAAACCAATAGTTGTTGTTACATGCACTGCACCTGTAAACATAGCCGTCG<br>TTAAGTACTGGGGTAAAAGAGACGAGGAACTGATATTACCAATTAACTCTTCACTATCTGT<br>CACGCTTCACCAAGATCAGTTGAAAACTACAACAACAGCCGCTATTTCAAGAGATTTCACG<br>GAAGATAGAATTTGGTTAAATGGTAGAGAGGAGGATATGGGACATCCAAGATTACAAGCCT<br>GTTTGAGAGAAATCAGAAGGTTGGCCAGAAAGAGAAGATCAGACGGGCATGAAGATCCAC<br>TACCTTTGAGTCTGAGTTACAAAGTTCACGTGGCTAGTGAAAACAATTTTCCAACTGCTGC<br>TGGTCTGGCTTCTTCTGCCGCTGGTTACGCCTGTCTTGCATATACATTAGCCAGAGTGTAC<br>GGGGTCGACTCCGATCTGTCTGAAGTTGCCAGGAGAGGATCTGGATCCGCTTGTAGAAGT<br>TTGTACGGCGGATTCGTAGAATGGCAAATGGGCGAAAGACCTGACGGTAAGGATAGTGTG<br>GCTTGTCAAGTTGCCCCAGAATCCCATTGGCCAGAACTTAGAGTATTGATTCTAGTCGTTT<br>CCGCTGAAAGGAAACCTATGGGGTCCACAGCTGGTATGCAAACATCCGTGGAAACTTCAG<br>CATTGTTAAAGTTTAGAGCTGAGGCACTGGTTCCACCAAGGATGGCAGAAATGACTAGGT<br>GCATCAGAGAGAGAAACTTTCAGGCTTTCGGCCAGTTGACTATGAAGGACTCAAATCAATT<br>TCACGCTACTTGTTTGGATACCTTCCCTCCTATCTCTTATCTATCAGATACATCTAGAAGGA<br>TCATTCAACTAGTTCACAGATTCAATGCCCATCACGGTCAAACGAAAGTCGCATATACCTT<br>CGACGCCGGACCTAACGCTGTCGTTTTCACTTTGGATGACACAGTAGCCGAGTTCGTGGC<br>TGCCGTAAGACATTCTTTTCCTCCAGAATCAAATGGTGATAAGTTTCTGAAGGGCTTACCT<br>GTGGAGCCAGTACTTTTATCTGATGAGTTGAAAGCCGTACTTGGTATGGATCCTGTTCCAG<br>GTTCTATTAGATATATCATTGCAACCCAAGTTGGACCAGGACCTCAAGTGTTGGATGATCC<br>TGGTGCCCATTTGTTAGGGCAGATGGCTTACCTAAGCCAGCTGCTTAA |
| 28 | MEV-28 | ATGTCTGGTGAACAAAGAGAACTTAACTCTTGGGTATTCATGGTAACAGCTAGAGCACCTA<br>CCAACATAGCTGTAATCAAGTACTGGGGTAAAAGAGACGAAAAGTTAATCTTACCTATCAA<br>TGACTCTATCTCTGTTACATTGGATCCAGATCACTTGAGTGCTACAACCACGGTGGCCGTA<br>TCACCATCCTTTTCTAGTGATAGAATGTGGCTTAATGGTAAGGAAGTTAGTTTGGGTGGGG<br>AGAGATATCAAAATTGCTTGAGAGAAATCAGATCTAGGGGAAGAGATGTGGTGGATGAAA<br>AGTCCGGTACTTTGATCAAAAAGGAGGACTGGCAGACACTACATTTGCACATTGCTTCCCA |

TABLE 6-continued

DNA Sequences of Optimized Mevalonate Pathway Gene Analogs

| SEQ ID. NO: | Optimized Gene | DNA Sequence |
|---|---|---|
| | | TAACAACTTTCCAACTGCTGCCGGATTAGCCTCATCTGCCGCTGGATTTGCCTGTTTAGTT<br>TACGCCCTAGCAAAATTGATGGATATTGAGGAAAGATATGCTGGGGAACTGTCCGCTATTG<br>CTAGACAAGGAAGTGGTTCTGCTTGTAGATCTTTGTACGGTGGCTTCGTCAAGTGGGATAT<br>GGGTAAAGAGAGAGACGGCTCTGACTCTATAGCTGTTCAACTAGCCACAGAAGAGCATTG<br>GGAGGAACTGGTCATTTTAGTTGCCGTCGTCTCTTCAAGACAAAAGGAAACATCTTCCACT<br>ACTGGGATGAGAGAATCTGTTGAAACTAGTGAACTATTACACCATAGGGCACAAGAGGTA<br>GTTCCTAAGAGAATTGTTCAAATGCAGGAAGCTATTGCCAACCATGATTTCGCCTCTTTTG<br>CCAGAATTACGTGTGTAGATTCCAATCAATTCCACGCCGTCTGTTTGGATGCATCTCCTCC<br>AATCTTCTACATGAACGATACGTCCCACAGAATCATAAACTGCATAGAAAAATGGAATAGG<br>TTTGAGGGCACCCCTCAAGTATCTTATACATTTGACGCAGGACCAAACGCCGTTATATGTG<br>CCCCTAGTAGAAAAGTAGCAGGCTTACTACTTCAGAGATTGTTGTACTATTTTCCACCAGA<br>TTCATCTAAAGAGTTATCTTCATACGTGATTGGCGATACATCAATCCTTGGGGAAATAGGT<br>CTTAAATCTATGAAGGATGTGGAATCACTGATTGCTCCTCCAGAATTCAGGTCACAAAATT<br>CCTCATCAATTCATCCTGGTGAAGTCGACTACTTCATTTGCACAAGACCAGGTAAAGGACC<br>AATTATCCTGAGGAACGAGGATCAGGCTTTCTTCAACAATAAGACTGGTTTCCCTTTCAGA<br>ATTAGTGAAACATAA |
| 29 | MEV-29 | ATGTCTGATCAATGTGTGACAGTTGAAGCCCCAATTAACATCGCTTTTATCAAATACTGGG<br>GTAAGAGAGAAGGAGGTGAAACTTTGATACTACCAACAAATGACTCTTTCTCTATTACTTTG<br>TCCGCCTCTCCTTTTAGATCAAAGACATCAGTAGAACTAAGAGATGACATCGAAACAGATA<br>CATTAAGATTAAACGGGACAGAAGTGGATGTGGGCAAAACACCAAGAGTTCAATCAATGTT<br>ATTGCACCTAAGATCCACATGTCCAGAAGATCTGAAAAACAAAAAGGTCAATATTGTAAGT<br>GAAAACAATTTTCCTACTGCTGCTGGTATGGCTTCCTCAGCCTCTGGTTATTGCGCCATGA<br>GTGCCGCTCTGATTAGAGCCTTCAAGTCCACCACAAACGTCTCCATGCTGGCCAGGTTAG<br>GATCTGGTTCTGCTTGTAGAAGTGCCTTCGGTGGATTCGTAATCTGGAATAAGGGCGAAA<br>AACCTGATGGGTCTGACTGCGTTGCCACGCAGTTTGTAGACGAAACACATTGGCCTGAAA<br>TACAGGTCATGTGTGCAGTTCTTAAGGGAGCTCAAAAGGATGTGTCATCTACTAAAGGTAT<br>GCAACAATCTCTGAAAACCTCTCCATTGATGAAAAAGAGAATTAGTGAGACGGTTCCAGAG<br>AGGATGAAAATTGCTTCTAGAGCCATTAAGGCTAGAGATTTCGCTACTTTTGCTGAGATAG<br>CTATGCTAGAATCTGACGACTTGAAGAGATCTGTGCAACAACTGAACCAAAGATAACTTA<br>CGCAACCGAAGATTCCTATGCCATGATCAGATTGGTGAAAGCATACAACGCCAAAAAGGG<br>AAGGACAGCATTAGCCTATACCTTTGATGCTGGTGCCAACTGTTTCTTATTTGTTCTTAAAG<br>AGGATTTGCCTGAAGCAGTTGCTATGTTGATGGAGCATTTCCCTACGCCATTTGAGAAGTT<br>CTTCTTCGGGGATAGAGAATTACTAGAGAAGGTGAAAGTCGTCTCTTTGCCTGATGAATAC<br>AAAAAGTTGATTGATCACCCTAAAAAGCCATTCGAAATGCTGCTTCAAAGTCCTGTTGGAT<br>GCGGCGTTAAGTACCTTGGCCCATCCGAATCATTGATTCCACCAAGAGTATAA |
| 30 | MEV-30 | ATGATCAAGTCTGGTAAAGCAAGAGCTCATACAAACATTGCCCTAATCAAGTACTGGGGTA<br>AAAAGGATGAGGCTTTGATTATTCCTATGAATAACTCTATCAGTGTAACCTTGGAGAAATTC<br>TACACAGAAACAAAGGTGACTTTCAACGATCAATTAACACAAGACCAATTCTGGTTAAATA<br>GCGAAAAAGTGTCCGGGAAGGAACTTGAGAAGATATCAAAGTACATGGATATTGTCAGAA<br>ACAGAGCTGGTATCGACTGGTACGCTGAAATCGAATCTGATAACTTCGTACCTACAGCCG<br>CTGGCCTGGCTTCATCTGCCTCCGCTTATGCTGCTTTAGCTGCCGCATGCAACCAGGCTT<br>TAGACTTACAATTGTCAGATAAGGATCTAAGTAGACTGGCTAGAATTGGCTCAGGTTCTGC<br>CTCTAGATCTATCTACGGTGGATTTGCCGAGTGGGAGAAAGGTTATAACGATGAAACGTC<br>CTACGCAGTACCACTAGAATCTAATCACTTTGAAGATGACTTGGCAATGATTTTTGTTGTCA<br>TAAATCAACATTCCAAAAAGGTGCCAAGTAGATATGGAATGTCTCTTACTAGAAACACTTCA<br>AGGTTCTATCAATATTGGTTGGATCATATTGACGAAGATTTGGCCGAACAAAAGCTGCAA<br>TACAAGATAAAGATTTCAAAAGATTGGGTGAAGTCATTGAGGAAAATGGGCTTAGAATGCA<br>TGCCACAAATTTGGGAAGTACCCCACCTTTTACTTACCTGGTTCAGGAATCCTACGATGTG<br>ATGGCCTTAGTTCATGAATGTAGGGAAGCCGGATACCCATGTTATTTCACGATGGATGCC<br>GGTCCTAATGTTAAGATTCTGGTTGAGAAGAAAAACAAGCAACAGATAATTGATAAGTTGC<br>TAACACAATTTGACAATAACCAAATCATTGATTCTGACATTATCGCCACAGGGATAGAAATC<br>ATTGAGTAA |
| 31 | MEV-31 | ATGTCATCTCAACAGGAGAAAAAGGATTACGACGAGGAACAATTGAGACTAATGGAGGAA<br>GTGTGTATAGTAGTTGACGAGAACGATGTGCCACTAAGATACGGGACTAAAAAGGAATGC<br>CATCTGATGGAAAACATCAATAAGGGCTTGTTGCATAGGGCTTTCTCTATGTTTATCTTCGA<br>TGAACAAAACAGACTTTTGCTACAACAAAGAGCTGAGGAAAAGATAACATTCCCATCTCTG<br>TGGACTAATACATGTTGTAGTCATCCACTTGATGTTGCTGGTGAACGTGGTAATACCTTAC<br>CAGAAGCTGTTGAAGGTGTCAAAAACGCAGCTCAGAGAAAATTGTTCCACGAATTGGGTAT<br>ACAAGCCAAGTACATCCCTAAAGATAAGTTCCAATTCTTGACCAGAATTCATTACCTTGCAC<br>CTTCTACAGGAGCCTGGGGTGAGCATGAAATTGATTACATCTTATTCTTTAAGGGAAAGGT<br>CGAATTAGACATTAATCCTAACGAAGTTCAGGCATATAAGTACGTTACAATGGAAGAGTTA<br>AAGGAAATGTTTTCCGATCCACAGTACGGCTTTACTCCATGGTTCAAACTGATTTGCGAGC<br>ACTTTATGTTTAAGTGGTGGCAAGATGTAGACCATGCCTCAAAATTCCAAGATACTTTAATC<br>CACAGATGTTAA |
| 32 | MEV-32 | ATGTGGAGAGCATTGGCCCCAGCTAGAGCTATCGGTAGAGCTGCATCCGGAGGTGGCGC<br>TAGAATTGGCGGAGGTGCCAGAGCATTGGGAAGATCTTTGAAAGACACACCTCCTGCTGT<br>TCAACCAACAGTTGATGGCTCTTGCTTAAGGTTTCCTGGTAGAAGAGGCGGGTGGGCTGC<br>TATGCCAGAAGTTTCAACTGATGATTTGGATGAAAGACAGGTACAACTAATGGCCGAAATG<br>TGTATTCTTGTGGATGAAAACGATAGAAGGATTGGTGCTGAAACAAAGAAGAATTGTCATT<br>TGAACGAAAACATTGAAAGAGGGTTATTGCATAGAGCTTTCTCTGTTTTCCTATTCAATACA |

TABLE 6-continued

DNA Sequences of Optimized Mevalonate Pathway Gene Analogs

| SEQ ID. NO: | Optimized Gene | DNA Sequence |
|---|---|---|
| | | GAAAACAAGTTATTACTACAGCAAAGATCTGATGCCAAAATCACTTTTCCTGGTTGTTTCAC<br>TAATACATGCTGTTCACATCCACTTTCAAATCCAAGTGAATTGGAGGAAAACGATGCCATC<br>GGGGTGAGAAGAGCAGCCCAAAGGAGACTGAAGGCCGAATTGGGTATACCAATGGAGGA<br>AGTCCCTCCAGAAGAGATCAACTATCTGACAAGGATTCACTATAAAGCTCAATCTGACAGT<br>ATATGGGGTGAACATGAAATCGACTACATTCTGCTGGTCAAGAAAAATGTGACCTTGAATC<br>CAGATCCTAATGAGATTAAGTCCTACTGTTACGTCACGAAAGAGGAACTTGAGGAGCTAAT<br>TGGTAAAGCAGCCCATGGAGAAATCAAGATCACGCCTTGGTTCCAAATCATAGCTGACACT<br>TTCTTGTTTAAGTGGTGGGACAACTTAAACAGATTAAACTTATTTGTAGATCACGAGAAAAT<br>ACACAGAATGTAA |
| 33 | MEV-33 | ATGGCCGAAACCTTAGTTTCCAAATGCTCCTCTCAGTTCACAAAATTGAGTTCCTTCTCACT<br>TACTTCTTCATCTTCTAATTTGTACCAGAGACAATTCGTCACATTCAAACCAAGGAGTTCAT<br>TTGCTGCTTCAGTTTCTTCATCCACTACCATTCTAACTGATGCCGACTCTAACATGGACGC<br>CGTTCAAAGGAGATTGATGTTTGAAGATGAATGCATCCTGGTGGATGCTAACGACGCAGT<br>AGTTGGCCATGATACAAAGTATAACTGTCATTTGATGGAAAAGATTCAATCTGAGAACCTG<br>CTACACAGAGCTTTCAGTGTCTTTCTGTTCAATTCCAAGTACGAATTGCTGTTACAACAAAG<br>ATCTGCTACAAAAGTTACATTTCCTTTGGTTTGGACTAACACCTGTTGTTCTCACCCATTGT<br>ATAGAGAATCAGAGCTTATTGAGGAGAACTACTTAGGGGTGAGAAACGCTGCTCAGAGAA<br>AGTTGTTAGATGAATTAGGTATCCCATCTGATGAGCTACCTGTTAATGAGTTTATCCCATTG<br>GGACGTATACTATACAAAGCACCTTCTGATGGAAAGTGGGGTGAACATGAACTTGATTACT<br>TGTTATTCATAGTAAGAGATGTTTCTATGGCACCAAATCCTGATGAAGTAGCAGAAGTCAA<br>ATACGTGAATAGAACAATTGAAGGAGTTAGTCATGAAGGCCGATCTTGGCGAAGAGGG<br>TCTTAAGTTATCACCATGGTTCAGAATCGTAGTGGACAATTTCTTGTTTAAGTGGTGGGATC<br>ATGTTGAAAACGGTTCACTATTAGAAGCCTGTGTATATGAAAACAATTCACAACTTATAA |
| 34 | MEV-34 | ATGACACAAGGTTCTGGATTCAACAAGGAAGATATCGTTAGAAGAAGGAAAAAGGATCACA<br>TTGATATCTGTTTGCATAAAGTAGTCGAACCTTACAAAAACGGTCCATCTATATGGGAGAA<br>GTACAAAATACCTTATACTGCCTTACCTGAAATCTCCATGGGGAAAATTGATACCAGATGC<br>GAATTCATGGGCTGGACTCTATCATTTCCTTTGATTATCAGTTCCATGACTGGCGGAGAAG<br>AGCATGGGAGAATAATCAACGAGAATTTGGCCAAAGCCTGTGAAGCCGAAGGCATACCAT<br>TCGGTTTAGGAAGTATGAGAATTGTTAACAGATATGCTGTGGCTATTCATACATTTGATGTC<br>AAAAAGTTCTGTCCATCTGTTCCAATGTTCGCCAATATAGGATTAGTACAGCTGAATTATGG<br>ATTCGGTGTCAAGGAAGTGAATAATCTTATCAAGTGCGTAAATGCAGACGGATTGTTTATT<br>CATCTAAACCACACAAGAGGCATGTCAACCAGAAGGTGATACAAACTTCGAATCCCTGC<br>TACACAAGTTAGAAGAGTTGTTACCTCACATTAAAGTGCCAGTAATCGTTAAGGGTGTTGG<br>GCATGGTATTGAAAAGAGATCTGTTATGGCCTTGCAAAGAGTTGGTGTCAAATACATCGAC<br>GTATCTGGTTGTGGAGGAACTTCTTGGGCTTGGATTGAAGGGTGGAGACATCCAGATCTA<br>CCAGATGACCAAAACTTGGGTTACATCTTCAGAGATGTTGGTATAACGACGGACAGGTCAT<br>TGCAAGAGTGTGCTCCTCTGACACAAGCATCTGACCTGAGACTTATCGCCGGAGGCGGGA<br>TTAGAACCGGTTTGGATATCGCCAAGTCTCTTATGATGGGCGCTGAATGCGCTACAGCCG<br>CTCTGCCATTTTTGAAAGCAGCTTTGGAATCACCTGAAAGAGTCAGAGGCGTGATTCAAAG<br>ATTCAAAAAGGAGTTAATAGTGGCTATGTTTGCTTGTGGTGCCTCTACTATTGAAGAGCTTA<br>GAAAGATGTCATTAAGTGTTTCATCATCTTTATAA |
| 35 | MEV-35 | ATGTCTGATTTCCAGAGAGAACAAAGGAAAAACGAGCATGTTGAAATTGCTATGGCACAAT<br>CTGATGCTATGCATTCTGATTTCGATAAGATGAGATTTGTGCATCATTCAATTCCATCAATT<br>AACGTTAACGATATTGATTTGACATCACAAACACCTGATTTGACGATGACATATCCAGTTTA<br>CATTAACGCTATGACAGGTGGATCTGAATGGACCAAAAACATAAATGAGAAATTAGCTGTA<br>GTCGCCAGAGAAACAGGCTTGGCCATGGCCGTCGGTTCTACTCACGCTGCCCTTAGAAAT<br>CCTAGAATGGCTGAAACCTTCACTATTGCCAGAAAGATGAATCCAGAAGGCATGATTTTCT<br>CCAATGTAGGAGCTGATGTACCTGTAGAAAAGGCCTTAGAAGCAGTAGAACTATTGGAAG<br>CTCAAGCCTTACAGATCCACGTTAACTCCCCTCAGGAACTGGTGATGCCAGAAGGTAATA<br>GAGAATTTGTTACATGGCTAGACAACATTGCTTCCATCGTCAGTAGAGTCTCAGTTCCAGT<br>AATCATAAAGGAGGTGGGGTTTGGTATGAGTAAGGAATTGATGCACGATCTTCAACAAATT<br>GGGGTGAAGTACGTTGACGTGTCTGGCAAAGGTGGAACAAACTTCGTCGATATAGAAAAT<br>GAGAGAAGAGCAAACAAGGACATGGATTACCTTTCCTCCTGGGGCCAATCCACTGTTGAA<br>TCTTTGCTAGAAACGACTGCTTACCAATCTGAAATATCAGTGTTCGCCTCAGGTGGGCTGA<br>GGACTCCATTAGCGCCATCAAATCATTAGCCTTGGGTGCTAAAGCAACTGGAATGTCTAG<br>ACCTTTTCTGAATCAAGTTGAGAATAATGGAATCGCACATACGGTCGCCTATGTTGAGAGT<br>TTCATAGAGCATATGAAGTCTATTATGACAATGTTAGATGCTAAAAACATTGATGATCTAAC<br>ACAAAAACAGATAGTTTTCTCTCCAGAAATCCTGAGTTGGATCGAGCAAAGGAATTTGAAC<br>ATCCATAGAGGTTAA |

TABLE 7

Protein Sequences of Optimized Mevalonate Pathway Gene Analogs

| SEQ ID. NO: | Optimized Gene | Amino Acid Sequence |
|---|---|---|
| 36 | MEV-1 | MVNTEVYIVSAVRTPMGSFGGSFASLPATKLGSIAIKGALERVNIKPSDVDEVFMGNVVSANLG QNPARQCALGAGLPRSIVCTTVNKVCASGMKATILGAQTIMTGNAEIVVAGGTESMSNAPYYA PKNRFGAKYGNVELVDGLLRDGLSDAYDGLPMGNAAELCAEEHSIDRASQDAFAISSYKRAQ NAQATKAFEQEIVPVEVPVGRGKPNKLVTEDEEPKNLNEDKLKSVRAVFKSNGTVTAANASTL NDGASALVLMSAAKVKELGLKPLAKIIGWGEAAQDPERFTTSPSLAIPKALKHAGIEASQVDYY EINEAFSVVAVANTKILGLDPERVNINGGGVAMGHPLGSSGSRIICTLAYILAQKDAKIGVAAVC NGGGGASSIVIERV |
| 37 | MEV-2 | MPVLAALLRRGPLLQRRVQEIRYAERSYVSKPTLNEVVIVSAIRTPIGSFLGSLSSLPATKLGSIA IQGAIEKAGIPKEEVKEAYMGNVLQGGEGQAPTRQAVLGAGLPISTPCTTINKVCASGMKAIMM ASQNLMCGHQDVMVAGGMESMSNVPYVMNRGATPYGGVKLEDLIVKDGLTDVYNKIHMGNC AENTAKKLNITREEQDTYALNSYTRSKAAWEAGRFGNEVVPVTITVKGKPDVVVKEDEEYKRV DFSKIPKLKTVFQRENGTVTAANASTLNDGAAAVVLMTADAAKRLNVKPLARIAAFADAAVEPI DFPLAPAYAVPKVLKDAGLKKEDITMWEVNEAFSVVVLANIKMLEMDPQKVNINGGAVSLGHPI GMSGARIVVHLAHALKQGEYGLASICNGGGGASAMLIQKL |
| 38 | MEV-3 | MAHSADSSDNPRDVCIVGVARTPMGGFLGSLSSLPATKLGSLAITAALKREMLTRLWSKEVVF GNVLSANLGQAPARQAALGAGISNSVICTTVNKVCASGMKAVMIAAQSIQLGINDVVVAGGME SMSNTPKYLAEARKGSRFGHDSLVDGMLKDGLWDVYNDCGMGSCAELCAEKFEITREQQDD YAVQSFERGIAAQESGAFTWEIVPVEVSGGRGRPSTIVDKDEGLGKFDAAKLRKLRPSFKENG GTVTAGNASSISDGAAAIVLVSGEKALQLGLQVLAKVKGYGDAAQEPEFFTTAPALAIPKAIAPN SPYSESYQVDYYEINEAFAVVALANQKLLGISPEKVNVNGGAVSLGHPLGCSGARILITLLGILK KRNGKYGVGGVCNGGGGASALVLEVV |
| 39 | MEV-4 | MHSTRHILRQRAVLVTGARTPFVKSFGALMKADTLELASASVAGLLNKTSLDPRDIDHIVWGNV VLQGSAHNCAREIVIDLNMPKKIIGNLTSMACASGLSSLSQACMLIEGGHADVVIAGGSDSVSN TEVPLRSVTYGLMMAQRKGVMGFFKEAGYNPFKWPGGIALTERSTGKTMGWHGDLIAELN SISRDDQEALAVASHANAARAEKAGYFKEEIVPVTIDKKGKKTEVTCDDVMQRDTEKMKAKMP SLKPVFRKEGGTITAATSSTLTDGGSAMLVMSEEKAKKLGYPTDVCVKSWYFSGIDPYPQLLL APVLGWGPALKKAGLTPKDIDLYEIHEAFAAQVLATIKCLKSQEFFDRYANGAKPVLTEDIDLSK LNVGGSLALGHPFAATGGRIVISLANELRRSGKRHGLVSICAAGGLGGVAILEHTASK |
| 40 | MEV-5 | MNQAVIVAAKRTAFGKYGGTLKHIEPEQLLKPLFQHFKEKYPEVISKIDDVVLGNVVGNGGNIA RKALLEAGLKDSIPGVTIDRQCGSGLESVQYSCRMIQAGAGKVYIAGGVESTSRAPWKIKRPH SVYETALPEFYERASFAPEMSDPSMIQGAENAAKMYDVSRELQDEFAYRSHQLTAENVKNGN ISQEILPITVKGEIFNTDESLKSHIPKDNFGRFKPVIKGGTVTAANSCMKNDGAVLLLIMEKDMAY ELDFEHGLLFKDGVTVGVDSNFPGIGPVPAISNLLKRNQLTIENIEVIEINEAFSAQVVACQQALN ISNTQLNIWGGALASGHPYGASGAQLVTRLFYMFDKETMIASMGIGGGLGNAALFTRF |
| 41 | MEV-6 | MTIPLATAVADIELPRPKDVGVLGIEVYFPPRRCVSEADLEVFDGVSTGKYTIGLGQEYMAWPDD REDINSFALNAVSGLLEKYNIDPKSIGRIDVGTETIIDKSKSVKTTLMDLFAEAGNYDIEGIDSKNA CYGGTAALFNAINWIESSSWDGRNAIVVSGDIAVYAEGAARPAGGAGACAILIGPNAPVVFEPV HGTYMANTYDFYKPNLSSEYPEVDGPVSVVTYVAALDAAYTTFKEKFAKAAKRAQVAGKEVS SATFSLEDLDYAIFHSPYGKQAVKGHARMLYNDFITNPKDPRFANVPNPESFISQSHAQSLTDK NVEKTFVALSKASFAKKTDPGMACSKRLGNMYTASLYGCLASLLGTVEPSELGGKRVSLFSFG SGCAATFFTARIKGDTSEIKEKLKLKERLAAMTVAPPEEFVAALALREKNHNAVDFTPEGSVDNI WPGAYYLEHVDSKFRRKYVRAPVA |
| 42 | MEV-7 | MQRLLTPVRQVLQVKRVMQEASLLPARLLPAAHPSFSTVPAVPLAKTDTWPKDVGILAMEVYF PAQYVDQTELEKFNKVEAGRYTVGLGQTQMGFCSVQEDVNSLCLTVVQQLMERTQLPWDSV GRLEVGTETIIDKSKAVKTVLMELFQDSGNTDIEGIDTTNACYGGTASLFNAANWMESSSWDG RYALVVCGDIAVYPSGNARPTGGAGAVAMLVGPEAPLVLERGLRGTHMENVYDFYKPDVTSE YPLVDGKLSIQCYLRALDKCYAFYRQKIEKQWKQAGIDRPFTLDDVQYMIFHTPFCKLVQKSLA RLMFNDFLLASGDTQTGIYKGLEAFRGLKLEDTYTNKDVDKAFLKASLNMFKKTKNSLYLSTY NGNMYTSSLYGCLASLLAHHSAQDLAGSRIGAFSYGSGLAASFFSFRVSQDASPGSPLEKLVS STSDLQKRLASRKRVSPEEFTEIMNQREQYYHKMNFSPPGDKNSLFPGTWYLERVDELYRRK YARRPV |
| 43 | MEV-8 | MASQPKNVGILAMEIYFPPTCLQQEVLEAHDGASKGKYTIGLGQDCMGFCTEVEDVISMSLTA VTSLPEKYAIDPKQIGRLEVGSETVIDKSKSIKTFLMQIFEKHGNTDIEGVDSTNACYGGTAALF NCVNWVESSSWDGRYGLVVCTDSAVYAEGPARPTGGAAAIAMLVGPDAPIVFESKIRASHMS HAYDFYKPILDSEYPVVDGKLSQTCYLMALDSCYKSLCNKYEKLEGKQFSMADAAYFVRHSPY NKLVQKSFGRLLFNDFLRNASSVDESAKQILAPFESLAGDESYQSRDLEKASQQVAKPFYDEK VQPTTLIPKQVGNMYTASLYAAFASLIHNKHNTLAGQRVIVFSYGSGLTATMFSLKFNEGQHPF SLSNIASVMNVSEKLKSRHEFTPEKFVEIMKLMEHRYGAKDFVTSKDCSLLAPGTYYLTEVDSK YRRFYAQKAPEHGLVNGH |
| 44 | MEV-9 | MMRNTCLSLAGVSGMAVYAPHCRVDLEQWCKWTGNSWDKVSSVVGQSFRITSHNENAYTM AANAVLRLIVNNNIDPTKIGFLGLGTESSSDNSAGAIIVKGMVDKGLRAMNMPAMSRHCEVPEF KHACLAGVYAMESATRFVNADGKDRMAIAVASDIAEYALGSTGEQTQGAGATAMVLEHDPKL FEVQLQHSGSASDYRGPDFRKPHRRHFMNLEEYTKSSANGKMADFPVFSGPYSTLVYQEEV TVAVEHMLERLQQSPGKYYDDVTALFFHRPYNMMPIQAMSFLYARGLARATSEEHKAHFAEL |

TABLE 7-continued

Protein Sequences of Optimized Mevalonate Pathway Gene Analogs

| SEQ ID. NO: | Optimized Gene | Amino Acid Sequence |
|---|---|---|
| | | CKQGKADPAAVVKELDVNPHYFQQIESGGEPKDAFPATGKVAKVLRKDKKFIDLLEKKMSMG SPAMGNFGNLYTASLPCWLAAGFEEAYTRKLDITGKPMVMVGYGSGDASMSIPILPVPGWEN AAANINVSKALENPVNLDKAQYEALHTGAEKNDLAKDRRKMEFVIDRLGNREAAFQDVGIEY YRYIQ |
| 45 | MEV-10 | MTIGIDKINFYVPKYYVDMAKLAEARQVDPNKFLIGIGQTEMAVSPVNQDIVSMGANAAKDIITD EDKKKIGMVIVATESAVDAAKAAAVQIHNLLGIQPFARCFEMKEACYAATPAIQLAKDYLATRPN EKVLVIATDTARYGLNSGGEPTQGAGAVAMVIAHNPSILALNEDAVAYTEDVYDFWRPTGHKY PLVDGALSKDAYIRSFQQSWNEYAKRQGKSLADFASLCFHVPFTKMGKKALESIIDNADETTQ ERLRSGYEDAVDYNRYVGNIYTGSLYLSLISLLENRDLQAGETIGLFSYGSGSVGEFYSATLVE GYKDHLDQAAHKALLNNRTEVSVDAYETFFKRFDDVEFDEEQDAVHEDRHIFYLSNIENNVRE YHRPE |
| 46 | MEV-11 | MRAVLRLLSTHTVFSPIETIVSVFVLATLAYFHILSGIKHSSFFASSHPPAIRPAFAHLTNGEWVA VSQHDWTEAWKHPGGSLDALELQQVVFTLDDKTQPSAVLDASAISQHLVSNVPALSGKAYSS LCHHPNVSGTSCFTSVSGPGASPILTLSFKPGTRDDWLGSLRKEKTITLDGVKYDVGAGKRQE SIGDMESSKWVAYALSALVLRFWELTKADSLDILVVLTGYILMHVTFMRLFLASRALGSNFWLS AGIFSSATISFLFTLPMCRSMDIPLDPIALTEALPFLVCTVGFDKPLRLARAVMAHPNILKPQDDG RMKAAGDVILEALDRVGNMILRDYALEIAVLFVGVNSRVGGLKEFCAVAAALLAMDRLMTFTLY TAVLTIMVEVRRIKKVRDMTKARSRSSSITAVTANGTAIRGVLSRKSSKQSVTEPETTKNLRQR ATDSAIGVKGSLLKDGGRLQEAEENPMARLKLLLIASFLTHILNFCTTLTSATANARHQRHPFR TVQEVVPIPRVDITTPAIANILSHLAVAQEPMFTVVGSEPIELLVKVAAPVYVHALPLAPALRASN TNTGEAIENFMSSWSSLVGDPVVSKWIVALLAVSVALNGYLLKGIAAGSGLAAMRAVRSQGVR FRSRARSIVKISDEPEPEPENSIDPAPVVFFASAAPAVEAPAPAPAPEPEPPVNRPPPLTIFSRP LNLETVDKKLQDALPIRSPPPVEPITPESREVEPTQVEVRSLAECVDVFENGPRPVSVALKTLN DEEVILLCQTGKIAPYALVKMLADFDRAVRVRRALISRASRTKTLENSLVPMKDYDYARVMGAC CENVIGYMPLPLGIAGPLKIDGLMYPIPMATAEGTLVASTSRGCKALNAGGGVTTVLTADGMTR GPAIDFPSIVRAAEAKAFIESEDGYATIREAFESTSRFAKLQKIKCALAGRTLFVRFATRTGDAM GMNMISKATEKALDVLSHEFPEMVVLALSGNYCTDKKPAAISWIEGRGKSIVAAEAVIPGKVVKS VLKTTVESLCNVNTKKNLIGSAMAGSVGGFNAHAANILTAVFLATGQDPAQNVESSNCMTLME PTNGGEDLLMTISMPCIEVGTVGGGTILEPQGAVLDLLGVRGAHPTNPGQNAQQLARIIASAVM AGELSLISALAAGHLVRAHLAHNRSQLNTPMPSRPHTPGPEDVSHVQQLPTPSASDDKGVTA QGYVVEAK |
| 47 | MEV-12 | MLSRLFRMHGLFVASHPWEVIVGTVTLTICMMSMNMFTGNNKICGWNYECPKLEEDVLSSDIII LTITRCIAILYIYFQFQNLRQLGSKYILGIAGLFTIFSSFVFSTVVINFLDKELTLGNLPFFLLLVD LSRASALAKFALSSNSQDEVRENIARGMAILGPTFTLDALVECLVIGVGTMSGVRQLEIMCCFG CMSVLANYFVFMTFFPACVSLVLELSRESREGRPIWQLSHFARVLEEEENKPNPVTQRVKMIM SLGLVLVHAHSRWIADPSPQNSTADNSKVSLGLDENVSKRIEPSVSLWQFYLSKMISMDIEQVI TLSLALLLAVKYIFFEQAETESTLSLKNPITSPVVTQKKITDDCCRRDPVLVRNDQKFHAMEEET RKNNERKVEVIKPLLAENDTSHRATFVVGNSSLLGTSLELETQEPEMELPVEPRPNEECLQILE NAEKGAKFLSDAEIIQLVNAKHIPAYKLETLMETHERGVSIRRQLLSKKLPEPSSLQYLPYRDYN YSLVMGACCENVIGYMPIPVGVAGPLCLDGKEFQVPMATTEGCLVASTNRGCRAIGLGGGAS SRVLADGMTRGPVVRFPRACDSAEVKAWLETPEGFTVIKEAFDSTSRVARLQKLHMSVAGRN LYIRFQSRSGDAMGMNMISKGTEKALSKLQEYFPEMQILAVSGNYCTDKKPAAINWIEGRGKS VVCEAVIPAKVVREVLKTTTEAMIEVNINKNLVGSAMAGSIGGYNAHAANIVTAIYIACGQDAAQ NVGSSNCITLMEASGPTNEDLYISCTMPSIEIGTVGGGTNLLPQQACLQMLGVQGACRDNPGE NARQLARIVCGTVMAGELSLMAALAAGHLVRSHMIHNRSKINLQDLQGTCTKKAA |
| 48 | MEV-13 | MDLRRKLPPKPPSSTTTKQPSHRSHSPTPIPKASDALPLPLYLTNTFFFTLFFSVAYYLLHRWR DKIRSGTPLHVVTLTELSAIVLLIASFIYLLGFFGIDFVQSFTSRENEQLNNDDHNVVSTNNVLSD RRLVYDYGFDVTGDNDNDNDDDVIVKSVVSGEVNSYSLEASLGDCYRAAKIRKRAVERIVGRE VLGLGFEGFDYESILGQCCEMPIGYVQPVPVGVAGPLLLNGGEFMVPMATTEGCLVASTNRGC KAICLSGGATAILLKDGMTRAPVVRFATAERASQLKFYLEDGVNFDTLSVVFNKSSRFARLQNI QCSIAGKNLYIRFTCSTGDAMGMNMVSKGVQNVLDFLQNDFPDMDVIGISWKFCSDKKPTAV NWIEGRGKSVVFQAVITKKVVRKSALNPQTCTCRTLTCLRPLLVLLLLVLLVDLMHMLHIVSAVF IATGQDPAQNIESSHCITMMEAVNNGKDLHVNVTMPSIEVGTVGGGTQLASQSACLNLLGVKG ACIESPGSNAQLLARIVAGSVLAGELSLMSAISAGQLVKSHMKYNRSSRDMSAIASKV |
| 49 | MEV-14 | MFRRAILLGCSAAKTPWSECSNAQLVDAVKSRKISFYGLEQALEPDYRRAIEVRREVVSEIASQ QPEAKKKQSALHTIPFENYDWNKVVGQNCENIIGYVPIPLGVAGPILIDGKEYPIPMATTEGALV ASTHRGARAITRSGGCKTLLLGEGMTRAPVVELPSLEEAGRLHKYCNENFLSLKEAFESTTQY GKLNSLKCVLAGRKAYLRFRATTGDAMGMNMITKGVDKALSVLQQHFPSMEILALSGNYCTDK KPSAVNWIDGRGKSVVAEATLLADVVEDTLKCTVDSLVSLNIDKNLVGSAMAGSVGGFNAQAA NAVAAIFIATGQDPAQVVESSMCITTMSKVGNDLLISVTMPSIEVGVVGGGTGLAAQRGCLELI GCGGPSKESPGTNAQLLSRVVAAGVLSAELSLMSGLAAGHLLSAHMRLNRKKK |
| 50 | MEV-15 | MQSLDKNFRHLSRQQKLQQLVDKQWLSEEQFNILLNHPLIDEEVANSLIENVIAQGALPVGLLP NIIVDDKAYVVPMMVEEPSVVAAASYGAKLVNQTGGFKTVSSERIMIGQIVFDGVDDTEKLSAD IKALEKQIHQIADEAYPSIKARGGGYQRIAIDTFPEQQLLSLKVFVDTKDAMGANMLNTILEAITA FLKNEFPQSDILMSILSNHATASVVKVQGEIDVKDLARGERTGEEVAKRMERASVLAQVDIHRA ATHNKGVMNGIHAVVLATGNDTRGAEASAHAYASKDGQYRGIATWRYDQERQRLIGTIEVPM TLAIVGGGTKVLPIAKASLELLNVESAQELGHVVAAVGLAQNFAACRALVSEGIQQGHMSLQYK SLAIVVGAKGDEIAQVAEALKQEPRANTQVAERILQDLRSQQ |

TABLE 7-continued

Protein Sequences of Optimized Mevalonate Pathway Gene Analogs

| SEQ ID. NO: | Optimized Gene | Amino Acid Sequence |
|---|---|---|
| 51 | MEV-16 | MTPPKPLETKQPLHDLPTPGPESPFRERRPYRFSTLCATVDNPDMKDQYGSSSVPIYQTATFK GVGNEYDYTRSGNPTRSHLQHHIAKISSAAHAFTVSSGMAALDVILRLLKPGDEVIAGDDLYGG TNRLLTYIRSHLGVTVHHVDTTDPTSLHKYINPTKTGMVLLESPTNPLLKIADLATISKDVKERAP NAIIVVDNTMMTSYLQRPLEHGADIVYDSATKYLSGHHDLMAGVVTCNRDDIAQRLAFTINAVG NALTPIDSFMLLRGIKTLAIRMDRQQTTAQLVAEYLYNLGFTVHYPGLPSHPGRDVHLRIADGN GAVLSFETGNKELSERIVAATRLWGISVSFGCVNSLISMPCVMSHASIDAATRAARGLPEDLITRL CVGIEDPHDLLDDLEHALLEAGAIELNAAQNKFVRAPDPDALSQAVHDLDLDDGRNQLEWFVS APGKVILFGEHAVVHGVTAIAASVDLRCYGLTTPRTDNKLSAHFKDLGNFYHEWDIDSLPWDA LTPIPPGEEHPEELDQRLIEALSQSVLAELGDENKQARAATLAFLYLYMTLARGQHRPSFNFTA RATLPVGAGLGSSASFSACAATALLLLHRRISVPAKPAPSTETHIHVSHEGRRALPASVAEDVN RWAFVAEKILHGNPSGVDNSVAVFGGALAYTRPGFGKKGGMEQIQGFKSLKFLLTNSQVPRD TKKLVAGVGEKKENEPELVNGILAAIQSISDEARRALADPELSRDALLSALQELIKENHDHLVTL GVSHPSLEKIREKTSEPYGLKTKLTGAGGGGCAVTLIPDDFKEEVLNGLIDELIREGFHPYLTSV GGSGLGILSPYPEHRTRGSDPQPPREDVGGGQVTPPDTPRAEIVERHTKHGVTFDPLRPTFE TAATTDISDWASSLGRWLYV |
| 52 | MEV-17 | MLSEVLLVSAPGKVILHGEHAVVHGKVALAVALNLRTFLRLQPHSNGRVGLNLPNIGVRRAWD VASLQLLDTSFLGHGDSAALTAKHVEKLKEVAGFPKDCVDPEHLAVLAFLYLYLSICQSQRALP SLDITVWSELPTGAGLGSSAAYSVCLAAALLTACEEIPNPLKDGEAAGRWTEENLELINKWAFQ GERVINGNPSGVDNAVSTWGGALRYQQGKISSLKRPPVLKILLINTKVPRSTKVLVANVRSRLL KFPEIVAPLLTSIDAISLECERVLGEMAAAPTPEHYLTLEELIDMNQHHLNALGVGHASLDQLCQ VTTAHGLHSKLTGAGGGGCGITLLRPDVERPAVEATKRALSGCGFDCWETSVGAPGVSVHTA ASLDASVQQGLDSL |
| 53 | MEV-18 | MEVKARAPGKIILSGEHAVVNGSTAVAASINLYTYVTLSFATAENDDSLKLQLKDLALEFSWPIG RIREALSNLGAPSSSTRTSCSMESIKTISALVEEENIPEAKIALTSGVSAFLWLYTSIQGFKPATV VVTSDLPLGSGLGSSAAFCVALSAALLAFSDSVNVDTKHLGWSIFGESDLELLNKWALEGEKII HGKPSGIDNTVSAYGNMIKFKSGNLTRIKSNMPLKMLVTNTRVGRNTKALVAGVSERTLRHPN AMSFVFNAVDSISNELANIIQSPAPDDVSITEKEEKLEELMEMNQGLLQCMGVSHASIETVLRTT LKYKLASKLTGAGGGGCVLTLLPTLLSGTVVDKAIAELESCGFQCLIAGIGGNGVEFCFGGSS |
| 54 | MEV-19 | MHVAVKDKTTRHHIGYGKVILFGEHFVVYGAESIVAGINEYTTCEISRLKHKPNVVEVIDERPAV PGYIKEKREEQRVAHGLVLRHLNIDTSKDGLLVKLGGPLVPSSGIGASASDVVSLSRALNELYS LNLSEEAVNRSAYAGECGYHGTPSGVDNTAATYGGIILFRRALKKSVFSRLALGKTLSIIVCSTG ITASTTKVVADVARLKAAQPSWFDDLFEQYNACVREAKKALQSGNLRRVGELMNINHTLCQKL TVSCPELDAIATCCRTFGALGAKMSGTGRGGLVVALAANTQERDRIAKAVREQCKEAKFVWR YSVQPGGSKL |
| 55 | MEV-20 | MTRKGYGESTGKIILIGEHAVTFGEPAIAVPFNAGKIKVLIEALESGNYSSIKSDVYDGMLYDAPD HLKSLVNRFVELNNITEPLAVTIQTNLPPSRGLGSSAAVAVAFVRASYDFLGKSLTKEELIEKAN WAEQIAHGKPSGIDTQTIVSGKPVWFQKGHAETLKTLSLDGYMVVIDTGVKGSTRQAVEDVHK LCEDPQYMSHVKHIGKLVLRASDVIEHHNFEALADIFNECHADLKALTVSHDKIEQLMKIGKEN GAIAGKLTGAGRGGSMLLLAKDLPTAKNIVKAVEKAGAAHTWIENLGG |
| 56 | MEV-21 | MVRTTVVSAPGKVLIAGGYLVLDPAYPGTVVSTSSRFYTVIQSQELLSKNTIRVRSPQFLEATW SYSVLFEPAVAVEASPENSSKNKFVHLALQKTIALAVELRGAAQIQEALTHGFDIAIVGDNDFYS QRAKLESLGLPRTLDSLTEITPFCATEVHLSDVHKTGLGSSAALITSLTSAILVHLSVISESSLAE DDSRDRRQAHNLAQYVHCLAQGKVGSGFDVSAAVFGSHLYSRFDPAVIQDLMSDDALPSQLP SVLSPSNAAWNYRIEPFKLPPLTRIVLADVDAGSDTPSLVGKVLKWRKENSTEAEALWKNLDQ QNQSLAQTLLHLGKLAEDDYENYASAVKYICSLQPVQQILYSPLRSNQSLQHSMKPTISAIREK MREMGNLSGVPIEPIEQTTLLLDACASQAGVIGGGVPGAGGYDAIWLLVCDPPSCAPDQSPLER IEHLWSHYEKLDVSPLSAQESTAKGVRVEALDDIPGLKNAISVS |
| 57 | MEV-22 | MAPLGGVPGLVLLFSGKRKSGKDFVTEALQSRLGADVCAILRLSGPLKEQYAQEHGLDFQRL MDASTYKEAYRSDMIRWGEEKRQADPGFFCRKIVEGVCQPVWLVSDTRRVSDIQWFQEAYG AVTQTVRVVATEESRQQRGWVFTPGVDDAESECGLDNFRTFDWVIENHGDEQHLEEQLEHLI EFIRSRL |
| 58 | MEV-23 | MAVVASAPGKVLMTGGYLILERPNAGIVLSTNARFYAIVKPIYDEIKPDSWAWAWTDVKLTSPQ LARESLYKLSLKNLALQCVSSSASRNPFVEQAVQFAVAAAHATLDKDKKNVLNKLLLQGLDITIL GTNDFYSYRNEIEACGLPLTPESLAALPSFSSITFNVEEANGQNCKPEVAKTGLGSSAAMTTAV VAALLHHLGLVDLSSSCKEKKFSDLDLVHIIAQTAHCIAQGKVGSGFDVSSAVYGSHRYVRFSP EVLSSAQDAGKGIPLQEVISNILKGKWDHERTMFSLPPLMSLLLGEPGTGGSSTPSMVGALKK WQKSDTQKSQETWRKLSEANSALETQFNILSKLAEEHWDAYKCVIDSCSTKNSEKWIEQATE PSREAVVKALLGSRNAMLQIRNYMRQMGEAAGVPIEPESQTRLLDTTMNMDGVLLAGVPGAG GFDAVFAVTLGDSGTNVAKAWSSLNVLALLVREDPNGVLLESGDPRTKEITTAVFAVHI |
| 59 | MEV-24 | MVVASCPGKVLILGGYLIVEEPNVGISVGTTARFVTRVASWKKCSDGKCRVHIVSSQFNKEFTF ECAAEEDSDSTIKIVQLEGASPSPFLFYGILYSVAGALLFGGDIFRDVTLELLADNDFYSQRNYLE SQGKPVTAANLRLIPRYTPLLGEVSKTGLGSSAAMTTSVVACLLQLYVFDSKKNNATESVERA PELPLRLEDVTEFIHRISQVAHCVAQGKVGSGFDVYTATFGTCVYRRFSARVLEKLVKGNEPP KRVTIPLLRECVETEDEVWVQRIPFRLPTGLQLLLGDVHKGGTETPGMVSKVMSWRRSVTTDP NSLWERLRMSNEKYVEALQGLIKQSQEAPVAYTEAVKNLKSVVLAKHNPSTEAERLWVEAAS |

TABLE 7-continued

Protein Sequences of Optimized Mevalonate Pathway Gene Analogs

| SEQ ID. NO: | Optimized Gene | Amino Acid Sequence |
|---|---|---|
| | | VASTSRRYLREMGEAAQVQIEPPELTSLLDATCSIPGVFAVGCPGAGGYDAVFALVLGEEVCS AVERFWECYNDLQVCPLLVRGDANGLVLD |
| 60 | MEV-25 | MIQVKAPGKLYIAGEYAVTEPGYKSVLIALDRFVTATIEEADQYKGTIHSKALHHNPVTFSRDED SIVISDPHAAKQLNYVVTAIEIFEQYAKSCDIAMKHFHLTIDSNLDDSNGHKYGLGSSAAVLVSVI KVLNEFYDMKLSNLYIYKLAVIANMKLQSLSSCGDIAVSVYSGWLAYSTFDHEWVKHQIEDTTV EEVLIKNWPGLHIEPLQAPENMEVLIGWTGSPASSPHFVSEVKRLKSDPSFYGDFLEDSHRCV EKLIHAFKTNNIKGVQKMVRQNRTIIQRMDKEATVDIETEKLKYLCDIAEKYHGASKTSGAGGG DCGITIINKDVDKEKIYDEWTKHGIKPLKFNIYHGQ |
| 61 | MEV-26 | MSEPIYEATASAPVNIAVIKYWGKRDTSLILPTNSSLSVTLSQDHLRSTTTSRASSSFDKDRLWL NGQEDVIKPGSRLETCIREMKKLRKELVEDKDANAPKLSTLPVHIASYNNFPTAAGLASSASGF AALVSSLAHLYTLTPPLTSPSTLSLIARQGSGSACRSLFGGFVAWEMGSTPTGTDSLAVQIADE AHWPEMHALICVVSDDKKGTSSTAGMQRTVETSTLLQHRIKDVVPRRMDEMIRAIKEKDFDSF ARITMADSNSFHAVALDTEPPIFYMNDVSRAIIALIVELNRVSLEKGEGYKAAYTYDAGPNAVIYT LDKNVKEVIQLIVKYFPQKAGEFKDNLQVLGGGVADINQVAQVPEGFNEKVAVVREVGAVKGLI HTKVGDGPRRLGDEESLLGKDGFPKTLVA |
| 62 | MEV-27 | MASEKPIVVVTCTAPVNIAVVKYWGKRDEELILPINSSLSVTLHQDQLKTTTTAAISRDFTEDRI WLNGREEDMGHPRLQACLREIRRLARKRRSDGHEDPLPLSLSYKVHVASENNFPTAAGLASS AAGYACLAYTLARVYGVDSDLSEVARRGSGSACRSLYGGFVEWQMGERPDGKDSVACQVA PESHWPELRVLILVVSAERKPMGSTAGMQTSVETSALLKFRAEALVPPRMAEMTRCIRERNFQ AFGQLTMKDSNQFHATCLDTFPPISYLSDTSRRIIQLVHRFNAHHGQTKVAYTFDAGPNAVVFT LDDTVAEFVAAVRHSFPPESNGDKFLKGLPVEPVLLSDELKAVLGMDPVPGSIRYIIATQVGPG PQVLDDPGAHLLGPDGLPKAA |
| 63 | MEV-28 | MSGEQRELNSWVFMVTARAPTNIAVIKYWGKRDEKLILPINDSISVTLDPDHLSATTTVAVSPSF SSDRMWLNGKEVSLGGERYQNCLREIRSRGRDVVDEKSGTLIKKEDWQTLHLHIASHNNFPT AAGLASSAAGFACLVYALAKLMDIEERYAGELSAIARQGSGSACRSLYGGFVKWDMGKERDG SDSIAVQLATEEHWEELVILVAVVSSRQKETSSTTGMRESVETSELLHHRAQEVVPKRIVQMQ EAIANHDFASFARITCVDSNQFHAVCLDASPPIFYMNDTSHRIINCIEKWNRFEGTPQVSYTFDA GPNAVICAPSRKVAGLLLQRLLYYFPPDSSKELSSYVIGDTSILGEIGLKSMKDVESLIAPPEFRS QNSSSIHPGEVDYFICTRPGKGPIILRNEDQAFFNNKTGFPPFRISET |
| 64 | MEV-29 | MSDQCVTVEAPINIAFIKYWGKREGGETLILPTNDSFSITLSASPFRSKTSVELRDDIETDTLRLN GTEVDVGKTPRVQSMLLLHLRSTCPEDLKNKKVNIVSENNFPTAAGMASSASGYCAMSAALIRA FKSTTNVSMLARLGSGSACRSAFGGFVIWNKGEKPDGSDCVATQFVDETHWPEIQVMCAVLK GAQKDVSSTKGMQQSLKTSPLMKKRISETVPERMKIASRAIKARDFATFAEIAMLESDDLQEIC ATTEPKITYATEDSYAMIRLVKAYNAKKGRTALAYTFDAGANCFLFVLKEDLPEAVAMLMEHFP TPFEKFFFGDRELLEKVKVVSLPDEYKKLIDHPKKPFEMLLQSPVGCGVKYLGPSESLIPPRV |
| 65 | MEV-30 | MIKSGKARAHTNIALIKYWGKKDEALIIPMNNSISVTLEKFYTETKVTFNDQLTQDQFWLNGEKV SGKELEKISKYMDIVRNRAGIDWYAEIESDNFVPTAAGLASSASAYAALAAACNQALDLQLSDK DLSRLARIGSGSASRSIYGGFAEWEKGYNDETSYAVPLESNHFEDDLAMIFVVINQHSKKVPS RYGMSLTRNTSRFYQYWLDHIDEDLAEAKAAIQDKDFKRLGEVIEENGLRMHATNLGSTPPFT YLVQESYDVMALVHECREAGYPCYFTMDAGPNVKILVEKKNKQQIIDKLLTQFDNNQIIDSDIIA TGIEIIE |
| 66 | MEV-31 | MSSQQEKKDYDEEQLRLMEEVCIVVDENDVPLRYGTKKECHLMENINKGLLHRAFSMFIFDEQ NRLLLQQRAEEKITFPSLWTNTCCSHPLDVAGERGNTLPEAVEGVKNAAQRKLFHELGIQAKYI PKDKFQFLTRIHYLAPSTGAWGEHEIDYILFFKGKVELDINPNEVQAYKYVTMEELKEMFSDPQ YGFTPWFKLICEHFMFKWWQDVDHASKFQDTLIHRC |
| 67 | MEV-32 | MWRALAPARAIGRAASGGGARIGGGARALGRSLKDTPPAVQPTVDGSCLRFPGRRGGWAA MPEVSTDDLDERQVQLMAEMCILVDENDRRIGAETKKNCHLNENIERGLLHRAFSVFLFNTEN KLLLQQRSDAKITFPGCFTNTCCSHPLSNPSELEENDAIGVRRAAQRRLKAELGIPMEEVPPEE INYLTRIHYKAQSDSIWGEHEIDYILLVKKNVTLNPDPNEIKSYCYVTKEELEELIGKAAHGEIKIT PWFQIIADTFLFKWWDNLNRLNLFVDHEKIHRM |
| 68 | MEV-33 | MAETLVSKCSSQFTKLSSFSLTSSSSNLYQRQFVTFKPRSSFAASVSSSTTILTDADSNMDAV QRRLMFEDECILVDANDAVVGHDTKYNCHLMEKIQSENLLHRAFSVFLFNSKYELLLQQRSAT KVTFPLVWTNTCCSHPLYRESELIEENYLGVRNAAQRKLLDELGIPSDELPVNEFIPLGRILYKA PSDGKWGEHELDYLLFIVRDVSMAPNPDEVAEVKYVNREQLKELVMKADLGEEGLKLSPWFR IVVDNFLFKWWDHVENGSLLEACDMKTIHNL |
| 69 | MEV-34 | MTQGSGFNKEDIVRRRKKDHIDICLHKVVEPYKNGPSIWEKYKIPYTALPEISMGKIDTRCEFM GWTLSFPLIISSMTGGEEHGRIINENLAKACEAEGIPFGLGSMRIVNRYAVAIHTFDVKKFCPSV PMFANIGLVQLNYGFGVKEVNNLIKCVNADGLFIHLNHTQEACQPEGDTNFESLLHKLEELLPHI KVPVIVKGVGHGIEKRSVMALQRVGVKYIDVSGCGGTSWAWIEGWRHPDLPDDQNLGYIFRD VGITTDRSLQECAPLTQASDLRLIAGGGIRTGLDIAKSLMMGAECATAALPFLKAALESPERVR GVIQRFKKELIVAMPACGASTIEELRKMSLSVSSSL |
| 70 | MEV-35 | MSDFQREQRKNEHVEIAMAQSDAMHSDFDKMRFVHHSIPSINVNDIDLTSQTPDLTMTYPVYI NAMTGGSEWTKNINEKLAVVARETGLAMAVGSTHAALRNPRMAETFTIARKMNPEGMIFSNV |

TABLE 7-continued

Protein Sequences of Optimized Mevalonate Pathway Gene Analogs

| SEQ ID NO: | Optimized Gene | Amino Acid Sequence |
|---|---|---|
| | | GADVPVEKALEAVELLEAQALQIHVNSPQELVMPEGNREFVTWLDNIASIVSRVSVPVIIKEVGF GMSKELMHDLQQIGVKYVDVSGKGGTNFVDIENERRANKDMDYLSSWGQSTVESLLETTAYQ SEISVFASGGLRTPLDAIKSLALGAKATGMSRPFLNQVENNGIAHTVAYVESFIEHMKSIMTMLD AKNIDDLTQKQIVFSPEILSWIEQRNLNIHRG |

TABLE 8

DNA Sequences of Genes Introduced for β-carotene Production.

| SEQ ID NO: | Gene | DNA Sequence |
|---|---|---|
| 71 | CAR-1 | ATGGATTACGCGAACATCCTCACAGCAATTCCACTCGAGTTTACTCCTCAGATGATATCGT GCTCCTTGAACCGTATCACTACCTAGGAAAGAACCCTGGAAAAGAAATTCGATCACAACTC ATCGAGGCTTTCAACTATTGGTTGGATGTCAAGAAGGAGGATCTCGAGGTCATCCAGAAC GTTGTTGGCATGCTACATACCGCTAGCTTATTAATGGACGATGTGGAGGATTCATCGGTCC TCAGGCGTGGGTCGCCTGTGCCCATCTAATTTACGGGATTCCGCAGACAATAAACACTG CAAACTACGTCTACTTTCTGGCTTATCAAGAGATCTTCAAGCTTCGCCAACACCGATACC CATGCCTGTAATTCCTCCTTCATCTGCTTCGCTTCAATCATCCGTCTCCTCTGCATCCTCCT CCTCCTCGGCCTCGTCTGAAAACGGGGGCACGTCAACTCCTAATTCGCAGATTCCGTTCT CGAAAGATACGTATCTTGATAAAGTGATCACAGACGAGATGCTTTCCCTCCATAGAGGGCA AGGCCTGGAGCTATTCTGGAGAGATAGTCTGAGTGTCCTAGCGAAGAGGAATATGTGAAA AGGTTCTTGGAAAGACGGGAGGTTTGTTCCGTATAGCGGTCAGATTGATGATGGCAAAGT CAGAATGTGACATAGACTTTGTCCAGCTTGTCAACTTGATCTCAATATACTTCCAGATCAG GGATGACTATATGAACCTTCAGTCTTCTGAGTATGCCCATAATAAGAATTTTGCAGAGGAC CTCACAGAAGGAAAATTCAGTTTTCCCACTATCCACTCGATTCATGCCAACCCCTCATCGA GACTCGTCATCAATACGTTGCAGAAGAAATCGACCTCTCCTGAGATCCTTCACCACTGTGT AAACTACATGCGCACAGAAACCCACTCATTCGAATATACTCAGGAAGTCCTCAACACCTTG TCAGGTGCACTCGAGAGAGAACTAGGAAGGCTTCAAGGAGAGTTCGCAGAAGCTAACTCA AAGATTGATCTTGGAGACGTAGAGTCGGAAGGAAGAACGGGGAAGAACGTCAAATGGAA GCGATCCTGAAAAAGCTAGCCGATATCCCTCTGTGA |
| 72 | CAR-2 | ATGACGGCTCTCGCATATTACCAGATCCATCTGATCTATACTCTCCCAATTCTTGGTCTT CTCGGCCTGCTCACTTCCCCGATTTTGACAAAATTTGACATCTACAAAATATCGATCCTC GTATTTATTGCGTTTAGTGCAACCACACCATGGGACTCATGGATCATCAGAAATGGCGCA TGGACATATCCATCAGCGGAGAGTGGCCAAGGCGTGTTTGGAACGTTTCTAGATGTTCCA TATGAAGAGTACGCTTTCTTTGTCATTCAAACCGTAATCACCGGCTTGGTCTACGTCTTG GCAACTAGGCACCTTCTCCCATCTCTCGCGCTTCCCAAGACTAGATCGTCCGCCCTTTCT CTCGCGCTCAAGGCGCTCATCCCTCTGCCCATTATCTACCTATTTACCGCTCACCCCAGC CCATCGCCCGACCCGCTCGTGACAGATCACTACTTCTACATGCGGGCACTCTCCTTACTC ATCACCCCACCTACCATGCTCTTGGCAGCATTATCAGGCGAATATGCTTTCGATTGGAAA AGTGGCCGAGCAAAGTCAACTATTGCAGCAATCATGATCCCGACGGTGTATCTGATTTGG GTAGATTATGTTGCTGTCGGTCAAGACTCTTGGTCGATCAACGATGAGAAGATTGTAGGG TGGAGGCTTGGAGGTGTACTACCCATTGAGGAAGCTATGTTCTTCTTACTGACGAATCTA ATGATTGTTCTGGGTCTGTCTGCCTGCGATCATACTCAGGCCCTATACCTGCTACACGGT CGAACTATTTATGGCAACAAAAAGATGCCATCTTCATTTCCCCTCATTACACCGCCTGTG CTCTCCCTGTTTTTTAGCAGCCGACCATACTCTTCTCAGCCAAAACGTGACTTGGAACTG GCAGTCAAGTTGTTGGAGGAAAAGAGCCGGAGCTTTTTTGTTGCCTCGGCTGGATTTCCT AGCGAAGTTAGGGAGAGGCTGGTTGGACTATACGCATTCTGCCGGGTGACTGATGATCTT ATCGACTCTCCTGAAGTATCTTCCAACCCGCATGCCACAATTGACATGGTCTCCGATTTT CTTACCCTACTATTTGGGCCCCCGCTACACCCTTCGCAACCTGACAAGATCCTTTCTTCG CCTTTACTTCCTCCTTCGCACCCTTCCCGACCCACGGGAATGTATCCCCTCCCGCCTCCT CCTTCGCTCTCGCCTGCCGAGCTCGTTCAATTCCTTACCGAAAGGGTTCCCGTTCAATAC CATTTCGCCTTCAGGTTGCTCGCTAAGTTGCAAGGGCTGATCCCTCGATACCCACTCGAC GAACTCCTTAGAGGATACACCACTGATCTTATCTTTCCCTTATCGACAGAGGCAGTCCAG GCTCGGAAGACGCCTATCGAGACCACAGCTGACTTGCTGGACTATGGTCTATGTGTAGCA GGCTCAGTCGCCGAGCTATTGGTCTATGTCTCTTGGGCAAGTGCACCAAGTCAGGTCCGT GCCACCATAGAAGAAAGAGAAGCTGTGTTAGTGGCAAGCCGAGAGATGGGAACTGCCCTT CAGTGGTGAACATTGCTAGGGACATTAAAGGGGACGCAACAGAAGGGAGATTTTACCTA CCACTCTCATTCTTTGGTCTTCGGGATGAATCAAAGCTTGCGATCCCGACTGATTGGACG GAACCTCGGCCTCAAGATTTCGACAAACTCCTCAGTCTATCTCCTTCGTCCACATTACCA TCTTCAAACGCCTCAGAAAGCTTCCGGTTCGAATGGAAGACGTACTCGCTTCCATTAGTC GCCTACGCAGAGGATCTTGCCAAACATTCTTATAAGGGAATTGACCGACTTCCTACCGAG GTTCAAGCGGGAATGCGAGCGGCTTGCGCGAGCTACCTACTGATCGGCCGAGAGATCAA AGTCGTTTGGAAAGGAGACGTCGGAGAGAGAAGGACAGTTGCCGGATGGAGGAGAGTAC GG |
| 73 | CAR-3 | ATGGCTGAGACTCAGAGACCACGAAGCGCCATTATCGTTGGCGCAGGAGCAGGCGGTAT CGCCGTCGCGGCCCGTCTGGCCAAAGCCGGAGTAGACGTCACAGTTCTCGAAAAGAACG ACTTCACAGGAGGCCGCTGCAGTCTCATCCACACAAAAGCTGGCTACCGCTTCGACCAAG |

TABLE 8-continued

DNA Sequences of Genes Introduced for β-carotene Production.

| SEQ ID. NO: | Gene | DNA Sequence |
|---|---|---|
| | | GTCCCTCACTCCTCCTCCTACCGGGTCTCTTCCGCGAGACCTTTGAAGATTTAGGCACCA<br>CTCTCGAGCAGGAAGATGTCGAGCTCCTCCAATGTTTCCCCAACTACAACATCTGGTTCTC<br>CGACGGCAAGCGCTTCTCGCCCACCACCGACAACGCCACCATGAAGGTCGAGATCGAAA<br>AGTGGGAAGGCCCCGACGGCTTCCGCCGCTACCTCTCGTGGCTCGCCGAGGGCCACCA<br>ACACTACGAGACCAGCTTGCGACACGTTCTGCACCGCAACTTCAAGTCCATCCTCGAGCT<br>GGCGGACCCCCGCCTTGTCGTCACGTTGCTCATGGCTCTTCACCCCTTCGAGAGCATCTG<br>GCACCGCGCCGGGCGTTACTTCAAGACGGATCGATGCAGCGCGTCTTTACTTTTGCGAC<br>CATGTACATGGGCATGAGCCCGTTCGATGCGCCGGCGACGTACAGTCTGCTTCAATACTC<br>GGAGTTGGCCGAGGGTATCTGGTATCCCGCGGAGGCTTCCACAAGGTGTTGGACGCTT<br>TGGTCAAAATTGGAGAGAGGATGGGCGTCAAGTACAGACTCAACACGGGCGTGTCCCAG<br>GTTCTCACGGACGGAGGCAAGAACGGAAAGAAGCCAAAGGCTACGGGTGTCCAGCTTGA<br>GAACGGCGAGGTGCTGAACGCCGATCTGGTGGTGGTTAACGCCGACTTGGTATATACGTA<br>CAACAACCTCCTGCCGAAGGAGATCGGGGGCATCAAGAAGTATGCGAACAAACTCAACAA<br>CCGCAAGGCGTCGTGCAGTTCTATTTCTTTTTACTGGAGTTTGTCGGGTATGGCCAAAGAG<br>TTGGAGACGCACAATATCTTTTTGGCGGAGGAGTACAAGGAGTCCTTTGACGCTATCTTTG<br>AGAGGCAGGCCCTGCCTGATGATCCCAGCTTCTACATCCACGTCCCCTCCCGCGTTGACC<br>CTCGGCCGCCCCTCCCGACCGCGACGCCGTCATCGCCCTCGTCCCGTTGGCCACCTT<br>CTCCAAAACGGCCAACCAGAGCTCGACTGGCCTACTCTCGTCTCCAAAGCCCGTGCCGG<br>CGTTCTGGCCACCATCCAAGCCCGTACCGGCCTGTCCCTGTCCCCCCTTATCACCGAAGA<br>AATCGTCAACACCCCTTACACCTGGGAGACCAAGTTCAACCTCAGCAAGGGCGCCATCCT<br>CGGTTTGGCCCACGACTTCTTCAACGTGCTGGCCTTCCGCCCGCGCACCAAAGCCCAAG<br>GCATGGATAACGCCTACTTTGTCGGCGCTAGCACCCATCCGGGAACCGGCGTGCCGATT<br>GTCCTTGCAGGTGCCAAGATCACTGCCGAGCAGATTCTTGAGGAGACGTTTCCTAAGAAC<br>ACAAAGGTGCCGTGGACGACGAACGAGGAGAGGAACAGTGAGCGGATGAGGAAGGAGA<br>TGGATGAGAAGATTACGGAGGAGGGGATTATTATGAGGAGTAACAGCAGTAAGCCGGGC<br>AGGAGGGGGAGTGATGCTTTTGAGGGCGCCATGGAGGTGGTTAATCTCTTGTCGCAGAG<br>GGCGTTCCCTTTGTTGGTGGCGTTGATGGGGGTGCTGTATTTCTTGCTATTTGTGAGGTA<br>G |

TABLE 9

Protein Sequences of Enzymes Introduced for β-carotene Production.

| SEQ ID. NO: | Gene | Protein Sequence |
|---|---|---|
| 74 | CAR-1 | MDYANILTAIPLEFTPQDDIVLLEPYHYLGKNPGKEIRSQLIEAFNYWLDVKKEDLEVIQNVVGM<br>LHTASLLMDDVEDSSVLRRGSPVAHLIYGIPQTINTANYVYFLAYQEIFKLRPTPIPMPVIPPSSA<br>SLQSSVSSASSSSSASSENGGTSTPNSQIPFSKDTYLDKVITDEMLSLHRGQGLELFWRDSLT<br>CPSEEEYVKMVLGKTGGLFRIAVRLMMAKSECDIDFVQLVNLISIYFQIRDDYMNLQSSEYAHN<br>KNFAEDLTEGKFSFPTIHSIHANPSSRLVINTLQKKSTSPEILHHCVNYMRTETHSFEYTQEVLN<br>TLSGALERELGRLQGEFAEANSKIDLGDVESEGRTGKNVKLEAILKKLADIPL |
| 75 | CAR-2 | MTALAYYQIHLIYTLPILGLLGLLTSPILTKFDIYKISILVFIAFSATTPWDSWIIRNGAWTYPSAES<br>GQGVFGTFLDVPYEEYAFFVIQTVITGLVYVLATRHLLPSLALPKTRSSALSLALKALIPLPIIYLFT<br>AHPSPSPDPLVTDHYFYMRALSLLITPPTMLLAALSGEYAFDWKSGRAKSTIAAIMIPTVYLIWV<br>DYVAVGQDSWSINDEKIVGWRLGGVLPIEEAMFFLLTNLMIVLGLSACDHTQALYLLHGRTIYG<br>NKKMPSSFPLITPPVLSLFFSSRPYSSQPKRDLELAVKLLEEKSRSFFVASAGFPSEVRERLVG<br>LYAFCRVTDDLIDSPEVSSNPHATIDMVSDFLTLLFGPPLHPSQPDKILSSPLLPPSHPSRPTGM<br>YPLPPPPSLSPAELVQFLTERVPVQYHFAFRLLAKLQGLIPRYPLDELLRGYTTDLIFPLSTEAV<br>QARKTPIETTADLLDYGLCVAGSVAELLVYVSWASAPSQVPATIEEREAVLVASREMGTALQLV<br>NIARDIKGDATEGRFYLPLSFFGLRDESKLAIPTDWTEPRPQDFDKLLSLSPSSTLPSSNASESF<br>RFEWKTYSLPLVAYAEDLAKHSYKGIDRLPTEVQAGMRAACASYLLIGREIKVVWKGDVGERR<br>TVAGWRRVRKVLSVVMSGWEGQ |
| 76 | CAR-3 | MAETQRPRSAIIVGAGAGGIAVAARLAKAGVDVTVLEKNDFTGGRCSLIHTKAGYRFDQGPSLL<br>LLPGLFRETFEDLGTTLEQEDVELLQCFPNYNIWFSDGKRFSPTTDNATMKVEIEKWEGPDGF<br>RRYLSWLAEGHQHYETSLRHVLHRNFKSILELADPRLVVTLLMALHPFESIWHRAGRYFKTDR<br>MQRVFTFATMYMGMSPFDAPATYSLLQYSELAEGIWYPRGGFHKVLDALVKIGERMGVKYRL<br>NTGVSQVLTDGGKNGKKPKATGVQLENGEVLNADLVVVNADLVYTYNNLLPKEIGGIKKYANK<br>LNNRKASCSSISFYWSLSGMAKELETHNIFLAEEYKESFDAIFERQALPDDPSFYINVPSRVDP<br>SAAPPDRDAVIALVPVGHLLQNGQPELDWPTLVSKARAGVLATIQARTGLSLSPLITEEIVNTPY<br>TWETKFLSKGAILGLAHDFFNVLAFRPRTKAQGMDNAYFVGASTHPGTGVPIVLAGAKITAEQI<br>LEETFPKNTKVPWTTNEERNSERMRKEMDEKITEEGIIMRSNSSKPGRRGSDAFEGAMEVVN<br>LLSQRAFPLLVALMGVLYFLLFVR |

What is claimed is:

1. A method of producing an isoprenoid compound in a yeast cell, comprising cultivating the yeast cell in a suitable medium, wherein the yeast cell comprises:
   a) one or more heterologous nucleic acids encoding MEV-1 of SEQ ID. NO: 36, MEV-6 of SEQ ID. NO: 41, MEV-15 of SEQ ID. NO: 50, MEV-18 of SEQ ID. NO: 53, MEV-21 of SEQ ID. NO: 56, or MEV-23 of SEQ ID. NO: 58;
   b) a heterologous promoter substituted for the endogenous promoter of the cellular aconitase (ACO1) gene; and
   c) a heterologous nucleotide sequence encoding an ATP-citrate lyase enzyme;
wherein the yeast cell has reduced inherent aconitase (ACO1) expression relative to an unaltered yeast cell.

2. The method of claim 1, wherein the yeast cell further comprises one or more heterologous nucleotide sequences encoding a product set forth in MEV-6 of SEQ ID. NO: 41, MEV-15 of SEQ ID. NO: 50, MEV-18 of SEQ ID. NO: 53, MEV-21 of SEQ ID. NO: 56, or MEV-23 of SEQ ID. NO: 58.

3. The method of claim 1, wherein the yeast cell further comprises one or more heterologous nucleotide sequences encoding a product involved in the biosynthesis pathway leading to an isoprenoid compound of one or more MEVs set forth in SEQ ID NOS: 36 to 70.

4. The method of claim 1, wherein the yeast cell further comprises one or more nucleic acids of SEQ ID NOS: 1-35.

5. The method of claim 1, wherein the heterologous promoter substituted for the endogenous promoter of the cellular aconitase (ACO1) gene is a CUP1 gene promoter.

6. The method of claim 1, further comprising recovering the isoprenoid compound.

7. The method of 1, wherein the isoprenoid compound is β-carotene, antheraxanthin, adonirubin, adonixanthin, astaxanthin, canthaxanthin, capsorubrin, β-cryptoxanthin, α-carotene, β,ψ-carotene, Δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, or C30 carotenoids.

8. The method of claim 1, wherein each heterologous nucleic acid comprises one or more of MEV-1 of SEQ ID. NO: 1, MEV-6 of SEQ ID. NO: 6, MEV-15 of SEQ ID. NO: 15, MEV-18 of SEQ ID. NO: 18, MEV-21 of SEQ ID. NO: 21, or MEV-23 of SEQ ID. NO: 23.

9. The method of claim 1, wherein the yeast cell further comprises reduced inherent ERG9 expression relative to an unaltered yeast cell.

10. The method of claim 1, wherein the yeast host cell produces at least about 25 fold more isoprenoid compound relative to an unaltered yeast cell.

11. The method of claim 1, wherein the isoprenoid compound is produced in a recoverable amount of at least 150 mg/g dry weight (DW).

12. The method of claim 1, wherein the ATP-citrate lyase enzyme is a *Chlamydomonas rheinhardtii* or *Yarrowia lipolytica* ATP-citrate lyase enzyme.

13. A method for making a yeast host cell with increased synthesis of isoprenoid compounds relative to an unaltered yeast cell, the method comprising
   a) introducing one or more heterologous nucleotide sequences encoding MEV-1 of SEQ ID. NO: 36, MEV-6 of SEQ ID. NO: 41, MEV-15 of SEQ ID. NO: 50, MEV-18 of SEQ ID. NO: 53, MEV-21 of SEQ ID. NO: 56, or MEV-23 of SEQ ID. NO: 58;
   b) a heterologous promoter substituted for the endogenous promoter of the cellular aconitase (ACO1) gene; and
   c) a heterologous nucleotide sequence encoding an ATP-citrate lyase enzyme;
wherein the yeast host cell has reduced inherent aconitase (ACO1) expression relative to an unaltered yeast cell.

14. A yeast host cell comprising
   a) one or more heterologous nucleotide sequences encoding MEV-1 of SEQ ID. NO: 36, MEV-6 of SEQ ID. NO: 41, MEV-15 of SEQ ID. NO: 50, MEV-18 of SEQ ID. NO: 53, MEV-21 of SEQ ID. NO: 56, or MEV-23 of SEQ ID. NO: 58;
   b) a heterologous promoter substituted for the endogenous promoter of the cellular aconitase (ACO1) gene; and
   c) a heterologous nucleotide sequence encoding an ATP-citrate lyase enzyme;
wherein the yeast host cell has reduced inherent aconitase (ACO1) expression relative to an unaltered yeast cell.

15. The yeast host cell of claim 14, wherein the nucleotide sequence comprises one or more of MEV-1 of, MEV-6 of SEQ ID. NO: 6, MEV-15 of SEQ ID. NO: 15, MEV-18 of SEQ ID. NO: 18, MEV-21 of SEQ ID. NO: 21, or MEV-23 of SEQ ID. NO: 23.

16. The yeast cell of claim 14, wherein the yeast cell further comprises one or more heterologous nucleotide sequences encoding a product set forth in MEV-6 of SEQ ID. NO: 41, MEV-15 of SEQ ID. NO: 50, MEV-18 of SEQ ID. NO: 53, MEV-21 of SEQ ID. NO: 56, or MEV-23 of SEQ ID. NO: 58.

* * * * *